(12) United States Patent
Sato et al.

(10) Patent No.: US 8,030,327 B2
(45) Date of Patent: Oct. 4, 2011

(54) FUSED IMIDAZOLE DERIVATIVE

(75) Inventors: Yoshiyuki Sato, Hanamigawa-ku (JP); Hideki Kurihara, Tsukuba (JP); Kaori Kamijo, Tsukuba (JP); Yu Onozaki, Tsukuba (JP); Toshiaki Tsujino, Tsukuba (JP); Tetsuya Sugimoto, Tsukuba (JP); Akiko Watanabe, Tsukuba (JP); Morihiro Mitsuya, Tsukuba (JP); Hideya Komatani, Toride (JP)

(73) Assignee: MDS K.K., Chiyoda-Ku (JP)

( * ) Notice: Subject to any disclaimer, the term of this patent is extended or adjusted under 35 U.S.C. 154(b) by 386 days.

(21) Appl. No.: 11/667,282

(22) PCT Filed: Nov. 7, 2005

(86) PCT No.: PCT/JP2005/020763
§ 371 (c)(1),
(2), (4) Date: May 7, 2007

(87) PCT Pub. No.: WO2006/049339
PCT Pub. Date: May 11, 2006

(65) Prior Publication Data
US 2008/0103136 A1 May 1, 2008

(30) Foreign Application Priority Data
Nov. 8, 2004 (JP) ................................ 2004-323438

(51) Int. Cl.
| | |
|---|---|
| A01N 43/42 | (2006.01) |
| A01N 43/38 | (2006.01) |
| A01N 43/06 | (2006.01) |
| A61K 31/44 | (2006.01) |
| A61K 31/40 | (2006.01) |
| A61K 31/38 | (2006.01) |
| C07D 513/02 | (2006.01) |
| C07D 515/02 | (2006.01) |
| C07D 333/02 | (2006.01) |
| C07D 333/34 | (2006.01) |
| C07D 333/22 | (2006.01) |

(52) U.S. Cl. ........ 514/300; 514/413; 514/414; 514/445; 546/121; 549/62; 549/70
(58) Field of Classification Search .................. 514/300, 514/314, 414, 445; 546/121; 549/62, 70
See application file for complete search history.

(56) References Cited

U.S. PATENT DOCUMENTS
7,074,801 B1  7/2006 Yoshida et al.

FOREIGN PATENT DOCUMENTS
| | | |
|---|---|---|
| EP | 1277754 | 7/2005 |
| WO | WO 01/46196 | 6/2001 |
| WO | WO 02/34748 | 5/2002 |
| WO | WO 02/076983 | 10/2002 |
| WO | WO 03/092595 | 11/2003 |
| WO | WO 03/092595 A2 * | 11/2003 |
| WO | WO 2004/014899 | 2/2004 |

OTHER PUBLICATIONS

Sausville, Edward et al., "Contributions of Human Tumor Xenografts to Anticancer Drug Development," Cancer Research, vol. 66, pp. 3351-3354(2006).*
Cecil Textbook of Medicine, edited by Lee Goldman and J. Claude Bennett, 21st Edition, vol. 1, Chapter 14, pp. 1060-1074 (2000).*

* cited by examiner

*Primary Examiner* — Sreeni Padmanabhan
*Assistant Examiner* — Sarah Pihonak
(74) *Attorney, Agent, or Firm* — Nicole M. Beeler; David A. Muthard

(57) ABSTRACT

The present invention relates to a compound represented by the Formula [I]:

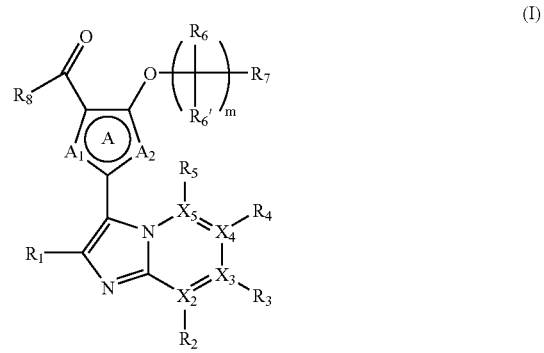

Wherein:
the A ring is a 5-membered aromatic heterocyclic group containing at least one hetero atom selected from a nitrogen atom, and the like; $A_1$ and $A_2$, are each a nitrogen atom, and the like; $X_2$, $X_3$, $X_4$, and $X_5$ are all carbon atoms, or alternatively any one of $X_2$, $X_3$, $X_4$, and $X_5$ is a nitrogen atom and the rest are all carbon atoms; $R_1$ is a hydrogen atom, or the like; $R_2$, $R_3$, $R_4$, and $R_5$, are each a hydrogen atom, or the like; $R_6$ and $R_6'$, are each a hydrogen atom, and the like; $R_7$ is an aryl group and the like; and $R_8$ is an amino group or a hydroxy group,
or a pharmaceutically acceptable salt or ester thereof.

10 Claims, 1 Drawing Sheet

FUSED IMIDAZOLE DERIVATIVE

PRIORITY CLAIM

This application is a §371 National Stage Application of PCT/JP2005/020763 that was filed on Nov. 7, 2005, which claims priority from the Japanese Priority Application No. Japan 2004-323438, filed on Nov. 8, 2004, now expired.

TECHNICAL FIELD

The present invention relates to a novel fused imidazole derivative useful in the field of medicine, which inhibits proliferation of tumor cells in response to an inhibitory effect against PLK1, thereby exhibiting an antitumor effect, and to a PLK1 inhibitor and an antitumor agent, containing the same.

BACKGROUND ART

Proliferation is known to be active generally in cancerous cells compared with normal cells, and in many cases, it is thought that the disorderliness of proliferation due to an abnormality in the cell cycle control mechanism is the cause of cancer. A mitotic phase (M phase) of the cell cycle is the step of equally partitioning a chromosome into daughter cells, and a strict control in the process is essential for cell proliferation and survival. Therefore, it is believed that the inhibition of M phase progression is an effective means for inhibiting cell proliferation, and in practical, antitumor agents targeting M phase such as taxol, vincristine, or the like are achieving clinically effective results.

It has been known that many steps in the M phase progression are controlled by protein kinase which phosphorylates proteins. A PLK (polo-like kinases) family is serine-threonine kinase playing an important role in controlling the cell cycle including M phase, and this family includes four similar proteins of PLK1, PLK2, PLK3, and SAK (Nature. Review. Molecular. Cell Biology (Nat. Rev. Mol. Cell. Biol.), Vol. 5, 429, (2004)). Of these, PLK1 is known to participate in number of important stages at M phase in mammalian cells: PLK1 has been reported to be participated in each step of: the entering into the M phase, the control of centrosome, the separation of chromosome, and cytokinesis, by phosphorylating various substrates (Nature. review. Molecular. Cell Biology.) (Nat. Rev. Mol. Cell. Biol.), Vol. 5, 429, (2004)).

Moreover, there are many reports suggesting that PLK1 is overexpressed in various cancerous tissues in human. For example, PLK1 is acknowledged to be overexpressed in non-small-cell lung cancer ((Oncogene), Vol. 14, 543, (1997)) and head and neck cancer ((Cancer Research), Vol. 15, 2794, (1999)), and there are data showing that the overexpression of PLK1 is in relation with a prognosis of patients with those diseases. It is also reported that the expression of PLK1 is increased in other types of cancer such as in colon cancer, esophageal cancer, ovarian cancer, and melanoma. Such reports suggest that the overexpression of PLK1 is related to malignant alteration of cells in one way or another, and also that the function of PLK1 is important particularly in the progression of M phase in cancer cells.

From the facts, PLK1 is thought to be a possible target for antitumor approach. In fact, there are many reports on experiments for examining the inhibitory effect on the function of PLK1 against cancerous cells by using various experimental techniques. For example, from the experiment of expressing a function-inhibited PLK1 mutant in a cell by using a viral vector, it is realized that PLK1 inhibition promotes the cancerous cell-selective apoptosis (Cell growth & Differentiation (Cell growth & Diff.), Vol. 11, 615, (2000)). There is also a report showing that PLK1 siRNA induces cancer cell growth inhibition and apoptosis (Journal of National Cancer Institute (J. Natl. Cancer Inst.), Vol. 94, 1863 (2002)). In addition, it is reported that PLK1 shRNA (Journal of National Cancer Institute (J. Natl. Cancer Inst.), Vol. 96, 862, (2004)), or antisense oligonucleotide (Oncogene, Vol. 21, 3126 (2002)) gives an antitumor effect in a mouse xenograft model. Those experimental results show that inhibition of the PLK1 activity causes the promotion of cancer cell growth inhibition and apoptosis, and strongly suggest that a PLK1 inhibitor is an effective antitumor agent.

In the past, there are filed patent applications related to a compound having a PLK inhibitory effect (Pamphlet of International Publication Nos. 2004/014899, etc.). However, there has not yet been reported a fused imidazole derivative having an excellent PLK1 inhibitory effect.

DISCLOSURE OF THE INVENTION

It is an object of the present invention to provide a novel fused imidazole derivative for the purpose of developing an antitumor agent based on a PLK1 inhibitory effect, which exhibits a PLK1 inhibitory effect and excellent cytostatic activity based on the inhibitory effect.

In order to solve the object, the inventors of the present invention synthesized a wide range of novel fused imidazole derivatives, and discovered that a compound represented by Formula [I]-exhibits excellent PLK1 inhibitory effect and cell-growth inhibitory activity based on the PLK1 inhibitory effect, thus completing the invention.

That is, the invention relates to a compound represented by the Formula [I]:

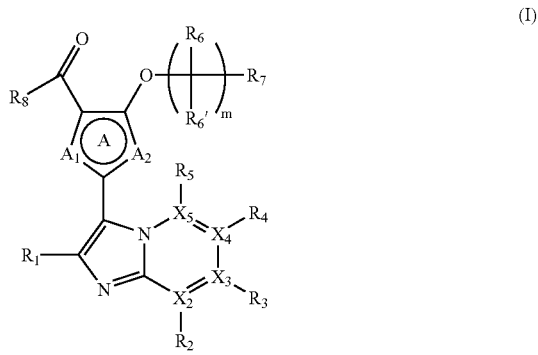

wherein
the A ring is a 5-membered aromatic heterocyclic group containing at least one hetero atom selected from the group consisting of a nitrogen atom, a sulfur atom, and an oxygen atom;

$A_1$ and $A_2$, which may be the same or different, are each CH, a nitrogen atom, NH, a sulfur atom, or an oxygen atom, with the proviso that the $A_1$ and $A_2$ cannot be simultaneously CH;

$X_2$, $X_3$, $X_4$, and $X_5$ are all carbon atoms, or alternatively any one of $X_2$, $X_3$, $X_4$, and $X_5$ is a nitrogen atom and the rest are all carbon atoms, with the proviso that when $X_i$ (where i is one of 2, 3, 4 and 5) is a nitrogen atom, the corresponding $R_i$ (where i is one of 2, 3, 4 and 5) together with the $X_i$ forms a nitrogen atom;

m is an integer of 1 or 2;

$R_1$ is a hydrogen atom, a methyl group which may be substituted with one or more halogen atom(s), or a substituent selected from <substituent group α>;

$R_2$, $R_3$, $R_4$, and $R_5$, which may be the same or different, are each a hydrogen atom or —$Y_1$—$Y_2$—$Y_3$—$Y_4$, wherein
- $Y_1$ is a single bond, $CH_2$, $CH(CH_3)$, O, S, SO, $SO_2$, CO, CONH, or NHCO;
- $Y_2$ is a single bond or $(CW_1W_1')_n$, wherein n is an integer of 1 to 4; i is an integer of 1 to n; and $(CW_iW_i')_n$ represents, $(CW_1W_1')$ when n is equal to 1, $(CW_1W_1')$—$(CW_2W_2')$ when n is equal to 2, $(CW_1W_1')$—$(CW_2W_2')$—$(CW_3W_3')$ when n is equal to 3, and $(CW_1W_1')$—$(CW_2W_2')$—$(CW_3W_3')$—$(CW_4W_4')$ when n is equal to 4, where $W_1$, $W_2$, $W_3$, and $W_4$, and $W_1'$, $W_2'$, $W_3'$, and $W_4'$, which may be the same or different, are each a hydrogen atom, a lower alkyl group, or a substituent selected from <substituent group $β_1$>;
- $Y_3$ is a single bond, NH, $NR_a$, S, O, or COO, wherein $R_a$ is a substituent selected from the <substituent group $β_1$>; or a lower alkyl group which may be substituted with one or more of the same or different substituents selected froth the <substituent group $β_1$>;
- $Y_4$ is a hydrogen atom, a substituent selected from the <substituent group $β_1$>, a lower alkyl group which may be substituted with one or more of the same or different substituents selected from the <substituent group $β_1$>, $R_bC(=O)NR_c$—$(CHZ_2)_p$—, $NR_dR_d'$—$(CHZ_2)_q$—$C(=O)NR_c$—$(CHZ_1)_p$—, $NR_eR_e'$—$(CHZ_3)_r$—$C(=O)$—$(CHZ_1)_p$—, a cycloalkyl group, an aliphatic heterocyclic group, an aryl group, an aralkyl group, a heteroaryl group, or a lower alkyl substituted with the heteroaryl group, wherein
    the cycloalkyl group, the aliphatic heterocyclic group, the aryl group, the aralkyl group, and the heteroaryl group may be substituted with one or more of the same or different substituents selected from the following:
    1) a lower alkyl group,
    2) a substituent selected from the <substituent group $β_1$>,
    3) a lower alkyl group substituted with a substituent selected from the <substituent group $β_1$>,
    4) $R_bC(=O)NR_c$—$(CHZ_1)_p$—,
    5) $NR_dR_d'$—$(CHZ_2)_q$—$C(=O)NR_c$—$(CHZ_1)_p$—,
    6) $NR_eR_e'$—$(CHZ_3)$, —$C(=O)$—$(CHZ_1)_p$—, and
    7) a cycloalkyl group which may be substituted, and two hydrogen atoms, which bind to the same carbon atom, in the aliphatic heterocyclic group may be substituted with an oxo group;

p, q, and r, which may be the same or different, are each 0, 1, or 2;

$Z_1$, $Z_2$, and $Z_3$, which may be the same or different, are each a hydrogen atom or a lower alkyl group;

$R_b$ is a substituent selected from <substituent group $β_2$>, a lower alkyl group which may be substituted with one or more of the same or different substituents selected from the <substituent group $β_2$>, or a cycloalkyl group which may be substituted;

$R_c$ is a hydrogen atom, a substituent selected from the <substituent group $β_2$>, or a lower alkyl group which may be substituted with one or more of the same or different substituents selected from the <substituent group $β_2$>;

$R_d$ and $R_d'$, which may be the same or different, are each a hydrogen atom or a lower alkyl group; and $R_e$ and $R_e'$ are each a hydrogen atom or a lower alkyl group, or alternatively $R_e$ and $R_e'$, together with the nitrogen atom to which they bind, form an aliphatic heterocyclic group selected from a pyrrolidinyl group, a piperidinyl group, and a piperazinyl group;

provided, however, that:

when $X_i$ (where i is one of 2, 3, 4 and 5) is a nitrogen atom, the corresponding R; (where is one of 2, 3, 4 and 5) together with the $X_1$ forms a nitrogen atom;

$R_6$ and $R_6'$, which may be the same or different, are each a hydrogen atom, a substituent selected from the <substituent group $β_1$>, a lower alkyl group which may be substituted with one or more of the same or different substituents selected from the <substituent group $β_1$>, or a cycloalkyl group; or alternatively $R_6$ and $R_6'$ are combined together to form an oxo group; however, when m is 2, then two sets of $R_6$ and $R_6'$ which are adjacent to each other cannot together form an oxo group;

$R_7$ is an aryl group or a heteroaryl group any of which may be substituted;

$R_8$ is an amino group or a hydroxy group; and the <substituent group α>, the <substituent group $β_1$>, and the <substituent group $β_2$> are defined as follows:
- <substituent group α>: a halogen atom, a hydroxy group, and an amino group,
- <substituent group $β_1$>: a halogen atom, a hydroxy group, a nitro group, a cyano group, a formyl group, an amino group, a lower alkylamino group, a dilower alkylamino group, a lower alkylsulfonyl group, a lower alkylsulfonylamino group, an aminosulfonyl group, an N-lower alkylaminosulfonyl group, an N,N-dilower alkylaminosulfonyl group, a lower alkoxy group, a lower alkoxycarbonyl group, a lower alkanoyl group, and a carboxyl group,
- <substituent group $β_2$>: a halogen atom, a hydroxy group, a nitro group, a cyano group, a formyl group, a lower alkoxy group, a lower alkylsulfonyl group, and a lower alkanoyl group, or a pharmaceutically acceptable salt or ester thereof.

The compound represented by the above Formula (I) includes all of the existing enantiomers and diastereomers in addition to racemates of the compound.

Hereinafter, the symbols and terms described in the present specification will be explained.

The "lower alkyl group" in the above Formula (I) refers to a straight-chained or branched alkyl group having 1 to 6 carbon atom(s), and examples thereof include a methyl group, an ethyl group, a propyl group, an isopropyl group, a butyl group, an isobutyl group, a sec-butyl group, a tert-butyl group, a pentyl group, a hexyl group, and the like.

The "5-membered aromatic heterocyclic group" in the above Formula (I) refers to a 5-membered aromatic heterocyclic group having at least one atom selected from a nitrogen atom, an oxygen atom, and a sulfur atom, in addition to carbon atoms, and examples thereof include a thienyl group, a pyrrolyl group, a furyl group, a thiazolyl group, an imidazolyl group, an oxazolyl group, and the like.

The "cycloalkyl group" in the above Formula (I) refers to a 3- to 8-membered aliphatic heterocyclic group, and examples thereof include a cyclopropyl group, a cyclobutyl group, a cyclopentyl group, a cyclohexyl group, a cycloheptyl group, a cyclooctyl group, and the like.

The "aryl group" in the above Formula (I) refers to a monocyclic, bicyclic, or tricycle aromatic hydrocarbon group having 6 to 14 carbon atoms, and examples thereof include a phenyl group, a naphthyl group, an indenyl group, an anthranil group, and the like.

The "heteroaryl group" in the above Formula (I refers to an aromatic heterocyclic group having at least one atom selected from a nitrogen atom, an oxygen atom, and a sulfur atom, in addition to carbon atoms, and examples thereof include a 5- to 7-membered monocyclic heterocyclic group, a fused-ring heterocyclic group formed by the fusion of a 3- to 8-membered ring to the monocyclic heterocyclic group, and the like. Concretely, a thienyl group, a pyrrolyl group, a furyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzoimidazolyl group, a benzofuranyl group, and the like may be mentioned.

The "aliphatic heterocyclic group" in the above Formula (I) refers to a saturated or unsaturated aliphatic heterocyclic group having at least one atom selected from a nitrogen atom, an oxygen atom, and a sulfur atom, in addition to carbon atoms, which is a mono-, di-, or tricyclic fused ring. Examples include an azetidyl group, a pyrrolidinyl group, a piperidinyl group, a piperazinyl group, a morpholino group, a tetrahydrofuranyl group, an imidazolidinyl group, a thiomorpholino group, a tetrahydroquinolyl group, a tetrahydroisoquinolyl group, and the like. In addition, two hydrogen atoms, which bind to the same carbon atom, in the aliphatic heterocyclic group may be substituted with an oxo group, and —S— in the aliphatic heterocyclic group may be substituted with —SO$_2$—.

The "halogen atom" in the above Formula (I) may be exemplified by a fluorine atom, a chlorine atom, a bromine atom, an iodine atom, or the like, and among these, for example, a fluorine atom, a chlorine atom, and a bromine atom are preferred.

The "lower alkylamino group" in the above Formula (I) refers to a group formed by N-substitution of the above "lower alkyl group" to a nitrogen atom of an amino group, and examples thereof include an N-methylamino group, an N-ethylamino group, an N-propylamino group, an N-isopropylamino group, an N-butylamino group, an N-isobutylamino group, an N-tert-butylamino group, an N-pentylamino group, an N-hexylamino group, and the like.

The "di-lower alkylamino group" in the above Formula (I) refers to a group formed by N,N-disubstitution of the above "lower alkyl group" to a nitrogen atom of an amino group, and examples thereof include an N,N-dimethylamino group, an N,N-diethylamino group, an N,N-dipropylamino group, an N,N-diisopropylamino group, an N,N-dibutylamino group, an N,N-diisobutylamino group, an N,N-ditert-butylamino group, an N,N-dipentylamino group, an N,N-dihexylamino group, an N-ethyl-N-methylamino group, an N-methyl-N-propylamino group, and the like.

The "N-lower alkylcarbamoyl group" in the above Formula (I) refers to a group formed by N-substitution of the above "lower alkyl group" to a nitrogen atom of a carbamoyl group, and examples thereof include an N-methylcarbamoyl group, an N-ethylcarbamoyl group, an N-propylcarbamoyl group, an N-isopropylcarbamoyl group, an N-butylcarbamoyl group, an N-isobutylcarbamoyl group, an N-tert-butylcarbamoyl group, an N-pentylcarbamoyl group, an N-hexylcarbamoyl group, and the like.

The "N,N-dilower alkylcarbamoyl group" in the above Formula (I) refers to a group formed by N,N-disubstitution of the above "lower alkyl group" to a nitrogen atom of a carbamoyl group, and examples thereof include an N,N-dimethylcarbamoyl group, an N,N-diethylcarbamoyl group, an N,N-dipropylcarbamoyl group, an N,N-diisopropylcarbamoyl group, an N,N-dibutylcarbamoyl group, an N,N-diisobutylcarbamoyl group, an N,N-ditert-butylcarbamoyl group, an N,N-dipentylcarbamoyl group, an N,N-dihexylcarbamoyl group, an N-ethyl-N-methylcarbamoyl group, an N-methyl-N-propylcarbamoyl group, and the like.

The "lower alkylsulfonyl group" in the above Formula (I) refers to a group formed by bonding the above "lower alkyl group" to a sulfur atom of a sulfonyl group, and examples thereof include a methylsulfonyl group, an ethylsulfonyl group, a butylsulfonyl group, and the like.

The "lower alkylsulfonylamino group" in the above Formula (I) refers to a group formed by N-substitution of the above "lower alkylsulfonyl group" to a nitrogen atom of an amino group, and examples thereof include a methylsulfonylamino group, an ethylsulfonylamino group, a butylsulfonylamino group, and the like.

The "N-lower alkylaminosulfonyl group" in the above Formula (I) refers to a group formed by bonding the above "lower alkylamino group" to a sulfur atom of a sulfonyl group, and examples thereof include an N-methylaminosulfonyl group, an N-ethylaminosulfonyl group, an N-propylaminosulfonyl group, an N-isopropyl-aminosulfonyl group, an N-butylaminosulfonyl group, an N-isobutylaminosulfonyl group, an N-tert-butylaminosulfonyl group, an N-pentylaminosulfonyl group, an N-hexylaminosulfonyl group, and the like.

The "N,N-dilower alkylaminosulfonyl group" in the above Formula (I) refers to a group formed by bonding the above "dilower alkylamino group" to a sulfur atom of a sulfonyl group, and examples thereof include an N,N-dimethylaminosulfonyl group, an N,N-diethylaminosulfonyl group, an N,N-dipropylaminosulfonyl group, an N,N-diisopropylaminosulfonyl group, an N,N-dibutylaminosulfonyl group, an N,N-diisobutylaminosulfonyl group, an N,N-ditert-butylaminosulfonyl group, an N,N-dipentylaminosulfonyl group, an N,N-dihexylaminosulfonyl group, an N-ethyl-N-methylaminosulfonyl group, an N-methyl-N-propylaminosulfonyl group, and the like.

The "lower alkoxy group" in the above Formula (I) refers to a group formed by bonding the "lower alkyl group" to an oxygen atom, and examples thereof include a methoxy group, an ethoxy group, a propoxy group, an isopropoxy group, a butoxy group, an isobutoxy group, a sec-butoxy group, a tert-butoxy group, a pentyloxy group, a neopentyloxy group, a hexyloxy group, an isohexyloxy group, and the like.

The "lower alkoxycarbonyl group" in the above Formula (I) refers to a group formed by bonding the "lower alkoxy group" to a carbon atom of a carbonyl group, and specific examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a neopentyloxycarbonyl group, a hexyloxycarbonyl group, an isohexyloxycarbonyl group, and the like.

The "lower alkanoyl group" in the above Formula (I) refers to a group formed by bonding the "lower alkyl group" to a carbon atom of a carbonyl group, and is preferably a group in which the alkyl group having 1 to 5 carbon atom(s) is bonded to a carbon atom of a carbonyl group. For example, an acetyl group, a propionyl group, a butyryl group, an isobutyryl group, a valeryl group, an isovaleryl group, a pivaloyl group, a pentanoyl group, and the like may be mentioned.

The term "PLK" represents a polo-like kinase.

The term "PLK1 inhibitor" represents a drug for inhibiting polo-like kinase 1.

The terms "pharmaceutically acceptable salt or ester" and "pharmaceutically acceptable carrier or diluent" will be explained later.

Embodiments of the compound represented by the above Formula (I) will be described in more detail.

The A ring is a 5-membered aromatic heterocyclic group having at least one hetero atom selected from the group consisting of a nitrogen atom, a sulfur atom, and an oxygen atom; and $A_1$ and $A_2$, which may be the same or different, are each CH, a nitrogen atom, NH, a sulfur atom, or an oxygen atom; however, $A_1$ and $A_2$ cannot be simultaneously CH.

Examples of the A ring are shown below:

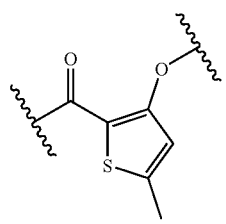 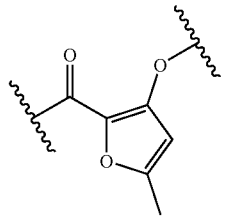

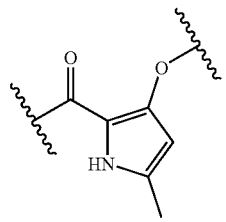 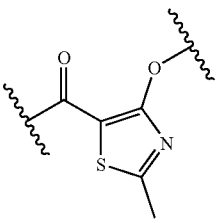

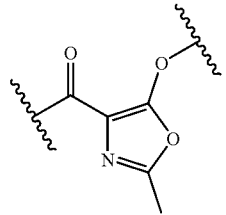 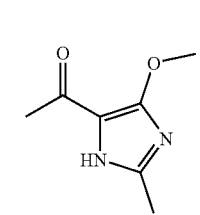

For $A_1$ and $A_2$, it is preferable that $A_1$ is a sulfur atom and $A_2$ is CH or a nitrogen atom.

$X_2$, $X_3$, $X_4$, and $X_5$ are all carbon atoms, or alternatively any one of $X_2$, $X_3$, $X_4$, and $X_5$ is a nitrogen atom and the rest are all carbon atoms, with the proviso that when $X_i$ (where i is one of 2, 3, 4 and 5) is a nitrogen atom, the corresponding $R_i$ (where i is one of 2, 3, 4 and 5) together with the $X_i$ forms a nitrogen atom.

Examples of the following partial structure of the Formula (I):

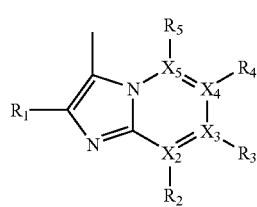

with relation to $X_2$, $X_3$, $X_4$, and $X_5$ are shown as follows.

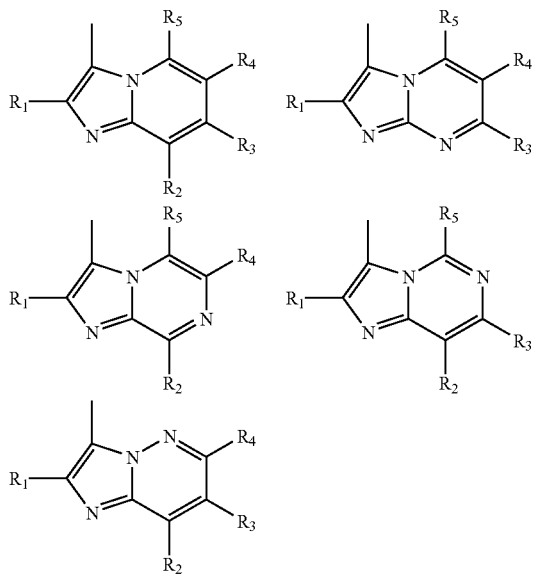

For $X_2$, $X_3$, $X_4$, and $X_5$, it is preferable that $X_2$, $X_3$, $X_4$, and $X_5$ are all carbon atoms, or alternatively $X_2$, $X_4$, and $X_5$ are all carbon atoms and $X_3$ is a nitrogen atom.

m is an integer of 1 or 2, which is preferably 1.

$R_1$ is a hydrogen atom, a methyl group which may be substituted with one or more halogen atom(s), or a substituent selected from the group consisting of a halogen atom, a hydroxy group, and an amino group (hereinafter, the group is referred to as <substituent group α>); and $R_1$ is preferably a hydrogen atom or a halogen atom, more preferably a hydrogen atom.

$R_2$, $R_3$, $R_4$, and $R_5$, which may be the same or different, are each a hydrogen atom or —$Y_1$—$Y_2$—$Y_3$—$Y_4$, wherein:

$Y_1$ is a single bond, $CH_2$, $CH(CH_3)$, O, S, SO, $SO_2$, CO, CONH, or NHCO;

$Y_2$ is a single bond or $(CW_iW_i')$, (wherein n is an integer of 1 to 4; i is an integer of 1 to n; and $(CW_iW_i')$, represents, $(CW_1W_1')$ when n is equal to 1, $(CW_1W_1')$—$(CW_2W_2')$ when n is equal to 2, $(CW_1W_1')$—$(CW_2W_2')$—$(CW_3W_3')$ when n is equal to 3, and $(CW_1W_1')$—$(CW_2W_2')$—$(CW_3W_3')$—$(CW_4W_4')$ when n is equal to 4, where $W_1$, $W_2$, $W_3$, and $W_4$, and $W_1'$, $W_2'$, $W_3'$, and $W_4'$, which may be the same or different, are each a hydrogen atom; a lower alkyl group; or a substituent selected from the group consisting of a halogen atom, a hydroxy group, a nitro group, a cyano group, a formyl group, an amino group, a lower alkylamino group, a dilower alkylamino group, a lower alkylsulfonyl group, a lower alkylsulfonylamino group, an aminosulfonyl group, an N-lower alkylaminosulfonyl group, an N,N-dilower alkylaminosulfonyl group, a lower alkoxy group, a lower alkoxycarbonyl group, a lower alkanoyl group, and a carboxyl group (hereinafter, the group is referred to as <substituent group $β_1$>));

$Y_3$ is a single bond, NH, $NR_a$, S, O, or COO (wherein $R_a$ is a substituent selected from the <substituent group $β_1$>, or a lower alkyl group which may be substituted with one or more of the same or different substituents selected from the <substituent group $β_1$>);

$Y_4$ is a hydrogen atom, a substituent selected from the <substituent group $β_1$>, a lower alkyl group which may be substituted with one or more of the same or different substituents selected from the <substituent group β$_1$>, R$_b$C(=O)NR$_c$—(CHZ$_2$)$_p$—, NR$_d$R$_d$'—(CHZ$_2$)$_q$—C(=O)NR$_c$—(CHZ$_2$)$_p$—, NR$_e$R$_e$'—(CHZ$_3$)$_r$—C(=O)—(CHZ$_1$)$_p$—, a cycloalkyl group, an aliphatic heterocyclic group, an aryl group, an aralkyl group, a heteroaryl group, or a lower alkyl substituted with the heteroaryl group, (wherein the cycloalkyl group, the aliphatic heterocyclic group, the aryl group, the aralkyl group, and the heteroaryl group may be substituted with one or more of the same or different substituents selected from the following:
1) a lower alkyl group,
2) a substituent selected from the <substituent group β$_1$>,
3) a lower alkyl group substituted with a substituent selected from the <substituent group β$_1$>,
4) R$_b$C(=O)NR$_c$—(CHZ$_1$)$_p$—,
5) NR$_d$R$_d$'—(CHZ$_2$)$_q$—C(=O)NR$_c$—(CHZ$_1$)$_p$—,
6) NR$_e$'—(CHZ$_3$)$_r$—C(=O)—(CHZ$_1$)$_p$—, and
7) a cycloalkyl group which may be substituted, and two hydrogen atoms, which bind to the same carbon atom, in the aliphatic heterocyclic group may be substituted with an oxo group;

p, q, and r, which may be the same or different, are each 0, 1, or 2;
Z$_1$, Z$_2$, and Z$_3$, which may be the same or different, are each a hydrogen atom or a lower alkyl group;
R$_b$ is a substituent selected from the group consisting of a halogen atom, a hydroxy group, a nitro group, a cyano group, a formyl group, a lower alkoxy group, a lower alkoxycarbonyl group, a lower alkylsulfonyl group, and a lower alkanoyl group (hereinafter, the group is referred to as <substituent group β$_2$>), a lower alkyl group which may be substituted with one or more of the same or different substituents selected from the <substituent group β$_2$>, or a cycloalkyl group which may be substituted;
R$_c$ is a hydrogen atom, a substituent selected from the <substituent group β$_2$>, or a lower alkyl group which may be substituted with one or more of the same or different substituents selected from the <substituent group β$_2$>;
R$_d$ and R$_d$', which may be the same or different, are each a hydrogen atom or a lower alkyl group; and
R$_e$ and R$_e$' are each a hydrogen atom or a lower alkyl group, or alternatively R$_e$ and R$_e$', together with the nitrogen atom to which they bind, form an aliphatic heterocyclic group selected from a pyrrolidinyl group, a piperidinyl group, and a piperazinyl group).

As mentioned above, when X$_1$ (where i is one of 2, 3, 4 and 5) is a nitrogen atom, the corresponding R$_i$ (where i is one of 2, 3, 4 and 5) together with the X$_1$ forms a nitrogen atom.

Here, it is preferable that R$_2$ and R$_5$, which may be the same or different, are each a hydrogen atom, a halogen atom, a hydroxyl group, an amino group, or a methyl group which may be substituted with 1 to 3 halogen atom(s); and it is more preferable that R$_2$ and R$_5$ are both hydrogen atoms.

It is preferable that R$_3$ and R$_4$, which may be the same or different, are each a hydrogen atom or —Y$_1$—Y$_2$—Y$_3$—Y$_4$, wherein <substituent group β$_{1a}$> is:
a halogen atom, a hydroxy group, an amino group, a cyano group, a lower alkylamino group, a dilower alkylamino group, a lower alkylsulfonyl group, and a carboxyl group;

Y$_1$ is a single bond, CH$_2$, or O;
Y$_2$ is a single bond or (CW$_1$W$_1$'), (wherein W$_i$, W$_i$', and n are the same as defined above);
Y$_3$ is a single bond, NH, or N(CH$_3$);
Y$_4$ is a substituent selected from the <substituent group β$_{1a}$>; a lower alkyl group which may be substituted with one or more of the same or different substituents selected from the <substituent group β$_{1a}$>; an aliphatic heterocyclic group selected from an azetidyl group, a pyrrolidinyl group, a piperidinyl group, a piperazinyl group, and a morpholino group; a heteroaryl group selected from a pyrrolyl group, an imidazolyl group, a pyridyl group, and a pyrimidinyl group; or a lower alkyl group substituted with the heteroaryl group. The aliphatic heterocyclic group and the heteroaryl group may be substituted with one or more of the same or different substituents selected from the following:
1) a lower alkyl group,
2) a substituent selected from the <substituent group β$_{1a}$>, and
3) a lower alkyl group substituted with a substituent selected from the <substituent group β$_{1a}$>.

Here, when one or both of R$_3$ and R$_4$, which may be the same or different, is/are —Y$_1$—Y$_2$—Y$_3$—Y$_4$, examples of the Y$_1$, Y$_2$, Y$_3$, and Y$_4$ combination are defined by Cases 1 to 14. In descriptions of Cases 1 to 14, the term "aliphatic heterocyclic group which may be substituted" refers to an aliphatic heterocyclic group selected from the group consisting of an azetidyl group, a pyrrolidinyl group, a piperidinyl group, a piperazinyl group, and a morpholino group, which is a group that may be substituted with one or more of the same or different substituents selected from the following:
1) a lower alkyl group,
2) a substituent selected from the <substituent group β$_{1a}$>, and
3) a lower alkyl group substituted with a substituent selected from the <substituent group β$_{1a}$> In addition, two hydrogen atoms, which bind to the same carbon atom, in the aliphatic heterocyclic group may be substituted with an oxo group. The binding form of the "aliphatic heterocyclic group which may be substituted" can be exemplified as below.

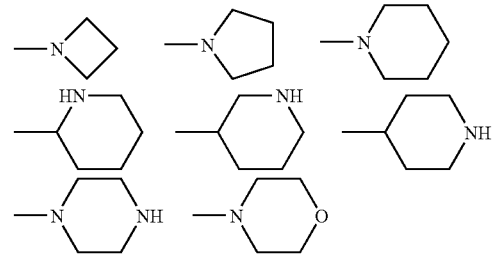

Case 1: case where Y$_1$ is a single bond; Y$_2$ is a single bond; Y$_3$ is a single bond; and Y$_4$ is either a substituent selected from the <substituent group β$_1$>, or a lower alkyl group which may be substituted with one or more of the same or different substituents selected from the <substituent group β$_1$>.

Case 2: case where Y$_1$ is a single bond; Y$_2$ is a single bond; Y$_3$ is a single bond; and Y$_4$ is an aliphatic heterocyclic group which may be substituted.

Case 3: case where Y$_1$ is a single bond; Y$_2$ is a single bond; Y$_3$ is NH or N(CH$_3$); and Y$_4$ is a lower alkyl group which may be substituted with one or more of the same or different substituents selected from the <substituent group β$_1$>.

Case 4: case where $Y_1$ is O; $Y_2$ is a single bond; $Y_3$ is a single bond; and $Y_4$ is an aliphatic heterocyclic group which may be substituted.

Case 5: case where $Y_1$ is O; $Y_2$ is $(CH_2)_n$; $Y_3$ is a single bond; and $Y_4$ is a substituent selected from the <substituent group $\beta_1$>.

Case 6: case where $Y_1$ is O; $Y_2$ is $(CH_2)_n$; $Y_3$ is a single bond; and $Y_4$ is an aliphatic heterocyclic group which may be substituted.

Case 7: case where $Y_1$ is O; $Y_2$ is $(CH_2)_n$; $Y_3$ is NH or $N(CH_3)$; and $Y_4$ is a lower alkyl group which may be substituted with one or more of the same or different substituents selected from the <substituent group $\beta_1$>.

Case 8: case where $Y_1$ is $CH_2$; $Y_2$ is a single bond; $Y_3$ is a single bond; and $Y_4$ is a lower alkyl group which may be substituted with one or more of the same or different substituents selected from the <substituent group 1>.

Case 9: case where $Y_1$ is $CH_2$; $Y_2$ is a single bond; $Y_3$ is a single bond; and $Y_4$ is an aliphatic heterocyclic group which may be substituted.

Case 10: case where $Y_1$ is $CH_2$; $Y_2$ is a single bond; $Y_3$ is NH; and $Y_4$ is a lower alkyl group which may be substituted with one or more of the same or different substituents selected from the <substituent group $\beta_1$>.

Case 11: case where $Y_1$ is CONH; $Y_2$ is $(CH_2)_n$; $Y_3$ is a single bond; and $Y_4$ is an aliphatic heterocyclic group which may be substituted.

Case 12: case where $Y_1$ is NHCO; $Y_2$ is $(CH_2)_n$; $Y_3$ is a single bond; and $Y_4$ is a substituent selected from the <substituent group 1>.

Case 13: case where $Y_1$ is $CH_2$; $Y_2$ is a single bond; $Y_3$ is $NR_a$ (where $R_a$ is either a substituent selected from the <substituent group P>, or a lower alkyl group which may be substituted with one or more of the same or different substituents selected from the <substituent group $\beta_1$>); and $Y_4$ is either a substituent selected from the <substituent group $\beta_1$>, or a lower alkyl group which may be substituted with one or more of the same or different substituents selected from the <substituent group. $\beta_1$>.

Case 14: case where $Y_1$ is $CH_2$; $Y_2$ is a single bond; $Y_3$ is $NR_a$ (where $R_a$ is the same as defined above); and $Y_4$ is either a heteroaryl group selected from a pyrrolyl group, an imidazolyl group, a pyridyl group, and a pyrimidinyl group, or a lower alkyl group substituted with the heteroaryl group.

For $R_3$ and $R_4$, it is more preferable that $R_3$ is a hydrogen atom, and $R_4$ is a hydrogen atom, a substituent selected from the <substituent group $\beta_{1b}$>, a lower alkyl group which may be substituted with one or more of the same or different substituents selected from the <substituent group $\beta_{1b}$>, or a lower alkyl group substituted with a piperazinyl group which may be substituted, wherein the <substituent group $\beta_{1b}$> is a hydroxy group, an amino group, a cyano group, and a methylsulfonyl group.

For $R_2$, $R_3$, $R_4$, and $R_5$, it is particularly preferable that $R_2$, $R_3$, and $R_5$ are all hydrogen atoms and $R_4$ is a hydrogen atom, a substituent selected from the <substituent group $\beta_{1b}$>, or a lower alkyl group which may be substituted with one or more of the same or different substituents selected from the <substituent group $\beta_{1b}$>, wherein the <substituent group $\beta_{1b}$> is a hydroxy group, an amino group, a cyano group, and a methylsulfonyl group.

For $R_2$, $R_3$, $R_4$, and $R_5$, it is even more preferable that $R_2$, $R_3$, and $R_5$ are all hydrogen atoms and $R_4$ is a hydrogen atom, a cyano group, a hydroxymethyl group, or a methylsulfonylmethyl group.

The partial structure of the following Formula (I):

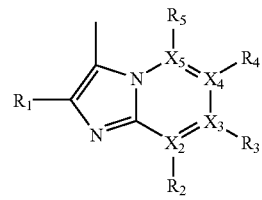

can be particularly preferably exemplified by imidazo[1,2-a]pyridin-3-yl, 6-cyanoimidazo[1,2-a]pyridin-3-yl, 6-(hydroxymethyl)imidazo[1,2-a]pyridin-3-yl, 6-[(methylsulfonyl)methyl])imidazo[1,2-a]pyridin-3-yl, imidazo[1,2-a]pyrazin-3-yl, 6-(hydroxymethyl)imidazo[1,2-a]pyrazin-3-yl, 6-[(methylsulfonyl)methyl])imidazo[1,2-a]pyrazin-3-yl, or the like.

As is evident from the above, the <substituent group $\beta_1$> is preferably a halogen atom, a hydroxy group, an amino group, a cyano group, a lower alkylamino group, a dilower alkylamino group, a lower alkylsulfonyl group, and a carboxyl group (this corresponds to the <substituent group $\beta_{1a}$>), and more preferably a hydroxy group, an amino group, a cyano group, and a methylsulfonyl group (this corresponds to the <substituent group $\beta_{1b}$>).

$R_6$ and $R_6'$, which may be the same or different, are each a hydrogen atom, a substituent selected from the <substituent group $\beta_1$>, a lower alkyl group which may be substituted with one or more of the same or different substituents selected from the <substituent group $\beta_1$>, or a cycloalkyl group; or alternatively $R_6$ and $R_6'$ are combined together to form an oxo group; however, when m is 2, two sets of $R_6$ and $R_6'$ which are adjacent to each other cannot together form an oxo group.

When m is 1, and $R_6$ and $R_6'$ are not simultaneously hydrogen atoms, then the carbon atom to which $R_6$ and $R_6'$ bind is an asymmetric carbon atom. In this case, the compound represented by the Formula (I) may exist as a racemate, or in the form of R- or S-form. The prepared form depends upon the kind of substituents of $R_6$ and $R_6'$, but the compound represented by the Formula (I) is preferably in the R- or S-form from the viewpoint of PLK1 inhibitory activity.

It is preferable that $R_6$ and $R_6'$, which may be the same or different, are each a hydrogen atom or a methyl group, with the proviso that they cannot be simultaneously a methyl group; and it is more preferable that one of $R_6$ and $R_6'$ is a hydrogen atom and the other one is a methyl group. In this case, the compound represented by the Formula (I) is preferably in the R-form from the viewpoint of PLK1 inhibitory activity.

$R_7$ is an aryl group or a heteroaryl group any of which may be substituted.

$R_7$ is preferably a phenyl group, a pyridyl group, a pyridazyl group, a pyrazinyl group, a pyrimidinyl group, a furyl group, a thienyl group, or a pyrrolyl group. The binding form of a pyridyl group, a pyridazinyl group, a pyrazinyl group, a pyrimidinyl group, a furyl group, a thienyl group, and a pyrrolyl group can be exemplified as below.

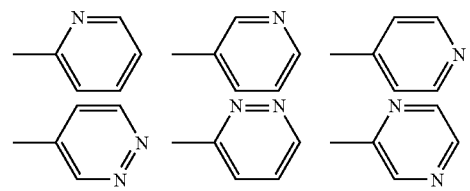

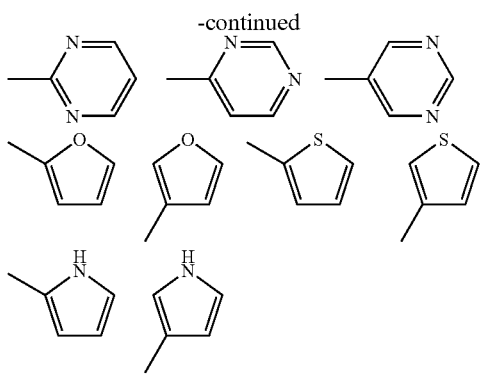

In the above R₇, the phenyl group, the pyridyl group, the pyridazinyl group, the pyrazinyl group, the pyrimidinyl group, the furyl group, the thienyl group, or the pyrrolyl group, may be substituted with one or more of the same or different substituents selected from the following:

1) a substituent selected from the group consisting of a halogen atom, a hydroxy group, a formyl group, a nitro group, a cyano group, a trifluoromethyl group, an amino group, a lower alkylamino group, a dilower alkylamino group, a carbamoyl group, an N-lower alkylcarbamoyl group, an N,N-dilower alkylcarbamoyl group, a lower alkoxy group which may be substituted with one or more halogen atom(s), a lower alkoxycarbonyl group, a lower alkanoyl group, a lower alkylsulfonyl group, a carboxyl group, and $R_aCONR_b$— (wherein $R_a$ is a lower alkyl group, and $R_b$ is a hydrogen atom or a lower alkyl group) (hereinafter, the group is referred to as <substituent $\gamma_1$>);

2) a lower alkyl group, which may be substituted with one or more of the same or different substituents (wherein the substituent may be further substituted with a hydroxy lower alkyl group; the lower alkyl group may be substituted with one or more halogen atom(s); and two lower alkyl groups, which bind to the same carbon atom, in the lower alkyl group, may together form a ring structure having 3 to 5 carbon atoms) selected from the group consisting of a halogen atom, a hydroxy group, a formyl group, a nitro group, a cyano group, a trifluoromethyl group, a carbamoyl group, an N-lower alkylcarbamoyl group, an N,N-dilower alkylcarbamoyl group, a lower alkoxy group which may be substituted with one or more halogen atom(s), a lower alkoxycarbonyl group, a lower alkanoyl group, a lower alkylsulfonyl group, a carboxyl group, and $R_aCONR_b$— (wherein $R_a$ is a lower alkyl group, and $R_b$ is a hydrogen atom or a lower alkyl group) (hereinafter, the group is referred to as <substituent $\gamma_4$>);

3) an aliphatic heterocyclic group (wherein two hydrogen atoms, which bind to the same carbon atom, in the aliphatic heterocyclic group may be substituted with an oxo group) selected from the group consisting of a pyrrolidinyl group, a piperidinyl group, a piperazinyl group, a morpholino group, and a thiomorpholino group (hereinafter, the group is referred to as <substituent $\gamma_2$>), which may be substituted with one or more of, the same or different substituents selected from the <substituent group $\gamma_1$> and/or a lower alkyl group optionally substituted with the same or different substituents selected from the <substituent group $\gamma_1$> (wherein two hydrogen atoms, which bind to the same carbon atom, in the aliphatic heterocyclic group may be substituted with an oxo group, and —S— in the aliphatic heterocyclic group may be substituted with —SO₂—);

4) a lower alkyl group substituted with an aliphatic heterocyclic group (wherein, the lower alkyl group may be substituted with one or more halogen atom(s), and two hydrogen atoms, which bind to the same carbon atom, in the aliphatic heterocyclic group may be substituted with an oxo group) selected from the <substituent $\gamma_2$> optionally substituted with one or more of, the same or different substituents selected from the <substituent group $\gamma_1$> and/or a lower alkyl group optionally substituted with the same or different substituents selected from the <substituent group $\gamma_1$>;

5) —$CR_fR_f'$)$_k$—$NR_9R_{10}$ (wherein
k is 1, 2, or 3;
$R_f$ and $R_f'$, which may be the same or different, are each a hydrogen atom or a lower alkyl group, and when the $R_f$ and $R_f'$ are both lower alkyl groups, then $R_f$ and $R_f'$ binding to the same carbon atom may together form a ring structure having 3 to 5 carbon atoms;
the hydrogen atom(s) of —$(CR_fR_f')_k$— may be substituted with one or more halogen atom(s);
$R_9$ is a hydrogen atom or a lower alkyl group; and
$R_{10}$ is a hydrogen atom; a lower alkyl group which may be substituted with one or more of the same or different substituents selected from the <substituent group $\gamma_1$>; a cycloalkyl group; an aromatic heterocyclic group selected from the group consisting of a pyridyl group, a pyrazinyl group, and a pyrimidinyl group; a lower alkyl group substituted with an aromatic heterocyclic group selected from the group consisting of a pyridyl group, a pyrazinyl group, and a pyrimidinyl group; or an aliphatic heterocyclic group selected from the group consisting of a pyrrolidinyl group, a piperidinyl group, a piperazinyl group, a morpholino group, an oxoranyl group, and a thioranyl group (hereinafter, the group is referred to as <substituent $\gamma_3$>) (wherein two hydrogen atoms, which bind to the same carbon atom, in the aliphatic heterocyclic group may be substituted with an oxo group, and —S— in the aliphatic heterocyclic group may be substituted with —SO₂—), wherein the cycloalkyl group, the aromatic heterocyclic group, and the aliphatic heterocyclic group, may be substituted with one or more of, the same or different substituents selected from the <substituent group $\gamma_1$> and/or a lower alkyl group optionally substituted with the same or different substituents selected from the <substituent group $\gamma_1$>); and 6) —$OR_{11}$ (wherein $R_{11}$ is the following a) or b):
a) —$(CH_2)_l$—$NR_{12}R_{13}$ (wherein
l is 2 or 3;
$R_{12}$ and $R_{13}$, which may be the same or different, are each a hydrogen atom, a lower alkyl group, or a lower alkyl group substituted with one or more of the same or different substituents selected from the <substituent group $\gamma_1$>; or alternatively
$R_{12}$ and $R_{13}$ with the nitrogen atom to which they bind together form an aliphatic heterocyclic group selected from <substituent $\gamma_2$>, wherein the aliphatic heterocyclic group may be substituted with one or more of, the same or different substituents selected from the <substituent group $\gamma_1$> and/or a lower alkyl group which may be substituted with the same or different substituents selected from the <substituent group $\gamma_1$>); or
b) a lower alkyl group substituted with one or more of the same or different substituents selected from the <substituent group $\gamma_1$>).

R₇ is more preferably a phenyl group, wherein the phenyl group may be substituted with one or more of the same or different substituents selected from the following:

1) a substituent selected from the group consisting of a halogen atom, a hydroxy group, a formyl group, a nitro group, a cyano group, an amino group, a lower alkylamino group, a dilower alkylamino group, a lower alkoxy group which may be substituted with one or more halogen atom(s), a lower alkylsulfonyl group, and a carboxyl group, (hereinafter, the group is referred to as <substituent $\gamma_{1a}$>);

2) a lower alkyl group which may be substituted with one or more of the same or different substituents selected from the group consisting of a halogen atom, a hydroxy group, a formyl group, a nitro group, a cyano group, a lower alkoxy group which may be substituted with one or more halogen atom(s), a lower alkylsulfonyl group, and a carboxyl group, (hereinafter, the group is referred to as <substituent $\gamma_{4a}$>);

3) a lower alkyl group substituted with an aliphatic heterocyclic group selected from the group consisting of a pyrrolidinyl group, a piperidinyl group, and a piperazinyl group (hereinafter, the group is referred to as <substituent $\gamma_2 a$>) which may be substituted with one or more of, the same or different substituents selected from the <substituent group $\gamma_{1a}$> and/or a lower alkyl group;

4) —$(CH_2)_k$—$NR_9R_{10}$ (wherein
k is 1, 2, or 3;
$R_9$ is a hydrogen atom or a lower alkyl group; and
$R_{10}$ is a hydrogen atom, a lower alkyl group which may be substituted with one or more of the same or different substituents selected from the <substituent group $\gamma_{1a}$>, or a cycloalkyl group having 5 to 6 carbon atoms, wherein the cycloalkyl group may be substituted with one or more of, the same or different substituents selected from the <substituent group $\gamma_1$> and/or a lower alkyl group which may be substituted with the same or different substituents selected from the <substituent group $\gamma_1$>); and 5) —O—$R_{11}$ (wherein $R_{11}$ is —$(CH_2)_l$—$NR_{12}R_{13}$, wherein
l is 2 or 3; and
$R_{12}$ and $R_{13}$, which may be the same or different, are each a hydrogen atom, a lower alkyl group, or a lower alkyl group substituted with one or more of the same or different substituents selected from the <substituent group $\gamma_{1a}$>).

As is evident from the above, the <substituent group $\gamma_1$> is preferably a halogen atom, a hydroxy group, a formyl group, a nitro group, a cyano group, an amino group, a lower alkylamino group, a dilower alkylamino group, a lower alkoxy group which may be substituted with one or more halogen atom(s), a lower alkylsulfonyl group, and a carboxyl group (this corresponds to the <substituent group $\gamma_{1a}$>). The <substituent group $\gamma_2$> is preferably a pyrrolidinyl group, a piperidinyl group, and a piperazinyl group (this applies to the <substituent group $\gamma_{2a}$>). The <substituent group $\gamma_4$> is preferably a halogen atom, a hydroxy group, a formyl group, a nitro group, a cyano group, a lower alkoxy group which may be substituted with one or more halogen atom(s), a lower alkylsulfonyl group, and a carboxyl group (this corresponds to the <substituent group $\gamma_{4a}$>).

$R_7$ is particularly preferably a phenyl group substituted at least at the $2^{nd}$ position with a halogen atom, a difluoromethoxy group, or a trifluoromethyl group.

$R_7$ is further preferably a phenyl group further substituted at the $4^{th}$ position with —$CH_2OH$ or —$CH_2$—$NR_9R_{10}$ (wherein $R_9$ is a hydrogen atom or a lower alkyl group; and $R_{10}$ is a lower alkyl group which may be substituted with a hydroxy group).

Preferred examples of $R_7$ include:
2-chlorophenyl, 4-{[(2-hydroxy-1,1-dimethylethyl)amino]methyl}phenyl, 2-chloro-4-(hydroxymethyl)phenyl, 2-chloro-4-[(methylamino)methyl]phenyl, 2-chloro-4-[(dimethylamino)methyl]phenyl, 2-chloro-4-{[(2-hydroxy-1,1-dimethylethyl)amino]methyl}phenyl, 4-[(t-butylamino)methyl]-2-chlorophenyl, 4-[(t-butylamino)methyl]-2-(difluoromethoxy)phenyl, and the like.

$R_8$ is an amino group or a hydroxy group, and is preferably an amino group.

The compound represented by the Formula (I) is preferably:

(a) 3-[1-(2-chlorophenyl)ethoxy]-5-imidazo[1,2-a]pyridin-3-ylthiophene-2-carboxyamide (Example 38), (b) 5-imidazo[1,2-a]pyridin-3-yl-3-[1-(2-nitrophenyl)ethoxy]thiophene-2-carboxyamide (Example 44), (c) 3-[(1R)-1-(2-chlorophenyl)ethoxy]-5-[6-(2-hydroxyethoxy)imidazo[1,2-a]pyridin-3-yl]thiophene-2-carboxyamide (Example 66), (d) 3-[(1R)-1-(2-chlorophenyl)ethoxy]-5-[6-(hydroxymethyl)imidazo[1,2-a]pyridin-3-yl]thiophene-2-carboxyamide (Example 107), (e) 3-[(1R)-1-(2-chlorophenyl)ethoxy]-5-[6-(piperazin-1-ylmethyl)imidazo[1,2-a]pyridin-3-yl]thiophene-2-carboxyamide (Example 119), (f) 3-{1-[2-chloro-4-(hydroxymethyl)phenyl]ethoxy}-5-imidazo[1,2-a]pyridin-3-ylthiophen-2-carboxyamide (Examples 166 and 167), (g) 3-[(1R)-1-(2-chloro-4-{[(2-hydroxy-1,1-dimethylethyl)amino]methyl}phenyl)ethoxy]-5-imidazo[1,2-a]pyridin-3-ylthiophene-2-carboxyamide (Example 174), (h) 3-((1R)-1-{4-[(t-butylamino)methyl]-2-chlorophenyl}ethoxy)-5-imidazo[1,2-a]pyridin-3-ylthiophene-2-carboxyamide (Example 177), (i) 3-{(1R)-1-[4-[(t-butylamino)methyl]-2-(difluoromethoxy)phenyl]ethoxy}-5-imidazo[1,2-a]pyridin-3-ylthiophene-2-carboxyamide (Example 180), (j) 3-[(1R)-1-(2-(difluoromethoxy)-4-{[(2-hydroxy-1,1-dimethylethyl)amino]methyl}phenyl)ethoxy]-5-imidazo[1,2-a]pyridin-3-ylthiophene-2-carboxyamide (Example 181), (k) 3-[(1R)-1-(2-chloro-4-{[(2-hydroxy-1,1-dimethylethyl)amino]methyl}phenyl)ethoxy]-5-(6-cyanoimidazo[1,2-a]pyridin-3-yl)thiophene-2-carboxyamide (Example 184), (l) 3-((1R)-1-{4-[(t-butylamino)methyl]-2-chlorophenyl}ethoxy)-5-(6-cyanoimidazo[1,2-a]pyridin-3-yl)thiophene-2-carboxyamide (Example 186), (m) 3-{(1R)-1-[4-[(t-butylamino)methyl]-2-(difluoromethoxy)phenyl]ethoxy}-5-(6-cyanoimidazo[1,2-a]pyridin-3-yl)thiophene-2-carboxyamide (Example 187), (n) 3-((1R)-1-{2-chloro-4-[(methylamino)methyl]phenyl}ethoxy)-5-[6-(hydroxymethyl)imidazo[1,2-a]pyridin-3-yl]thiophene-2-carboxyamide (Example 197), (o) 3-{(1R)-1-[4-[(t-butylamino)methyl]-2-chlorophenyl}ethoxy)-5-[6-(hydroxymethyl)imidazo[1,2-a]pyridin-3-yl]thiophene-2-carboxyamide (Example 201), (p) 3-{(1R)-1-[4-[(t-butylamino)methyl]-2-(difluoromethoxy)phenyl]ethoxy}-5-[6-(hydroxymethyl)imidazo[1,2-a]pyridin-3-yl]thiophene-2-carboxyamide (Example 202), (q) 3-[(1R)-1-(2-chlorophenyl)ethoxy]-5-{6-[(methylsulfonyl)methyl]imidazo[1,2-a]pyridin-3-yl}thiophene-2-carboxyamide (Example 203), (r) 3-((1R)-1-{2-chloro-4-[(dimethylamino)methyl]phenyl}ethoxy)-5-{6-[(methylsulfonyl)methyl]imidazo[1,2-a]pyridin-3-yl}thiophene-2-carboxamide (Example 207),
(s) 3-((1R)-1-{4-[(t-butylamino)methyl]-2-chlorophenyl}ethoxy)-5-{6-[(methylsulfonyl)(methyl)imidazo[1,2-a]pyridin-3-yl}thiophene-2-carboxamide (Example 208),
(t) 4-{(1R)-1-[4-[(t-butylamino)methyl]-2-(difluoromethoxy)phenyl]ethoxy}-2-imidazo[1,2-a]pyridin-3-yl-1,3-thiazole-5-carboxamide (Example 220),
(u) 4-((1R)-1-{2-chloro-4-[(dimethylamino)methyl]phenyl}ethoxy)-2-[6-(hydroxymethyl)imidazo[1,2-a]pyridin-3-yl]-1,3-thiazole-5-carboxamide (Example 221),
(v) 4-((1R)-1-{2-chloro-4-[(methylamino)methyl]phenyl}ethoxy)-2-{6-[(methylsulfonyl)methyl]imidazo[1,2-a]pyridin-3-yl}-1,3-thiazole-5-carboxamide (Example 224),
(w) 3-{(1R)-1-[2-chloro-4-(hydroxymethyl)phenyl]ethoxy}-5-{6-[(4-methylpiperazin-1-yl)methyl]imidazo[1,2-a]pyrazin-3-yl}thiophene-2-carboxamide (Example 230), or
(x) 4-{(1R)-1-[2-chloro-4-(hydroxymethyl)phenyl]ethoxy}-2-{6-[(4-methylpiperazin-1-yl)methyl]imidazo[1,2-a]pyrazin-3-yl}-1,3-thiazole-5-carboxamide (Example 235), or a pharmaceutically acceptable salt or ester thereof.

The compound represented by the Formula (I) is more preferably
(aa) 3-{(1R)-1-[4-[(t-butylamino)methyl]-2-(difluoromethoxy)phenyl]ethoxy}-5-imidazo[1,2-a]pyridin-3-ylthiophene-2-carboxamide (Example 180),
(bb) 3-[(1R)-1-(2-(difluoromethoxy)-4-{[(2-hydroxy-1,1-dimethylethyl)amino]methyl}phenyl)ethoxy]-5-imidazo[1,2-a]pyridin-3-ylthiophene-2-carboxamide (Example 181),
(cc) 3-((1R)-1-{4-[(t-butylamino)methyl]-2-chlorophenyl}ethoxy)-5-(6-cyanoimidazo[1,2-a]pyridin-3-yl)thiophene-2-carboxamide (Example 186),
(dd) 3-((1R)-1-{2-chloro-4-[(methylamino)methyl]phenyl}ethoxy)-5-[6-(hydroxymethyl)imidazo[1,2-a]pyridin-3-yl]thiophene-2-carboxamide (Example 197),
(ee) 3-((1R)-1-{2-chloro-4-[(dimethylamino)methyl]phenyl}ethoxy)-5-{6-[(methylsulfonyl)methyl]imidazo[1,2-a]pyridin-3-yl}thiophene-2-carboxamide (Example 207),
(ff) 4-{(1R)-1-[4-[(t-butylamino)methyl]-2-(difluoromethoxy)phenyl]ethoxy}-2-imidazo[1,2-a]pyridin-3-yl-1,3-thiazole-5-carboxamide (Example 220),
(gg) 4-{(1R)-1-[2-chloro-4-(hydroxymethyl)phenyl]ethoxy}-2-{6-[(4-methylpiperazin-1-yl)methyl]imidazo[1,2-a]pyrazin-3-yl}-1,3-thiazole-5-carboxamide (Example 235), or a pharmaceutically acceptable salt or ester thereof.

The preferred embodiment of the present specification can also be represented as follows:
(1) the compound of the above Formula (I), or a pharmaceutically acceptable salt or ester thereof, wherein
$R_1$ is a hydrogen atom; and $R_2$ and $R_5$, which may be the same or different, are each a hydrogen atom, a halogen atom, a hydroxyl group, an amino group, or a methyl group which may be substituted with 1 to 3 halogen atom(s); or
(2) the compound of (1) above, or a pharmaceutically acceptable salt or ester thereof, wherein
$R_7$ is a phenyl group, a pyridyl group, a pyridazinyl group, a pyrazinyl group, a pyrimidinyl group, a furyl group, a thienyl group, or a pyrrolyl group, wherein the phenyl group, the pyridyl group, the pyridazinyl group, the pyrazinyl group, the pyrimidinyl group, the furyl group, the thienyl group, and the pyrrolyl group may be substituted with one or more of the same or different substituents selected from the following:
1) a substituent selected from the <substituent $\gamma_1$>;
2) a lower alkyl group which may be substituted with one or more of the same or different substituents selected from the <substituent $\gamma_4$>, wherein the substituent may be further substituted with a hydroxy lower alkyl group; the lower alkyl group may be substituted with one or more halogen atom(s); and two lower alkyl groups, which bind to the same carbon atom, in the lower alkyl group may together form a ring structure having 3 to 5 carbon atoms;
3) an aliphatic heterocyclic group selected from the <substituent $\gamma_2$>, which may be substituted with one or more of, the same or different substituents selected from the <substituent group $\gamma_1$> and/or a lower alkyl group optionally substituted with the same or different substituents selected from the <substituent group $\gamma_1$>, wherein two hydrogen atoms, which bind to the same carbon atom, in the aliphatic heterocyclic group may be substituted with an oxo group;
4) a lower alkyl group substituted with an aliphatic heterocyclic group selected from the <substituent $Y_2$> optionally substituted with one or more of, the same or different substituents selected from the <substituent group $\gamma_1$> and/or a lower alkyl group optionally substituted with the same or different substituents selected from the <substituent group $\gamma_1$>, wherein the lower alkyl group may be substituted with one or more halogen atom(s), and two hydrogen atoms, which bind to the same carbon atom, in the aliphatic heterocyclic group may be substituted with an oxo group;
5) —$(CR_fR_f')_k$—$NR_9R_{10}$, wherein
k is 1, 2, or 3;
$R_f$ and $R_f'$, which may be the same or different, are each a hydrogen atom or a lower alkyl group, and when the $R_f$ and $R_f'$ are both lower alkyl groups, then $R_f$ and $R_f'$ binding to the same carbon atom may together form a ring structure having 3 to 5 carbon atoms;
the hydrogen atom(s) of —$(CR_fR_f')_k$— may be substituted with one or more halogen atom(s);
$R_9$ is a hydrogen atom or a lower alkyl group; and
$R_{10}$ is a hydrogen atom; a lower alkyl group which may be substituted with one or more of the same or different substituents selected from the <substituent group $\gamma_1$>; a cycloalkyl group; an aromatic heterocyclic group selected from the group consisting of a pyridyl group, a pyrazinyl group, and a pyrimidinyl group; a lower alkyl group substituted with an aromatic heterocyclic group selected from the group consisting of a pyridyl group, a pyrazinyl group, and a pyrimidinyl group; or an aliphatic heterocyclic group selected from the <substituent $\gamma_3$>, wherein the cycloalkyl group, the aromatic heterocyclic group, and the aliphatic heterocyclic group, may be substituted with one or more of, the same or different substituents selected from the <substituent group $\gamma_1$> and/or a lower alkyl group optionally substituted with the same or different substituents selected from the <substituent group $\gamma_1$>; and
6) —$OR_{11}$, wherein $R_{11}$ is the following a) or b):
a) —$(CH_2)_l$—$NR_{12}R_{13}$, wherein
l is 2 or 3;
$R_{12}$ and $R_{13}$, which may be the same or different, are each a hydrogen atom, a lower alkyl group, or a lower alkyl group substituted with one or more of the same or different substituents selected from the <substituent group $\gamma_1$>, or alternatively, $R_{12}$ and $R_{13}$ together with the nitrogen atom to which they bind form an aliphatic heterocyclic group selected from the <substituent $\gamma_2$>, wherein the aliphatic heterocyclic group may be substituted with one or more of, the same or different substituents selected from the <substituent group $\gamma_1$> and/or a lower alkyl group which may be substituted with the same or different substituents selected from the <substituent group $\gamma_1$>; and b) a lower alkyl group substituted with one or more of the same or different substituents selected from the <substituent group $\gamma_1$>, wherein the <substituent group $\gamma_1$>, <substituent group $\gamma_2$>, <substituent group $\gamma_3$>, and <substituent group $\gamma_4$> are defined as follows:

<substituent group $\gamma_1$>: a halogen atom, a hydroxy group, a formyl group, a nitro group, a cyano group, a trifluoromethyl group, an amino group, a lower alkylamino group, a dilower alkylamino group, a carbamoyl group, an N-lower alkylcarbamoyl group, an N,N-dilower alkylcarbamoyl group, a lower alkoxy group which may be substituted with one or more halogen atom(s), a lower alkoxycarbonyl group, a lower alkanoyl group, a lower alkylsulfonyl group, a carboxyl group, and $R_a$CONR$_b$— (where $R_a$ is a lower alkyl group, and $R_b$ is a hydrogen atom or a lower alkyl group), <substituent group $\gamma_2$>: a pyrrolidinyl group, a piperidinyl group, a piperazinyl group, a morpholino group, and a thiomorpholino group, wherein two hydrogen atoms, which bind to the same carbon atom, in the aliphatic heterocyclic group may be substituted with an oxo group, and —S— in the aliphatic heterocyclic group may be substituted with —SO$_2$—, <substituent group $Y_3$>: a pyrrolidinyl group, a piperidinyl group, a piperazinyl group, a morpholino group, an oxoranyl group, and a thioranyl group, wherein two hydrogen atoms, which bind to the same carbon atom, in the aliphatic heterocyclic group may be substituted with an oxo group, and —S— in the aliphatic heterocyclic group may be substituted with —SO$_2$—, and <substituent group $\gamma_4$>: a halogen atom, a hydroxy group, a formyl group, a nitro group, a cyano group, a trifluoromethyl group, a carbamoyl group, an N-lower alkylcarbamoyl group, an N,N-dilower alkylcarbamoyl group, a lower alkoxy group which may be substituted with one or more halogen atom(s), a lower alkoxycarbonyl group, a lower alkanoyl group, a lower alkylsulfonyl group, a carboxyl group, and $R_a$CONR$_b$— (where $R_a$ is a lower alkyl group, and $R_b$ is a hydrogen atom or a lower alkyl group);

(3) the compound of (2) above, or a pharmaceutically acceptable salt or ester thereof, wherein $X_2$, $X_3$, $X_4$, and $X_5$ are all carbon atoms, or alternatively $X_2$, $X_4$, and $X_5$ are all carbon atoms and $X_3$ is a nitrogen atom; and $R_8$ is an amino group; or (4) the compound of (3) above, or a pharmaceutically acceptable salt or ester thereof, wherein $A_1$ is a sulfur atom and $A_2$ is CH or a nitrogen atom; and m is 1; or (5) the compound of (4) above, or a pharmaceutically acceptable salt or ester thereof, wherein $R_6$ and $R_6'$, which may be the same or different, are each a hydrogen atom or a methyl group, with the proviso that they cannot be simultaneously a methyl group; and $R_7$ is a phenyl group, wherein the phenyl group may be substituted with one or more of the same or different substituents selected from the following:
1) a substituent selected from the <substituent $\gamma_1$>;
2) a lower alkyl group which may be substituted with one or more of the same or different substituents selected from the <substituent $\gamma_4$>, wherein the lower alkyl group may be substituted with one or more halogen atom(s), and two lower alkyl groups, which bind to the same carbon atom, in the lower alkyl group may together form a ring structure having 3 to 5 carbon atoms;
3) a lower alkyl group substituted with an aliphatic heterocyclic group selected from the <substituent $\gamma_2$> optionally substituted with one or more of, the same or different substituents selected from the <substituent group $\gamma_1$> and/or a lower alkyl group;
4) —CH$_2$)$_k$—NR$_9$R$_{10}$, wherein
k is 1, 2, or 3;
$R_9$ is a hydrogen atom or a lower alkyl group; and
$R_{10}$ is a hydrogen atom, a lower alkyl group which may be substituted with one or more of the same or different substituents selected from the <substituent group $\gamma_1$>, or a cycloalkyl group having 5 to 6 carbon atoms, wherein the cycloalkyl group may be substituted with one or more of, the same or different substituents selected from the <substituent group $\gamma_1$> and/or a lower alkyl group which may be substituted with the same or different substituents selected from the <substituent group $\gamma_1$>; and
5) O—R$_{11}$, wherein R$_{11}$ is —CH$_2$)$_l$—NR$_{12}$R$_{13}$, wherein
l is 2 or 3; and
$R_{12}$ and $R_{13}$, which may be the same or different, are each a hydrogen atom, a lower alkyl group, or a lower alkyl group substituted with one or more of the same or different substituents selected from the <substituent group $\gamma_1$>, wherein the <substituent group $\gamma_1$>, <substituent group $\gamma_2$>, and <substituent group $\gamma_4$> are defined as follows:

<substituent group $\gamma_1$>: a halogen atom, a hydroxy group, a formyl group, a nitro group, a cyano group, an amino group, a lower alkylamino group, a dilower alkylamino group, a lower alkoxy group which may be substituted with one or more halogen atom(s), a lower alkylsulfonyl group, and a carboxyl group, <substituent group $\gamma_2$>: a pyrrolidinyl group, a piperidinyl group, and a piperazinyl group, and <substituent group $Y_4$>: a halogen atom, a hydroxy group, a formyl group, a nitro group, a cyano group, a lower alkoxy group which may be substituted with one or more halogen atom(s), a lower alkylsulfonyl group, and a carboxyl group; or (6) the compound of (5) above, or a pharmaceutically acceptable salt or ester thereof, wherein
$R_7$ is a phenyl group substituted at least at the $2^{nd}$ position with a halogen atom, a difluoromethoxy group, or a trifluoromethyl group; or (7) the compound of (6) above, or a pharmaceutically acceptable salt or ester thereof, wherein
$R_3$ and $R_4$, which may be the same or different, are each a hydrogen atom or —Y$_1$—Y$_2$—Y$_3$—Y$_4$, wherein
$Y_1$ is a single bond, CH$_2$, or O;
$Y_2$ is a single bond or (CW$_i$W$_i'$)$_n$, wherein W$_i$, W$_i'$, and n are the same as defined above;
$Y_3$ is a single bond, NH, or N(CH$_3$);
$Y_4$ is a substituent selected from the <substituent group $\beta_1$>; a lower alkyl group which may be substituted with one or more of the same or different substituents selected from the <substituent group β₁>; an aliphatic heterocyclic group selected from an azetidyl group, a pyrrolidinyl group, a piperidinyl group, a piperazinyl group, and a morpholino group; a heteroaryl group selected from a pyrrolyl group, an imidazolyl group, a pyridyl group, and a pyrimidinyl group; or a lower alkyl group substituted with the heteroaryl group, wherein the aliphatic heterocyclic group and the heteroaryl group may be substituted with one or more of the same or different substituents selected from the following:
1) a lower alkyl group,
2) a substituent selected from the <substituent group β₁>, and
3) a lower alkyl group substituted with a substituent selected from the <substituent group β₁>; and
the <substituent group β₁> is: a halogen atom, a hydroxy group, an amino group, a cyano group, a lower alkylamino group, a dilower alkylamino group, a lower alkylsulfonyl group, and a carboxyl group; or (8) the compound of (7) above, or a pharmaceutically acceptable salt or ester thereof, wherein $R_7$ is a phenyl group further substituted at the $4^{th}$ position with —$CH_2OH$ or —$CH_2$—$NR_9R_{10}$, wherein $R_9$ is a hydrogen atom or a lower alkyl group; and $R_{10}$ is a lower alkyl group which may be substituted with a hydroxy group; or (9) the compound of (8) above, or a pharmaceutically acceptable salt or ester thereof, wherein $R_2$, $R_3$, and $R_5$ are all hydrogen atoms;
$R_4$ is a hydrogen atom, a substituent selected from the <substituent group β₁>, or a lower alkyl group which may be substituted with one or more of the same or different substituents selected from the <substituent group β₁>; and
the <substituent group β₁> is a hydroxy group, an amino group, a cyano group, and a methylsulfonyl group.

In addition, the other embodiment of the present specification can be represented as follows. That is, a compound represented by the following Formula [I]:

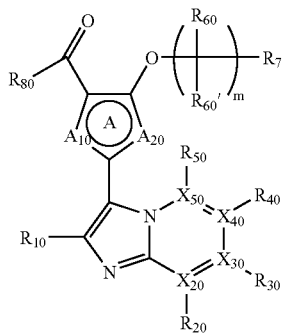

(I)

wherein
the A ring is a 5-membered aromatic heterocyclic group containing at least one hetero atom selected from the group consisting of a nitrogen atom, a sulfur atom, and an oxygen atom;

$A_{10}$ and $A_{20}$, which may be the same or different, are each CH, a nitrogen atom, NH, a sulfur atom, or an oxygen atom, with the proviso that the $A_{10}$ and $A_{20}$ cannot be simultaneously CH;

$X_{20}$, $X_{30}$, $X_{40}$, and $X_{50}$ are all carbon atoms, or alternatively any one of $X_{20}$, $X_{30}$, $X_{40}$, and $X_{50}$ is a nitrogen atom and the rest are all carbon atoms, with the proviso that when $X_{i0}$ (where i0 is one of 2, 3, 4 and 5) is a nitrogen atom, the corresponding $R_{i0}$ (where i0 is one of 2, 3, 4 and 5) together with the $X_{i0}$ forms a nitrogen atom;

m is an integer of 1 or 2;
$R_{10}$ is a hydrogen atom, a methyl group which may be substituted with one or more halogen atom(s), or a substituent selected from <substituent group α₀>;

$R_{20}$, $R_{30}$, $R_{40}$, and $R_{50}$, which may be the same or different, are each a hydrogen atom or —$Y_{10}$—$Y_{20}$—$Y_{30}$—$Y_{40}$, [wherein
$Y_{10}$ is a single bond, $CH_2$, $CH(CH_3)$, O, S, SO, $SO_2$, CO, CONH, or NHCO;
$Y_{20}$ is a single bond or $(CW_iW_i')_n$ (wherein n is an integer of 1 to 4; i is an integer of 1 to n; and $(CW_1W_1')$, represents, $(CW_1W_1')$ when n is equal to 1, $(CW_1W_1')$—$(CW_2W_2')$ when n is equal to 2, $(CW_1W_1')$—$(CW_2W_2')$—$(CW_3W_3')$ when n is equal to 3, and $(CW_1W_1')$—$(CW_2W_2')$—$(CW_3W_3')$—$(CW_4W_4')$ when n is equal to 4, where $W_1$, $W_2$, $W_3$, and $W_4$, and $W_1'$, $W_2'$, $W_3'$, and $W_4'$, which may be the same or different, are each a hydrogen atom, a lower alkyl group, or a substituent selected from <substituent group β₀>);
$Y_{30}$ is a single bond, NH, N(CH₃), S, O, or COO; and
$Y_{40}$ is a hydrogen atom, a substituent selected from the <substituent group β₀>, a lower alkyl group which may be substituted with the same or different substituents selected from the <substituent group β₀>, a cycloalkyl group, an aliphatic heterocyclic group, an aryl group, or a heteroaryl group (wherein the cycloalkyl group, the aliphatic heterocyclic group, the aryl group, and the heteroaryl group may be substituted with one or more of the same or different substituents selected from the following:
1) a lower alkyl group,
2) a substituent selected from the <substituent group β₀>, and
3) a lower alkyl group substituted with a substituent selected from the <substituent group β₀>, and also two hydrogen atoms, which bind to the same carbon atom, in the aliphatic heterocyclic group may be substituted with an oxo group)];

provided, however, that:
when $X_{i0}$ (where i0 is one of 2, 3, 4 and 5) is a nitrogen atom, the corresponding $R_{10}$ (where i0 is one of 2, 3, 4 and 5) together with the $X_{i0}$ forms a nitrogen atom;

$R_{60}$ and $R_{60}'$, which may be the same or different, are each a hydrogen atom, a substituent selected from the <substituent group β₀>, or a lower alkyl group which may be substituted with one or more of the same or different substituents selected from the <substituent group β₀>; or alternatively $R_{60}$ and $R_{60}'$ together form an oxo group (when m is 2, then two sets of $R_{60}$ and $R_{60}'$ which are adjacent to each other cannot together form an oxo group);

$R_{70}$ is an aryl group or a heteroaryl group any of which may be substituted;

$R_{80}$ is an amino group or a hydroxy group; and
the <substituent group α₀> and the <substituent group β₀> are defined as follows:
<substituent group α₀>: a halogen atom, a hydroxy group, and an amino group,
<substituent group β₀>: a halogen atom, a hydroxy group, a nitro group, a cyano group, a formyl group, an amino group, a lower alkylamino group, a dilower alkylamino group, a carbamoyl group, an N-lower alkylcarbamoyl group, an N,N-dilower alkylcarbamoyl group, a lower alkylsulfonyl group, a lower alkylsulfonylamino group, an aminosulfonyl group, an N-lower alkylaminosulfonyl group, an N,N-dilower alkylaminosulfonyl group, a lower alkoxy group, a lower alkoxycarbonyl group, a lower alkoxycarbonylamino group, a lower alkanoyl group, a lower alkanoylamino group, and a carboxyl group, or a pharmaceutically acceptable salt or ester thereof.

Next, representative processes for producing the compound of Formula (I) of the present invention will be described.

Scheme 1: Process for Producing Compound of Formula (I) from Compound of Formula (II)

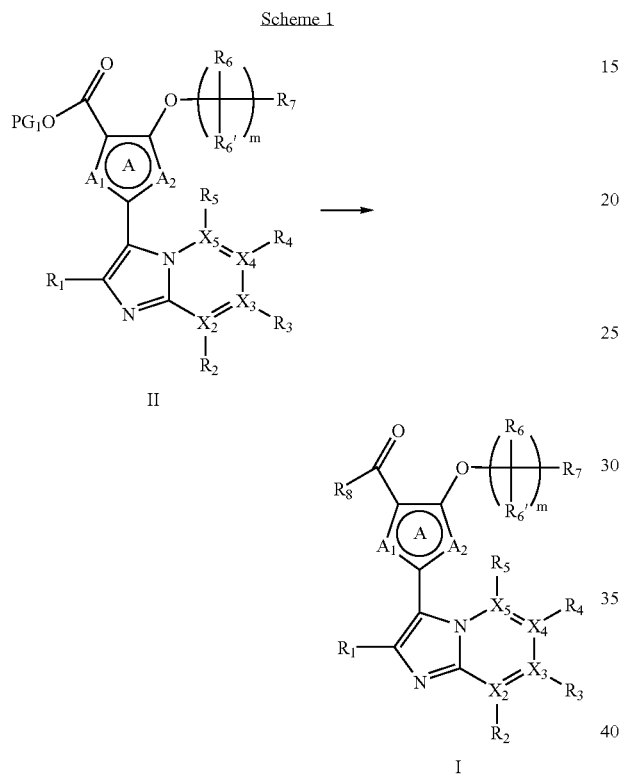

I

The compound of Formula (I) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $R_8$ is OH) can be obtained by eliminating a protective group $PG_1$ from the compound of Formula (U) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $PG_1$ is a protective group). Here $PG_1$ may be exemplified by methyl, ethyl, tert-butyl, benzyl, allyl, or the like, and preferably exemplified by methyl, tert-butyl, or the like. Elimination of the protective group $PG_1$ may be performed differently in accordance with the type of the protective group and stability of the compound, but can be performed by, for example, hydrolysis reaction with an alkali or solvolysis with an acid, according to the method described in the literature [See T. W. Greene, Protective Groups in Organic Synthesis, the third edition, published by John Wiley & Sons] or a method analogous thereto.

Further, the compound of Formula (I) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $R_8$ is $NH_2$) can be synthesized by subjecting the compound of the Formula (I) (wherein $A_1$, $A_2$, $X_2$, $X_3$, $X_4$, —$X_5$, m, $R_1$, —$R_2$, $R_3$, $R_4$, $R_5$, $R_6$, and $R_7$, are the same as defined above, and $R_8$ is OH), obtained according to the above method, to a condensation reaction with an amine such as ammonia, in a solvent such as tetrahydrofuran, N,N-dimethylformamide, dimethylsulfoxide, 1,4-dioxane, chloroform, or the like, preferably in the N,N-dimethylformamide, with the use of a condensing agent such as 1-(3-dimethylaminopropyl)-3-ethylcarbodiimide or the like, and 1-hydroxybenzotriazole. In this case, the reaction temperature can be appropriately selected by those having ordinary skill in the art in accordance with the starting compound used, but the reaction temperature is usually from room temperature to the boiling point of the solvent used. The reaction is usually completed between 1 to 24 hours, but the duration of the reaction can be appropriately increased or decreased.

The compound of Formula (I) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $R_8$ is $NH_2$) can be synthesized by reacting the compound of Formula (II) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $PG_1$ is a protective group) with an ammonia under heating in a sealed tube, in a solvent such as methanol, ethanol, propanol, 1,4-dioxane, or the like, preferably in the methanol or ethanol. The reaction temperature can be appropriately selected by those having ordinary skill in the art in accordance with the starting compound used, but the reaction temperature is usually from room temperature to the boiling point of the solvent used. The reaction is usually completed between 1 to 72 hours, but the duration of the reaction can be appropriately increased or decreased.

Scheme 2: Representative Process for Producing Compound of Formula (II)

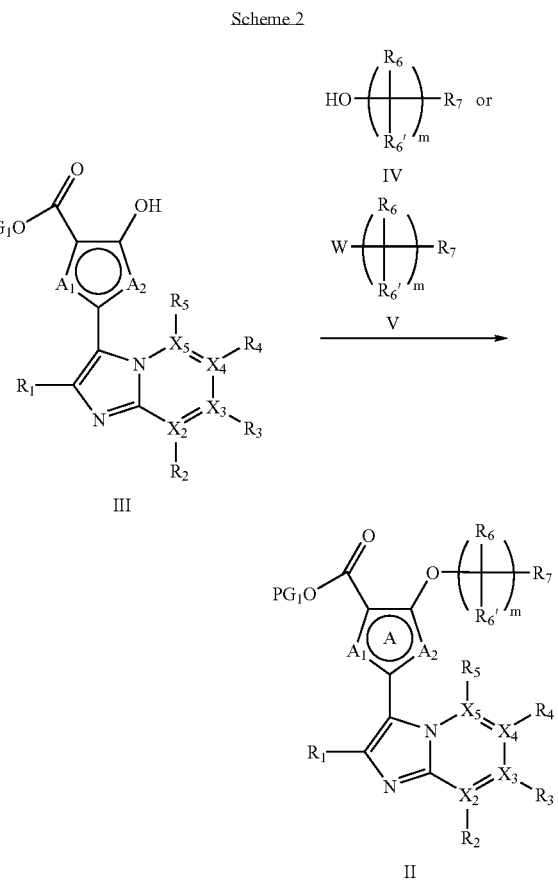

II

The compound of Formula (II) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $PG_1$ is a protective group) can be obtained by a Mitsunobu reaction (Synthesis, 1981, 1) of the compound of Formula (III) (wherein $A_1$, $A_2$, $X_2$, $X_3$, $X_4$, $X_5$, m, $R_1$, $R_2$, $R_3$, $R_4$, and $R_5$, are the same as defined above, and $PG_1$ is a protective group) with the compound of Formula (IV) (wherein m, $R_6$, and $R_7$, are the same as defined above). For example, the compound can be synthesized by reacting the compound of Formula (III) with the compound of Formula (IV), in a solvent such as tetrahydrofuran, 1,4-dioxane, methylene chloride, chloroform, toluene, or the like, with one of triphenylphosphine and tributylphosphine, and with one of diethyl azodicarboxylate and diisopropyl azodicarboxylate. In the reaction, 1 to 3 mole(s), preferably 1 mole of the compound of Formula (IV), to 1 mole of the compound of Formula (III) is used. In this case, the reaction temperature can be appropriately selected by those having ordinary skill in the art in accordance with the starting compound used or the reaction solvent, but the reaction temperature is usually from 0° C. to room temperature. The reaction is usually completed between 1 to 24 hours, but the duration of the reaction can be appropriately increased or decreased.

Alternatively, the compound of Formula (II) (wherein $A_1$, $A_2$, $X_2$, $X_3$, $X_4$, $X_5$, m, $R_1$, $R_2$, $R_3$, $R_4$, $R_5$, $R_6$ and $R_7$, are the same as defined above, and $PG_1$ is a protective group) can be synthesized by reacting the compound of Formula (III) with the compound of Formula (V) (wherein m, $R_6$, and $R_7$, are the same as defined above, and W is a leaving group such as an iodine atom, a bromine atom, a methanesulfonyloxy group, or the like) with a base such as potassium carbonate, in an aprotic polar solvent such as N,N-dimethylformamide, or the like. In the reaction, 1 to 3 mole(s), preferably 1 mole of the compound of Formula (V), to 1 mole of the compound of Formula (III) is used. In this case, the reaction temperature can be appropriately selected by those having ordinary skill in the art in accordance with the starting compound used or the reaction solvent, but the reaction temperature is usually from room temperature to 100° C., and preferably from 60 to 80° C. The reaction is usually completed between 1 to 24 hours, but the duration of the reaction can be appropriately increased or decreased.

The compound of the above Formula (IV), for example, is 4-methyl-benzyl alcohol, or the like, and the compound of the above Formula (V), for example, is 3-nitro-benzyl bromide, or the like, which are either commercially available or can be synthesized from a commercially available compound by a method generally known, or commonly known, by those having ordinary skill in the art.

Scheme 3: Representative Process for Producing Compound of Formula (III)

Scheme 3

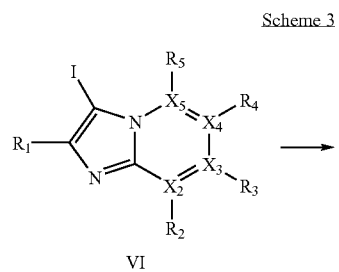

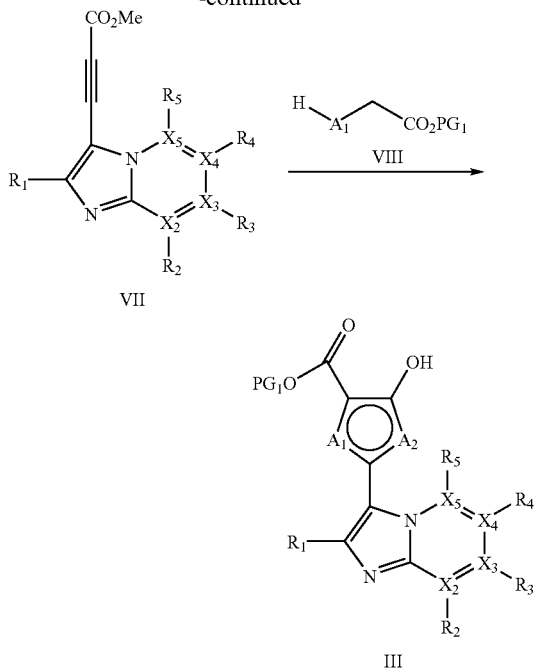

Firstly, the compound of Formula (VII) (wherein $X_2$, $X_3$, $X_4$, $X_5$, $R_1$, $R_2$, $R_3$, $R_4$, and $R_5$, are the same as defined above) can be obtained by subjecting the compound of Formula (VI) (wherein $X_2$, $X_3$, $X_4$, $X_5$, $R_1$, $R_2$, $R_3$, $R_4$, and $R_5$, are the same as defined above) to the Sonogashira reaction (Tetrahedron Lett., 50, 4467 (1975), Synth. Commun., 28, 327 (1998)). For example, by reacting the compound of Formula (VI) with methyl propiolate, in a solvent such as tetrahydrofuran, 1,4-dioxane, methylene chloride, chloroform, toluene, or the like, in the presence of a palladium catalyst such as bis(triphenylphosphine)palladium(II) dichloride, a copper catalyst such as copper iodide, and a base such s-potassium carbonate, or triethylamine, the corresponding compound of Formula (VII) can be synthesized. In this case, the reaction temperature can be appropriately selected by those having ordinary skill in the art in accordance with the starting compound used or the reaction solvent, but the reaction temperature is usually from room temperature to a boiling point of the solvent used in the reaction. The reaction is usually completed between 1 to 24 hours, but the duration of the reaction can be appropriately increased or decreased.

Next, the compound of Formula (III) (wherein $X_2$, $X_3$, $X_4$, $X_5$, $R_1$, $R_2$, $R_3$, $R_4$, and $R_5$, are the same as defined above, $A_1$ is S or NH, $A_2$ is CH, and $PG_1$ is a protective group) can be obtained by subjecting the compound of Formula (VII) and the compound of Formula (VIII) (wherein $A_1$ is S or NH, and $PG_1$ is a protective group) to a cycloaddition reaction (Chem. Ber., 99, 1558 (1966), Helv. Chim. Acta, 47, 1748 (1964) and the like). For example, the compound of Formula (III) can be synthesized by reacting the compound of Formula (VII) and the compound of Formula (VIII), with a base such as sodium methoxide or sodium ethoxide, in a solvent such as methanol, ethanol, tetrahydrofuran, 1,4-dioxane, toluene, or the like. In the reaction, 1 to 3 mole(s), preferably 1 mole of the compound of Formula (VIII), to 1 mole of the compound of Formula (VII) is used. In this case, the reaction temperature can be appropriately selected by those having ordinary skill in the art in accordance with the starting compound used or the reaction solvent, but the reaction temperature is usually from 0° C. to a boiling point of the solvent. The reaction is usually completed between 1 to 24 hours, but the duration of the reaction can be appropriately increased or decreased.

The compound of Formula (VIII), for example, is methyl thioglycolate, or the like, and is either commercially available or can be synthesized from a commercially available compound by a method generally known by those having ordinary skill in the art.

Scheme 4: Representative Process for Producing Compound of Formula (VI)

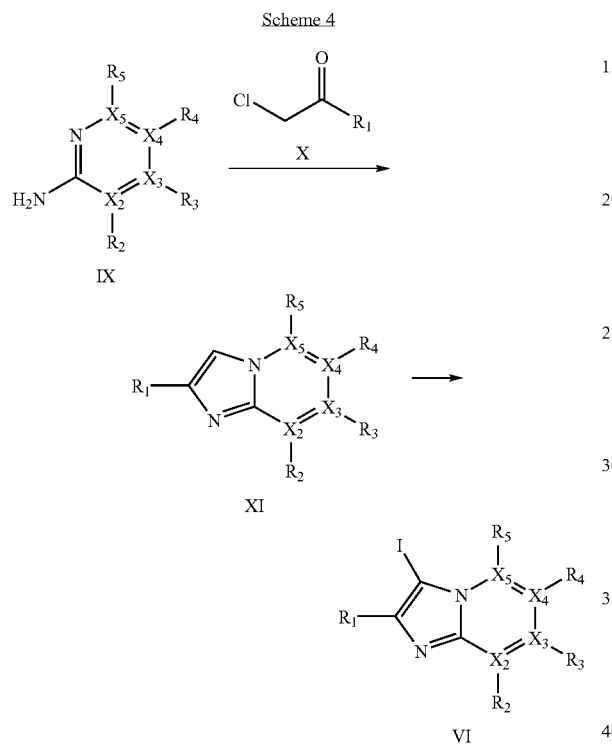

Firstly, a fused imidazole derivative of Formula ($X_1$) (wherein $X_2$, $X_3$, $X_4$, $X_5$, $R_1$, $R_2$, $R_3$, $R_4$, and $R_5$, are the same as defined above) can be easily prepared by reacting the compound of (IX) (wherein $X_2$, $X_3$, $X_4$, $X_5$, $R_2$, $R_3$, $R_4$, and $R_5$, are the same as defined above) with the α-halogenated carbonyl compound of Formula (X) (wherein $R_1$ is the same as defined above) in accordance with the known method (e.g., J. Med. Chem., 39, 2856 (1996)).

The compound of Formula (IX), for example, is 2-aminopyridine, or the like, and is either commercially available or can be synthesized from a commercially available compound by a method generally known by those having ordinary skill in the art or a method analogous thereto.

Next, the compound of Formula (VI) (wherein $X_2$, $X_3$, $X_4$, $X_5$, $R_1$, $R_2$, $R_3$, $R_4$, and $R_5$, are the same as defined above) can be prepared by reacting the compound of above ($X_1$) with N-iodosuccinimide, in 1,4-dioxane (J. Org. Chem., 654(20), 6572 (2000)). For the reaction, 1 to 3 mole(s), preferably 1 mole of the N-iodosuccinimide, to 1 mole of the compound of Formula ($X_1$) is used. In this case, the reaction temperature can be appropriately selected by those having ordinary skill in the art in accordance with the starting compound used, but the reaction temperature is usually from 0° C. to room temperature, and preferably room temperature. The reaction is usually completed between 1 to 12 hours, but the duration of the reaction can be appropriately increased or decreased.

Scheme 5: Another Process for Producing Compound of Formula (II)

The compound of Formula (II) (wherein $A_1$, $A_2$, $X_2$, $X_3$, $X_4$, $X_5$, m, $R_1$, $R_2$, $R_3$, $R_4$, $R_5$, $R_6$, and $R_7$, are the same as defined above, and $PG_1$ is a protective group) can also be synthesized by the following process.

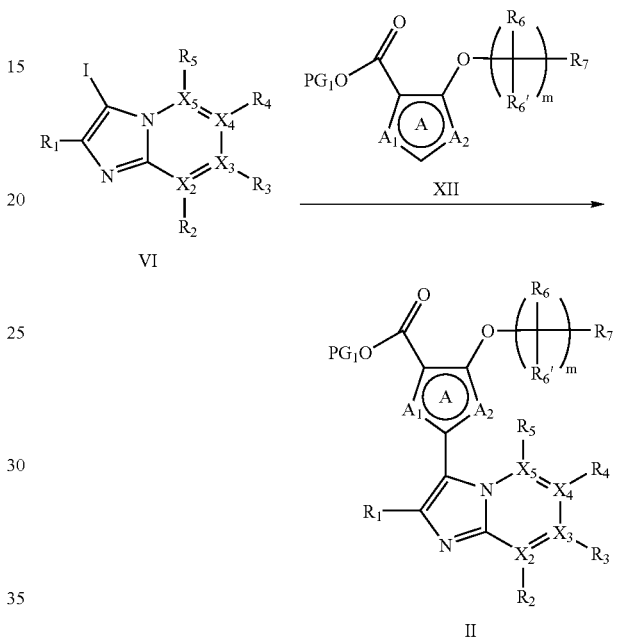

The compound of Formula (II) can be obtained by subjecting the compound of Formula (VI) (wherein $X_2$, $X_3$, $X_4$, $X_5$, $R_1$, $R_2$, $R_3$, 4, and $R_5$, are the same as defined above) and the compound of Formula (XII) (wherein $A_1$, $A_2$, m, $R_6$, and $R_7$, are the same as defined above, and $PG_1$ is a protective group) (Journal of synthetic organic chemistry society, 62 (4), 355 (2004)), to a coupling reaction.

For example, by reacting the compound of Formula (VI) with the compound of Formula (XII), in a solvent such as dimethylsulfoxide, N,N-dimethylformamide, or the like, in the presence of a palladium catalyst, such as bis(triphenylphosphine)palladium(II) dichloride, and a catalyst such as a tetrabutylammonium fluoride or silver fluoride catalyst, the corresponding compound of Formula (II) can be synthesized.

The compound of Formula (XII), for example, is 3-benzyloxy-2-thiophenecarboxylic acid methyl ester, and can be synthesized from a commercially available compound such as 3-hydroxy-2-thiophenecarboxylic acid methyl ester, by using the method shown in Scheme 2 or a method analogous thereto.

Scheme 6: Another Process for Producing Compound of Formula (II)

The compound of Formula (II) (wherein $A_1$, $A_2$, $X_2$, $X_3$, $X_4$, $X_5$, m, $R_2$, $R_3$, $R_4$, $R_5$, $R_6$, and $R_7$, are the same as defined above, $R_1$ is a hydrogen atom, and $PG_1$ is a protective group) can also be synthesized by the following process.

Scheme 6

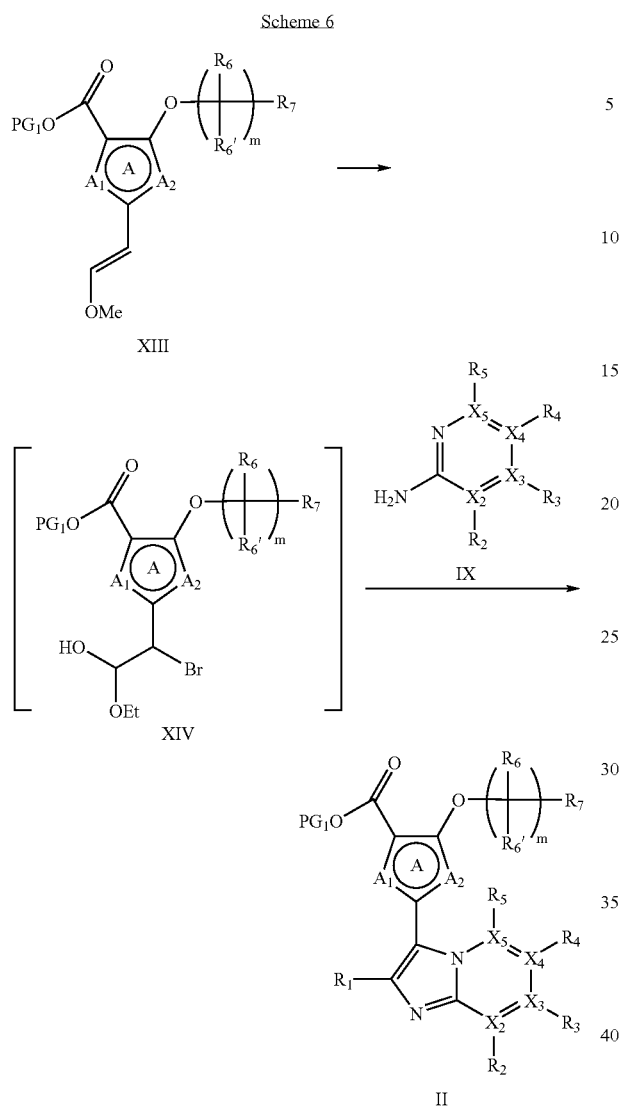

starting compound used, but the reaction temperature is usually from 0° C. to room temperature, and preferably room temperature. The reaction is usually completed between 1 to 12 hours, but the duration of the reaction can be appropriately increased or decreased. The obtained Compound of Formula (XIV) can be used in the subsequent reaction without further isolation and purification.

Scheme 7: Process for Producing Compound of Formula (XIII)

Scheme 7

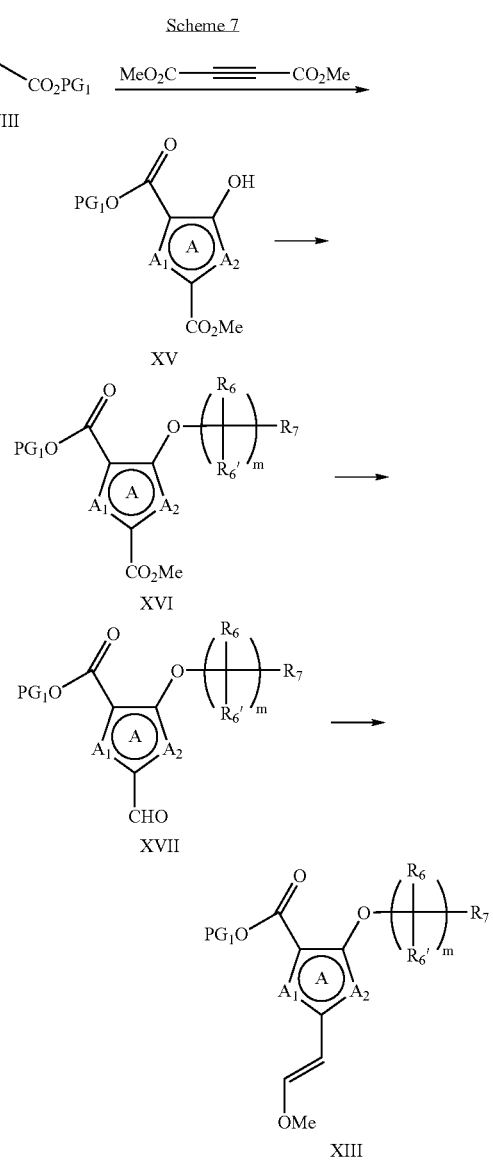

The compound of Formula (II) can be synthesized from the compound of Formula (XIV) (wherein $A_1$, $A_2$, m, $R_6$, and $R_7$, are the same as defined above, and $PG_1$ is a protective group) and the compound of Formula (IX) (wherein $X_2$, $X_3$, $X_4$, $X_5$, $R_2$, $R_3$, $R_4$, and $R_5$, are the same as defined above), in 1,4-dioxane. In the reaction, 1 to 3 mole(s), preferably 1 mole of the compound of Formula (IX), to 1 mole of the compound of Formula (XIV) is used. The reaction temperature can be appropriately selected by those having ordinary skill in the art in accordance with the starting compound used, but the reaction temperature is usually from room temperature to a boiling point of the solvent, and preferably from room temperature to 50° C. The reaction is usually completed between 1 to 24 hours, but the duration of the reaction can be appropriately increased or decreased.

Here, the compound of Formula (XIV) can be prepared by reacting the compound of above (XII) (wherein $A_1$, $A_2$, m, $R_6$, and $R_7$, are the same as defined above, and $PG_1$ is a protective group) with N-bromosuccinimide, in 1,4-dioxane. In the reaction, 1 to 3 mole(s), preferably 1 mole of N-bromosuccinimide, to 1 mole of the compound of Formula (XII) is used. The reaction temperature can be appropriately selected by those having ordinary skill in the art in accordance with the Firstly, the compound of Formula (XV) (wherein $A_1$ is the same as defined above, $A_2$ is CH, and $PG_1$ is t-butyl) can be synthesized by reacting the compound represented by Formula (VIII) (wherein $A_1$ is the same as defined above, and $PG_1$ is tert-butyl) and acetylenedicarboxylic acid dimethyl ester with a base such as sodium methoxide or sodium ethoxide, in a solvent such as methanol, ethanol, tetrahydrofuran, 1,4-dioxane, or toluene (Chem. Ber., 87, 1229 (1954)). In the reaction, 1 to 3 mole(s), preferably 1 mole of acetylenedicarboxylic acid dimethyl ester, to 1 mole of the compound of Formula (VIII) is used. In this case, the reaction temperature can be appropriately selected by those having ordinary skill in the art in accordance with the starting compound used or the reaction solvent, but the reaction temperature is usually from 0° C. to a boiling point of the solvent. The reaction is usually completed in 1 to 24 hours, but the duration of the reaction can be appropriately increased or decreased.

Secondly, the compound of Formula (XVI) (wherein $A_1$, m, $R_6$, and $R_7$, are the same as defined above, $A_2$ is CH, and $PG_1$ is tert-butyl) can be synthesized from the compound of Formula (XV) by using the method shown in Scheme 2 or a method analogous thereto.

Thirdly, the compound of Formula (XVII) (wherein $A_1$, m, $R_6$, and $R_7$, are the same as defined above, $A_2$ is CH, and $PG_1$ is t-butyl) can be obtained from the compound of Formula (XVI) by an appropriate method generally known by those having ordinary skill in the art (see Advanced Organic Chemistry, Fourth edition, written by Jerry March, WILEY. INTERSCIENCE publication) and/or a method exemplified below or method analogous thereto.

For example, the compound of Formula (XVI) (wherein $A_1$, m, $R_6$, and $R_7$, are the same as defined above, $A_2$ is CH, and $PG_1$ is t-butyl) is reacted with a base such as an aqueous solution of sodium hydroxide, in a solvent such as methanol, ethanol, tetrahydrofuran, or the like, to make a form of carboxylic acid methyl ester thereof a carboxylic compound. In this case, the reaction temperature can be appropriately selected by those having ordinary skill in the art in accordance with the starting compound used or the reaction solvent, but the reaction temperature is usually from 0° C. to a boiling point of the solvent. The reaction is usually completed between 1 to 24 hours, but the duration of the reaction can be appropriately increased or decreased.

Subsequently, the obtained carboxylic compound is reacted with a reducing agent such as boron hydride, in a solvent such as tetrahydrofuran, to obtain a hydroxymethyl form thereof. In this case, the reaction temperature can be appropriately selected by those having ordinary skill in the art in accordance with the starting compound used or the reaction solvent, but the reaction temperature is usually from 0° C. to a boiling point of the solvent. The reaction is usually completed between 1 to 24 hours, but the duration of the reaction can be appropriately increased or decreased.

Then, the obtained hydroxymethyl form is reacted with an oxidizing agent such as manganese dioxide, in a solvent such as chloroform or tetrahydrofuran, to obtain the compound of Formula (XVII). In this case, the reaction temperature can be appropriately selected by those having ordinary skill in the art in accordance with the starting compound used or the reaction solvent, but the reaction temperature is usually from 0° C. to a boiling point of the solvent. The reaction is usually completed in 1 to 24 hours, but the duration of the reaction can be appropriately increased or decreased.

Fourthly, the compound of Formula ($X_1$) (wherein $A_1$, $A_2$, m, $R_6$, and $R_7$, are the same as defined above, and $PG_1$ is tert-butyl) is obtained by subjecting the compound of Formula (XVII) (see Advanced Organic Chemistry, Fourth Edition, page 956, written by Jerry March, WILEY. INTERSCIENCE Publication), to the Wittig reaction. For example, the compound of Formula (XIII) is obtained by reacting methoxymethyl triphenylphosphonium chloride with a base such as n-butyllithium or lithium diisopropylamide, and then reacting the thus obtained compound with the compound (XVII). In this case, the reaction temperature can be appropriately selected by those having ordinary skill in the art in accordance with the starting compound used or the reaction solvent, but the reaction temperature is usually from −78° C. to room temperature. The reaction is usually completed between 1 to 96 hours, but the duration of the reaction can be appropriately increased or decreased.

Scheme 8: Process for Producing Compound of Formula (III) in which $A_1$ is S and $A_2$ is N

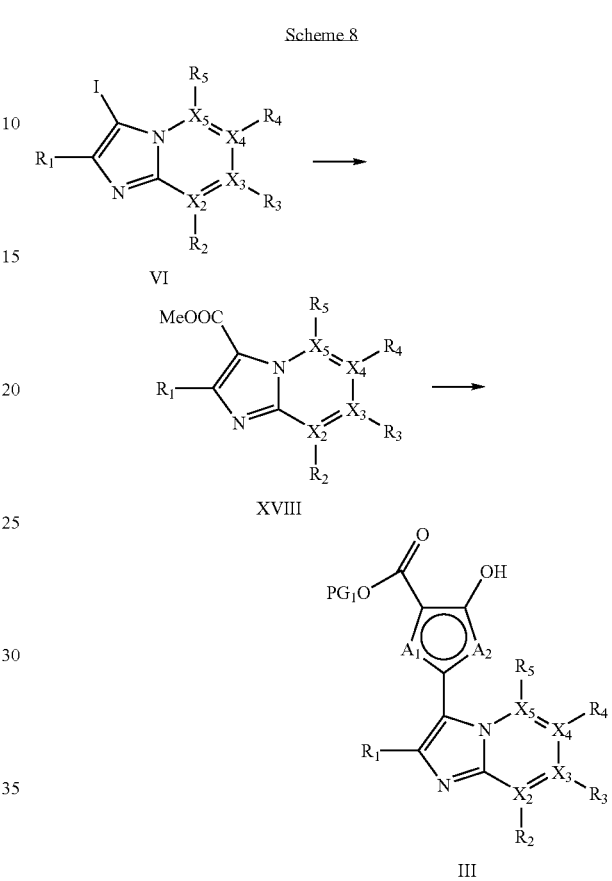

Firstly, the compound of Formula (XVIII) (wherein $X_2$, $X_3$, $X_4$, $X_5$, $R_1$, $R_2$, $R_3$, $R_4$, and $R_5$, are the same as defined above) can be synthesized by reacting the compound of Formula (VI) (wherein $X_2$, $X_3$, $X_4$, $X_5$, $R_1$, $R_2$, $R_3$, $R_4$, and $R_5$, are the same as defined above) with carbon monoxide, in a mixed solvent as prepared by adding an alcohol such as methanol to a solvent such as dimethylsulfoxide, N-methylpyrrolidone, or N,N-dimethylformamide, in the presence of a ligand such as 1,1'-bis(diphenylphosphino)ferrocene, a palladium catalyst such as palladium(II) acetate, and a base such as sodium hydrogen carbonate or triethylamine, thereby obtaining the corresponding compound of Formula (XVIII). In this case, the reaction temperature can be appropriately selected by those having ordinary skill in the art in accordance with the starting compound used or the reaction solvent, but the reaction temperature is usually from 50° C. to a boiling point of the solvent used in the reaction. The reaction is usually completed in 1 to 24 hours, but the duration of the reaction can be appropriately increased or decreased.

Secondly, the compound of Formula (III) (wherein $A_1$ is S; $A_2$ is N; $X_2$, $X_3$, $X_4$, $X_5$, $R_1$, $R_2$, $R_3$, $R_4$, and $R_5$, are the same as defined above; and $PG_1$ is a protective group) can be obtained from the compound of Formula (XVIII) by an appropriate method generally known by those having ordinary skill in the art (see Advanced Organic Chemistry, Fourth edition, written by Jerry March, WILEY. INTERSCIENCE publication) and/or a method exemplified below or method analogous thereto.

For example, the compound of Formula (XVIII) is reacted with a base such as an aqueous solution of sodium hydroxide, in a solvent such as methanol, ethanol, tetrahydrofuran, or the like, thereby to make a form of carboxylic acid methyl ester thereof a carboxylic compound. In this case, the reaction temperature can be appropriately selected by those having ordinary skill in the art in accordance with the starting compound used or the reaction solvent, but the reaction temperature is usually from 0° C. to a boiling point of the solvent. The reaction is usually completed between 1 to 24 hours, but the duration of the reaction can be appropriately increased or decreased.

Subsequently, the obtained carboxylic compound is subjected to a condensation reaction with an amine such as ammonia, in a solvent such as tetrahydrofuran, N,N-dimethylformamide, 1,4-dioxane, chloroform, or the like, preferably in N,N-dimethylformamide, with the use of a condensation agent such as 1-(3-dimethylaminopropyl)-3-ethylcarbodiimide or the like, and 1-hydroxybenzotriazole, thereby obtaining a carbamoyl compound. In this case, the reaction temperature can be appropriately selected by those having ordinary skill in the art in accordance with the starting compound used, but the reaction temperature is usually from room temperature to a boiling point of the solvent used. The reaction is usually completed in 1 to 24 hours, but the duration of the reaction can be appropriately increased or decreased.

Next, the obtained carbamoyl compound is reacted with a Lawesson's reagent, phosphorous pentasulphide, or the like, to obtain a thiocarbamoyl compound, and subsequently, thus obtained compound is reacted with an ester form of bromomalonic acid, in an alcohol solvent such as ethanol, to obtain the compound of Formula (III) (literature: J. Med. Chem. 1980, 23, 65, etc.).

Scheme 9: Another Process for Producing Compound of Formula (III) in which $A_1$ is S and $A_2$ is N The compound of Formula (III) (wherein $X_2$, $X_3$, $X_4$, $X_5$, m, $R_2$, $R_3$, $R_4$, $R_5$, $R_6$, and $R_7$, are the same as defined above, $R_1$ is a hydrogen atom, and $PG_1$ is a protective group) can also be synthesized by the following process.

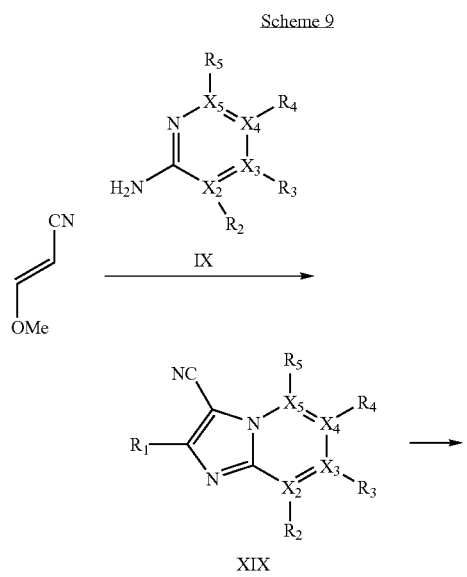

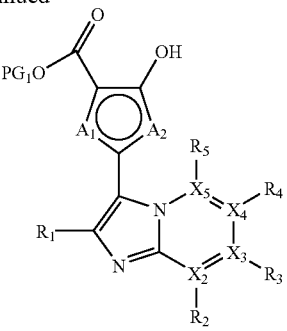

Firstly, the compound of Formula (XIX) (wherein $X_2$, $X_3$, $X_4$, $X_5$, $R_2$, $R_3$, $R_4$, and $R_5$, are the same as defined above, and $R_1$ is a hydrogen atom) is synthesized from alkoxyacrylonitrile such as 3-methoxyacrylonitrile and 3-ethoxyacrylonitrile by using the method shown in Scheme 6 or a method analogous thereto.

Secondly, the compound of Formula (III) (wherein $A_1$ is S; $A_2$ is N; $X_2$, $X_3$, $X_4$, $X_5$, $R_2$, $R_3$, $R_4$, and $R_5$, are the same as defined above; $R_1$ is a hydrogen atom; and $PG_1$ is a protective group) is obtained by either: applying a hydrogen sulfide gas to a nitrile group of the compound of Formula (XIX) in the presence of a base such as pyridine or triethylamine; or reacting with a base such as bis(trimethylsilyl)sulfide or sodium methoxide so as to give a thiocarbamoyl compound, and then reacting the obtained thiocarbamoyl compound with an ester form of the bromomalonic acid in an alcohol solvent such as ethanol.

In the production processes described in the above Schemes 1 to 9, when a defined functional group is modified under reaction conditions, those having ordinary skill in the art if necessary can apply a method commonly used in synthetic organic chemistry, for example a means for protecting or deprotecting a functional group [for example, see Protective Groups in Organic Synthesis, the third edition, written by T. W. Greene, John Wiley & Sons Publication], thus to obtain a desired compound.

Next, the PLK 1 inhibitory effect and cell proliferation inhibitory effect (cell-growth inhibitory effect) of the compound according to the present invention will be explained.

Measurement of Effect of Inhibitory Activity Against PLK 1

(1) Preparation of PLK 1

PLK1 was prepared in accordance with the method disclosed in [Cell Signal, Vol. 12, 405-411 (2000)].

First, a baculovirus expressing full-length human PLK1 of which the N terminus is fused with GST (glutathione S-transferase) was prepared, and then the PLK1 transfected into a Spodoptera frugiperda(Sf)9 insect cell was highly expressed as a GST-fused protein. The cells were recovered and suspended in a lysis buffer (50 mM tris-hydrochloric acid buffer (pH 7.4)/150 mM sodium chloride/1 mM EDTA (ethylenediamine tetraacetic acid)/1 mM dithiothreitol/0.1% polyoxyethylene sorbitan monolaurate) to break open cells with a sonicator, and supernatant was recovered after a centrifugation. The supernatant was reacted on glutathione sepharose beads, and then the beads were washed with a lysis buffer. Thereafter, the beads were reacted in a lysis buffer containing Precision Protease to recover supernatant.

(2) Preparation of PLK1-T210D

It has been known that $210^{th}$ codon of human PLK1 which originally codes for threonine can be changed to an active type by altering the site so as to code aspartic acid [Molecular and Cell Biology (Mol. Cell. Biol.), Vol. 17, 3408 (1997)]. In order to obtain a human active type PLK1 protein, cDNA of mutated PLK1 (PLK1-T210D) in which the $210^{th}$ codon codes for aspartic acid due to a base substitution in the $210^{th}$ codon of human PLK1 cDNA, was prepared. This PLK1-T210D cDNA was incorporated into a baculovirus expression vector in the same manner as in the above, expressed in insect cells, and then purified.

(3) Measurement of PLK 1 and PLK1-T210D Activity

For the measurement of the PLK1 and PLK1-T210D activity, a synthetic peptide (aspartic acid-glutamic acid leucine-methionine-glutamic acid-alanine-serine-phenylalanine-alanine-aspartic acid-glutamine-aspartic acid-alanine-lysine) in which the serine surrounding sequence of the amino acid sequence No. 198 of CDC25C having been reported as the site for PLK1 substrate [EMBO Report, Vol. 3, 341 (2002)] is altered, was used as a substrate.

The reaction was carried out in accordance with the method of Toyoshima-Morimoto et al. [Nature, Vol. 410, 215-220, (2001)]. The volume of the reaction solution was 21.1 µL and the composition of the reaction buffer was 20 mM tris-hydrochloric acid buffer (pH 7.4)/10 mM magnesium chloride/0.5 mM dithiothreitol/1 mM EGTA (ethylene glycol-bis(beta-aminoethylether)-N,N,N',N',-tetraacetic acid). Thereto, purified PLK 1, 50 µM of the substrate peptide, 50 µM of non-labeled adenosine triphosphate (ATP), and 1 µCi of [$\gamma$-$^{33}$P]-labeled ATP (2000 to 4000 Ci/mmole) were added to carry out the reaction at 25° C. for 20 minutes. Then, 10 µL of 350 mM phosphate buffer was added to the reaction system to terminate the reaction. The resultant solution was spotted onto a multi-screen phosphocellulose filter on a 96-well plate. After washing the phosphocellulose filter with 75 mM phosphate buffer, the filter was dried to measure the radioactivity with a liquid scintillation counter. The non-labeled ATP and [$\gamma$-$^{33}$P]-labeled ATP were purchased from Amersham Bioscience Corp., and the multi-screen phosphocellulose filter was purchased from Millipore Corp.

The addition of the compound according to the invention to the reaction system was carried out by adding 1.1 µL of the solution prepared by preliminarily dissolving in dimethylsulfoxide at a 20-fold concentration of the final concentration. A control was provided by adding 1.1 µL of dimethylsulfoxide to the reaction system.

$IC_{50}$ value of the compound according to the invention against the PLK 1 and PLK1-T210D activity was determined, and the results are shown in Table 1 below.

TABLE 1

| | PLK1 inhibitory activity (nM) | PLK1-T210D inhibitory activity (nM) |
|---|---|---|
| Compound of Example 38 | 20 | 7.9 |
| Compound of Example 44 | 12 | 12 |
| Compound of Example 107 | 12 | 8.4 |
| Compound of Example 119 | 28 | 22 |

As above, it is clear that the inhibitory activity of the compound according to the invention against PLK1 and PLK1-T210D is remarkably high.

Measurement of the inhibitory effect against cell proliferation: Measurement of the inhibitory activity against PLK1 at Cellular Level (1) Method of Cell Culture For the measurement of the PLK 1 inhibitory activity of the compound at the cellular level, human uterine cervix cell lines HeLaS3 cells were used. The HeLaS3 cell was obtained from American Type Culture Collection (ATTC), and cultured in a $CO_2$-incubator of saturated steam, in the presence of 5% $CO_2$, by using Dulbecco's Modified Eagle's Medium containing 10% fetal calf serum at 37° C.

(2) Measurement of Inhibitory Activity of the Compound According to the Invention It has been reported that PLK 1 plays an important role in various stages of mitotic phase (M-phase) in mammalian cells (Nature Review Molecular Cell Biology (Nat. Rev. Mol. Cell. Biol.), Vol. 5, 429, (2004)). In fact, when the mammalian cells are treated with PLK 1 siRNA to control the expression level, the cell cycle progression is inhibited and thus the cell is arrested at M phase. In addition, when examining the phosphorylation level of serine (10th residue on histone H3) which is thought to be required for a chromosome condensation in M phase, is examined, it is observed that the level is enhanced to a high level. Thus, after treating the cell with the compound according to the invention, the phosphorylation level of histone H3 was examined by the indirect fluorescent antibody technique, the cells arrested at M phase were identified by using the level thereof as an indicator to analyze the ratio of cells arrested at M phase, and then EC50 value of each compound was calculated to evaluate the PLK 1 inhibitory activity at a cellular level.

First, HeLaS3 cells synchronized at the G1/S phase by the double-thymidine method were seeded into a lysine-treated 96-well plate (Falcon Corp.) in the ratio of 8,000 per one well, and allowed to stand still in the above-mentioned $CO_2$ incubator. 4 hours after the seeding, the compound according to the invention, which is diluted in series, was added into each well of the plate, and further allowed to stand still in the $CO_2$ incubator. 12 hours after the addition of the compound according to the invention, the culture medium containing the compound according to the invention in each well of the plate was removed, and then 100 µL of ice-cold 100% methanol (Wako Pure Chemical Industries, Ltd.) was added, to carry out cell fixation for 10 minutes and treatment for increasing the membrane permeability. Subsequently, to the wells in which the methanol was removed, 50 µL of 1% BSA/PBS was added, and then blocking was carried out for 30 minutes. Thereafter, for the primary antibody reaction, 50 µL of 1% BSA/PBS containing a 2.5 mg/mL Anti-phospho Histone H3 (Ser10) antibody (Upstate Corp.) was added, and the plate was left over at room temperature for 90 minutes. After terminating the reaction, each well was once washed with PBS, and for the second antibody reaction, 50 µL of 1% BSA/PBS containing 1.5 mg/mL Cy5-labelled anti-rabbit IgG (H+ L) antibody (Chemicon) and 10 ug/mL DAPI (Sigma) which is a nucleus staining regent, was added to the wells, and further left over at room temperature for 90 minutes. After terminating the reaction, the reaction solution in wells was removed and replaced with 100 µL of PBS, and then fluorescence images were captured by using IN Cell Analyzer 1000 (manufactured by GE Amersham) to analyze the ratio of the cells arrested at M phase (Mitotic index) in each view. When the maximum value of the ratio of cells arrested at M phase which can be induced by each drug is assumed as 100%, the drug concentration required for inducing 50% out of that 100% is defined as $EC_{50}$.

$EC_{50}$ values obtained by the above-mentioned method are shown in Table 2 below.

TABLE 2

| | PLK1 inhibitory activity at cellular level (EC$_{50}$, μM) |
|---|---|
| Compound of Example 44 | 0.07 |
| Compound of Example 66 | 0.36 |
| Compound of Example 107 | 0.21 |
| Compound of Example 119 | 0.21 |
| Compound of Example 161 | 0.49 |
| Compound of Example 163 | 0.66 |
| Compound of Example 188 | 0.39 |
| Compound of Example 236 | 0.10 |

From the fact that the compound according to the invention exhibits a strong inhibitory effect against cell proliferation, it is believed to be extremely useful as an antitumor agent.

As discussed in the above, the compound according to the invention has an excellent PLK 1 inhibitory activity and also has a strong inhibitory effect against cell proliferation. Therefore, it is believed to be useful as an antitumor agent for strongly inhibiting the proliferation of cancerous cells. That is, a pharmaceutical composition containing the novel fused imidazole derivative according to the invention or a pharmaceutically acceptable salt or ester thereof, or an antitumor agent containing the novel fused imidazole derivative according to the invention or a pharmaceutically acceptable salt or ester thereof, is believed to be effective for the treatment of cancer patients.

In addition, the pharmaceutical composition or the antitumor agent may contain pharmaceutically acceptable carriers or diluents. Here, the term "pharmaceutically acceptable carriers or diluents" refers to excipients [e.g., fats, bees wax, semi-solid or liquid polyol, natural or hydrogenated oil, etc.]; water [e.g., distilled water, especially distilled water for injection, etc.], physiological brine, alcohol (e.g., ethanol), glycerol, polyol, aqueous glucose solution, mannitol, vegetable oil, or the like; additives [e.g. bulking agent, disintegrant, binder, lubricant, wetting agent, stabilizer, emulsifier, dispersant, preservative, sweetener, colorant, flavoring agent or aromatic substance, thickening agent, diluent, buffering substance, solvent or solubilizer, drug for attaining storage effect, salt for adjusting osmotic pressure, coating agent, or antioxidant], and the like.

The compound according to the invention can also be used as a prodrug containing ester. Here, the term 'prodrug' generally refers to a derivative of a certain drug molecule which is chemically modified, which itself shows no physiological activity but after being injected in vivo, transforms back to its original drug molecule to exhibit drug efficacy. As the prodrug of the compound according to the invention, a compound of the above Formula (I) in which the hydroxyl group is acylated, for example, with a phosphate group can be exemplified. The prodrug/ester can be produced in accordance with the method commonly known or used by those having ordinary skill in the art.

Furthermore, as for tumors suitable for expecting a therapeutic effect of the compound according to the invention, for example, human solid tumors and the like may be mentioned. Examples of the human solid tumors include cerebral cancer, head and neck cancer, esophageal cancer, thyroid cancer, small cell cancer, non-small cell cancer, breast cancer, gastric cancer, gall bladder/bile duct cancer, hepatic cancer, pancreatic cancer, colon cancer, rectal cancer, ovarian cancer, chorioepithelioma, uterine cancer, cervical cancer, renal pelvic/ureteral cancer, urinary bladder cancer, prostate cancer, penile cancer, testicular cancer, embryonal cancer, Wilms' tumor, skin cancer, malignant melanoma, neuroblastoma, osteosarcoma, Ewing's sarcoma, soft tissue sarcoma, and the like.

Next, the "pharmaceutically acceptable salt or ester thereof" described above will be explained.

When the compound according to the invention is used as an antitumor agent or the like, the compound can be used in the form of a pharmaceutically acceptable salt thereof. Typical examples of the pharmaceutically acceptable salt include inorganic salts such as salts with alkali metals, e.g., sodium, potassium, and the like, hydrochloride, sulfate, nitrate, phosphate, carbonate, hydrogen carbonate, and hyperchlorate; organic salts such as acetate, propionate, lactate, maleate, fumarate, tartrate, malate, citrate, and ascorbate; sulfonates such as methanesulfonate, isethionate, benzenesulfonate, and toluenesulfonate; acidic amino acid salts such as aspartate, and glutamate; and the like.

Preparation of the Pharmaceutically Acceptable Salts of the Compound According to the invention can be carried out by appropriately combining methods that are conventionally used in the field of organic synthetic chemistry. Specifically, a method of neutrally titrating a solution of the compound according to the invention in a free form using an alkaline solution or an acidic solution, or the like may be mentioned.

Examples of the ester of the compound according to the invention include methyl ester, ethyl ester, and the like. These esters can be prepared by esterifying a free carboxyl group according to commonly used methods.

For the administration form used when using the compound according to the invention as an antitumor agent or the like, various forms can be selected. For example, oral formulations such as tablet, capsule, powder, granule, and liquid; and sterilized liquid parenteral formulations such as solution, and suspension, and the like may be mentioned.

Here, solid preparations can be prepared, without modifications, in the form of tablet, capsule, granule or powder according to commonly used methods, but can be also prepared using appropriate additives. Examples of the additives include sugars such as lactose and glucose; starches such as those from corn, wheat, and rice; fatty acids such as stearic acid; inorganic salts such as sodium metasilicate, magnesium aluminate, and anhydrous calcium phosphate; synthetic polymers such as polyvinylpyrrolidone and polyalkylene glycol; fatty acid salts such as calcium stearate and magnesium stearate; alcohols such as stearyl alcohol and benzyl alcohol; and synthetic cellulose derivatives such as methylcellulose, carboxymethylcellulose, ethylcellulose, and hydroxypropylethylcellulose; and in addition to these, generally used additives such as water, gelatin, talc, vegetable oils, and gum arabic, and in the like, may also be mentioned.

These solid preparations such as tablet, capsule, granule, and powder may usually contain 0.1 to 100% by weight, preferably 5 to 100% by weight, more preferably 5 to 85% by weight, and particularly preferably 5 to 30% by weight, of the active ingredient.

Liquid preparations can be prepared in the form of suspension, syrup, injectable preparation, or the like, using appropriate additives which are generally used for liquid preparations, such as water, alcohols, plant-derived oils e.g., soybean oil, peanut oil, sesame oil, and the like.

In particular, examples of appropriate solvent or diluent useful in the case of parenterally administering via intramuscular injection, intravenous injection, or subcutaneous injection, include distilled water for injection, aqueous solution of lidocaine hydrochloride (for intramuscular injection), physiological brine, aqueous glucose solution, ethanol, fluid for intravenous injection (e.g., aqueous solution of citric acid, sodium citrate, and the like), electrolyte solution (e.g., fluid for infusion or for intravenous injection), and the like, and mixed solutions thereof.

These injectable preparations may be in a form that the active ingredient is preliminarily dissolved, or in a form of powder or compound with suitable additives which is to be dissolved at the time of use. Such injectable liquid can usually contain 0.1 to 10% by weight, preferably 1 to 5% by weight, of the active ingredient.

The liquid for oral administration, such as suspension, syrup or the like, can contain 0.5 to 10% by weight, preferably 1 to 5% by weight, of the active ingredient.

The preferred amount of the compound according to the invention to be administered in practice can be appropriately increased or decreased in accordance with the kind of the compound to be used, the kind of the composition mixed, the frequency of application, the specific site to be treated, and the conditions of the patient. For example, the daily dose for an adult is, in the case of oral administration, 10 to 500 mg, preferably 10 to 200 mg, and in the case of parenteral administration, preferably intravenous injection, 10 to 100 mg, preferably 10 to 30 mg, per day. In addition, the dose frequency may vary depending on the mode of administration and symptoms, but the administration can be conducted once, or divided into 2 to 5 portions, and preferably 2 to 3 portions.

In addition, formulations including a therapeutically effective amount of the compound represented by Formula [I] above according to the invention, or a pharmaceutically acceptable salt or ester thereof can be administered simultaneously, separately, or in order, in combination with a therapeutically effective amount of an antitumor agent, selected from the group consisting of anticancer alkylating agents, anticancer antimetabolites, anticancer antibiotics, plant-derived antitumor agents, anticancer platinum coordination compounds, anticancer camptothecine derivatives, anticancer tyrosine kinase inhibitors, monoclonal antibodies, interferons, biological response modifiers, and other antitumor agents, or a pharmaceutically acceptable salt or ester thereof. Here, the term "formulations" includes oral formulations and parenteral formulations. The oral formulations are exemplified by tablet, capsule, powder, granule, or the like, and the parenteral formulations are exemplified by sterilized liquid formulations such as solution, suspension, and the like, specifically injectable preparations, drip infusion, and the like.

The term "anticancer alkylating agents" above means an alkylating agent having anticancer activity, and the "alkylating agent" here in general refers to the agent providing an alkyl group in an alkylation reaction of an organic compound in which the hydrogen atom is substituted with an alkyl group. Examples of the "anticancer alkylating agents" include nitrogen mustard N-oxide, cyclophosphamide, iphosphamide, melphalan, busulfan, mitobronitol, carboquone, thiotepa, ranimustine, nimustine, temozolomide, carmustine, and the like.

The term "anticancer antimetabolites" above refers to a metabolic antagonist having anticancer activity, and the "metabolic antagonist" here, in a wide sense, includes substances which interfere a normal metabolic change to take place and substances which interfere high-energy intermediates to be produced by inhibiting an electron transport system, as the substances are similar in structure or function, which are the important factors in organisms, to metabolites (vitamins, coenzymes, amino acids, sugars, etc.). Examples of the "anticancer antimetabolites" include methotrexate, 6-mercaptopurine riboside, mercaptopurine, 5-fluorouracil, tegafur, doxifluridine, carmofur, cytarabine, cytarabine ocphosphate, enocitabine, S-1, gemcitabine, fludarabine, pemetrexed disodium, and the like, and preferably 5-fluorouracil, S-1, gemcitabine, and the like.

The term "anticancer antibiotics" above refers to an antibiotic having anticancer activity, and the "antibiotics" here includes substances prepared by microorganisms, that inhibit the growth or other functions of cells in microorganisms or other organisms. Examples of the "anticancer antibiotics" include actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, valrubicin, and the like.

The term "plant-derived antitumor agents" includes compounds having anticancer activity exhibited by using plants as a source, and those compounds to which the chemical modification are further added. Examples of the "plant-derived antitumor agents" includes vincristine, vinblastine, vindesine, etoposide, sobuzoxane, docetaxel, paclitaxel, vinorelbine, and the like, and preferably docetaxel and paclitaxel.

The term "anticancer camptothecine derivatives" includes camptothecine per se, and refers to an inhibitory compound against proliferation of cancerous cells, which is structurally related to camptothecine. The "anticancer camptothecine derivatives" is not particularly limited to, but may be exemplified by camptothecine, 10-hydroxy camptothecine, topotecan, irinotecan, 9-aminocamptothecine, or the like, and preferably camptothecine, topotecan, or irinotecan. The irinotecan is metabolized in vivo and exhibits anticancer activity as SN-38. The camptothecine derivative is thought to have the same mechanism of action and activity as in the camptothecine (Nitta et al, cancer and chemotherapeutics, 14, 850-857 (1987), etc.).

The term "anticancer platinum coordination compounds" above refers to a platinum coordination compound having anticancer activity, and the "platinum coordination compound" here means a platinum coordination compound that provides platinum in the form of ion. Preferred examples of the platinum compound include cisplatin; cis-diammine diaquo platinum(II)-ion; chloro(diethylenetriamine)-platinum(II) chloride; dichloro(ethylenediamine)-platinum(II); diammine(1,1-cyclobutanedicarboxylato)platinum(II) (carboplatin); spiroplatin; iproplatin; diammine(2-ethylmalonato)-platinum(I); ethylenediamine malonato platinum(II); aqua(1,2-diamino dicyclohexane)sulphato platinum(II); aqua(1,2-diamino dicyclohexane)malonato platinum(II); (1,2-diaminocyclohexane)malonato platinum (II); (4-carboxyphthalate)(1,2-diaminocyclohexane)platinum(II); (1,2-diaminocyclohexane)-(isocitrate)platinum(II); (1,2-diaminocyclohexane)oxalato platinum(II); ormaplatin; tetraplatin; carboplatin; nedaplatin; and oxaliplatin; and preferably include carboplatin and oxaliplatin. In addition, other anticancer platinum coordination compounds exemplified in the present specification are generally known and is commercially available, and/or can be produced by those having ordinary skill in the art in accordance with conventional techniques.

The term "anticancer tyrosine kinase inhibitors" above refers to a tyrosine kinase inhibitor having anticancer activity, and the "tyrosine kinase inhibitor" here refers to a chemical substance for inhibiting "tyrosine kinase" which involves replacing a γ-phosphate group of ATP to a hydroxyl group of specific tyrosine in proteins. Examples of the "anticancer tyrosine kinase inhibitors" include gefitinib, imatinib, erlotinib, and the like.

The term "monoclonal antibodies" refers to an antibody produced from a monoclonal antibody-forming cell, and examples include cetuximab, bevacizumab, rituximab, alemtuzumab, trastuzumab, and the like.

The term "interferons" refers to an interferon having anticancer activity, and generally, in the case of viral infection, is a glycoprotein having the molecular weight of about 20,000, that is produced/secreted from the most of animal cells. The interferon, known as one of cytokines, not only inhibits viral proliferation, but also has various immunity effector functions including, for example, that for inhibiting proliferation of cells (tumor cells in particular) and that for enhancing the natural killer activity. Examples of the "interferon" include interferon a, interferon a-2a, interferon a-2b, interferon β, interferon γ-1a, interferon γ-n1, and the like.

The term "biological response modifiers" above is also known as BRM, and generally is a generic term of substances or drugs for driving to achieve individual benefits against tumors, infections, or other diseases by regulating biological reactions such as a defense mechanism possessed by organisms, and survival, proliferation, or differentiation of tissue cells. Examples of the "biological response modifiers" include krestin, lentinan, schizophyllan, picibanil, ubenimex, and the like.

The term "other antitumor agents" refers to an antitumor agent having anticancer activity which is not included in any of the above. Examples of the "other antitumor agents" include mitoxantrone, L-asparaginase, procarbazine, dacarbazine, hydroxycarbamide, pentostatin, tretinoin, alefacept, darbepoetin alfa, anastrozole, exemstane, bicalutamide, leuproreline, flutamide, fulvestrant, pegaptanib octasodium, denileukin diftitox, aldesleukin, thyrotropin alfa, arsenic trioxide, bortezomib, capecitabine, goserelin, and the like.

All of the above "anticancer alkylating agents", "anticancer antimetabolites", "anticancer antibiotics", "plant-derived antitumor agents", "anticancer platinum coordination compounds", "anticancer camptothecine derivatives", "anticancer tyrosine kinase inhibitors", "monoclonal antibodies", "interferons", "biological response modifiers", and "other antitumor agents" are generally known and commercially available, or can be produced by those having ordinary skill in the art in accordance with methods known per se or commonly known/used methods.

BEST MODE FOR CARRYING OUT THE INVENTION

Examples

Figure 1:
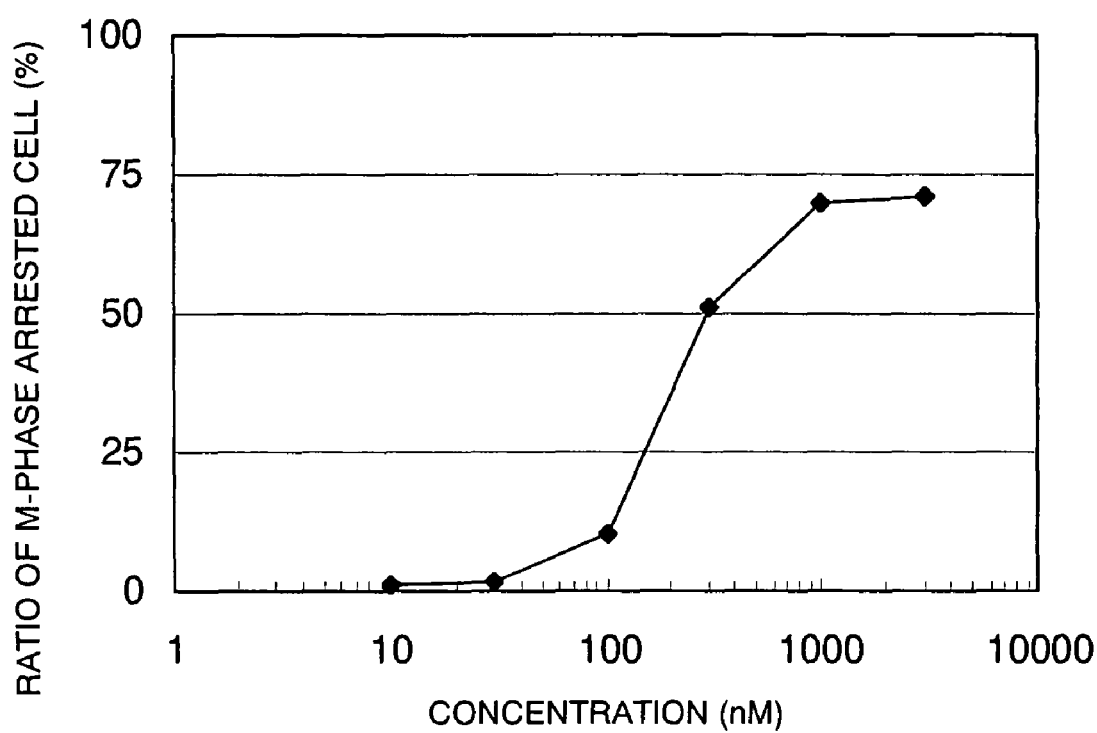
FIG. 1 shows a dose-dependent curved line showing the M phase arresting inducibility of the compound of Example 119 against a HeLaS3 cell. The vertical axis is a ratio of M-phase arrested cell (%) and a horizontal axis is a concentration of the compound of Example 119 (nM).

Hereinafter, the present invention will be described in more detail with reference to Examples, but the invention is not intended to be limited to the Examples. In Examples, thin layer chromatography was performed using Silica gel $_{60}F_{254}$ (Merck & Co., Inc.) for the plate, and a UV detector for the detection. Wakogel™C-300 or C-200 (Wako Pure Chemical Industries, Ltd.) or NH (Fuji Silysia Chemical, Ltd.) was used as a silica gel for column. In a preparative reversed phase liquid chromatography, CombiPrep Pro C18 (YMC) was used for a column, and 0.1% trifluoroacetic acid aqueous solution and 0.1% trifluoroacetic acid acetonitrile solution were used for a mobile phase. For the MS spectra, JMS-SX102A (JEOL, Co. Ltd.), or QUATTRO II (Micromass) was used, or for the LC-MS, ZMD (Micromass) was used, for the measurement. For the NMR spectra, a spectrometer such as Gemini-300 (300 MHz; Varian, Inc.), Mercury 400 (400 MHz; Varian, Inc.), or Inova 400 (400 MHz; Varian, Inc.), was used for the measurement. All δ values were expressed in ppm. For the NMR spectra, dimethylsulfoxide was used as the internal standard in the case of measuring in a deuterated dimethylsulfoxide solution, tetramethylsilane was used as the internal standard in the case of measuring in a deuterated chloroform solution, and methanol as used as the internal standard in the case of measuring in a deuterated methanol solution.

The meanings of the abbreviations used in Examples are given below.

TABLE 3

| | |
|---|---|
| s: | Singlet |
| d: | Doublet |
| dd: | Double doublet |
| ddd: | Double double doublet |
| t: | Triplet |
| dt: | Double triplet |
| q: | Quartet |
| dq: | Double quartet |
| quin: | Quintet |
| m: | Multiplet |
| br: | Broad |
| J: | Coupling constant |
| Hz: | Hertz |
| DMSO-$d_6$: | Deuterated dimethylsulfoxide |
| CDCl$_3$: | Deuterated chloroform |
| CD$_3$OD: | Deuterated methanol |
| RT: | Retention time |

TABLE 3

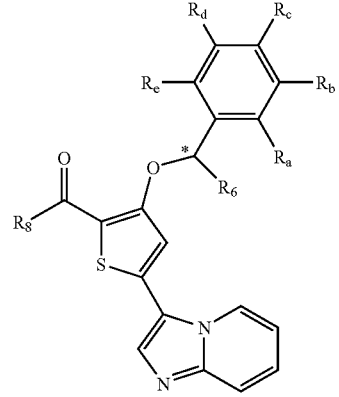

| Examples | $R_a$ | $R_b$ | $R_c$ | $R_d$ | $R_e$ | $R_6$ | $R_8$ |
|---|---|---|---|---|---|---|---|
| 1 | H | H | H | H | H | H | OH |
| 2 | CF$_3$ | H | H | H | H | H | OH |
| 3 | Cl | H | H | H | H | H | OH |
| 4 | CH$_3$ | NH$_2$ | H | H | H | H | OH |
| 5 | NO$_2$ | H | H | H | H | CH$_3$ (racemate) | OH |
| 6 | Cl | H | H | H | Cl | CH$_3$ (racemate) | OH |
| 7 | CF$_3$ | H | H | H | H | CH$_3$ (racemate) | OH |
| 8 | H | H | H | H | H | H | NH$_2$ |
| 9 | CF$_3$ | H | H | H | H | H | NH$_2$ |
| 10 | H | H | CF$_3$ | H | H | H | NH$_2$ |
| 11 | H | CF$_3$ | H | H | H | H | NH$_2$ |
| 12 | Br | H | H | H | H | H | NH$_2$ |
| 13 | NO$_2$ | H | H | H | H | H | NH$_2$ |
| 14 | H | NO$_2$ | H | H | H | H | NH$_2$ |
| 15 | F | H | H | H | H | H | NH$_2$ |
| 16 | H | F | H | H | H | H | NH$_2$ |
| 17 | H | H | F | H | H | H | NH$_2$ |
| 18 | Cl | H | H | H | Cl | H | NH$_2$ |

TABLE 3-continued
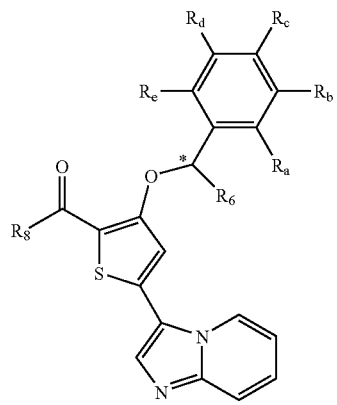
| Examples | R$_a$ | R$_b$ | R$_c$ | R$_d$ | R$_e$ | R$_6$ | R$_8$ |
|---|---|---|---|---|---|---|---|
| 19 | H | CONH$_2$ | H | H | H | H | NH$_2$ |
| 20 | H | NH$_2$ | H | H | H | H | NH$_2$ |
| 21 | OH | H | H | H | H | H | NH$_2$ |
TABLE 4
| Examples | R$_6$ | R$_7$ | R$_8$ |
|---|---|---|---|
| 22 | H | 3-pyridyl | NH$_2$ |
TABLE 4-continued
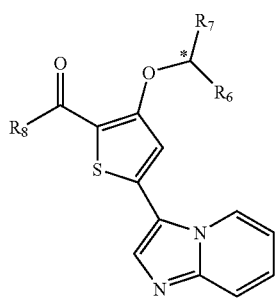
| Examples | R$_6$ | R$_7$ | R$_8$ |
|---|---|---|---|
| 23 | H | 2-pyridyl | NH$_2$ |
| 24 | H | 4-pyridyl | NH$_2$ |
| 25 | H | 3-furyl | NH$_2$ |
| 26 | H | 2-furyl | NH$_2$ |
| 56 | CH$_3$ (racemate) | 3-chloro-4-pyridyl | NH$_2$ |
TABLE 5
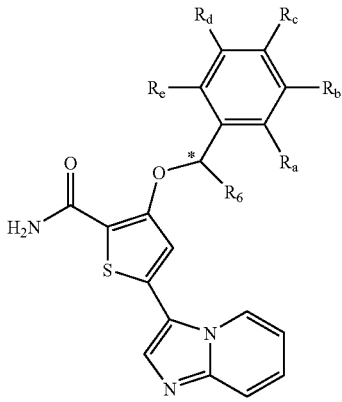
| Examples | R$_a$ | R$_b$ | R$_c$ | R$_d$ | R$_e$ | R$_6$ |
|---|---|---|---|---|---|---|
| 27 | OCH$_3$ | H | H | H | H | H |
| 28 | H | OCH$_3$ | H | H | H | H |
| 29 | H | H | OCH$_3$ | H | H | H |

TABLE 5-continued

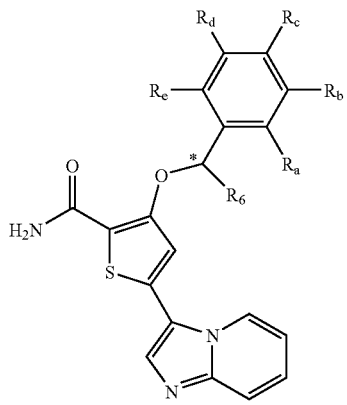

| Examples | $R_a$ | $R_b$ | $R_c$ | $R_d$ | $R_e$ | $R_6$ |
|---|---|---|---|---|---|---|
| 30 | Cl | H | H | H | H | H |
| 31 | CH$_3$ | H | H | H | H | H |
| 32 | CH$_3$ | NH$_2$ | H | H | Cl | H |
| 33 | Cl | H | H | NH$_2$ | H | H |
| 34 | Cl | H | H | H | Cl | CH$_3$ (racemate) |
| 35 | CF$_3$ | H | H | H | H | CH$_3$ (racemate) |
| 36 | CH$_3$ | H | H | H | H | CH$_3$ (racemate) |
| 37 | Cl | H | H | H | H | CH$_3$ (one of R form and S form) |
| 38 | Cl | H | H | H | H | CH$_3$ (the other one of R form and S form) |
| 39 | NO$_2$ | H | H | N(CH$_3$)$_2$ | H | CH$_3$ (racemate) |
| 40 | NO$_2$ | H | H | —N(morpholine) | H | CH$_3$ (racemate) |
| 41 | Br | H | H | H | H | CH$_3$ (S form) |
| 42 | Br | H | H | H | H | CH$_3$ (R form) |
| 43 | NO$_2$ | H | H | H | H | CH$_3$ (one of R form and S form) |
| 44 | NO$_2$ | H | H | H | H | CH$_3$ (the other one of R form and S form) |

TABLE 6

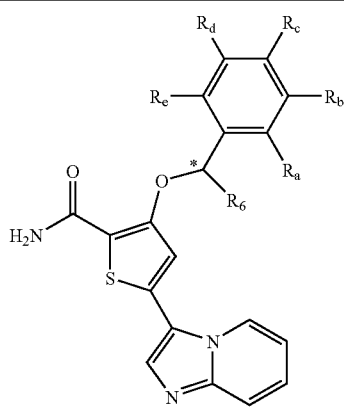

| Examples | $R_a$ | $R_b$ | $R_c$ | $R_d$ | $R_e$ | $R_6$ |
|---|---|---|---|---|---|---|
| 45 | COOCH$_3$ | H | H | H | H | CH$_3$ (S form) |
| 46 | CN | H | H | H | H | CH$_3$ (S form) |
| 47 | CN | H | H | H | H | CH$_3$ (R form) |
| 48 | CH$_2$OH | H | H | H | H | CH$_3$ (S form) |
| 49 | CH$_2$OH | H | H | H | H | CH$_3$ (R form) |

TABLE 6-continued

[Structure: thiophene-2-carboxamide with 3-(imidazo[1,2-a]pyridin-3-yl) substituent and 3-O-CH(R6)-phenyl(Ra,Rb,Rc,Rd,Re) group]

| Examples | $R_a$ | $R_b$ | $R_c$ | $R_d$ | $R_e$ | $R_6$ |
|---|---|---|---|---|---|---|
| 50 | CH$_2$NHCH$_3$ | H | H | H | H | CH$_3$ (R form) |
| 51 | CH$_2$NH(CH$_2$)$_2$OH | H | H | H | H | CH$_3$ (R form) |
| 52 | 4-ethyl-morpholine | H | H | H | H | CH$_3$ (R form) |
| 53 | Cl | H | H | H | H | CH$_2$CH$_3$ (racemate) |
| 54 | Cl | H | H | H | H | CH$_2$OH (racemate) |
| 55 | Cl | H | CH$_2$OH | H | H | CH$_3$ (racemate) |
| 57 | Cl | H | 1-ethyl-pyrrolidine | H | H | CH$_3$ (racemate) |
| 58 | Cl | H | 4-ethyl-morpholine | H | H | CH$_3$ (racemate) |
| 59 | Cl | H | 1-ethyl-piperazine | H | H | CH$_3$ (racemate) |
| 60 | Cl | H | 1-ethyl-4-hydroxy-piperidine | H | H | CH$_3$ (racemate) |
| 61 | Cl | H | CH$_2$NH(CH$_2$)$_2$OH | H | H | CH$_3$ (racemate) |

TABLE 7

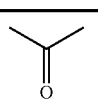

| Examples | R_a | R_b | R_c | R_d | R_e | Z |
|---|---|---|---|---|---|---|
| 62 | Cl | H | H | H | Cl | acetyl (C=O with methyl) |
| 63 | CF_3 | H | H | H | H | acetyl (C=O with methyl) |
| 64 | OCH_3 | H | H | H | H | acetyl (C=O with methyl) |
| 65 | H | H | Cl | H | H | propanoyl (C=O with ethyl) |
| 241 | Cl | H | H | H | H | (S)-2-hydroxybutyl (HO-CH with ethyl and methyl) |

TABLE 8

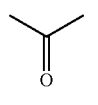

| Examples | R_a | R_4 | R_6 |
|---|---|---|---|
| 66 | Cl | O(CH_2)_2OH | CH_3 (R form) |
| 67 | CF_3 | OCH_3 | H |
| 68 | CF_3 | OCH_2-(4-piperidinyl-NH) | H |

TABLE 8-continued

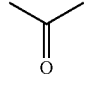

| Examples | R_a | R_4 | R_6 |
|---|---|---|---|
| 69 | Cl | O(CH_2)_2OCH_3 | CH_3 (racemate) |
| 70 | Cl | O—(CH_2)_2—N(morpholine) | CH_3 (racemate) |
| 71 | Cl | O—(CH_2)_2—N(pyrrolidine) | CH_3 (racemate) |
| 72 | Cl | O—(CH_2)_2—N(pyrrolidine) | CH_3 (racemate) |
| 73 | Cl | O—(CH_2)_2—N(piperazine)NCH_3 | CH_3 (racemate) |
| 74 | Cl | O—(CH_2)_2—N(piperazine)NCOOC(CH_3)_3 | CH_3 (racemate) |
| 75 | Cl | O—(CH_2)_2—N(piperazine)NH | CH_3 (racemate) |
| 76 | Cl | O(CH_2)_2—N(piperidine)-4-OH | CH_3 (racemate) |

TABLE 9

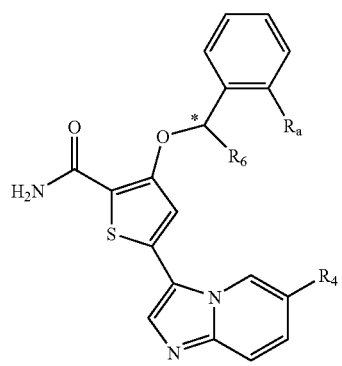

| Examples | $R_a$ | $R_4$ | $R_6$ |
|---|---|---|---|
| 77 | Cl | O(CH$_2$)$_2$NH(CH$_2$)$_2$OH | CH$_3$ (racemate) |
| 78 | Cl | O(CH$_2$)$_2$N(CH$_3$)(CH$_2$)$_2$OH | CH$_3$ (racemate) |
| 79 | Cl | O—(CH$_2$)$_2$—N-piperidinyl-3-OH | CH$_3$ (racemate) |
| 80 | Cl | O—(CH$_2$)$_2$—N-piperidinyl-3-OH | CH$_3$ (racemate) |
| 81 | Cl | O—(CH$_2$)$_2$—N-pyrrolidinyl-3-OH | CH$_3$ (R form) |
| 82 | Cl | O—(CH$_2$)$_2$—N-pyrrolidinyl-3-OH | CH$_3$ (racemate) |
| 83 | Cl | O(CH$_2$)$_3$OH | CH$_3$ (racemate) |
| 84 | Cl | O—(CH$_2$)$_3$—N-morpholinyl | CH$_3$ (racemate) |
| 85 | Cl | O(CH$_2$)$_4$OH | CH$_3$ (racemate) |
| 86 | Cl | O—(CH$_2$)$_4$—N-piperidinyl | CH$_3$ (racemate) |

TABLE 10

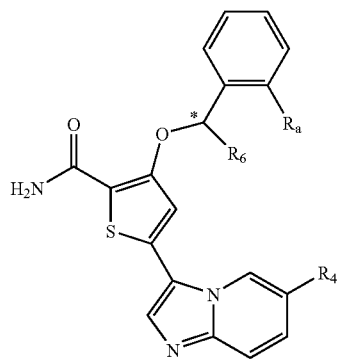

| Examples | $R_a$ | $R_4$ | $R_6$ |
|---|---|---|---|
| 87 | Cl | O—(CH$_2$)$_4$—N-pyrrolidinyl | CH$_3$ (racemate) |
| 88 | Cl | O(CH$_2$)$_4$N(CH$_3$)$_2$ | CH$_3$ (racemate) |
| 89 | Cl | O—(CH$_2$)$_4$—N-morpholinyl | CH$_3$ (racemate) |
| 90 | Cl | O—(CH$_2$)$_4$—N-piperazinyl-NCH$_3$ | CH$_3$ (racemate) |
| 91 | Cl | O—(CH$_2$)$_4$—N-piperazinyl-NCOOC(CH$_3$)$_3$ | CH$_3$ (racemate) |
| 92 | Cl | O—(CH$_2$)$_4$—N-piperazinyl-NH | CH$_3$ (racemate) |
| 93 | Br | O(CH$_2$)$_2$OH | CH$_3$ (R form) |
| 94 | NO$_2$ | O(CH$_2$)$_2$OH | CH$_3$ (racemate) |
| 95 | CN | O(CH$_2$)$_2$OH | CH$_3$ (R form) |
| 96 | NO$_2$ | O—(CH$_2$)$_2$—N-piperidinyl-3-OH | CH$_3$ (racemate) |
| 97 | CN | O—(CH$_2$)$_2$—N-piperidinyl-3-OH | CH$_3$ (R form) |

TABLE 11

[Structure: thiophene-2-carboxamide with 3-O-CH(R6)(2-Ra-phenyl) and 5-(imidazo[1,2-a]pyridin-3-yl with R4 at 6-position)]

| Examples | R_a | R_4 | R_6 |
|---|---|---|---|
| 98 | Cl | 3-(piperidinyloxy) (NH piperidine, O-linked at 3) | CH₃ (racemate) |
| 99 | Cl | NH(CH₂)₂OH | CH₃ (racemate) |
| 100 | Cl | NCH₃(CH₂)₂OH | CH₃ (racemate) |
| 101 | Cl | NH₂ | CH₃ (R form) |
| 102 | Cl | 4-methylpiperazin-1-yl (N-methyl piperazine, NH) | CH₃ (R form) |
| 103 | Cl | 4-methylpiperazin-1-yl (N-methyl, N'-methyl) | CH₃ (R form) |
| 104 | Cl | N(CH₃)₂ | CH₃ (R form) |
| 105 | Cl | 1-methyl-3-hydroxypiperidinyl | CH₃ (R form) |
| 106 | Cl | 1-methyl-3-hydroxypyrrolidinyl | CH₃ (R form) |
| 107 | Cl | CH₂OH | CH₃ (R form) |
| 108 | Cl | CHO | CH₃ (racemate) |

TABLE 12

[Structure: same core as Table 11]

| Examples | R_a | R_4 | R_6 |
|---|---|---|---|
| 109 | Cl | CH₂—N(pyrrolidinyl) | CH₃ (racemate) |
| 110 | Cl | CH₂—N(morpholinyl) | CH₃ (racemate) |
| 111 | Cl | CH₂—N(piperidinyl) | CH₃ (racemate) |
| 112 | Cl | CH₂N(CH₂CH₃)₂ | CH₃ (racemate) |
| 113 | Cl | CH₂—N(4-methylpiperazin-1-yl) | CH₃ (racemate) |
| 114 | Cl | CH₂N(CH₃)₂ | CH₃ (racemate) |
| 115 | Cl | CH₂NHCH₃ | CH₃ (racemate) |
| 116 | Cl | 1-ethyl-3-hydroxypiperidinyl | CH₃ (racemate) |
| 117 | Cl | 1-ethyl-3-hydroxypyrrolidinyl | CH₃ (racemate) |
| 118 | Cl | 1-ethyl-3-hydroxypyrrolidinyl | CH₃ (racemate) |
| 119 | Cl | CH₂—N(piperazinyl-NH) | CH₃ (R form) |

TABLE 13

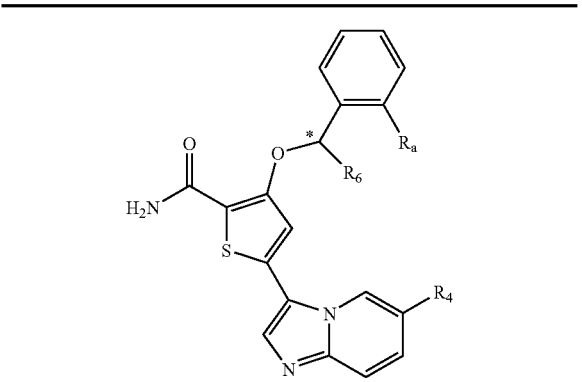

| Examples | $R_a$ | $R_4$ | $R_6$ |
|---|---|---|---|
| 120 | Cl | CH₂–N(piperidine)–OH | CH₃ (racemate) |
| 121 | Cl | CH₂NH₂ | CH₃ (R form) |
| 122 | Cl | CH₂–N(pyrrolidine)–NHCOOC(CH₃)₃ | CH₃ (R form) |
| 123 | Cl | CH₂–N(pyrrolidine)–NHCOOC(CH₃)₃ | CH₃ (R form) |
| 124 | Cl | CH₂–N(pyrrolidine)–NH₂ | CH₃ (R form) |
| 125 | Cl | CH₂–N(pyrrolidine)–NH₂ | CH₃ (R form) |
| 126 | Cl | CH₂NH(CH₂)₂NH₂ | CH₃ (R form) |
| 127 | Cl | CH₂NH(CH₂)₂N(CH₃)₂ | CH₃ (R form) |
| 128 | Cl | CH₂–N(piperazine)–CHO | CH₃ (R form) |
| 129 | Cl | CH₂–N(piperazine)–COCH₃ | CH₃ (R form) |
| 130 | Cl | CH₂–N(piperazine)–(CH₂)₂OH | CH₃ (R form) |

TABLE 14

| Examples | $R_a$ | $R_4$ | $R_6$ |
|---|---|---|---|
| 131 | Cl | CH₂NCH₃(CH₂)₂N(CH₃)₂ | CH₃ (R form) |
| 132 | Cl | CH₂–N(pyrrolidine)–NHCOCH₃ | CH₃ (R form) |
| 133 | Cl | CH₂–N(pyrrolidine)–NHCOOCH₃ | CH₃ (R form) |
| 134 | Cl | CH₂–N(piperazinone) | CH₃ (R form) |
| 135 | Cl | CH₂–N(piperazine)–CH₂COOCH₃ | CH₃ (R form) |
| 136 | Cl | CH₂–N(pyrrolidine)–N(CH₃)₂ | CH₃ (R form) |
| 137 | Cl | CH₂–N(azetidine) | CH₃ (R form) |
| 138 | Cl | CH₂OH | CH₂OH (racemate) |
| 139 | Br | CH₂OH | CH₃ (R form) |
| 140 | CN | CH₂OH | CH₃ (R form) |
| 141 | NO₂ | CH₂OH | CH₃ (racemate) |
| 142 | Cl | COOH | CH₃ (R form) |

TABLE 15

| Examples | $R_a$ | $R_3$ | $R_6$ |
|---|---|---|---|
| 143 | $CF_3$ | $COOCH_3$ | H |
| 144 | $CF_3$ | COOH | H |
| 145 | $CF_3$ | CONH(CH$_2$)$_2$—N(morpholine) | H |
| 146 | $CF_3$ | $CONH_2$ | H |
| 147 | Cl | $NH_2$ | $CH_3$ (racemate) |
| 148 | Cl | $CH_2OH$ | $CH_3$ (racemate) |
| 149 | Cl | $CH_2$—N(morpholine) | $CH_3$ (racemate) |

TABLE 16

| Examples | $R_a$ | $R_1$ | $R_2$ | $R_5$ | $R_6$ |
|---|---|---|---|---|---|
| 150 | Cl | $NH_2$ | H | H | $CH_3$ (racemate) |
| 151 | Cl | $CHF_2$ | H | H | $CH_3$ (racemate) |
| 152 | Cl | H | $CH_3$ | H | $CH_3$ (R form) |
| 153 | Cl | H | H | $COOCH_3$ | $CH_3$ (racemate) |
| 154 | Cl | H | H | COOH | $CH_3$ (racemate) |
| 155 | Cl | H | H | $NH_2$ | $CH_3$ (racemate) |
| 156 | Cl | H | H | $CH_2OH$ | $CH_3$ (racemate) |

TABLE 17

| Examples | (A ring) | $X_3$—$R_3$ | $X_5$—$R_5$ | Z | $R_a$ | $R_4$ | $R_6$ | $R_8$ |
|---|---|---|---|---|---|---|---|---|
| 157 | 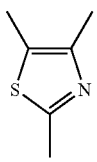 | CH | CH | CH | $CF_3$ | H | H | OH |

TABLE 17-continued

| Examples | A ring | $X_3$—$R_3$ | $X_5$—$R_5$ | Z | $R_a$ | $R_4$ | $R_6$ | $R_8$ |
|---|---|---|---|---|---|---|---|---|
| 158 | thiazole (2,4,5-trimethyl) | | CH | CH | CF$_3$ | H | H | NH$_2$ |
| 159 | thiazole (2,4,5-trimethyl) | | CH | CH | F | H | H | NH$_2$ |
| 160 | thiazole (2,4,5-trimethyl) | | CH | CH | N | Cl | H | H | NH$_2$ |
| 161 | thiazole (2,4,5-trimethyl) | | CH | CH | CH | Cl | H | CH$_3$ (racemate) | NH$_2$ |
| 162 | oxazole (2,4,5-trimethyl) | | CH | CH | CH | Cl | H | CH$_3$ (racemate) | NH$_2$ |
| 163 | thiophene (2,3,5-trimethyl) | | N | CH | CH | Cl | H | CH$_3$ (racemate) | NH$_2$ |

TABLE 17-continued

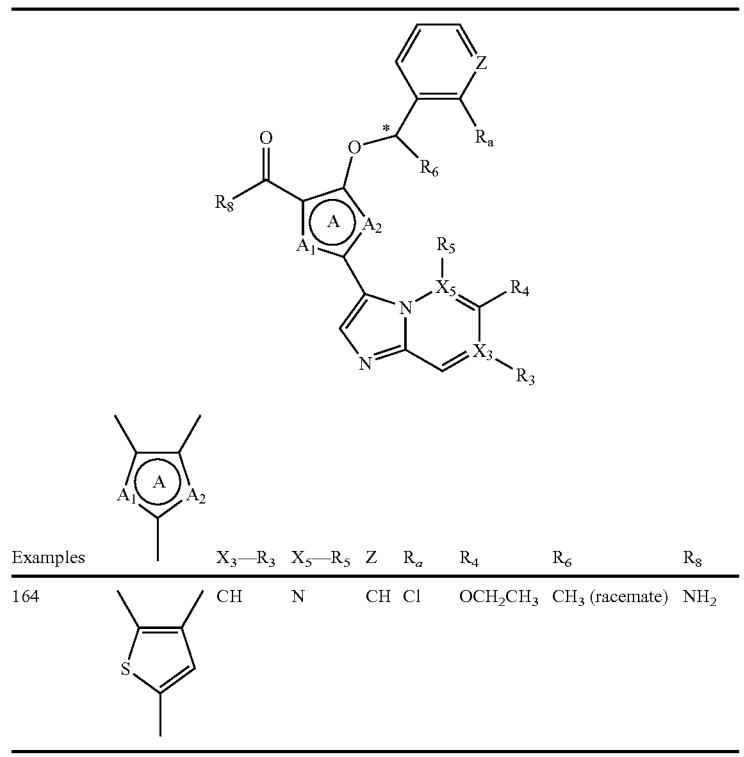

| Examples | (A) | $X_3$—$R_3$ | $X_5$—$R_5$ | Z | $R_a$ | $R_4$ | $R_6$ | $R_8$ |
|---|---|---|---|---|---|---|---|---|
| 164 | 2,5-dimethylthiophene | CH | N | CH | Cl | OCH$_2$CH$_3$ | CH$_3$ (racemate) | NH$_2$ |

TABLE 18

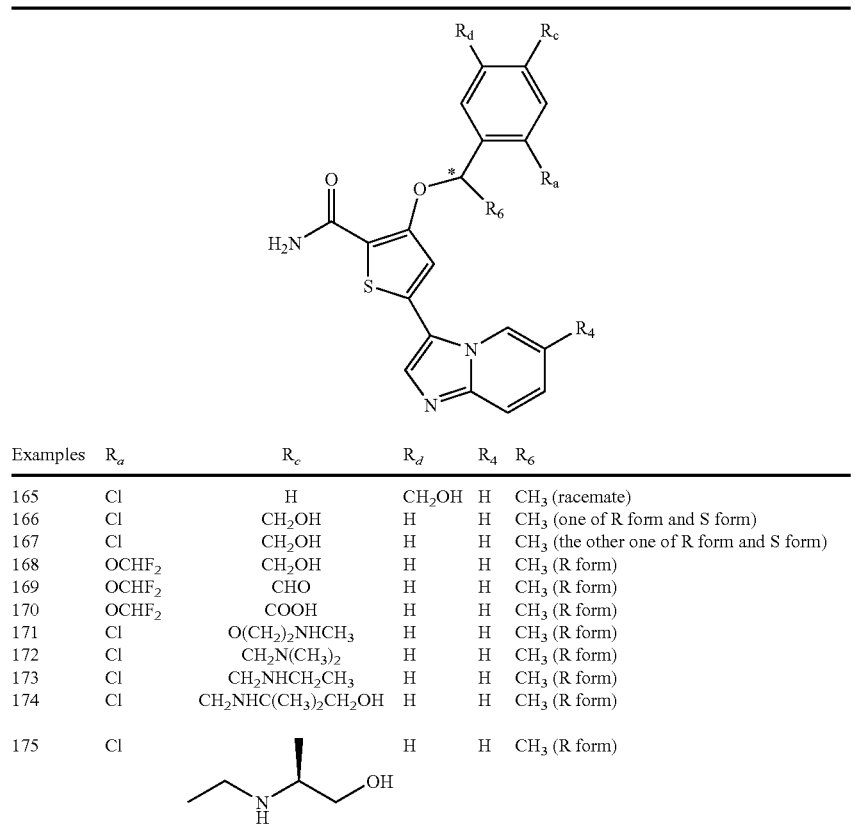

| Examples | $R_a$ | $R_c$ | $R_d$ | $R_4$ | $R_6$ |
|---|---|---|---|---|---|
| 165 | Cl | H | CH$_2$OH | H | CH$_3$ (racemate) |
| 166 | Cl | CH$_2$OH | H | H | CH$_3$ (one of R form and S form) |
| 167 | Cl | CH$_2$OH | H | H | CH$_3$ (the other one of R form and S form) |
| 168 | OCHF$_2$ | CH$_2$OH | H | H | CH$_3$ (R form) |
| 169 | OCHF$_2$ | CHO | H | H | CH$_3$ (R form) |
| 170 | OCHF$_2$ | COOH | H | H | CH$_3$ (R form) |
| 171 | Cl | O(CH$_2$)$_2$NHCH$_3$ | H | H | CH$_3$ (R form) |
| 172 | Cl | CH$_2$N(CH$_3$)$_2$ | H | H | CH$_3$ (R form) |
| 173 | Cl | CH$_2$NHCH$_2$CH$_3$ | H | H | CH$_3$ (R form) |
| 174 | Cl | CH$_2$NHC(CH$_3$)$_2$CH$_2$OH | H | H | CH$_3$ (R form) |
| 175 | Cl | CH$_3$CH$_2$NHCH(CH$_2$OH)— | H | H | CH$_3$ (R form) |

TABLE 18-continued

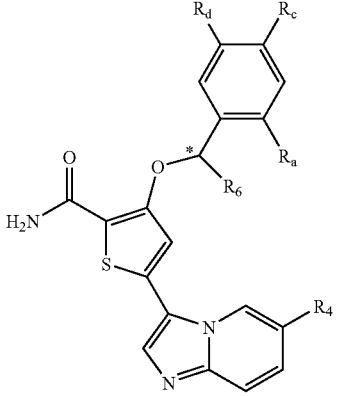

| Examples | $R_a$ | $R_c$ | $R_d$ | $R_4$ | $R_6$ |
|---|---|---|---|---|---|
| 176 | Cl | —CH$_2$NH—cyclopentyl | H | H | CH$_3$ (R form) |
| 177 | Cl | CH$_2$NHC(CH$_3$)$_3$ | H | H | CH$_3$ (R form) |
| 178 | CF$_3$ | CH$_2$NHCH$_3$ | H | H | CH$_3$ (racemate) |
| 179 | OCHF$_2$ | CH$_2$NHCH$_3$ | H | H | CH$_3$ (R form) |
| 180 | OCHF$_2$ | CH$_2$NHC(CH$_3$)$_3$ | H | H | CH$_3$ (R form) |
| 181 | OCHF$_2$ | CH$_2$NHC(CH$_3$)$_2$CH$_2$OH | H | H | CH$_3$ (R form) |
| 182 | Cl | CH$_2$NHCH$_3$ | H | CN | CH$_3$ (R form) |
| 183 | Cl | CH$_2$N(CH$_3$)$_2$ | H | CN | CH$_3$ (R form) |
| 184 | Cl | CH$_2$NHC(CH$_3$)$_2$CH$_2$OH | H | CN | CH$_3$ (R form) |
| 185 | Cl | ethyl-piperazine-N-CH$_3$ | H | CN | CH$_3$ (R form) |
| 186 | Cl | CH$_2$NHC(CH$_3$)$_3$ | H | CN | CH$_3$ (R form) |
| 187 | OCHF$_2$ | CH$_2$NHC(CH$_3$)$_3$ | H | CN | CH$_3$ (R form) |
| 188 | OCHF$_2$ | CH$_2$NHC(CH$_3$)$_2$CH$_2$OH | H | CN | CH$_3$ (R form) |

TABLE 19

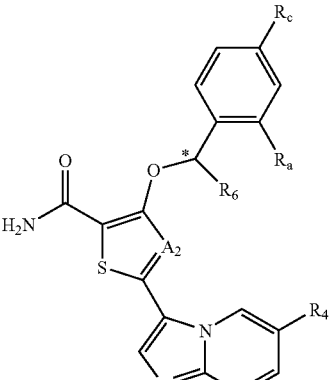

| Examples | $A_2$ | $R_a$ | $R_c$ | $R_4$ | $R_6$ |
|---|---|---|---|---|---|
| 189 | CH | Cl | H | NHCOCH$_2$N(CH$_3$)$_2$ | CH$_3$ (R form) |
| 190 | CH | Cl | H | CH(CH$_3$)OH | CH$_3$ (R form) |
| 191 | CH | Cl | H | CH(OH)CF$_3$ | CH$_3$ (R form) |
| 192 | CH | Cl | H | CH$_2$N(CH$_3$)(CH$_2$)$_2$OH | CH$_3$ (R form) |
| 193 | CH | Cl | H | CH$_2$N(CH$_3$)(CH$_2$)$_2$F | CH$_3$ (R form) |

TABLE 19-continued

| Examples | A$_2$ | R$_a$ | R$_c$ | R$_4$ | R$_6$ |
|---|---|---|---|---|---|
| 194 | CH | Cl | H | N-ethyl-N-methyl-2-aminopyridine | CH$_3$ (R form) |
| 195 | CH | Cl | H | N-ethyl-N-methyl-aminomethyl-imidazole | CH$_3$ (R form) |
| 196 | CH | OCHF$_2$ | H | 4-ethyl-1-methylpiperazine | CH$_3$ (racemate) |
| 197 | CH | Cl | CH$_2$NHCH$_3$ | CH$_2$OH | CH$_3$ (R form) |
| 198 | CH | Cl | CH$_2$NHCH(CH$_3$)$_2$ | CH$_3$OH | CH$_3$ (R form) |
| 199 | CH | Cl | 1-ethylpyrrolidine | CH$_2$OH | CH$_3$ (R form) |
| 200 | CH | Cl | CH$_2$N(CH$_3$)$_2$ | CH$_2$OH | CH$_3$ (R form) |
| 201 | CH | Cl | CH$_2$NHC(CH$_3$)$_3$ | CH$_2$OH | CH$_3$ (R form) |
| 202 | CH | OCHF$_2$ | CH$_2$NHC(CH$_3$)$_3$ | CH$_2$OH | CH$_3$ (R form) |
| 203 | CH | Cl | H | CH$_2$SO$_2$CH$_3$ | CH$_3$ (R form) |
| 204 | CH | CF$_3$ | H | CH$_2$SO$_2$CH$_3$ | CH$_3$ (racemate) |
| 205 | CH | OCHF$_2$ | H | CH$_2$SO$_2$CH$_3$ | CH$_3$ (one of R form and S form) |
| 206 | CH | OCHF$_2$ | H | CH$_2$SO$_2$CH$_3$ | CH$_3$ (the other one of R form and S form) |
| 207 | CH | Cl | CH$_2$N(CH$_3$)$_2$ | CH$_2$SO$_2$CH$_3$ | CH$_3$ (R form) |
| 208 | CH | Cl | CH$_2$NHC(CH$_3$)$_3$ | CH$_2$SO$_2$CH$_3$ | CH$_3$ (R form) |
| 209 | CH | Cl | CH$_2$OH | CH$_2$N(CH$_3$)$_2$ | CH$_3$ (R form) |
| 210 | CH | Cl | CH$_2$SO$_2$CH$_3$ | CH$_2$N(CH$_3$)(CH$_2$)$_2$OH | CH$_3$ (R form) |
| 211 | N | Cl | H | CH$_2$N(CH$_3$)(CH$_2$)$_2$N(CH$_3$)$_2$ | CH$_3$ (R form) |
| 212 | N | Cl | H | CH$_2$SO$_2$CH$_3$ | CH$_3$ (R form) |
| 213 | N | Cl | H | NH$_2$ | CH$_3$ (R form) |

TABLE 20

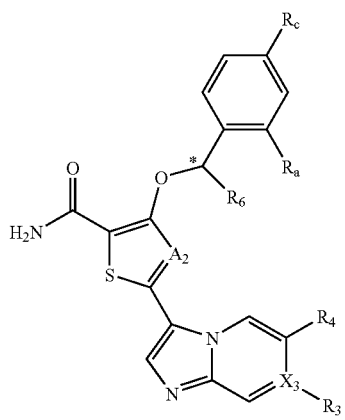

| Examples | A₂ | Rₐ | R_c | X₃—R₃ | R₄ | R₆ |
|---|---|---|---|---|---|---|
| 214 | N | Cl | H | CH | —O—⟨azetidine-NH⟩ | $CH_3$ (R form) |
| 215 | N | Cl | $CH_2OH$ | CH | $CH_2N(CH_3)(CH_2)_2F$ | $CH_3$ (R form) |
| 216 | N | Cl | $CH_2OH$ | CH | $CH_2N(CH_3)_2$ | $CH_3$ (R form) |
| 217 | N | Cl | $CH_2NHCH_3$ | CH | H | $CH_3$ (R form) |
| 218 | N | Cl | $CH_2NHCH(CH_3)_2$ | CH | H | $CH_3$ (R form) |
| 219 | N | Cl | $CH_2NHC(CH_3)_2CH_2OH$ | CH | H | $CH_3$ (R form) |
| 220 | N | $OCHF_2$ | $CH_2NHC(CH_3)_3$ | CH | H | $CH_3$ (R form) |
| 221 | N | Cl | $CH_2N(CH_3)_2$ | CH | $CH_2OH$ | $CH_3$ (R form) |
| 222 | N | $OCHF_2$ | $CH_2NHC(CH_3)_3$ | CH | $CH_2OH$ | $CH_3$ (R form) |
| 223 | N | Cl | $CH_2N(CH_3)_2$ | CH | $CH_2SO_2CH_3$ | $CH_3$ (R form) |
| 224 | N | Cl | $CH_2NHCH_3$ | CH | $CH_2SO_2CH_3$ | $CH_3$ (R form) |
| 225 | CH | Cl | H | N | $CH_2N(CH_3)_2$ | $CH_3$ (R form) |
| 226 | CH | Cl | H | N | $CH_2N(CH_3)(CH_2)_2F$ | $CH_3$ (R form) |
| 227 | CH | $OCHF_2$ | H | N | $CH_2N(CH_3)_2$ | $CH_3$ (R form) |
| 228 | CH | Cl | $CH_2NHCH_3$ | N | H | $CH_3$ (R form) |
| 229 | CH | Cl | $CH_2NHCH(CH_3)_2$ | N | H | $CH_3$ (R form) |
| 230 | CH | Cl | $CH_2OH$ | N | 4-ethyl-1-methylpiperazinyl | $CH_3$ (R form) |
| 231 | CH | Cl | $CH_2N(CH_3)_2$ | N | $CH_2OH$ | $CH_3$ (R form) |
| 232 | CH | Cl | $CH_2N(CH_3)_2$ | N | $CH_2SO_2CH_3$ | $CH_3$ (R form) |
| 233 | N | Cl | H | N | $CH_2N(CH_3)_2$ | $CH_3$ (R form) |
| 234 | N | Cl | $CH_2NHCH_3$ | N | H | $CH_3$ (R form) |
| 235 | N | Cl | $CH_2OH$ | N | 4-ethyl-1-methylpiperazinyl | $CH_3$ (R form) |
| 236 | N | Cl | $CH_2N(CH_3)_2$ | N | $CH_2SO_2CH_3$ | $CH_3$ (R form) |
| 237 | N | Cl | $CH_2NHC(CH_3)_3$ | N | $CH_2SO_2CH_3$ | $CH_3$ (R form) |
| 238 | N | Cl | $CH_2N(CH_3)_2$ | N | $CH_2OH$ | $CH_3$ (R form) |
| 239 | N | $OCHF_2$ | $CH_2OH$ | N | 4-ethyl-1-methylpiperazinyl | $CH_3$ (R form) |

TABLE 21

| Examples | $R_a$ | $R_c$ | $X_2$—$R_2$ | $R_4$ | $X_5$—$R_5$ | $R_6$ |
|---|---|---|---|---|---|---|
| 240 | Cl | H | CH | H | CH | $CH_2OH$ (S form) |
| 242 | Cl | H | CH | H | CH |  (racemate) |
| 243 | Cl | H | CH | $CH_2SO_2CH_3$ | N | $CH_3$ (R form) |
| 244 | Cl | H | CH | $CH_2N(CH_3)_2$ | N | $CH_3$ (R form) |
| 245 | Cl | H | N | H | CH | $CH_3$ (R form) |
| 246 | $CH_3$ | $CH_2NHC(CH_3)_3$ | CH | H | CH | $CH_3$ (R form) |
| 247 |  | $CH_2NHCH(CH_3)_2$ | CH | H | CH | $CH_3$ (R form) |
| 248 | $CHF_2$ | $CH_2NHC(CH_3)_3$ | CH | H | CH | $CH_3$ (R form) |
| 249 | Cl | $CH_2CH_2OH$ | CH | H | CH | $CH_3$ (R form) |
| 250 | Cl | $CH_2CH_2NHCH_3$ | CH | H | CH | $CH_3$ (R form) |
| 251 | Cl | $CH_2CH_2CH_2OH$ | CH | H | CH | $CH_3$ (R form) |
| 252 | Cl | $CH_2CH_2CH_2NHCH_3$ | CH | H | CH | $CH_3$ (R form) |
| 253 | Cl | $CH(CH_3)NHC(CH_3)_3$ | CH | H | CH | $CH_3$ (R form) |
| 254 | Cl | (cyclopropyl with $NH_2$) | CH | H | CH | $CH_3$ (R form) |

Example 1

Synthesis of 3-(benzyloxy)-5-imidazo[1,2-a]pyridin-3-yl-2-thiophencarboxylic acid [1] (hereinafter, referred to as the compound [1])

(1) 10.0 g of imidazo[1,2-a]pyridine was dissolved in 80 mL of acetonitrile, and 19.0 g of N-iodosuccinimide was added thereto at room temperature. After stirring at room temperature for two hours, the precipitated powders were taken by filtration and washed with ether to obtain 17.2 g of 3-iodoimidazo[1,2-a]pyridine [1-1] (hereinafter, referred to as the compound [1-1]) as a pale yellow solid.

(2) 3.66 g of the compound [1-1] was dissolved in 80 mL of tetrahydrofuran, then 4.15 g of potassium carbonate, 1.05 g of bis(triphenylphosphine)palladium(II) dichloride, 571 mg of copper iodide, and 2.67 mL of methyl propiolic acid were added thereto, and the mixture was stirred for 4 hours at 60° C. under a nitrogen atmosphere. The insolubles were filtered through celite, the filtrate was concentrated under reduced pressure, and thus obtained residue was purified by silica gel column chromatography, to obtain 1.70 g of methyl 3-imidazo[1,2-a]pyridin-3-ylpropi-2-noate [1-2] (hereinafter, referred to as the compound [1-2]) as a light brown oily product.

(3) 394 mg of sodium methoxide was dissolved in 10 mL of methanol, 685 μL of methyl thioglycolate was added thereto, and the mixture was stirred for 10 minutes at room temperature. Next, 10 mL of methanol solution containing 1.46 g of the compound [1-2] was added to neutralize the solution and stirred for 6 hours at the same temperature. Thereto, 561 μL of trifluoroacetic acid was added to be neutralized, and the solution was concentrated under reduced pressure. The residue was added with water, and extracted with chloroform. The organic layer was washed with saturated brine, and dried over anhydrous sodium sulfate. The insolubles were filtered, the filtrate was concentrated under reduced pressure, and thus obtained residue was purified by silica gel column chromatography, to obtain 1.32 g of methyl 3-hydroxy-5-imidazo[1,2-a]pyridin-3-yl-2-thiophenecarboxylic acid [1-3] (hereinafter, referred to as the compound [1-3]) as a colorless solid.

(4) 17 mg of the compound [1-3] was dissolved in 1 mL of tetrahydrofuran and 1 mL of methanol, then 6 μL of benzyl alcohol, 37 μL of tributylphosphine, and 30 μL of diisopropyl azodicarboxylate were added thereto, and the mixture was stirred for 1 hour at room temperature. The solvent was concentrated under reduced pressure, and thus obtained residue was purified by preparative thin-layer chromatography, to obtain methyl 3-(benzyloxy)-5-imidazo[1,2-a]pyridin-3-yl-2-thiophenecarboxylic acid [1-4] (hereinafter, referred to as the compound [1-4]) as a colorless solid.

(5) The compound [1-4] was dissolved in tetrahydrofuran, 1 mL of a 1N aqueous sodium hydroxide solution was added thereto, and the mixture was stirred overnight at room temperature. The reaction mixture was directly purified by preparative reverse-phase liquid chromatography, and 17 mg of a trifluoroacetate salt as the target compound [1] was obtained as a colorless solid.

A spectral data of the compound [1] is presented below.
$^1$H-NMR (DMSO-d$_6$) δ: 8.91 (m, 2H), 8.41 (s, 1H), 7.96 (dt, J=9.0, 1.0 Hz, 1H), 7.82 (dt, J=1.2, 7.2 Hz, 1H), 7.73 (s, 1H), 7.54 (m, 2H), 7.47-7.35 (m, 4H), 5.41 (s, 2H).
mass: 351 (M+1)$^+$.

Example 2

Synthesis of 5-imidazo[1,2-a]pyridin-3-yl-3-{[2-(trifluoromethyl)benzyl]oxy}thiophene-2-carbonxylic acid [2] (hereinafter, referred to as the compound [2])

The target compound [2] was obtained as a colorless oily product from the compound [1-3] and 2-trifluoromethyl-benzyl alcohol according to the methods of Example 1-(4) and (5).
The target compound was confirmed by LC-MS.
mass: 419 (M+1)$^+$.

Example 3

Synthesis of 3-[(2-chlorobenzyl)oxy]-5-imidazo[1,2-a]pyridin-3-ylthiophene-2-carboxylic acid [3] (hereinafter, referred to as the compound [3])

A trifluoroacetate salt of the target compound [3] was obtained as a colorless oily product from the compound [1-3] and m-chlorobenzyl alcohol according to the methods of Example 1-(4) and (5).
A spectral data of the compound [3] is presented below.
$^1$H-NMR (DMSO-d$_6$) δ: 8.94 (d, J=7.0 Hz, 1H), 8.39 (s, 1H), 7.94 (d, J=9.0 Hz, 1H), 7.79-7.75 (m, 3H), 7.56 (m, 1H), 7.48-7.39 (m, 3H), 5.46 (s, 2H).
mass: 385, 387 (M+1)$^+$.

Example 4

Synthesis of 3-[(3-amino-2-methylbenzyl)oxy]-5-imidazo[1,2-a]pyridin-3-ylthiophene-2-carbonxylic acid [4] (hereinafter, referred to as the compound [4])

A trifluoroacetate salt of the target compound [4] was obtained as a colorless oily product from the compound [1-3] and 3-amino-2-methylbenzyl alcohol according to the methods of Example 1-(4) and (5).
A spectral data of the compound [4] is presented below.
$^1$H-NMR (DMSO-d$_6$) δ: 9.00, 8.94 (each brs, 2H), 8.89 (d, J=7.1 Hz, 1H), 8.37 (s, 1H), 7.93 (d, J=9.1 Hz, 1H), 7.79-7.75 (m, 2H), 7.41 (dt, J=1.2, 7.0 Hz, 1H), 7.34 (d, J=7.9 Hz, 1H), 7.22 (t, J=7.6 Hz, 1H), 7.14 (d, J=8.2 Hz, 1H), 5.38 (s, 2H), 2.26 (s, 3H).
mass: 380 (M+1)$^+$.

Example 5

Synthesis of 5-imidazo[1,2-a]pyridin-3-yl-3-[1-(2-nitrophenyl)ethoxy]thiophene-2-carboxylic acid [5] (hereinafter, referred to as the compound [5])

(1) 165 mg of o-nitroacetophenone was dissolved in 3 mL of methanol, 43 mg of sodium boronhydride was added thereto, and the mixture was stirred for 2 hours at room temperature. Thereto, ethyl acetate was added, washed with saturated brine, and dried over anhydrous sodium sulfate. The insolubles were filtered, the filtrate was concentrated under reduced pressure, and thus obtained compound 1-(2-nitrophenyl)-1-ethanol [5-1] (hereinafter, referred to as the compound [5-1]) was used in the subsequent reaction without further purification.

(2) A trifluoroacetate salt of the target compound [5] was obtained as a yellow oily product from the compound [1-3] and the compound [5-1] according to the methods of Example 1-(4) and (5).

A spectral data of the compound [5] is presented below.
$^1$H-NMR (DMSO-d$_6$) δ: 8.70 (d, J=6.9 Hz, 1H), 8.31 (s, 1H), 8.05 (d, J=8.3 Hz, 1H), 8.00 (d, J=8.0 Hz, 1H), 7.92 (d, J=9.0 Hz, 1H), 7.85-7.75 (m, 2H), 7.60 (m, 1H), 7.52 (s, 1H), 7.39 (dt, J=1.1, 6.9 Hz, 1H), 6.21 (q, J=6.2 Hz, 1H), 1.75 (d, J=6.1 Hz, 3H).
mass: 410 (M+1)$^+$.

Example 6

Synthesis of 3-[1-(2,6-dichlorophenyl)ethoxy]-5-imidazo[1,2-a]pyridin-3-ylthiophene-2-carboxylic acid [6] (hereinafter, referred to as the compound [6])

A trifluoroacetate salt of the target compound [6] was obtained as a colorless oily product from 2,6-dichloroacetophenone according to the method of Example 5.

A spectral data of the compound [6] is presented below.
$^1$H-NMR (DMSO-d$_6$) δ: 8.47 (d, J=6.8 Hz, 1H), 8.17 (s, 1H), 7.86 (d, J=9.0 Hz, 1H), 7.67 (m, 1H), 7.49 (d, J=7.8 Hz, 2H), 7.37-7.30 (m, 2H), 7.06 (s, 1H), 6.24 (q, J=6.6 Hz, 1H), 1.79 (d, J=6.6 Hz, 3H).
mass: 433, 435 (M+1)$^+$.

Example 7

Synthesis of 5-imidazo[1,2-a]pyridin-3-yl-3-{1-[2-(trifluoromethyl)phenyl]ethoxy}thiophene-2-carboxylic acid [7] (hereinafter, referred to as the compound [7])

A trifluoroacetate salt of the target compound [7] was obtained as a colorless oily product from 2-trifluoromethylacetophenone according to the method of Example 5.

A spectral data of the compound [7] is presented below.
$^1$H-NMR (DMSO-d$_6$) δ: 8.65 (d, J=7.0 Hz, 1H), 8.23 (s, 1H), 7.98 (d, J=7.8 Hz, 1H), 7.88 (d, J=9.3 Hz, 1H), 7.76-7.69 (m, 3H), 7.51 (t, J=7.8 Hz, 1H), 7.36 (s, 1H), 7.34 (t, J=6.8 Hz, 1H), 6.00 (q, J=6.3 Hz, 1H), 1.64 (d, J=6.3 Hz, 3H).
mass: 433 (M+1)$^+$.

Example 8

Synthesis of 3-(benzyloxy)-5-imidazo[1,2-a]pyridin-3-ylthiophene-2-carboxyamide [8] (hereinafter, referred to as the compound [8])

12 mg of the compound [1] was dissolved in 1 mL of N,N-dimethylformamide, then 12 mg of ammonium chloride, 34 mg of 1-hydroxybenzotriazole, 44 μL of diisopropylethylamine, and 48 mg of 1-(3-dimethylaminopropyl)-3-ethylcarbodiimide were added thereto, and the mixture was stirred overnight at room temperature. The insolubles were filtered, the filtrate was purified by preparative reverse-phase liquid chromatography, and 5.8 mg of a trifluoroacetate salt as the target compound [8] was obtained as a colorless solid.

A spectral data of the compound [8] is presented below.
$^1$H-NMR (DMSO-$d_6$) δ: 8.88 (d, J=7.0 Hz, 1H), 8.39 (s, 1H), 7.96 (d, J=9.0 Hz, 1H), 7.83 (t, J=7.7 Hz, 1H), 7.76 (m, 2H), 7.58-7.55 (m, 2H), 7.48-7.38 (m, 4H), 7.07 (brs, 1H), 5.47 (s, 2H).
mass: 350 (M+1)$^+$.

Example 9

Synthesis of 5-imidazo[1,2-a]pyrdin-3-yl-3-{[2-(trifluoromethyl)benzyl]oxy}thiophene-2-carboxyamide [9] (hereinafter, referred to as the compound [9])

The target compound [9] was obtained as a colorless oily product from the compound [2] according to the method of Example 8.
The target compound was confirmed by LC-MS.
mass: 418 (M+1)$^+$.

Example 10

Synthesis of 5-imidazo[1,2-a]pyridin-3-yl-3-{[4-(trifluoromethyl)benzyl]oxy}thiophene-2-carboxyamide [10] (hereinafter, referred to as the compound [10])

(1) 16 mg of the compound [1-3] was dissolved in 0.75 mL of dimethylsulfoxide, then 29 mg of 4-trifluoromethylbenzylbromide and 17 mg of potassium carbonate were added thereto, and the mixture was stirred for 2 hours at room temperature. The insolubles were filtered, the reaction mixture was purified by preparative reverse-phase liquid chromatography, and methyl 5-imidazo[1,2-a]pyridin-3-yl-3-[4-(trifluoro)benzyl]oxy-2-thiophene-carboylic acid [10-1] (hereinafter, referred to as the compound [10-1]) was obtained.

(2) The compound [10-1] was dissolved in 1 mL of tetrahydrofuran and 1 mL of methanol, 1 mL of a 1N aqueous sodium hydroxide solution was added thereto, and the mixture was stirred for 5 hours at room temperature. After the reaction was completed, the reaction solution was adjusted to pH 7 with 1N hydrochloric acid, and concentrated under reduced pressure. From the obtained residue, 9 mg of a trifluoroacetate salt as the target compound [10] was obtained as a colorless solid according to the method of Example 8.

A spectral data of the compound [10] is presented below.
$^1$H-NMR (DMSO-$d_6$) δ: 8.88 (d, J=6.9 Hz, 1H), 8.40 (s, 1H), 7.97 (d, J=9.2 Hz, 1H), 7.86-7.77 (m, 6H), 7.73 (s, 1H), 7.45 (m, 1H), 7.15 (br, 1H), 5.58 (s, 2H).
mass: 418 (M+1)$^+$.

Example 11

Synthesis of 5-imidazo[1,2-a]pyridin-3-yl-3-{[3-(trifluoromethyl)benzyl]oxy}thiophene-2-carboxyamide [11] (hereinafter, referred to as the compound [11])

A trifluoroacetate salt of the target compound [11] was obtained as a colorless oily product from the compound [1-3] and 3-trifluoromethylbenzylbromide according to the method of Example 10.

A spectral data of the compound [11] is presented below.
$^1$H-NMR (CD$_3$OD) δ: 8.84 (d, J=7.0 Hz, 1H), 8.30 (s, 1H), 7.99 (m, 2H), 7.90 (s, 1H), 7.84 (d, J=8.0 Hz, 1H), 7.75-7.67 (m, 3H), 7.53 (m, 1H), 5.58 (s, 2H).
mass: 418 (M+1)$^+$.

Example 12

Synthesis of 3-[(2-bromobenzyl)oxy]-5-imidazo[1,2-a]pyridin-3-ylthiophene-2-carboxyamide [12] (hereinafter, referred to as the compound [12])

A trifluoroacetate salt of the target compound [12] was obtained as a colorless oily product from the compound [1-3] and 2-bromobenzylbromide according to the method of Example 10.

A spectral data of the compound [12] is presented below.
$^1$H-NMR (DMSO-$d_6$) δ: 8.93 (d, J=6.9 Hz, 1H), 8.37 (s, 1H), 7.94 (d, J=9.0 Hz, 1H), 7.81-7.75 (m, 4H), 7.69 (dd, J=1.6, 7.6 Hz, 1H), 7.50 (dt, J=1.2, 7.6 Hz, 1H), 7.45-7.37 (m, 2H), 6.96 (br s, 1H), 5.51 (s, 2H).
mass: 428, 430 (M+1)$^+$.

Example 13

Synthesis of 5-imidazo[1,2-a]pyridin-3-yl-3-[(2-nitrobenzyl)oxy]thiophene-2-carboxyamide [13] (hereinafter, referred to as the compound [13])

A trifluoroacetate salt of the target compound [13] was obtained as a yellow oily product from the compound [1-3] and 2-nitrobenzylbromide according to the method of Example 10. The target compound was confirmed by LC-MS.
mass: 395 (M+1)$^+$.

Example 14

Synthesis of 5-imidazo[1,2-a]pyridin-3-yl-3-[(3-nitrobenzyl)oxy]thiophene-2-carboxyamide [14] (hereinafter, referred to as the compound [14])

A trifluoroacetate salt of the target compound [14] was obtained as a yellow oily product from the compound [1-3] and 3-nitrobenzylbromide according to the method of Example 10. The target compound was confirmed by LC-MS.
mass: 395 (M+1)$^+$.

Example 15

Synthesis of 3-[(2-fluorobenzyl)oxy]-5-imidazo[1,2-a]pyridin-3-ylthiophene-2-carboxyamide [15] (hereinafter, referred to as the compound [15])

A trifluoroacetate salt of the target compound [15] was obtained as a colorless oily product from the compound [1-3]

and 2-fluorobenzylbromide according to the method of Example 10. The target compound was confirmed by LC-MS.
mass: 368 (M+1)$^+$.

Example 16

Synthesis of 3-[(3-fluorobenzyl)oxy]-5-imidazo[1,2-a]pyridin-3-ylthiophene-2-carboxyamide [16] (hereinafter, referred to as the compound [16])

A trifluoroacetate salt of the target compound [16] was obtained as a colorless oily product from the compound [1-3] and 3-fluorobenzylbromide according to the method of Example 10. The target compound was confirmed by LC-MS.
mass: 368 (M+1)$^+$.

Example 17

Synthesis of 3-[(4-fluorobenzyl)oxy]-5-imidazo[1,2-a]pyridin-3-ylthiophene-2-carboxyamide [17] (hereinafter, referred to as the compound [17])

A trifluoroacetate salt of the target compound [17] was obtained as a colorless oily product from the compound [1-3] and 4-fluorobenzylbromide according to the method of Example 10. The target compound was confirmed by LC-MS.
mass: 368 (M+1)$^+$.

Example 18

Synthesis of 3-[(2,6-dichlorobenzyl)oxy]-5-imidazo[1,2-a]pyridin-3-ylthiophene-2-carboxyamide [18] (hereinafter, referred to as the compound [18])

A trifluoroacetate salt of the target compound [18] was obtained as a colorless oily product from the compound [1-3] and 2,6-dichlorobenzylbromide according to the method of Example 10. The target compound was confirmed by LC-MS.
mass: 418, 420 (M+1)$^+$.

Example 19

Synthesis of 3-{[3-(Aminocarbonyl)benzyl]oxy}-5-imidazo[1,2-a]pyridin-3-ylthiophene-1-2-carboxyamide [19] (hereinafter, referred to as the compound [19])

A trifluoroacetate salt of the target compound. [19] was obtained as a colorless oily product from the compound [1-3] and 3-(bromomethyl)methylbenzoate according to the method of Example 10. The target compound was confirmed by LC-MS.
mass: 393 (M+1)$^+$.

Example 20

Synthesis of 3-[(3-aminobenzyl)oxy]-5-imidazo[1,2-a]pyridin-3-ylthiophene-2-carboxyamide [20] (hereinafter, referred to as the compound [20])

(1) Methyl 3-[(3-aminobenzyl)oxy]-5-imidazo[1,2-a]pyridin-3-ylthiophene-2-carboxylic acid [20-1] (hereinafter, referred to as the compound [20-1]) was obtained from the compound [1-3] and 3-aminobenzyl alcohol according to the method of Example 1-(4).
(2) A trifluoroacetate salt of the target compound [20] was obtained as a colorless oily product from the compound [20-1] according to the method of Example 10-(2). The target compound was confirmed by LC-MS.
mass: 365 (M+1)$^+$.

Example 21

Synthesis of 3-[(2-hydroxybenzyl)oxy]-5-imidazo[1,2-a]pyridin-3-ylthiophene-2-carboxyamide [21] (hereinafter, referred to as the compound [21])

(1) 5-imidazo[1,2-a]pyridin-3-yl-3-{[2-(methoxymethoxy)benzyl]oxy}thiophene-2-carboxyamide [21-1] (hereinafter, referred to as the compound [21-1]) was obtained from the compound [1-3] and [2-(methoxymethoxy)phenyl]methanol according to the method of Example 20.
(2) The compound [21-1] was dissolved in trifluoroacetate, and the solution was stirred for 1 hour. The reaction solution was concentrated under reduced pressure, and the residue was purified by preparative reverse-phase liquid chromatography, to obtain a trifluoroacetate salt of the target compound [21] as a colorless oily product. The target compound was confirmed by LC-MS.
mass: 366 (M+1)$^+$.

Example 22

Synthesis of 5-imidazo[1,2-a]pyridin-3-yl-3-(pyridin-3-ylmethoxy)thiophene-2-carboxyamide [22] (hereinafter, referred to as the compound [22])

The target compound [22] was obtained as a colorless solid from the compound [1-3] and 3-hydroxymethylpyridine according to the method of Example 20. The target compound was confirmed by LC-MS.
mass: 351 (M+1)$^+$.

Example 23

Synthesis of 5-imidazo[1,2-a]pyridin-3-yl-3-(pyridin-2-ylmethoxy)thiophene-2-carboxyamide [23] (hereinafter, referred to as the compound [23])

The target compound [23] was obtained as a colorless solid from the compound [1-3] and 2-hydroxymethylpyridine according to the method of Example 20. The target compound was confirmed by LC-MS.
mass: 351 (M+1)$^+$.

Example 24

Synthesis of 5-imidazo[1,2-a]pyridin-3-yl-3-(pyridin-4-ylmethoxy)thiophene-2-carboxyamide [24] (hereinafter, referred to as the compound [24])

A trifluoroacetate salt of the target compound [24] was obtained as a colorless solid from the compound [1-3] and 4-hydroxymethylpyridine according to the method of Example 20. The target compound was confirmed by LC-MS.
mass: 351 (M+1)$^+$.

Example 25

Synthesis of 3-(3-furylmethoxy)-5-imidazo[1,2-a]pyridin-3-ylthiophene-2-carboxyamide [25] (hereinafter, referred to as the compound [25])

A trifluoroacetate salt of the target compound [25] was obtained as a colorless oily product from the compound [1-3]

and 3-furylmethanol according to the method of Example 20. The target compound was confirmed by LC-MS.
mass: 340 (M+1)⁺.

Example 26

Synthesis of 3-(2-furylmethoxy)-5-imidazo[1,2-a]pyridin-3-ylthiophene-2-carboxyamide [26] (hereinafter, referred to as the compound [26])

A trifluoroacetate salt of the target compound [26] was obtained as a colorless oily product from the compound [1-3] and furfuryl alcohol according to the method of Example 20. The target compound was confirmed by LC-MS.
mass: 340 (M+1)⁺.

Example 27

Synthesis of 5-imidazo[1,2-a]pyridin-3-yl-3-[(2-methoxybenzyl)oxy]thiophene-2-carboxyamide [27] (hereinafter, referred to as the compound [27])

A trifluoroacetate salt of the target compound [27] was obtained as a colorless oily product from the compound [1-3] and 2-methoxybenzyl alcohol according to the method of Example 20. The target compound was confirmed by LC-MS.
mass: 380 (M+1)⁺.

Example 28

Synthesis of 5-imidazo[1,2-a]pyridin-3-yl-3-[(3-methoxybenzyl)oxy]thiophene-2-carboxyamide [28] (hereinafter, referred to as the compound [28])

A trifluoroacetate salt of the target compound [28] was obtained as a colorless oily product from the compound [1-3] and 3-methoxybenzyl alcohol according to the method of Example 20. The target compound was confirmed by LC-MS.
mass: 380 (M+1)⁺.

Example 29

Synthesis of 5-imidazo[1,2-a]pyridin-3-yl-3-[(4-methoxybenzyl)oxy]thiophene-2-carboxyamide [29] (hereinafter, referred to as the compound [29])

A trifluoroacetate salt of the target compound [29] was obtained as a colorless oily product from the compound [1-3] and 4-methoxybenzyl alcohol according to the method of Example 20. The target compound was confirmed by LC-MS.
mass: 380 (M+1)⁺.

Example 30

Synthesis of 3-[(2-chlorobenzyl)oxy]-5-imidazo[1,2-a]pyridin-3-ylthiophene-2-carboxyamide [30] (hereinafter, referred to as the compound [30])

A trifluoroacetate salt of the target compound [30] was obtained as a colorless oily product from the compound [1-3] and 2-chlorobenzyl alcohol according to the method of Example 20.
A spectral data of the compound [30] is presented below.
¹H-NMR (DMSO-d₆) δ: 8.95 (d, J=6.9 Hz, 1H), 8.44 (s, 1H), 7.98 (d, J=8.0 Hz, 1H), 7.86 (t, J=6.8 Hz, 1H), 7.82 (s, 1H), 7.78 (brs, 1H), 7.70 (m, 1H), 7.59 (m, 1H), 7.50-7.44 (m, 3H), 6.97 (brs, 1H), 5.54 (s, 2H).
mass: 384, 386 (M+1)⁺.

Example 31

Synthesis of 5-imidazo[1,2-a]pyridin-3-yl-3-[(2-methylbenzyl)oxy]thiophene-2-carboxyamide [31] (hereinafter, referred to as the compound [31])

A trifluoroacetate salt of the target compound [31] was obtained as a colorless oily product from the compound [1-3] and 2-methylbenzyl alcohol according to the method of Example 20.
A spectral data of the compound [31] is presented below.
¹H-NMR (DMSO-d₆) δ: 8.95 (d, J=7.0 Hz, 1H), 8.48 (s, 1H), 8.02 (d, J=9.0 Hz, 1H), 7.92 (dt, J=1.2, 6.8 Hz, 1H), 7.81 (s, 1H), 7.77 (brs, 1H), 7.54-7.49 (m, 2H), 7.34-7.25 (m, 3H), 6.94 (brs, 1H), 5.48 (s, 2H), 2.41 (s, 3H).
mass: 364 (M+1)⁺.

Example 32

Synthesis of 3-[(3-amino-2-methylbenzyl)oxy]-5-imidazo[1,2-a]pyridin-3-ylthiophene-2-carboxyamide [32] (hereinafter, referred to as the compound [32])

The target compound [32] was obtained as a colorless oily product from the compound [1-3] and 3-amino-2-methylbenzyl alcohol according to the method of Example 20.
A spectral data of the compound [32] is presented below.
¹H-NMR (DMSO-d₆) δ: 8.74 (d, J=6.8 Hz, 1H), 8.00 (s, 1H), 7.74 (d, J=9.2 Hz, 1H), 7.69 (s, 1H), 7.61 (brs, 1H), 7.42 (m, 1H), 7.15 (dt, J=1.1, 6.8 Hz, 1H), 6.96 (t, J=7.6 Hz, 1H), 6.83 (brs, 1H), 6.74 (d, J=7.4 Hz, 1H), 6.70 (d, J=7.9 Hz, 1H), 5.38 (s, 2H), 2.12 (s, 3H).
mass: 379 (M+1)⁺.

Example 33

Synthesis of 3-[(5-amino-2-chlorobenzyl)oxy]-5-imidazo[1,2-a]pyridin-3-ylthiophene-2-carboxyamide [33] (hereinafter, referred to as the compound [33])

(1) To 10 mL of tetrahydrofuran solution containing 296 mg of lithium aluminum hydride, 684 mg of 5-amino-2-chlorobenzoic acid was added, and the mixture was stirred for 1 hour at 60° C. Thereto, 2N hydrochloric acid was added, the insolubles were filtered, and then the filtrate was extracted with chloroform. The organic layer was washed with saturated brine, and dried over anhydrous sodium sulfate. The insolubles were filtered, the filtrate was concentrated under reduced pressure, and thus obtained residue was purified by silica gel column chromatography, to obtain 340 mg of (5-amino-2-chlorophenyl)methanol [33-1] (hereinafter, referred to as the compound [33-1]) as a light brown oily product.

(2) A trifluoroacetate salt of the target compound [33] was obtained as a pale yellow substance from the compound [33-1] and the compound [1-3] according to the method of Example 20.
A spectral data of the compound [33] is presented below.
¹H-NMR (DMSO-d₆) δ: 8.91 (dd, J=1.0, 5.8 Hz, 1H), 8.38 (s, 1H), 7.94 (d, J=9.1 Hz, 1H), 7.82 (t, J=7.6 Hz, 1H), 7.75 (brs, 1H), 7.71 (s, 1H), 7.70 (d, J=8.2 Hz, 1H), 7.44 (d, J=6.9

Hz, 1H), 7.36 (dd, J=0.6, 8.4 Hz, 1H), 7.25 (br s, 1H), 7.17 (d, J=8.6 Hz, 1H), 6.84 (d, J=2.7 Hz, 1H), 6.64 (dd, J=2.8, 8.6 Hz, 1H), 5.37 (s, 2H).

mass: 399, 401 $(M+1)^+$.

Example 34

Synthesis of 3-[1-(2,6-dichlorophenyl)ethoxy]-5-imidazo[1,2-a]pyridin-3-ylthiophene-2-carboxamide [34] (hereinafter, referred to as the compound [34])

A trifluoroacetate salt of the target compound [34] was obtained as a colorless oily product from the compound [6] according to the method of Example 8.

A spectral data of the compound [34] is presented below.
$^1$H-NMR (DMSO-$d_6$) δ: 8.61 (d, J=6.9 Hz, 1H), 8.25 (s, 1H), 7.92 (d, J=8.8 Hz, 1H), 7.88 (brs, 1H), 7.74 (d, J=8.4 Hz, 1H), 7.57 (d, J=7.9 Hz, 2H), 7.46-7.37 (m, 2H), 7.23 (s, 1H), 7.14 (brs, 1H), 6.35 (q, J=6.7 Hz, 1H), 1.89 (d, J=6.7 Hz, 3H).

mass: 432, 434 $(M+1)^+$.

Example 35

Synthesis of 5-imidazo[1,2-a]pyridin-3-yl-3-{1-[2-(trifluoromethyl)phenyl]ethoxy}thiophene-2-carboxamide [35] (hereinafter, referred to as the compound [35])

A trifluoroacetate salt of the target compound [35] was obtained as a colorless oily product from the compound [7] according to the method of Example 8.

A spectral data of the compound [35] is presented below.
$^1$H-NMR (DMSO-$d_6$) δ: 8.72 (d, J=7.0 Hz, 1H), 8.34 (s, 1H), 7.98-7.76 (m, 6H), 7.57 (t, J=7.6 Hz, 1H), 7.46 (t, J=6.8 Hz, 1H), 7.26 (s, 1H), 7.23 (brs, 1H), 6.02 (m, 1H), 1.78 (d, J=6.3 Hz, 3H).

mass: 432 $(M+1)^+$.

Example 36

Synthesis of 5-imidazo[1,2-a]pyridin-3-yl-3-[1-(2-methylphenyl)ethoxy]thiophene-2-carboxamide [36] (hereinafter, referred to as the compound [36])

A trifluoroacetate salt of the target compound [36] was obtained as a colorless oily product from 2-methylacetophenone according to the method of Example 5.

A spectral data of the compound [36] is presented below.
$^1$H-NMR (DMSO-$d_6$) δ: 8.65 (d, J=7.1 Hz, 1H), 8.42 (s, 1H), 7.99 (d, J=9.2 Hz, 1H), 7.93-7.89 (m, 2H), 7.49-7.45 (m, 2H), 7.32 (s, 1H), 7.27-7.19 (m, 4H), 5.94 (q, J=6.5 Hz, 1H), 2.41 (s, 3H), 1.71 (d, J=6.5 Hz, 3H).

mass: 378 $(M+1)^+$.

Examples 37 and 38

Synthesis of 3-[1-(2-chlorophenyl)ethoxy]-5-imidazo[1,2-a]pyridin-3-ylthiophene-2-carboxamide (any one of R-form and S-form enantiomers)[37] (hereinafter, referred to as the compound [37]) and 3-[1-(2-chlorophenyl)ethoxy]-5-imidazo[1,2-a]pyridin-3-ylthiophene-2-carboxamide [38] (enantiomer different from the compound [37]) (hereinafter, referred to as the compound [38])

(1) 3.12 g of 2-chloro-α-methylbenzyl alcohol was dissolved in 10 mL of tetrahydrofuran, and 5.57 mL of triethylamine and 1.85 mL of methanesulfonyl chloride were added thereto. The mixture was stirred for 1 hour at room temperature, the reaction mixture was added with water and extracted with ethyl acetate. The organic layer was washed with saturated brine and dried over anhydrous sodium sulfate. The insolubles were filtered, and the filtrate was concentrated under reduced pressure. Thus obtained residue was dissolved in N,N-dimethylformamide, 3.16 g of 3-hydroxy-2-thiophenecarboxylic acid methyl ester and 8.28 g of potassium carbonate were added, and the mixture was stirred for 2 hours at 70° C. Water was added thereto, and extracted with ethyl acetate. The organic layer was washed with water and saturated brine, and then dried over anhydrous sodium sulfate. The insolubles were filtered and the filtrate was concentrated under reduced pressure. Thus obtained residue was purified by silica gel chromatography to obtain 6.43 g of methyl 3-[1-(2-chlorophenyl)ethoxy]-2-thiophenecarboxylic acid [37-1] (hereinafter, referred to as the compound [37-1]) as a colorless solid.

(2) 312 mg of the compound [37-1] and 122 mg of the compound [1-1] were dissolved in 3 mL of dimethylsulfoxide, 22 mg of bis(triphenylphosphine)palladium(II) dichloride and 126 mg of silver fluoride were added thereto, and the mixture was stirred overnight at 60° C. The insolubles were filtered through celite, water was added to the filtrate, and extracted with ethyl acetate. The organic layer was washed with water and saturated brine, and then dried over anhydrous sodium sulfate. The insolubles were filtered, and the filtrate was concentrated under reduced pressure. Thus obtained residue was purified by silica gel chromatography to obtain 108 mg of methyl 3-[1-(2-chlorophenyl)ethoxy]-5-imidazo[1,2-a]pyridin-3-yl-2-thiophenecarboxylic acid [37-2] (hereinafter, referred to as the compound [37-2]) as a colorless solid.

(3) A racemic mixture of the compound [37] and the compound [38] were obtained from the compound [37-2] according to the method of Example 10-(2).

(4) 45 mg of the racemic mixture of the compound [37] and the compound [38] was optically resolved using Chiralcel OD (Daicel Chemical Industries Ltd.) and hexane/ethanol as an eluent. The assay conditions were as follows.

Assay Conditions:

column: Chiralcel OD (Daicel Chemical Industries Ltd.), diameter of 0.46 mm, length of 250 mm;

eluent: hexane/ethanol (65:35);

flow rate: 1.0 mL/min.

Thus obtained solution was concentrated under reduced pressure to obtain 21 mg of the target compound [37] (RT=11.5 min) as a colorless oily product and 22 mg of the target compound [38] (RT=16.7 min) as a colorless oily product.

A spectral data of the compound [37] is presented below.
$^1$H-NMR (DMSO-$d_6$) δ: 8.46 (d, J=8.9 Hz, 1H), 7.87 (s, 1H), 7.73-7.66 (m, 3H), 7.49 (dd, J=1.2, 6.8 Hz, 1H), 7.43-7.33 (m, 3H), 7.19 (s, 1H), 7.10-7.07 (m, 2H), 6.04 (q, J=6.5 Hz, 1H), 1.73 (d, J=6.5 Hz, 3H).

mass: 398, 400 $(M+1)^+$.

A spectral data of the compound [38] is presented below.
$^1$H-NMR (DMSO-$d_6$) δ: 8.46 (d, J=8.9 Hz, 1H), 7.87 (s, 1H), 7.73-7.66 (m, 3H), 7.49 (dd, J=1.2, 6.8 Hz, 1H), 7.43-7.33 (m, 3H), 7.19 (s, 1H), 7.10-7.07 (m, 2H), 6.04 (q, J=6.5 Hz, 1H), 1.73 (d, J=6.5 Hz, 3H).

mass: 398, 400 $(M+1)^+$.

Example 39

Synthesis of 3-{1-[5-(dimethylamino)-2-nitrophenyl]ethoxy}-5-imidazo[1,2-a]pyridin-3-ylthiophene-2-carboxyamide [39] (hereinafter, referred to as the compound [39])

(1) 169 mg of 5-fluoro-2-nitrobenzaldehyde was dissolved in 1 mL of dimethylsulfoxide, then 300 mg of potassium carbonate, 300 μL of water, and 300 μL of dimethylamine were added thereto, and the mixture was stirred in a sealed tube for 1 hour at 90° C. After cooling back to room temperature, 1N hydrochloric acid was added and thus precipitated crystal was taken to obtain 130 mg of 5-(dimethylamino)-2-nitrobenzaldehyde [39-1] (hereinafter, referred to as the compound [39-1]) as a yellow solid.

(2) 97 mg of the compound [39-1] was dissolved in 3 mL of tetrahydrofuran, and 591 μL of methyl magnesium bromide (0.93M tetrahydrofuran solution) was added thereto at −20° C. under a nitrogen atmosphere. After heating back to room temperature, the mixture was stirred for 6 hours, a saturated aqueous solution of ammonium chloride was added thereto, and extracted with ethyl acetate. The organic layer was washed with saturated brine, and dried over anhydrous sodium sulfate. The insolubles were filtered, the filtrate was concentrated under reduced pressure, and thus obtained residue was purified by silica gel column chromatography, to obtain 100 mg of 1-[5-(dimethylamino)-2-nitrophenyl]-1-ethanol [39-2] (hereinafter, referred to as the compound [39-2]) as a yellow oily product.

(3) A trifluoroacetate salt of the target compound [39] was obtained as a yellow oily product from the compound [1-3] and the compound [39-2] according to the method of Example 20.

A spectral data of the compound [39] is presented below.
$^1$H-NMR (DMSO-$d_6$) δ: 8.62 (d, J=6.8 Hz, 1H), 8.22 (s, 1H), 8.06 (d, J=9.6 Hz, 1H), 7.88 (m, 2H), 7.72 (t, J=7.6 Hz, 1H), 7.33 (m, 3H), 6.93 (d, J=2.9 Hz, 1H), 6.73 (dd, J=2.8, 9.4 Hz, 1H), 6.48 (q, J=6.2 Hz, 1H), 3.06 (s, 6H), 1.84 (d, J=6.2 Hz, 3H).
mass: 452 (M+1)$^+$.

Example 40

Synthesis of 5-imidazo[1,2-a]pyridin-3-yl-3-[1-(5-morpholin-4-yl-2-nitrophenyl)ethoxy]thiophene-2-carboxyamide [40] (hereinafter, referred to as the compound [40])

A trifluoroacetate salt of the target compound [40] was obtained as a yellow oily product from 5-fluoro-2-nitrobenzaldehyde and morpholine according to the methods of Example 39-(1) to (3).

A spectral data of the compound [40] is presented below.
$^1$H-NMR (DMSO-$d_6$) δ: 8.69 (d, J=6.9 Hz, 1H), 8.36 (s, 1H), 8.05 (d, J=9.4 Hz, 1H), 7.97-7.84 (m, 3H), 7.44 (t, J=6.9 Hz, 1H), 7.41 (s, 1H), 7.35 (br s, 1H), 7.24 (d, J=2.6 Hz, 1H), 7.00 (dd, J=3.0, 9.2 Hz, 1H), 6.42 (q, J=6.3 Hz, 1H), 3.75-3.71 (m, 4H), 3.47-3.34 (m, 4H), 1.84 (d, J=6.3 Hz, 3H).
mass: 494 (M+1)$^+$.

Example 41

Synthesis of 3-[(1S)-1-(2-bromophenyl)ethoxy]-5-imidazo[1,2-a]pyridin-3-ylthiophene-2-carboxyamide [41] (hereinafter, referred to as the compound [41])

A trifluoroacetate salt of the target compound [41] was obtained as a yellow oily product from the compound [1-3] and (R)-2-bromo-α-methylbenzyl alcohol according to the method of Example 20.

A spectral data of the compound [41] is presented below.
$^1$H-NMR (DMSO-$d_6$) δ: 8.69 (d, J=6.8 Hz, 1H), 8.38 (s, 1H), 7.99 (d, J=9.0 Hz, 1H), 7.90-7.86 (m, 2H), 7.68-7.65 (m, 2H), 7.47 (dd, J=1.2, 6.9 Hz, 2H), 7.28 (m, 1H), 7.26 (s, 1H), 7.21 (brs, 1H), 5.96 (q, J=6.4 Hz, 1H), 1.74 (d, J=6.4 Hz, 3H).
mass: 442, 444 (M+1)$^+$.

Example 42

Synthesis of 3-[(1R)-1-(2-bromophenyl)ethoxy]-5-imidazo[1,2-a]pyridin-3-ylthiophene-2-carboxyamide [42] (hereinafter, referred to as the compound [42])

A trifluoroacetate salt of the target compound [42] was obtained as a yellow oily product from the compound [1-3] and (S)-2-bromo-α-methylbenzyl alcohol according to the method of Example 20.

A spectral data of the compound [42] is presented below.
$^1$H-NMR (DMSO-$d_6$) δ: 8.69 (d, J=6.8 Hz, 1H), 8.38 (s, 1H), 7.99 (d, J=9.0 Hz, 1H), 7.90-7.86 (m, 2H), 7.68-7.65 (m, 2H), 7.47 (dd, J=1.2, 6.9 Hz, 2H), 7.28 (m, 1H), 7.26 (s, 1H), 7.21 (brs, 1H), 5.96 (q, J=6.4 Hz, 1H), 1.74 (d, J=6.4 Hz, 3H).
mass: 442, 444 (M+1)$^+$.

Examples 43 and 44

Synthesis of 5-imidazo[1,2-a]pyridin-3-yl-3-[1-(2-nitrophenyl)ethoxy]thiophene-2-carboxyamide (any one of R-form and S-form enantiomers)[43] (hereinafter, referred to as the compound [43]) and 5-imidazo[1,2-a]pyridin-3-yl-3-[1-(2-nitrophenyl)ethoxy]thiophene-2-carboxyamide [44] (Enantiomer Different from the Compound [43]) (hereinafter, referred to as the compound [44])

(1) A racemic mixture of the compound [43] and the compound [44] was obtained from the compound [5] according to the method of Example 8.

(2) 27 mg of the racemic mixture obtained in (1) was optically resolved using Chiralcel OD (Daicel Chemical Industries Ltd.) and hexane/ethanol as an eluent. The assay conditions were as follows.

Assay Conditions:
column: Chiralcel OD (Daicel Chemical Industries Ltd.), diameter of 0.46 mm, length of 250 mm;
eluent: hexane/ethanol (50:50);
flow rate: 1.0 mL/min.

Thus obtained solution was concentrated under reduced pressure to obtain 22 mg of the target compound [43] (RT=9.96 min) as a colorless oily product and 23 mg of the target compound [44] (RT=12.0 min) as a colorless oily product.

A spectral data of the compound [43] is presented below.
$^1$H-NMR (DMSO-$d_6$) δ: 8.44 (dd, J=1.0, 7.1 Hz, 1H), 8.04 (dd, J=1.2, 8.3 Hz, 1H), 7.90-7.87 (m, 2H), 7.81 (t, J=6.5 Hz, 1H), 7.76 (brs, 1H), 7.70 (d, J=9.0 Hz, 1H), 7.60 (m, 1H), 7.39 (m, 1H), 7.22 (s, 1H), 7.11-7.07 (m, 2H), 6.19 (q, J=6.3 Hz, 1H), 1.83 (d, J=6.3 Hz, 3H).

A spectral data of the compound [44] is presented below.
$^1$H-NMR (DMSO-$d_6$) δ: 8.44 (dd, J=1.0, 7.1 Hz, 1H), 8.04 (dd, J=1.2, 8.3 Hz, 1H), 7.90-7.87 (m, 2H), 7.81 (t, J=6.5 Hz, 1H), 7.76 (brs, 1H), 7.70 (d, J=9.0 Hz, 1H), 7.60 (m, 1H), 7.39 (m, 1H), 7.22 (s, 1H), 7.11-7.07 (m, 2H), 6.19 (q, J=6.3 Hz, 1H), 1.83 (d, J=6.3 Hz, 3H).
mass: 409 (M+1)$^+$.

Example 45

Synthesis of methyl 2-((1S)-1-{[2-(aminocarbonyl)-5-imidazo[1,2-a]pyridin-3-yl-3-thienyl]oxy}ethyl)benzoate [45] (hereinafter, referred to as the compound [45])

The compound [41] was dissolved in 1 mL of N,N-dimethylformamide and 1 mL of methanol, then 7 mg of palladium acetate (II), 17 mg of 1,1'-bisdiphenylphosphino ferrocene, and 78 µL of diisopropylethylamine were added thereto, and the mixture was stirred overnight at 130° C. under a carbon monoxide atmosphere (3.5 atmospheric pressure). After cooling back to the room temperature, the insolubles were separated by filtration, and ethyl acetate was added. The organic layer was washed with saturated brine and dried over anhydrous sodium sulfate. The insolubles were filtered, the filtrate was concentrated under reduced pressure, and thus obtained residue was purified by silica gel column chromatography, to obtain 127 mg of the target compound [45] as a light brown oily product. Further, 15 mg of the compound [45] was taken and purified by preparative reverse-phase liquid chromatography, to obtain 12 mg of a trifluoroacetate salt of the compound [45].

A spectral data of the compound [45] is presented below.
$^1$H-NMR (DMSO-$d_6$) δ: 8.60 (dd, J=1.0, 5.9 Hz, 1H), 8.32 (s, 1H), 7.95 (d, J=9.0 Hz, 1H), 7.87-7.82 (m, 3H), 7.76 (d, J=6.9 Hz, 1H), 7.67 (t, J=1.5, 7.6 Hz, 1H), 7.48-7.40 (m, 2H), 7.26 (s, 1H), 7.20 (brs, 1H), 6.41 (q, J=6.5 Hz, 1H), 3.87 (s, 3H), 1.76 (d, J=6.5 Hz, 3H).
mass: 422 (M+1)$^+$.

Example 46

Synthesis of 3-[(1S)-1-(2-cyanophenyl)ethoxy]-5-imidazo[1,2-a]pyridin-3-ylthiophene-2-carboxyamide [46] (hereinafter, referred to as the compound [46])

44 mg of the compound [41] was dissolved in 1 mL of N,N-dimethylformamide, then 22 mg of tetrakis(triphenylphosphine)palladium (0) and 46 mg of zinc cyanide were added thereto, and the mixture was stirred overnight at 130° C. under a nitrogen atmosphere. After cooling back to room temperature, the insolubles were separated by filtration, the filtrate was concentrated under reduced pressure, and thus obtained residue was purified by preparative reverse-phase liquid chromatography, to obtain 12 mg of a trifluoroacetate salt of the target compound [46] as a pale yellow oily product.

A spectral data of the compound [46] is presented below.
$^1$H-NMR (DMSO-$d_6$) δ: 8.78 (dd, J=1.0, 5.9 Hz, 1H), 8.40 (s, 1H), 7.99 (d, J=9.0 Hz, 1H), 7.93-7.70 (m, 5H), 7.56 (dt, J=1.6, 7.4 Hz, 1H), 7.53 (s, 1H), 7.48 (dt, J=1.0, 6.9 Hz, 1H), 7.15 (brs, 1H), 6.01 (q, J=6.4 Hz, 1H), 1.84 (d, J=6.4 Hz, 3H).
mass: 389 (M+1)$^+$.

Example 47

Synthesis of 3-[(1R)-1-(2-cyanophenyl)ethoxy]-5-imidazo[1,2-a]pyridin-3-ylthiophene-2-carboxyamide [47] (hereinafter, referred to as the compound [47])

A trifluoroacetate salt of the target compound [47] was obtained as a colorless oily product from the compound [42] according to the method of Example 46.

A spectral data of the compound [47] is presented below.
$^1$H-NMR (DMSO-$d_6$) δ: 8.78 (dd, J=1.0, 5.9 Hz, 1H), 8.40 (s, 1H), 7.99 (d, J=9.0 Hz, 1H), 7.93-7.70 (m, 5H), 7.56 (dt, J=1.6, 7.4 Hz, 1H), 7.53 (s, 1H), 7.48 (dt, J=1.0, 6.9 Hz, 1H), 7.15 (brs, 1H), 6.01 (q, J=6.4 Hz, 1H), 1.84 (d, J=6.4 Hz, 3H).
mass: 389 (M+1)$^+$.

Example 48

Synthesis of 3-{(1S)-1-[2-(hydroxymethyl)phenyl]ethoxy}-5-imidazo[1,2-a]pyridin-3-ylthiophene-2-carboxyamide [48] (hereinafter, referred to as the compound [48])

35 mg of the compound [45] was dissolved in 1 mL of tetrahydrofuran and 1 mL of methanol, then 500 µL of a 2N aqueous sodium hydroxide solution was added thereto, and the mixture was stirred overnight at room temperature. The reaction mixture was neutralized with 2N hydrochloric acid, and concentrated. The residue was added with ethyl acetate, washed with saturated brine, and dried over anhydrous sodium sulfate. The insolubles were filtered, thus obtained residue was dissolved in 3 mL of tetrahydrofuran, and 1 mL of borane-tetrahydrofuran complex (1.0M tetrahydrofuran solution) was slowly added dropwise. The mixture was stirred for 2 hours at room temperature, a saturated aqueous solution of sodium hydrogen carbonate was added thereto, and extracted with ethyl acetate. The organic layer was washed with saturated brine, and dried over anhydrous sodium sulfate. The insolubles were filtered, the filtrate was concentrated under reduced pressure, and thus obtained residue was purified by preparative reverse-phase liquid chromatography, to obtain 6 mg of a trifluoroacetate salt of the target compound [48] as a pale yellow oily product.

A spectral data of the compound [48] is presented below.
$^1$H-NMR (DMSO-$d_6$) δ: 8.57 (d, =7.0 Hz, 1H), 8.25 (s, 1H), 7.90 (d, J=9.0 Hz, 1H), 7.84 (br s, 1H), 7.77 (t, J=7.7 Hz, 1H), 7.51 (d, J=7.6 Hz, 1H), 7.49 (s, 1H), 7.38-7.20 (m, 5H), 6.08 (q, J=6.6 Hz, 1H), 4.74 (d, J=12.4 Hz, 1H), 4.57 (d, J=12.4 Hz, 1H), 1.73 (d, J=6.6 Hz, 3H).
mass: 394 (M+1)$^+$.

Example 49

Synthesis of 3-{(1R)-1-[2-(hydroxymethyl)phenyl]ethoxy}-5-imidazo[1,2-a]pyridin-3-ylthiophene-2-carboxyamide [49] (hereinafter, referred to as the compound [49])

(1) Methyl 2-((1R)-1-{[2-(aminocarbonyl)-5-imidazo[1,2-a]pyridin-3-yl-3-thienyl]oxy}ethyl)benzoate [49-1] was obtained as a pale yellow oily product from the compound [42] according to the method of Example 45 (hereinafter, referred to as the compound [49-1])

(2) A trifluoroacetate salt of the target compound [49] was obtained as a colorless oily product from the compound [49-1] according to the method of Example 48.

A spectral data of the compound [49] is presented below.

$^1$H-NMR (DMSO-d$_6$) δ: 8.57 (d, =7.0 Hz, 1H), 8.25 (s, 1H), 7.90 (d, J=9.0 Hz, 1H), 7.84 (brs, 1H), 7.77 (t, J=7.7 Hz, 1H) 7.51 (d, J=7.6 Hz, 1H), 7.49 (s, 1H), 7.38-7.20 (m, 5H), 6.08 (q, J=6.6 Hz, 1H), 4.74 (d, J=12.4 Hz, 1H), 4.57 (d, J=12.4 Hz, 1H), 1.73 (d, J=6.7 Hz, 3H).

mass: 394 (M+1)$^+$.

Example 50

Synthesis of 5-imidazo[1,2-a]pyridin-3-yl-3-((1R)-1-{2-[(methylamino)methyl]phenyl}ethoxy)thiophene-2-carboxyamide [50] (hereinafter, referred to as the compound [50])

13 mg of the compound [49] was dissolved in 2 mL of chloroform, and 30 μL of diisopropylethylamine and 7.8 μL of methanesulfonyl chloride were added thereto. The mixture was stirred for 4 hours at room temperature, and the reaction mixture was added with water and extracted with chloroform. The organic layer was washed with saturated brine and dried over anhydrous sodium sulfate. The insolubles were filtered, the filtrate was concentrated under reduced pressure, and thus obtained residue was dissolved in 0.5 mL of dimethylsulfoxide. 0.3 mL of methanol solution of methylamine was added thereto. The mixture was stirred overnight at room temperature, and the reaction solution was added with water and extracted with chloroform. The organic layer was washed with saturated brine and dried over anhydrous sodium sulfate. The insolubles were filtered and the filtrate was concentrated under reduced pressure. Thus obtained residue was purified by preparative reverse-phase liquid chromatography to obtain 10 mg of a trifluoroacetate salt of the target compound [50] as a colorless oily product.

A spectral data of the compound [50] is presented below.

$^1$H-NMR (DMSO-d$_6$) δ: 9.00 (brs, 2H), 8.70 (d, J=7.3 Hz, 1H), 8.23 (s, 1H), 7.89 (d, J=9.2 Hz, 1H), 7.81 (br s, 1H), 7.71 (t, J=7.8 Hz, 1H), 7.67 (dd, J=1.5, 7.8 Hz, 1H), 7.56-7.41 (m, 4H), 7.32 (dt, J=1.0, 6.9 Hz, 1H), 7.11 (brs, 1H), 6.03 (q, J=6.3 Hz, 1H), 4.41-4.13 (m, 2H), 2.68 (t, J=5.0 Hz, 3H), 1.69 (d, J=6.3 Hz, 3H).

mass: 407 (M+1)$^+$.

Example 51

Synthesis of 3-[(1R)-1-(2-{[(2-hydroxyethyl)amino] methyl}phenyl)ethoxy]-5-imidazo[1,2-a]pyridin-3-ylthiophene-2-carboxyamide [51] (hereinafter, referred to as the compound [51])

A trifluoroacetate salt of the target compound [51] was obtained as a colorless oily product from the compound [49] and 2-aminoethanol according to the method of Example 50.

A spectral data of the compound [51] is presented below.

$^1$H-NMR (DMSO-d$_6$) δ: 9.01 (brs, 2H), 8.71 (d, J=6.4 Hz, 1H), 8.20 (s, 1H), 7.87 (d, J=9.3 Hz, 1H), 7.80 (br s, 1H); 7.68-7.65 (m, 2H), 7.58 (dd, J=1.5, 7.0 Hz, 1H), 7.49-7.41 (m, 3H), 7.29 (dt, J=1.0, 6.8 Hz, 1H), 7.10 (s, 1H), 6.05 (q, J=5.8 Hz, 1H), 4.44-4.31 (m, 2H), 3.69 (t, J=5.8 Hz, 2H), 3.15 (m, 2H), 1.69 (d, J=5.8 Hz, 3H).

mass: 437 (M+1)$^+$.

Example 52

Synthesis of 5-imidazo[1,2-a]pyridin-3-yl-3-{(1R)-1-[2-(morpholin-4-ylmethyl)phenyl] ethoxy}thiophene-2-carboxyamide [52] (hereinafter, referred to as the compound [52])

A trifluoroacetate salt of the target compound [52] was obtained as a colorless oily product from the compound [49] and morpholine according to the method of Example 50.

A spectral data of the compound [52] is presented below.

$^1$H-NMR (DMSO-d$_6$) δ: 8.71 (br, 1H), 8.28 (s, 1H), 7.92 (d, J=9.2 Hz, 1H), 7.82 (brs, 1H), 7.78-7.73 (m, 2H), 7.57-7.43 (m, 4H), 7.35 (dt, J=1.0, 6.8 Hz, 1H), 7.10 (brs, 1H), 6.08 (q, J=6.4 Hz, 1H), 4.60-4.20 (m, 6H), 3.80-3.60 (m, 2H), 3.30-3.10 (m, 2H), 1.71 (d, J=6.4 Hz, 3H).

mass: 463 (M+1)$^+$.

Example 53

Synthesis of 3-[1-(2-chlorophenyl)propoxy]-5-imidazo[1,2-a]pyridin-3-ylthiophene-2-carboxyamide [53] (hereinafter, referred to as the compound [53])

(1) 210 mg of 2-chlorobenzaldehyde was dissolved in 3 mL of tetrahydrofuran, and 3 mL of ethyl magnesium bromide (1.0M tetrahydrofuran solution) was added at −20° C. under a nitrogen atmosphere. The mixture was stirred for 4 hours at the same temperature, a saturated aqueous solution of ammonium chloride was added thereto, and extracted with ethyl acetate. The organic layer was washed with saturated brine and dried over anhydrous sodium sulfate. The insolubles were filtered, the filtrate was concentrated under reduced pressure, and thus obtained residue was purified by silica gel column chromatography, to obtain 210 mg of 1-(2-chlorophenyl)-1-propanol [53-1] as a light brown oily product (hereinafter, referred to as the compound [53-1]).

(2) A trifluoroacetate salt of the target compound [53] was obtained as a colorless oily product from the compound [1-3] and the compound [53-1] according to the method of Example 20.

A spectral data of the compound [53] is presented below.

$^1$H-NMR (DMSO-d$_6$) δ: 8.64 (dt, J=6.8, 1.0 Hz, 1H), 8.28 (s, 1H), 7.91 (dt, J=9.0, 1.0 Hz, 1H), 7.86 (br, 1H), 7.79 (dt, J=1.0, 6.8 Hz, 1H), 7.63 (dd, J=1.8, 7.5 Hz, 1H), 7.48 (dd, J=1.8, 7.5 Hz, 1H), 7.32-7.42 (m, 3H), 7.21 (s, 1H), 7.19 (br, 1H), 5.82 (dd, J=5.7, 7.6 Hz, 1H), 1.90-2.22 (m, 2H), 1.01 (t, J=7.2 Hz, 3H).

mass: 412, 414 (M+1)$^+$.

Example 54

Synthesis of 3-[1-(2-chlorophenyl)-2-hydroxyethoxy]-5-imidazo[1,2-a]pyridin-3-ylthiophene-2-carboxyamide [54] (hereinafter, referred to as the compound [54])

(1) To 10 mL of tetrahydrofuran solution containing 296 mg of lithium aluminum hydride, 744 mg of 2-chloromandelic acid was added, and the mixture was stirred for 2 hours at 60° C. Thereto, 2N hydrochloric acid was added, and extracted with ethyl acetate. The organic layer was washed with saturated brine and dried over anhydrous sodium sulfate. The insolubles were filtered and the filtrate was concentrated under reduced pressure to obtain 688 mg of 1-(2-chlorophenyl)-1,2-ethandiol [54-1] (hereinafter, referred to as the compound [54-1]) as a light brown oily product.

(2) 80 mg of the compound [54-1] was dissolved in 2 mL of N,N-dimethylformamide, then 63 mg of imidazole and 77 mg of t-butyldimethylsilylchloride were added, and the mixture was stirred for 2 hours at room temperature. The reaction mixture was added with ethyl acetate, washed with saturated brine, and dried over anhydrous sodium sulfate. The insolubles were filtered and the filtrate was concentrated under reduced pressure to obtain 133 mg of 2-[t-butyl(dimethyl)silyl]oxy-1-(2-chlorophenyl)-1-ethanol [54-2] (hereinafter, referred to as the compound [54-2]) as a light brown oily product.

(3) A trifluoroacetate salt of the target compound [54] was obtained as a colorless oily product from the compound [1-3] and the compound [54-2] according to the method of Example 20.

A spectral data of the compound [54] is presented below.
$^1$H-NMR (DMSO-$d_6$) δ: 8.59 (dt, J=7.0, 1.0 Hz, 1H), 8.24 (s, 1H), 7.91-7.88 (m, 2H), 7.75 (m, 1H), 7.54 (dd, J=2.2, 7.3 Hz, 1H), 7.50 (m, 1H), 7.44 (brs, 1H), 7.41-7.33 (m, 3H), 7.11 (s, 1H), 5.86 (dd, J=3.3, 6.9 Hz, 1H), 3.90-3.79 (m, 2H).
mass: 414, 416 (M+1)$^+$.

Example 55

Synthesis of 3-{1-[2-chloro-4-(hydroxymethyl)phenyl]ethoxy}-5-imidazo[1,2-a]pyridin-3-ylthiophene-2-carboxyamide [55] (hereinafter, referred to as the compound [55])

(1) 4 mL of thionyl chloride was added to 1.5 g of 4-bromo-2-chlorobenzoic acid, and the mixture was stirred overnight at 80° C. The solvent was concentrated under reduced pressure and dissolved in 15 mL of chloroform. Thereto, 780 mg of N,O-dimethyl hydroxylamine and 3.48 mL of diisopropylethylamine were added under an ice-cold condition, and the mixture was stirred for 7 hours at the same temperature. The reaction solution was added with water and extracted with chloroform. The organic layer was washed with saturated brine and dried over anhydrous sodium sulfate. The insolubles were filtered and the filtrate was concentrated under reduced pressure. Thus obtained residue was purified by silica gel chromatography to obtain 2.05 g of 4-bromo-2-chloro-N-methoxy-N-methylbenzamide [55-1] (hereinafter, referred to as the compound [55-1]) as a colorless oily product.

(2) 940 mg of 1-(4-bromo-2-chlorophenyl)-1-ethanone [55-2] (hereinafter, referred to as the compound [55-2]) was obtained as a colorless oily product from 2.05 g of the compound [55-1] according to the method of Example 39-(2).

(3) 400 mg of methyl 4-acetyl-3-chlorobenzoic acid [55-3] (hereinafter, referred to as the compound [55-3]) was obtained as a pale yellow solid from 940 mg of the compound [55-2] according to the method of Example 45.

(4) 220 mg of 1-[2-chloro-4-(hydroxymethyl)phenyl]-1-ethanol [55-4] (hereinafter, referred to as the compound [55-4]) was obtained as a colorless oily product from 400 mg of the compound [55-3] according to the method of Example 33-(1).

(5) 213 mg of 1-[4-([t-butyl(dimethyl)silyl]oxymethyl)-2-chlorophenyl]-1-ethanol [55-5] (hereinafter, referred to as the compound [55-5]) was obtained as a colorless oily product from 220 mg of the compound [55-4] according to the method of Example 54-(2).

(6) The target compound [55] was obtained from the compound [55-5] and the compound [1-3] according to the method of Example 20.

A spectral data of the compound [55] is presented below.
$^1$H-NMR (DMSO-$d_6$) δ: 8.46 (dd, J=1.0, 5.9 Hz, 1H), 7.86 (s, 1H), 7.71 (brs, 1H), 7.68 (dd, J=1.0, 7.7 Hz, 1H), 7.61 (d, J=7.8 Hz, 1H), 7.40-7.31 (m, 3H), 7.18 (s, 1H), 7.10-7.06 (m, 2H), 6.01 (q, J=6.4 Hz, 1H), 5.29 (t, J=5.8 Hz, 1H), 4.46 (d, J=5.4 Hz, 2H), 1.71 (d, J=6.4 Hz, 3H).
mass: 428, 430 (M+1)$^+$.

Example 56

Synthesis of 3-[1-(3-chloropryidin-4-yl)ethoxy]-5-imidazo[1,2-a]pyridin-3-ylthiophene-2-carboxyamide [56] (hereinafter, referred to as the compound [56])

(1) 574 mg of 1-(3-chloro-4-pyridinyl)-1-ethanol [56-1] (hereinafter, referred to as the compound [56-1]) was obtained as a pale yellow oily product from 564 mg of 3-chloroisonicotinaldehyde according to the method of Example 39-(2).

(2) The target compound [56] was obtained from the compound [56-1] and the compound [1-3] according to the method of Example 20.

A spectral data of the compound [56] is presented below.
$^1$H-NMR (DMSO-$d_6$) δ: 8.65 (s, 1H), 8.57 (d, J=5.4 Hz, 1H), 8.54 (dd, J=1.0, 6.8 Hz, 1H), 7.88 (s, 1H), 7.75 (brs, 1H), 7.70-7.67 (m, 2H), 7.37 (m, 1H), 7.22 (s, 1H), 7.12-7.07 (m, 2H), 6.02 (q, J=6.4 Hz, 1H), 1.73 (d, J=6.7 Hz, 3H).
mass: 399, 401 (M+1)$^+$.

Example 57

Synthesis of 3-{1-[2-chloro-4-(pyrrolidin-1-ylmethyl)phenyl]ethoxy}-5-imidazo[1,2-a]pyridin-3-ylthiophene-2-carboxyamide [57] (hereinafter, referred to as the compound [57])

A trifluoroacetate salt of the target compound [57] was obtained from the compound [55] and pyrrolidine according to the method of Example 50.

A spectral data of the compound [57] is presented below.
$^1$H-NMR (DMSO-$d_6$) δ: 9.95 (brs, 1H), 8.68 (d, J=6.8 Hz, 1H), 8.18 (s, 1H), 7.86 (d, J=8.3 Hz, 1H), 7.82 (brs, 1H), 7.77 (d, J=7.8 Hz, 1H), 7.70-7.66 (m, 2H), 7.55 (dd, J=−1.5; 7.8 Hz, 1H), 7.33 (d, J=6.8 Hz, 1H), 7.30 (s, 1H), 7.15 (brs, 1H), 6.05 (q, J=6.3 Hz, 1H), 4.33 (m, 2H), 3.34 (m, 2H), 3.06 (m, 2H), 1.99 (m, 2H), 1.82 (m, 2H), 1.72 (d, J=6.3 Hz, 3H).
mass: 481, 483 (M+1)$^+$.

Example 58

Synthesis of 3-{1-[2-chloro-4-(morpholin-4-ylmethyl)phenyl]ethoxy}-5-imidazo[1,2-a]pyridin-3-ylthiophene-2-carboxyamide [58] (hereinafter, referred to as the compound [58])

A trifluoroacetate salt of the target compound [58] was obtained from the compound [55] and morpholine according to the method of Example 50.

A spectral data of the compound [58] is presented below.

$^1$H-NMR (DMSO-d$_6$) δ: 8.72 (d, J=6.8 Hz, 1H), 8.25 (s, 1H), 7.90 (d, J=8.8 Hz, 1H), 7.85 (brs, 1H), 7.79-7.73 (m, 2H), 7.66 (d, J=1.5 Hz, 1H), 7.52 (dd, J=1.5, 7.7 Hz, 1H), 7.37 (dd, J=5.9, 6.8 Hz, 1H), 7.33 (s, 1H), 7.16 (brs, 1H), 6.05 (q, J=6.3 Hz, 1H), 4.31 (s, 2H), 3.91 (m, 2H), 3.60 (m, 2H), 3.20-3.11 (m, 4H), 1.73 (d, J=6.3 Hz, 3H).

mass: 497, 499 (M+1)$^+$.

Example 59

Synthesis of 3-{1-[2-chloro-4-(piperazin-1-ylmethyl)phenyl]ethoxy}-5-imidazo[1,2-a]pyridin-3-ylthiophene-2-carboxyamide [59] (hereinafter, referred to as the compound [59])

A trifluoroacetate salt of the target compound [59] was obtained from the compound [55] and piperazine according to the method of Example 50.

A spectral data of the compound [59] is presented below.

$^1$H-NMR (CD$_3$OD) δ: 8.71 (d, J=6.8 Hz, 1H), 8.27 (s, 1H), 8.07-8.00 (m, 2H), 7.64 (d, J=7.9 Hz, 1H), 7.57-7.53 (m, 2H), 7.43 (d, J=7.6 Hz, 1H), 7.31 (s, 1H), 6.13 (q, J=6.3 Hz, 1H), 3.72 (s, 2H), 3.29-3.27 (m, 4H), 2.81 (m, 4H), 1.82 (d, J=6.3 Hz, 3H).

mass: 496, 498 (M+1)$^+$.

Example 60

Synthesis of 3-(1-{2-chloro-4-[(4-hydroxypiperidin-1-yl)methyl]phenyl}ethoxy)-5-imidazo[1,2-a]pyridin-3-ylthiophene-2-carboxyamide [60] (hereinafter, referred to as the compound [60])

A trifluoroacetate salt of the target compound [60] was obtained from the compound [55] and 4-hydroxypiperidine according to the method of Example 50.

A spectral data of the compound [60] is presented below.

$^1$H-NMR (DMSO-d$_6$) δ: 8.67 (d, J=5.8 Hz, 1H), 8.17 (s, 1H), 7.86 (d, J=9.3 Hz, 1H), 7.83 (br s, 1H), 7.76 (d, J=8.2 Hz, 1H), 7.69-7.65 (m, 2H), 7.53 (m, 1H), 7.31 (m, 2H), 7.15 (brs, 1H), 6.06 (q, J=6.3 Hz, 1H), 4.29 (m, 2H), 4.24 (m, 1H), 3.90 (m, 1H), 3.58 (m, 1H), 3.30 (m, 1H), 2.94 (m, 1H), 1.90 (m, 1H), 1.85-1.70 (m, 5H), 1.50 (m, 1H).

mass: 511, 513 (M+1)$^+$.

Example 61

Synthesis of 3-[1-(2-chloro-4-{[(2-hydroxyethyl)amino]methyl}phenyl)ethoxy]-5-imidazo[1,2-a]pyridin-3-ylthiophene-2-carboxyamide [61] (hereinafter, referred to as the compound [61])

A trifluoroacetate salt of the target compound [61] was obtained from the compound [55] and 2-aminoethanol according to the method of Example 50.

A spectral data of the compound [61] is presented below.

$^1$H-NMR (DMSO-d$_6$) δ: 8.88 (brs, 2H), 8.72 (dd, J=1.0, 6.8 Hz, 1H), 8.21 (s, 1H), 7.88 (d, J=9.2 Hz, 1H), 7.84 (brs, 1H), 7.75-7.70 (m, 2H), 7.65 (d, J=2.0 Hz, 1H), 7.51 (dd, J=1.4, 7.6 Hz, 1H), 7.35 (dt, J=1.0, 6.8 Hz, 1H), 7.31 (s, 1H), 7.15 (brs, 1H), 6.05 (q, J=6.3 Hz, 1H), 4.13 (m, 2H), 3.62 (t, J=5.4 Hz, 2H), 2.96 (m, 2H), 1.73 (d, J=6.3 Hz, 3H).

mass: 471, 473 (M+1)$^+$.

Example 62

Synthesis of 2-(aminocarbonyl)-5-imdiazo[1,2-a]pyridin-3-yl-3-thienyl-2,6-dichlorobenzoate [62] (hereinafter, referred to as the compound [62])

(1) 137 mg of the compound [1-3] was dissolved in 3 mL of N,N-dimethylformamide, then 138 mg of potassium carbonate and 42 μL of chloromethylmethyl ether were added, and the mixture was stirred for 1 hour at room temperature. The reaction mixture was added with ethyl acetate, washed with water and saturated brine, and dried over anhydrous sodium sulfate. The insolubles were filtered, the filtrate was concentrated under reduced pressure, and methyl 5-imidazo[1,2-a]pyridin-3-yl-3-(methoxymethoxy)-2-thiophenecarboxylic acid [62-1] (hereinafter, referred to as the compound [62-1]) was obtained. The obtained compound [62-1] was used in the subsequent reaction without further purification.

(2) 57 mg of 5-imidazo[1,2-a]pyridin-3-yl-3-(methoxymethoxy)-2-thiophenecarboxyamide [62-2] (hereinafter, referred to as the compound [62-2]) was obtained as a colorless solid from the compound [62-1] according to the method of Example 10-(2).

(3) 19 mg of the compound [62-2] in 10% hydrochloric acid/methanol solution was stirred for 3 hours at room temperature. The solvent was concentrated under reduced pressure, the residue was dissolved in 2 mL of tetrahydrofuran, then 90 μL of diisopropylethylamine and 6 μL of 2,6-dichlorobenzoyl chloride were added, and then stirred for 2 hours at room temperature. The reaction mixture was concentrated under reduced pressure and the residue was purified by preparative reverse-phase liquid chromatography to obtain 2.0 mg of a trifluoroacetate salt of the target compound [62] as a colorless solid.

A spectral data of the compound [62] is presented below.

$^1$H-NMR (DMSO-d$_6$) δ: 8.76 (d, J=6.8 Hz, 1H), 8.32 (s, 1H), 7.87 (m, 2H), 7.72-7.63 (m, 4H), 7.54 (m, 1H), 7.34 (m, 2H).

mass: 432, 434 (M+1)$^+$.

Example 63

Synthesis of 2-(aminocarbonyl)-5-imidazo[1,2-a]pyridin-3-yl-3-thienyl2-(trifluoromethyl)benzoate [63] (hereinafter, referred to as the compound [63])

A trifluoroacetate salt of the target compound [63] was obtained as a colorless oily product from the compound [62-2] and 2-trifluoromethylbenzoyl chloride according to the method of Example 62-(3).

A spectral data of the compound [63] is presented below.

$^1$H-NMR (DMSO-d$_6$) δ: 8.82 (d, J=6.8 Hz, 1H), 8.41 (s, 1H), 8.31 (d, J=7.3 Hz, 1H), 8.01-7.90 (m, 4H), 7.80 (t, J=6.8 Hz, 1H), 7.72 (s, 1H), 7.67 (br, 2H), 7.42 (t, J=7.0 Hz, 1H)

mass: 432 (M+1)$^+$.

Example 64

Synthesis of 2-(aminocarbonyl)-5-imidazo[1,2-a]pyridin-3-yl-3-thienyl2-methoxybenzoate [64] (hereinafter, referred to as the compound [64])

A trifluoroacetate salt of the target compound [64] was obtained as a colorless oily product from the compound [62-2] and 2-methoxybenzoyl chloride according to the method of Example 62-(3).

A spectral data of the compound [64] is presented below.
¹H-NMR (DMSO-d₆) δ: 8.83 (d, J=7.0 Hz, 1H), 8.41 (s, 1H), 8.06 (br, 1H), 8.00 (dd, J=1.8, 8.0 Hz, 1H), 7.93 (d, J=9.0 Hz, 1H), 7.82 (s, 1H), 7.79 (t, J=7.0 Hz, 1H), 7.72 (m, 1H), 7.58 (br, 1H), 7.40 (dt, J=1.1, 7.0 Hz, 1H), 7.31 (d, J=6.8 Hz, 1H), 7.17 (dt, J=1.0, 7.5 Hz, 1H), 3.93 (s, 3H).
mass: 394 (M+1)⁺.

Example 65

Synthesis of 3-[2-(4-chlorophenyl)-2-oxoethoxy]-5-imidazo[1,2-a]pyridin-3-ylthiophene-2-carboxamide [65] (hereinafter, referred to as the compound [65])

A trifluoroacetate salt of the target compound [65] was obtained as a colorless oily product from the compound [1-3] and 4-chlorophenyl bromide according to the method of Example 10. The target compound was confirmed by LC-MS.
mass: 412 (M+1)⁺.

Example 66

Synthesis of 3-[(1R)-1-(2-chlorophenyl)ethoxy]-5-[6-(2-hydroxyethoxy)imidazo[1,2-a]pyridin-3-yl]thiophene-2-carboxamide [66] (hereinafter, referred to as the compound [66])

(1) 1.04 g of 2-amino-5-iodopyridine was dissolved in 5 mL of chloroform, and 3.84 mL of chloroacetaldehyde (40% aqueous solution) and 795 mg of sodium hydrogen carbonate were added at room temperature. The mixture was stirred overnight at room temperature, and the reaction mixture was added with water and extracted with chloroform. The organic layer was washed with water and saturated brine, and dried over anhydrous sodium sulfate. The insolubles were filtered, the filtrate was concentrated under reduced pressure, and thus obtained residue was purified by silica gel column chromatography, to obtain 1.05 g of 6-iodoimidazo[1,2-a]pyridine [66-1] (hereinafter, referred to as the compound [66-1]) as a light brown solid.

(2) 1.0 g of the compound [66-1] was dissolved in 4 mL of toluene; then 1.4 g of 2-t-butyldimethylsiloxy ethanol synthesized according to the method disclosed in the literature (J.O.C., 51(17)3388 (1986)), 2.0 g of cesium carbonate, and 295-mg of 1,10-phenanthroline were added, the mixture was stirred overnight at 110° C. The insolubles were filtered, the filtrate was concentrated under reduced pressure, and thus obtained residue was purified by silica gel column chromatography, to obtain 650 mg of 6-(2-[t-butyl(dimethyl)silyl]oxyethoxy)imidazo[1,2-a]pyridine [66-2] (hereinafter, referred to as the compound [66-2]) as a light brown solid (Literature: Org. Lett., 4(6)973, (2002))

(3) 860 mg of 6-(2-[t-butyl(dimethyl)silyl]oxyethoxy)-3-iodoimidazo[1,2-a]pyridine [66-3] (hereinafter, referred to as the compound [66-3]) was obtained as a colorless solid from 650 mg of the compound [66-2] according to the method of Example 1-(1).

(4) 410 mg of methyl 5-[6-(2-[t-butyl(dimethyl)silyl]oxyethoxy)imidazo[1,2-a]pyridin-3-yl]-3-hydroxy-2-thiophenecarboxylic acid [66-4] (hereinafter, referred to as the compound [66-4]) was obtained as a pale yellow solid from 810 mg of the compound [66-3] according to the methods of Example 1-(2) and (3).

(5) 421 mg of methyl 5-[6-(2-[t-butyl(dimethyl)silyl]oxyethoxy)imidazo[1,2-a]pyridin-3-yl]-3-[(1R)-1-chlorophenylethyl]oxy-2-thiophenecarboxylic acid [66-5] (hereinafter, referred to as the compound [66-5]) was obtained as a colorless solid from 410 mg of the compound [66-4] and (S)-α-(2-chlorophenyl)ethyl alcohol synthesized according to the method disclosed in the literature (Tetrahedron, 52 (2), 589 (1996)) in accordance with the method of Example 1-(4).

(6) 46 mg of the target compound [66] was obtained as a pale yellow solid from 110 mg of the compound [66-5] according to the method of Example 10-(2).

A spectral data of the compound [66] is presented below.
¹H-NMR (CDCl₃) δ: 7.90 (d, J=2.4 Hz, 1H), 7.69 (s, 1H), 7.57 (d, J=9.6 Hz, 1H), 7.48 (dd, J=8.0, 1.6 Hz, 1H), 7.42 (dd, J=8.0, 1.6 Hz, 1H), 7.34-7.21 (m, 2H), 7.07 (dd, J=9.6, 2.4 Hz, 1H), 6.72 (s, 1H), 5.89 (q, J=6.4 Hz, 1H), 5.71 (brs, 1H), 4.01-4.00 (m, 4H), 2.17 (brs, 1H), 1.77 (d, J=6.4 Hz, 3H).
mass: 458, 460 (M+1)⁺.

Example 67

Synthesis of 5-(6-methoxyimidazo[1,2-a]pyridin-3-yl)-3-{[2-(trifluoromethyl)benzyl]oxy}thiophene-2-carboxamide [67] (hereinafter, referred to as the compound [67])

(1) Methyl 3-hydroxy-5-(6-methoxyimidazo[1,2-a]pyridin-3-yl)-2-thiophenecarboxylic acid [67-1] (hereinafter, referred to as the compound [67-1]) was obtained from the compound [66-1] and methanol according to the methods of Example 66-(2) to (4).

(2) The target compound [67] was obtained from the compound [67-1] and 2-trifluoromethylbenzyl alcohol according to the methods of Example 66-(5) and (6).

A spectral data of the compound [67] is presented below.
¹H-NMR (CDCl₃) δ: 8.00-7.98 (m, 1H), 7.81-7.75 (m, 2H), 7.70-7.50 (m, 4H), 7.09-7.02 (m, 2H), 7.01 (s, 1H), 5.60 (brs, 1H), 5.52 (s, 2H), 3.82 (s, 3H).
mass: 448 (M+1)⁺.

Example 68

Synthesis of 5-[6-(piperidin-4-ylmethoxy)imidazo[1,2-a]pyridin-3-yl]-3-{[2-(trifluoromethyl)benzyl]oxy}thiophene-2-carboxamide [68] (hereinafter, referred to as the compound [68])

(1) 5.0 g of 4-piperidinemethanol was dissolved in 100 mL of 1,4-dioxane, then 17 mL of a 3N aqueous sodium hydroxide solution and 8.5 g of di-t-butyl-dicarbonate were added, and the mixture was stirred for 5 hours at room temperature. The reaction mixture was added with water and extracted with ethyl acetate. The organic layer was washed with saturated brine and dried over anhydrous sodium sulfate. The insolubles were filtered and the filtrate was concentrated under reduced pressure to obtain 7.0 g of t-butyl 4-(hydroxymethyl)tetrahydro-1-(2H)-pyridinecarboxylate [68-1] hereinafter, referred to as the compound [68-1]) as a colorless substance.

(2) t-butyl 4-[(3-[5-(aminocarbonyl)-4-(2-trifluoromethylbenzyl)oxy-2-thienyl]imidazo[1,2-a]pyridin-6-yloxy)methyl]tetrahydro-1-(2H)-pyridinecarboxylic acid [68-2](hereinafter, referred to as the compound [68-2]) was obtained as a colorless oily product from the compound [66-1] and the compound [68-1] according to the method of Example 67.

(3) 4.1 mg of the compound [68-2] was dissolved in a mixed solution of chloroform/methanol (9:1), 1 mL of 4N hydrochloric acid-dioxane was added thereto, and the mixture was stirred overnight at room temperature. The solvent was concentrated under reduced pressure and thus obtained residue was purified by preparative reverse-phase liquid chromatography, to obtain 2 mg of a trifluoroacetate salt of the target compound [68] as a colorless oily product.

A spectral data of the compound [68] is presented below.
$^1$H-NMR (CD$_3$OD) δ: 8.25-8.20 (m, 1H), 8.11-8.05 (m, 1H), 7.85-7.68 (m, 4H), 7.60 (dd, J=7.5, 7.5 Hz, 1H), 7.54 (s, 1H), 7.54-7.50 (m, 1H), 5.60 (s, 2H), 4.02-3.99 (m, 2H), 3.59-3.43 (m, 2H), 3.19-3.01 (m, 2H), 2.26-2.07 (m, 3H), 1.73-1.58 (m, 2H).
mass: 531 (M+1)$^+$.

Example 69

Synthesis of 3-[1-(2-chlorophenyl)ethoxy]-5-[6-(2-methoxyethoxy)imidazo[1,2-a]pyridin-3-yl]thiophene-2-carboxyamide [69] (hereinafter, referred to as the compound [69])

(1) 32 mg of the compound [66] was dissolved in 3 mL of chloroform, and 60 μL of diisopropylethylamine and 16 μL of methanesulfonyl chloride were added thereto. The mixture was stirred for 1 hour at room temperature, the reaction mixture was added with water and extracted with chloroform. The organic layer was washed with saturated brine and dried over anhydrous sodium sulfate. The insolubles were filtered and the filtrate was concentrated under reduced pressure. Thus obtained 2-[(3-{5-(aminocarbonyl)-4-[1-(2-chlorophenyl)ethoxy]-2-thienyl}imidazo[1,2-a]pyridin-6-yl)oxy]ethyl-methanesulfonate [69-1] (hereinafter, referred to as the compound [69-1]) was used in the subsequent reaction without further purification.

(2) 4.2 mg of the compound [69-1] was dissolved in 1 mL of methanol, then 4.2 mg of sodium methoxide was added, and the mixture was stirred overnight at 70° C. The reaction mixture was added with water and extracted with chloroform. The organic layer was washed with saturated brine and dried over anhydrous sodium sulfate. The insolubles were filtered, the filtrate was concentrated under reduced pressure, and thus obtained residue was purified by preparative thin-layer chromatography, to obtain 2.2 mg of the target compound [69] as a pale yellow solid.

A spectral data of the compound [69] is presented below.
$^1$H-NMR (CDCl$_3$) δ: 7.90 (d, J=2.4 Hz, 1H), 7.68 (s, 1H), 7.55 (d, J=9.6 Hz, 1H), 7.48 (dd, J=7.6, 1.6 Hz, 1H), 7.42 (dd, J=7.6, 1.6 Hz, 1H), 7.32 (ddd, J=7.6, 7.6, 1.6 Hz, 1H), 7.29-7.25 (m, 1H), 7.09 (dd, J=9.6, 2.4 Hz, 1H), 6.72 (s, 1H), 5.89 (q, J=6.4 Hz, 1H), 5.71 (brs, 1H), 4.05-4.03 (m, 2H), 3.80-3.77 (m, 2H), 3.48 (s, 3H), 1.77 (d, J=6.4 Hz, 3H).
mass: 472, 474 (M+1)$^+$.

Example 70

Synthesis of 3-[1-(2-chlorophenyl)ethoxy]-5-[6-(2-morpholin-4-ylethoxy)imidazo[1,2-a]pyridin-3-yl]thiophene-2-carboxyamide [70] (hereinafter, referred to as the compound [70])

10 mg of the compound [69-1] was dissolved in 1 mL of N,N-dimethylformamide, 0.5 mL of morpholine was added, and the mixture was stirred for 4 hours at 50° C. The reaction mixture was added with water and extracted with chloroform. The organic layer was washed with saturated brine and dried over anhydrous sodium sulfate. The insolubles were filtered, the filtrate concentrated under reduced pressure, and thus obtained residue was purified by preparative thin-layer chromatography, to obtain 10 mg of the target compound [70] as a colorless solid.

A spectral data of the compound [70] is presented below.
$^1$H-NMR (CDCl$_3$) δ: 7.90 (d, J=2.4 Hz, 1H), 7.68 (s, 1H), 7.54 (d, J=9.6 Hz, 1H), 7.48 (dd, J=7.8, 1.8 Hz, 1H), 7.43 (dd, J=7.8, 1.8 Hz, 1H), 7.35-7.23 (m, 2H), 7.06 (dd, J=9.6, 2.4 Hz, 1H), 6.72 (s, 1H), 5.90 (q, J=6.3 Hz, 1H), 5.89 (brs, 1H), 4.03 (t, J=5.4 Hz, 2H), 3.77-3.74 (m, 4H), 2.84 (t, J=5.4 Hz, 2H), 2.61-2.58 (m, 4H), 1.77 (d, J=6.3 Hz, 3H).
mass: 527, 529 (M+1)$^+$.

Example 71

Synthesis of 3-[1-(2-chlorophenyl)ethoxy]-5-[6-(2-piperidin-1-ylethoxy)imidazo[1,2-a]pyridin-3-yl]thiophene-2-carboxyamide [71] (hereinafter, referred to as the compound [71])

The target compound [71] was obtained as a pale yellow solid from the compound [69-1] and piperidine according to the method of Example 70.

A spectral data of the compound [71] is presented below.
$^1$H-NMR (CDCl$_3$) δ: 7.87 (d, J=2.4 Hz, 1H), 7.57 (s, 1H), 7.54 (d, J=9.6 Hz, 1H), 7.48 (dd, J=7.8, 1.8 Hz, 1H), 7.43 (dd, J=7.8, 1.8 Hz, 1H), 7.35-7.25 (m, 2H), 7.07 (dd, J=9.6, 2.4 Hz, 1H), 6.72 (s, 1H), 5.90 (q, J=6.3 Hz, 1H), 5.82 (brs, 1H), 4.03 (t, J=5.4 Hz, 2H), 2.82 (t, J=5.4 Hz, 2H), 2.59-2.50 (m, 4H), 1.85-1.40 (m, 6H), 1.77 (d, J=6.3 Hz, 3H).
mass: 525, 527 (M+1)$^+$.

Example 72

Synthesis of 3-[1-(2-chlorophenyl)ethoxy]-5-[6-(2-pyrrolidin-1-ylethoxy)imidazo[1,2-a]pyridin-3-yl]thiophene-2-carboxyamide [72] (hereinafter, referred to as the compound [72])

The target compound [72] was obtained as a pale yellow solid from the compound [69-1] and pyrrolidine according to the method of Example 70.

A spectral data of the compound [72] is presented below.
$^1$H-NMR (CDCl$_3$) δ: 7.89 (d, J=2.4 Hz, 1H), 7.67 (s, 1H), 7.54 (d, J=9.6 Hz, 1H), 7.48 (dd, J=7.6, 1.6 Hz, 1H), 7.42 (dd, J=7.6, 1.6 Hz, 1H), 7.32 (ddd, J=7.6, 7.6, 1.6 Hz, 1H), 7.29-7.25 (m, 1H), 7.09 (dd, J=9.6, 2.4 Hz, 1H), 6.72 (s, 1H), 5.90 (q, J=6.4 Hz, 1H), 5.83 (brs, 1H), 4.05 (t, J=5.6 Hz, 2H), 2.97 (t, J=5.6 Hz, 2H), 2.75-2.65 (m, 4H), 1.90-1.75 (m, 4H), 1.77 (d, J=6.4 Hz, 3H).
mass: 511, 513 (M+1)$^+$.

Example 73

Synthesis of 3-[1-(2-chlorophenyl)ethoxy]-5-{6-[2-(4-methylpiperazin-1-yl)ethoxy]imidazo[1,2-a]pyridin-3-yl}thiophene-2-carboxyamide [73] (hereinafter, referred to as the compound [73])

The target compound [73] was obtained as a pale yellow solid from the compound [69-1] and N-methylpiperazine according to the method of Example 70.

A spectral data of the compound [73] is presented below.
$^1$H-NMR (CDCl$_3$) δ: 7.88 (d, J=2.4 Hz, 1H), 7.67 (s, 1H), 7.54 (d, J=9.6 Hz, 1H), 7.48 (dd, J=7.6, 1.6 Hz, 1H), 7.43 (dd, J=7.6, 1.6 Hz, 1H), 7.32 (ddd, J=7.6, 7.6, 1.6 Hz, 1H), 7.30-7.21 (m, 1H), 7.06 (dd, J=9.6, 2.4 Hz, 1H), 6.72 (s, 1H), 5.89

(q, J=6.4 Hz, 1H), 5.81 (brs, 1H), 4.02 (t, J=5.2 Hz, 2H), 2.85 (t, J=5.2 Hz, 2H), 2.75-2.40 (m, 8H), 2.31 (s, 3H), 1.77 (d, J=6.4 Hz, 3H).

mass: 540, 542 (M+1)$^+$.

Example 74

Synthesis of t-butyl 4-{2-[(3-{5-(aminocarbonyl)-4-[1-(2-chlorophenyl)ethoxy]-2-thienyl}imidazo[1,2-a]pyridin-6-yl)oxy]ethyl}piperazine-1-carboxylate [74] (hereinafter, referred to as the compound [74])

The target compound [74] was obtained as a pale yellow solid from the compound [69-1] and 1-t-butoxycarbonylpiperazine according to the method of Example 70.

A spectral data of the compound [74] is presented below.
$^1$H-NMR (CDCl$_3$) δ: 7.89 (d, J=2.4 Hz, 1H), 7.68 (s, 1H), 7.55 (d, J=9.6 Hz, 1H), 7.48 (dd, J=7.6, 1.6 Hz, 1H), 7.42 (dd, J=7.6, 1.6 Hz, 1H), 7.30 (ddd, J=7.6, 7.6, 1.6 Hz, 1H), 7.26-7.20 (m, 1H), 7.06 (dd, J=9.6, 2.4 Hz, 1H), 6.72 (s, 1H), 5.89 (q, J=6.4 Hz, 1H), 5.79 (brs, 1H), 4.03 (t, J=5.2 Hz, 2H), 3.45-3.42 (m, 4H), 2.85 (t, J=5.2 Hz, 2H), 2.95-2.55 (m, 4H), 1.77 (d, J=6.4 Hz, 3H), 1.47 (s, 9H).

mass: 626, 628 (M+1)$^+$.

Example 75

Synthesis of 3-[1-(2-chlorophenyl)ethoxy]-5-[6-(2-piperazin-1-ylethoxy)imidazo[1,2-a]pyridin-3-yl]thiophene-2-carboxyamide [75] (hereinafter, referred to as the compound [75])

The target compound [75] was obtained as a pale yellow solid from the compound [74] according to the method of Example 68-(3).

A spectral data of the compound [75] is presented below.
$^1$H-NMR (CDCl$_3$) δ: 7.89-7.88 (m, 1H), 7.67 (s, 1H), 7.54 (d, J=9.6 Hz, 1H), 7.47 (d, J=7.2 Hz, 1H), 7.43 (d, J=7.2 Hz, 1H), 7.35-7.22 (m, 2H), 7.07 (dd, J=9.6, 2.4 Hz, 1H), 6.72 (s, 1H), 5.90 (q, J=6.3 Hz, 1H), 5.72 (brs, 1H), 4.03 (t, J=5.4 Hz, 2H), 2.96-2.93 (m, 4H), 2.81 (t, J=5.4 Hz, 2H), 2.60-2.54 (m, 4H), 1.77 (d, J=6.3 Hz, 3H).

mass: 526, 528 (M+1)$^+$.

Example 76

Synthesis of 3-[1-(2-chlorophenyl)ethoxy]-5-{6-[2-(4-hydroxypiperidin-1-yl)ethoxy]imidazo[1,2-a]pyridin-3-yl}thiophene-2-carboxyamide [76] (hereinafter, referred to as the compound [76])

The target compound [76] was obtained as a pale yellow solid from the compound [69-1] and 4-hydroxypiperidine according to the method of Example 70.

A spectral data of the compound [76] is presented below.
$^1$H-NMR (CDCl$_3$) δ: 7.92 (d, J=2.4 Hz, 1H), 7.67 (s, 1H), 7.55 (d, J=9.6 Hz, 1H), 7.48 (dd, J=7.6, 1.6 Hz, 1H), 7.43 (dd, J=7.6, 1.6 Hz, 1H), 7.32 (ddd, J=7.6, 7.6, 1.6 Hz, 1H), 7.20 (m, 1H), 7.06 (dd, J=9.6, 2.4 Hz, 1H), 6.72 (s, 1H), 5.89 (q, J=6.4 Hz, 1H), 5.82 (brs, 1H), 4.03 (t, J=5.6 Hz, 2H), 3.80-3.72 (m, 1H), 2.91-2.85 (m, 2H), 2.84 (t, J=5.6 Hz, 2H), 2.40-2.30 (m, 2H), 2.00-1.90 (m, 2H), 1.77 (d, J=6.4 Hz, 3H), 1.70-1.60 (m, 2H).

mass: 541, 543 (M+1)$^+$.

Example 77

Synthesis of 3-[1-(2-chlorophenyl)ethoxy]-5-(6-{2-[(2-hydroxyethyl)amino]ethoxy}imidazo[1,2-a]pyridin-3-yl)thiophene-2-carboxyamide [77] (hereinafter, referred to as the compound [77])

The target compound [77] was obtained as a pale yellow solid from the compound [69-1] and 2-aminoethanol according to the method of Example 70.

A spectral data of the compound [77] is presented below.
$^1$H-NMR (CDCl$_3$) δ: 7.92 (d, J=2.4 Hz, 1H), 7.69 (s, 1H), 7.56 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.25 (m, 1H), 7.05 (dd, J=9.6, 2.4 Hz, 1H), 6.72 (s, 1H), 5.89 (q, J=6.4 Hz, 1H), 5.80 (brs, 1H), 4.01 (t, J=4.8 Hz, 2H), 3.72 (t, J=5.2 Hz, 2H), 3.08 (t, J=4.8 Hz, 2H), 2.90 (t, J=5.2 Hz, 2H), 1.76 (d, J=6.4 Hz, 3H).

mass: 501, 503 (M+1)$^+$.

Example 78

Synthesis of 3-[1-(2-chlorophenyl)ethoxy]-5-(6-{2-[(2-hydroxyethyl)(methyl)amino]ethoxy}imidazo[1,2-a]pyridin-3-yl)thiophene-2-carboxyamide [78] (hereinafter, referred to as the compound [78])

The target compound [78] was obtained as a pale yellow solid from the compound [69-1] and 2-methylaminoethanol according to the method of Example 70.

A spectral data of the compound [78] is presented below.
$^1$H-NMR (CDCl$_3$) δ: 7.91 (d, J=2.4 Hz, 1H), 7.68 (s, 1H), 7.55 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.25 (m, 1H), 7.05 (dd, J=9.6, 2.4 Hz, 1H), 6.73 (s, 1H), 5.90 (q, J=6.4 Hz, 1H), 5.81 (brs, 1H), 4.00 (t, J=4.8 Hz, 2H), 3.64 (t, J=5.2 Hz, 2H), 2.92 (t, J=4.8 Hz, 2H), 2.69 (t, J=5.2 Hz, 2H), 2.42 (s, 3H), 1.77 (d, J=6.4 Hz, 3H).

mass: 515, 517 (M+1)$^+$.

Example 79

Synthesis of 3-[1-(2-chlorophenyl)ethoxy]-5-(6-{2-[(3R)-3-hydroxypiperidin-1-yl]ethoxy}imidazo[1,2-a]pyridin-3-yl)thiophene-2-carboxyamide [79] (hereinafter, referred to as the compound [79])

The target compound [79] was obtained as a pale yellow solid from the compound [69-1] and (R)-3-hydroxypiperidine according to the method of Example 70.

A spectral data of the compound [79] is presented below.
$^1$H-NMR (CDCl$_3$) δ: 7.92-7.91 (m, 1H), 7.68-7.67 (m, 1H), 7.55 (d, J=9.6 Hz, 1H), 7.48 (dd, J=7.6, 1.6 Hz, 1H), 7.42 (dd, J=7.6, 1.6 Hz, 1H), 7.32 (ddd, J=7.6, 7.6, 1.6 Hz, 1H), 7.30-7.25 (m, 1H), 7.05 (dd, J=9.6, 2.4 Hz, 1H), 6.73 (s, 1H), 5.90 (q, J=6.4 Hz, 1H), 5.80 (brs, 1H), 4.03 (t, J=5.6 Hz, 2H), 3.90-3.80 (m, 1H), 2.85 (t, J=5.6 Hz, 2H), 2.75-2.42 (m, 4H), 1.90-1.50 (m, 4H), 1.77 (d, J=6.4 Hz, 3H).

mass: 541, 543 (M+1)$^+$.

Example 80

Synthesis of 3-[(1R)-1-(2-chlorophenyl)ethoxy]-5-(6-{2-[(3S)-3-hydroxypiperidin-1-yl]ethoxy}imidazo[1,2-a]pyridin-3-yl)thiophene-2-carboxyamide [80] (hereinafter, referred to as the compound [80])

The target compound [80] was obtained as a pale yellow solid from the compound [69-1] and (S)-3-hydroxypiperidine according to the method of Example 70.

A spectral data of the compound [80] is presented below.

$^1$H-NMR (CDCl$_3$) δ: 7.92-7.91 (m, 1H), 7.68-7.67 (m, 1H), 7.55 (d, J=9.6 Hz, 1H), 7.48 (dd, J=7.6, 1.6 Hz, 1H), 7.42 (dd, J=7.6, 1.6 Hz, 1H), 7.32 (ddd, J=7.6, 7.6, 1.6 Hz, 1H), 7.30-7.25 (m, 1H), 7.05 (dd, J=9.6, 2.4 Hz, 1H), 6.73 (s, 1H), 5.90 (q, J=6.4 Hz, 1H), 5.80 (brs, 1H), 4.03 (t, J=5.6 Hz, 2H), 3.90-3.80 (m, 1H), 2.85 (t, J=5.6 Hz, 2H), 2.75-2.42 (m, 4H), 1.90-1.50 (m, 4H), 1.77 (d, J=6.4 Hz, 3H).

mass: 541, 543 (M+1)$^+$.

Example 81

Synthesis of 3-[1-(2-chlorophenyl)ethoxy]-5-(6-{2-[(3R)-3-hydroxypyrrolidin-1-yl]ethoxy}imidazo[1,2-a]pyridin-3-yl)thiophene-2-carboxyamide [81] (hereinafter, referred to as the compound [81])

The target compound [81] was obtained as a pale yellow solid from the compound [69-1] and (R)-3-hydroxypyrrolidine according to the method of Example 70.

A spectral data of the compound [81] is presented below.

$^1$H-NMR (CDCl$_3$) δ: 7.93 (d, J=2.4 Hz, 1H), 7.68 (s, 1H), 7.55 (d, J=9.6 Hz, 1H), 7.47 (dd, J=7.6, 1.6 Hz, 1H), 7.42 (dd, J=7.6, 1.6 Hz, 1H), 7.32 (ddd, J=7.6, 7.6, 1.6 Hz, 1H), 7.29-7.25 (m, 1H), 7.07 (dd, J=9.6, 2.4 Hz, 1H), 6.73 (s, 1H), 5.90 (q, J=6.4 Hz, 1H), 5.83 (brs, 1H), 4.44-4.39 (m, 1H), 4.06 (t, J=5.6 Hz, 2H), 3.05-3.00 (m, 1H), 2.97 (t, J=5.6 Hz, 2H), 2.87-2.74 (m, 2H), 2.55-2.45 (m, 1H), 2.35-2.20 (m, 1H), 2.00-1.75 (m, 1H), 1.76 (d, J=6.4 Hz, 3H).

mass: 527, 529 (M+1)$^+$.

Example 82

Synthesis of 3-[1-(2-chlorophenyl)ethoxy]-5-(6-{2-[(3S)-3-hydroxypyrrolidin-1-yl]ethoxy}imidazo[1,2-a]pyridin-3-yl)thiophene-2-carboxyamide [82] (hereinafter, referred to as the compound [82])

The target compound [82] was obtained as a pale yellow solid from the compound [69-1] and (S)-3-hydroxypyrrolidine according to the method of Example 70.

A spectral data of the compound [82] is presented below.

$^1$H-NMR (CDCl$_3$) δ: 7.93 (d, J=2.4 Hz, 1H), 7.68 (s, 1H), 7.55 (d, J=9.6 Hz, 1H), 7.47 (dd, J=7.6, 1.6 Hz, 1H), 7.42 (dd, J=7.6, 1.6 Hz, 1H), 7.32 (ddd, J=7.6, 7.6, 1.6 Hz, 1H), 7.29-7.25 (m, 1H), 7.07 (dd, J=9.6, 2.4 Hz, 1H), 6.73 (s, 1H), 5.90 (q, J=6.4 Hz, 1H), 5.83 (brs, 1H), 4.44-4.39 (m, 1H), 4.06 (t, J=5.6 Hz, 2H), 3.05-3.00 (m, 1H), 2.97 (t, J=5.6 Hz, 2H), 2.87-2.74 (m, 2H), 2.55-2.45 (m, 1H), 2.35-2.20 (m, 1H), 2.00-1.75 (m, 1H), 1.76 (d, J=6.4 Hz, 3H).

mass: 527, 529 (M+1)$^+$.

Example 83

Synthesis of 3-[1-(2-chlorophenyl)ethoxy]-5-[6-(3-hydroxypropoxy)imidazo[1,2-a]pyridin-3-yl]thiophene-2-carboxyamide [83] (hereinafter, referred to as the compound [83])

The target compound [83] was obtained as a colorless solid from the compound [66-1] and 3-t-butyldimethylsiloxy propanol synthesized according to the method disclosed in the literature (J. Org. Chem., 51(17) 3388 (1986)) according to the methods of Example 66-(2) to (6).

A spectral data of the compound [83] is presented below.

$^1$H-NMR (CD$_3$OD) δ: 7.85 (d, J=2.4 Hz, 1H), 7.67 (s, 1H), 7.58 (dd, J=7.6, 1.6 Hz, 1H), 7.52 (d, J=9.6 Hz, 1H), 7.46 (dd, J=7.6, 1.6 Hz, 1H), 7.37 (ddd, J=7.6, 7.6, 1.6 Hz, 1H), 7.32 (ddd, J=7.6, 7.6, 1.6 Hz, 1H), 7.20 (dd, J=9.6, 2.4 Hz, 1H), 6.98 (s, 1H), 6.06 (q, J=6.4 Hz, 1H), 4.06-3.99 (m, 2H), 3.78 (t, J=6.0 Hz, 2H), 2.07-2.01 (m, 2H), 1.77 (d, J=6.4 Hz, 3H).

mass: 472, 474 (M+1)$^+$.

Example 84

Synthesis of 3-[1-(2-chlorophenyl)ethoxy]-5-[6-(3-morpholin-4-ylpropoxy)imidazo[1,2-a]pyridin-3-yl]thiophene-2-carboxyamide [84] (hereinafter, referred to as the compound [84])

The target compound [84] was obtained as a pale yellow solid from the compound [83] according to the method of Example 50.

A spectral data of the compound [84] is presented below.

$^1$H-NMR (CDCl$_3$) δ: 7.89 (d, J=2.4 Hz, 1H), 7.68 (s, 1H), 7.55 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.25 (m, 1H), 7.04 (dd, J=9.6, 2.4 Hz, 1H), 6.73 (s, 1H), 5.92-5.87 (m, 2H), 3.96 (t, J=6.0 Hz, 2H), 3.75-3.40 (m, 4H), 2.56 (t, J=7.2 Hz, 2H), 2.54-2.50 (m, 4H), 2.03-1.97 (m, 2H), 1.77 (d, J=6.4 Hz, 3H).

mass: 541, 543(M+1)$^+$.

Example 85

Synthesis of 3-[1-(2-chlorophenyl)ethoxy]-5-[6-(4-hydroxybutoxy)imidazo[1,2-a]pyridin-3-yl]thiophene-2-carboxyamide [85] (hereinafter, referred to as the compound [85])

The target compound [85] was obtained as a pale yellow solid from the compound [66-1] and 4-t-butyldimethylsiloxy butanol synthesized according to the method disclosed in the literature (J. Org. Chem., 51(17) 3388 (1986)) according to the methods of Example 66-(2) to (6).

A spectral data of the compound [85] is presented below.

$^1$H-NMR (CDCl$_3$) δ: 7.89 (d, J=2.4 Hz, 1H), 7.59 (s, 1H), 7.55 (d, J=9.6 Hz, 1H), 7.49 (dd, J=7.5, 1.8 Hz, 1H), 7.42 (dd, J=7.5, 1.8 Hz, 1H), 7.36-7.24 (m, 2H), 7.03 (dd, J=9.6, 2.4 Hz, 1H), 6.73 (s, 1H), 5.90 (q, J=6.6 Hz, 1H), 5.73 (brs, 1H), 3.95 (t, J=6.0 Hz, 2H), 3.77 (t, J=6.0 Hz, 2H), 2.00-1.91 (m, 2H), 1.84-1.71 (m, 2H), 1.77 (d, J=6.6 Hz, 3H).

mass: 486, 488 (M+1)$^+$.

Example 86

Synthesis of 3-[1-(2-chlorophenyl)ethoxy]-5-[6-(4-piperidin-1-ylbutoxy)imidazo[1,2-a]pyridin-3-yl]thiophene-2-carboxyamide [86] (hereinafter, referred to as the compound [86])

The target compound [86] was obtained as a pale yellow solid from the compound [85] and piperidine according to the method of Example 50.
A spectral data of the compound [86] is presented below.
$^1$H-NMR (CDCl$_3$) δ: 7.84 (d, J=2.4 Hz, 1H), 7.67 (s, 1H), 7.54 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.20 (m, 1H), 7.03 (dd, J=9.6, 2.4 Hz, 1H), 6.72 (s, 1H), 5.89 (q, J=6.4 Hz, 1H), 5.76 (brs, 1H), 3.89 (t, J=6.0 Hz, 2H), 2.60-2.40 (m, 6H), 1.90-1.40 (m, 10H), 1.77 (d, J=6.4 Hz, 3H).
mass: 553, 555 (M+1)$^+$.

Example 87

Synthesis of 3-[1-(2-chlorophenyl)ethoxy]-5-[6-(4-pyrrolidin-1-ylbutoxy)imidazo[1,2-a]pyridin-3-yl]thiophene-2-carboxyamide [87] (hereinafter, referred to as the compound [87])

The target compound [87] was obtained as a pale yellow solid from the compound [85] and pyrrolidine according to the method of Example 50.
A spectral data of the compound [87] is presented below.
$^1$H-NMR (CDCl$_3$) δ: 7.86 (d, J=2.4 Hz, 1H), 7.67 (s, 1H), 7.54 (d, J=9.6 Hz, 1H), 7.48 (dd, J=7.6, 1.6 Hz, 1H), 7.41 (dd, J=7.6, 1.6 Hz, 1H), 7.34-7.20 (m, 2H), 7.02 (dd, J=9.6, 2.4 Hz, 1H), 6.72 (s, 1H), 5.89 (q, J=6.4 Hz, 1H), 5.74 (brs, 1H), 3.91 (t, J=6.0 Hz, 2H), 3.00-2.75 (m, 6H), 2.00-1.60 (m, 8H), 1.77 (d, J=6.4 Hz, 3H).
mass: 539, 541 (M+1)$^+$.

Example 88

Synthesis of 3-[1-(2-chlorophenyl)ethoxy]-5-{6-[4-(dimethylamino)butoxy]imidazo[1,2-a]pyridin-3-yl}thiophene-2-carboxyamide [88] (hereinafter, referred to as the compound [88])

The target compound [88] was obtained as a pale yellow solid from the compound [85] and dimethylamine according to the method of Example 50.
A spectral data of the compound [88] is presented below.
$^1$H-NMR (CDCl$_3$) δ: 7.84 (d, J=2.4 Hz, 1H), 7.67 (s, 1H), 7.54 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.20 (m, 1H), 7.03 (dd, J=9.6, 2.4 Hz, 1H), 6.71 (s, 1H), 5.89 (q, J=6.4 Hz, 1H), 5.74 (brs, 1H), 3.89 (t, J=6.0 Hz, 2H), 2.36 (t, J=7.2 Hz, 2H), 2.26 (s, 6H), 1.89-1.82 (m, 2H), 1.76 (d, J=6.4 Hz, 3H), 1.75-1.60 (m, 2H).
mass: 513, 515 (M+1)$^+$.

Example 89

Synthesis of 3-[1-(2-chlorophenyl)ethoxy]-5-[6-(4-morpholin-4-ylbutoxy)imidazo[1,2-a]pyridin-3-yl]thiophene-2-carboxyamide [89] (hereinafter, referred to as the compound [89])

The target compound [89] was obtained as a pale yellow solid from the compound [85] and morpholine according to the method of Example 50.

A spectral data of the compound [89] is presented below.
$^1$H-NMR (CDCl$_3$) δ: 7.86 (d, J=2.4 Hz, 1H), 7.67 (s, 1H), 7.54 (d, J=9.6 Hz, 1H), 7.48 (d, J=-7.6, 1.6 Hz, 1H), 7.4 (dd, J=7.6, 0.6 Hz, 1H), 7.32 (ddd, J=7.6, 7.6, 1.6 Hz, 1H), 7.29-7.25 (m, 1H), 7.02 (dd, J=9.6, 2.4 Hz, 1H), 6.72 (s, 1H), 5.89 (q, J=6.4 Hz, 1H), 5.80 (brs, 1H), 3.90 (t, J=6.0 Hz, 2H), 3.74-3.7-2 (m, 4H), 2.48-2.41 (m, 6H), 1.88-1.80 (m, 2H), 1.77 (d, J=6.4 Hz, 3H), 1.73-1.65 (m, 2H).
mass: 555, 557 (M+1)$^+$.

Example 90

Synthesis of 3-[1-(2-chlorophenyl)ethoxy]-5-{6-[4-(4-methylpiperazin-1-yl)butoxy]imidazo[1,2-a]pyridin-3-yl}thiophene-2-carboxyamide [90] (hereinafter, referred to as the compound [90])

The target compound [90] was obtained as a pale yellow solid from the compound [85] and N-methylpiperazine according to the method of Example 50.
A spectral data of the compound [90] is presented below.
$^1$H-NMR (CDCl$_3$) δ: 7.84 (d, J=2.4 Hz, 1H), 7.67 (s, 1H), 7.54 (d, J=9.6 Hz, 1H), 7.48 (dd, J=7.6, 1.6 Hz, 1H), 7.41 (dd, J=7.6 Hz, 1.6 Hz, 1H), 7.32 (ddd, J=7.6, 7.6, 1.6 Hz, 1H), 7.29-7.22 (m, 1H), 7.02 (dd, J=9.6, 2.4 Hz, 1H), 6.72 (s, 1H), 5.89 (q, J=6.4 Hz, 1H), 5.74 (brs, 1H), 3.89 (t, J=6.0 Hz, 2H), 2.61-2.40 (m, 10H), 2.30 (s, 3H), 1.87-1.80 (m, 2H), 1.77 (d, J=6.4 Hz, 3H), 1.73-1.60 (m, 2H).
mass: 568, 570 (M+1)$^+$.

Example 91

Synthesis of t-butyl 4-{4-[(3-{5-(aminocarbonyl)-4-[1-(2-chlorophenyl)ethoxy]-2-thienyl}imidazo[1,2-a]pyridin-6-yl)oxy]butyl}piperazine-1-carboxylate [91] (hereinafter, referred to as the compound [91])

The target compound [91] was obtained as a pale yellow solid from the compound [85] and 1-t-butoxycarbonylpiperazine according to the method of Example 50.
A spectral data of the compound [91] is presented below.
$^1$H-NMR (CDCl$_3$) δ: 7.85-7.65 (m, 1H), 7.67 (s, 1H), 7.57-7.30 (m, 5H), 7.05-6.95 (m, 1H), 6.72 (s, 1H), 5.91-5.85 (m, 1H), 5.77 (brs, 1H), 3.91-3.85 (m, 2H), 3.50-3.35 (m, 4H), 2.50-2.35 (m, 6H), 1.90-1.80 (m, 2H), 1.80-1.50 (m, 5H), 1.46 (s, 9H).
mass: 654, 656 (M+1)$^+$.

Example 92

Synthesis of 3-[1-(2-chlorophenyl)ethoxy]-5-[6-(4-piperazin-1-ylbutoxy)imidazo[1,2-a]pyridin-3-yl]thiophene-2-carboxyamide [92] (hereinafter, referred to as the compound [92])

The target compound [92] was obtained as a pale yellow solid from the compound [91] according to the method of Example 68-(3).
A spectral data of the compound [92] is presented below.
$^1$H-NMR (CDCl$_3$) δ: 7.86 (d, J=2.4 Hz, 1H), 7.67 (s, 1H), 7.54 (d, J=9.6 Hz, 1H), 7.48 (dd, J=7.6, 1.6 Hz, 1H), 7.41 (dd, J=7.6, 1.6 Hz, 1H), 7.32 (ddd, J=7.6, 7.6, 1.6 Hz, 1H), 7.29-7.25 (m, 1H), 7.03 (dd, J=9.6, 2.4 Hz, 1H), 6.72 (s, 1H), 5.89 (q, J=6.4 Hz, 1H), 5.74 (brs, 1H), 3.90 (t, J=6.0 Hz, 2H), 2.93-2.91 (m, 4H), 2.50-2.40 (m, 6H), 1.90-1.80 (m, 2H), 1.77 (d, J=6.4 Hz, 3H), 1.73-1.60 (m, 2H).

mass: 554, 556 (M+1)$^+$.

Example 93

Synthesis of 3-[(1R)-1-(2-bromophenyl)ethoxy]-5-[6-(2-hydroxyethoxy)imidazo[1,2-a]pyridin-3-yl]thiophene-2-carboxyamide [93] (hereinafter, referred to as the compound [93])

The target compound [93] was obtained as a colorless solid from the compound [66-4] and (S)-2-bromo-α-methylbenzyl alcohol according to the methods of Example 66-(5) and (6).

A spectral data of the compound [93] is presented below.
$^1$H-NMR (CDCl$_3$) δ: 7.91 (d, J=2.4 Hz, 1H), 7.70 (s, 1H), 7.59 (d, J=7.6 Hz, 1H), 7.57 (d, J=9.6 Hz, 1H), 7.48 (d, J=6.8 Hz, 1H), 7.37 (dd, J=7.6, 7.6 Hz, 1H), 7.20 (dd, J=7.6, 6.8 Hz, 1H), 7.07 (dd, J=9.6, 2.4 Hz, 1H), 6.71 (s, 1H), 5.84 (q, J=6.4 Hz, 1H), 5.68 (brs, 1H), 4.02-4.00 (m, 4H), 2.17 (brs, 1H), 1.76 (d, J=6.4 Hz, 3H).

mass: 502, 504 (M+1)$^+$.

Example 94

Synthesis of 5-[6-(2-hydroxyethoxy)imidazo[1,2-a]pyridin-3-yl]-3-[1-(2-nitrophenyl)ethoxy]thiophene-2-carboxyamide [94] (hereinafter, referred to as the compound [94])

The target compound [94] was obtained as a colorless solid from the compound [66-4] and the compound [5-1] according to the methods of Example 66-(5) and (6).

A spectral data of the compound [94] is presented below.
$^1$H-NMR (CDCl$_3$) δ: 8.02 (d, J=8.0 Hz, 1H), 7.93 (d, J=2.4 Hz, 1H), 7.73 (dd, J=7.6, 6.0 Hz, 1H), 7.69 (d, J=6.0 Hz, 1H), 7.68 (s, 1H), 7.56 (d, J=9.6 Hz, 1H), 7.52 (dd, J=8.0, 7.6 Hz, 1H), 7.17 (brs, 1H), 7.08 (dd, J=9.6, 2.4 Hz, 1H), 6.73 (s, 1H), 6.24 (q, J=6.4 Hz, 1H), 5.78 (brs, 1H), 4.05-4.00 (m, 4H), 2.14 (brs, 1H), 1.84 (d, J=6.4 Hz, 3H).

mass: 469 (M+1)$^+$.

Example 95

Synthesis of 3-[(1R)-1-(2-cyanophenyl)ethoxy]-5-[6-(2-hydroxyethoxy)imidazo[1,2-a]pyridin-3-yl]thiophene-2-carboxyamide [95] (hereinafter, referred to as the compound [95])

The target compound [95] was obtained as a colorless solid from the compound [93] according to the method of Example 46.

A spectral data of the compound [95] is presented below.
$^1$H-NMR (CDCl$_3$) δ: 8.02 (d, J=2.4 Hz, 1H), 7.73 (d, J=7.6 Hz, 1H), 7.72 (s, 1H), 7.68 (dd, J=7.6, 7.2 Hz, 1H), 7.62 (d, J=7.2 Hz, 1H), 7.58 (d, J=9.6 Hz, 1H), 7.47 (ddd, J=7.6, 7.6, 1.6 Hz, 1H), 7.18 (brs, 1H), 7.10 (dd, J=9.6, 2.4 Hz, 1H), 6.83 (s, 1H), 5.88-5.82 (m, 2H), 4.11-4.02 (m, 4H), 2.40 (brs, 1H), 1.86 (d, J=6.4 Hz, 3H).

mass: 449 (M+1)$^+$.

Example 96

Synthesis of 5-(6-{2-[(3S)-3-hydroxypiperidin-1-yl]ethoxy}imidazo[1,2-a]pyridin-3-yl)-3-[1-(2-nitrophenyl)ethoxy]thiophene-2-carboxyamide [96] (hereinafter, referred to as the compound [96])

The target compound [96] was obtained as a pale yellow solid from the compound [94] and (S)-3-hydroxypiperidine according to the method of Example 50.

A spectral data of the compound [96] is presented below.
$^1$H-NMR (CDCl$_3$) δ: 8.02 (d, J=8.0 Hz, 1H), 7.92 (d, J=2.4 Hz, 1H), 7.74-7.66 (m, 3H), 7.55 (d, J=9.6 Hz, 1H), 7.51 (ddd, J=7.2, 7.2, 1.6 Hz, 1H), 7.18 (brs, 1H), 7.05 (dd, J=9.6, 2.4 Hz, 1H), 6.73 (s, 1H), 6.25 (q, J=6.4 Hz, 1H), 5.85 (brs, 1H), 4.09-4.01 (m, 2H), 3.90-3.82 (m, 1H), 2.86 (t, J=5.6 Hz, 2H), 2.80-2.42 (m, 4H), 1.83 (d, J=6.4 Hz, 3H), 1.83-1.50 (m, 4H).

mass: 552 (M+1)$^+$.

Example 97

Synthesis of 3-[(1R)-1-(2-cyanophenyl)ethoxy]-5-(6-{2-[(3S)-3-hydroxypiperidin-1-yl]ethoxy}imidazo[1,2-a]pyridin-3-yl)thiophene-2-carboxyamide [97] (hereinafter, referred to as the compound [97])

The target compound [97] was obtained as a pale yellow solid from the compound [95] and (S)-3-hydroxypiperidine according to the method of Example 50.

A spectral data of the compound [97] is presented below.
$^1$H-NMR (CDCl$_3$) δ: 7.96 (d, J=2.4 Hz, 1H), 7.74 (d, J=7.6 Hz, 1H), 7.70 (s, 1H), 7.68 (dd, J=7.6, 7.6 Hz, 1H), 7.61 (d, J=7.6 Hz, 1H), 7.56 (d, J=9.6 Hz, 1H), 7.47 (dd, J=7.6, 7.6 Hz, 1H), 7.20 (brs, 1H), 7.06 (dd, J=9.6, 2.4 Hz, 1H), 6.82 (s, 1H), 5.85 (q, J=6.4 Hz, 1H), 5.84 (brs, 1H), 4.12-4.02 (m, 2H), 3.90-3.83 (m, 1H), 2.86 (t, J=5.6 Hz, 2H), 2.76-2.44 (m, 4H), 1.86 (d, J=6.4 Hz, 3H), 1.85-1.50 (m, 4H).

mass: 532 (M+1)$^+$.

Example 98

Synthesis of 3-[1-(2-chlorophenyl)ethoxy]-5-[6-(piperidin-3-yloxy)imidazo[1,2-a]pyridin-3-yl]thiophene-2-carboxyamide [98] (hereinafter, referred to as the compound [98])

A hydrochloride salt of the target compound [98] was obtained as a pale yellow solid from the compound [66-1] and (S)-3-hydroxy-1-t-butoxycarbonylpiperidine according to the methods of Example 68-(2) and (3).

A spectral data of the compound [98] is presented below.
$^1$H-NMR (CD$_3$OD) δ: 8.41-8.38 (m, 1H), 8.24 (s, 1H), 7.96-7.94 (m, 2H), 7.63-7.58 (m, 1H), 7.42 (dd, J=7.6, 1.6 Hz, 1H), 7.37 (ddd, J=7.6, 7.6, 1.6 Hz, 1H), 7.31 (ddd, J=7.6, 7.6, 1.6 Hz, 1H), 7.24-7.23 (m, 1H), 6.09 (q, J=6.4 Hz, 1H) 4.95-4.80 (m, 1H), 3.75-3.10 (m, 4H), 2.20-1.90 (m, 3H), 1.90-1.70 (m, 1H), 1.79 (d, J=6.4 Hz, 3H).

mass: 497, 499 (M+1)$^+$.

Example 99

Synthesis of 3-[1-(2-chlorophenyl)ethoxy]-5-{6-[(2-hydroxyethyl)amino]imidazo[1,2-a]pyridin-3-yl}thiophene-2-carboxyamide [99] (hereinafter, referred to as the compound [99])

(1) 1.0 g of the compound [66-1] was dissolved in 1 mL of isopropyl alcohol, then 742 μL of 2-aminoethanol, 327 mg of sodium hydroxide, and 19 mg of copper iodide were added thereto, and the mixture was stirred overnight at 90° C. After cooling back to room temperature, the insolubles were filtered, the filtrate was concentrated under reduced pressure, and thus obtained residue was purified by silica gel column chromatography, to obtain 1.0 g of 2-(imidazo[1,2-a]pyridin-6-ylamino)-1-ethanol [99-1] (hereinafter, referred to as the compound [99-1]) as a dark brown oily product, (Literature: Org. Lett., 4(21) 3703 (2002)).

(2) The compound [99-1] was dissolved in 20 mL of N,N-dimethylformaide, then 1.95 g of imidazole and 2.88 g of t-butyldimethylsilylchloride were added, and the mixture was stirred overnight at room temperature. The reaction mixture was added with water and extracted with ethyl acetate. The organic layer was washed with water and saturated brine, and dried over anhydrous sodium sulfate. The insolubles were filtered, the filtrate was concentrated under reduced pressure, and thus obtained residue was purified by silica gel column chromatography, to obtain 0.65 g of N-(2-[t-butyl(dimethyl)silyl]oxymethyl)imidazo[1,2-a]pyridine-6-amine [99-2] (hereinafter, referred to as the compound [99-2]) as a light brown solid.

(3) 101 mg of the compound [99-2] was dissolved in 5 mL of chloroform, then 84 μL of pyridine and 66 μL of acetic anhydride were added, and the mixture was stirred overnight at room temperature. The reaction mixture was added with water and extracted with chloroform. The organic layer was washed with water and saturated brine, and dried over anhydrous sodium sulfate. The insolubles were filtered, the filtrate was concentrated under reduced pressure, and thus obtained residue was purified by preparative thin-layer chromatography, to obtain 108 mg of N-(2-[t-butyl(dimethyl)silyl]oxyethyl)-N-imidazo[1,2-a]pyridine-6-ylacetoamide [99-3] (hereinafter, referred to as the compound [99-3]) as a light brown oily product.

(4) 56 mg of methyl 5-6-[acetyl(2-[t-butyl(dimethyl)silyl]oxyethyl)amino]imidazo[1,2-a]pyridin-3-yl-3-hydroxy-2-thiophenecarboxylic acid [99-4] (hereinafter, referred to as the compound [99-4]) was obtained as a pale yellow amorphous from 108 mg of the compound [99-3] according to the methods of Example 1-(1) to (3).

(5) 40 mg of the target compound [99] was obtained as a pale yellow solid from 56 mg of the compound [99-4] and 2-chloro-α-methylbenzyl alcohol according to the method of Example 20.

A spectral data of the compound [99] is presented below.
$^1$H-NMR (CDCl$_3$) δ: 7.61 (s, 1H), 7.56 (d, J=2.4 Hz, 1H), 7.49-7.39 (m, 3H), 7.35-7.20 (m, 2H), 6.80 (dd, J=9.6, 2.4 Hz, 1H), 6.70 (s, 1H), 5.88 (q, J=6.4 Hz, 1H), 5.82 (brs, 1H), 4.00 (brs, 1H), 3.92 (t, J=5.2 Hz, 2H), 3.20-3.16 (m, 2H), 1.75 (d, J=6.4 Hz, 3H).
mass: 457, 459 (M+1)$^+$.

Synthesis of 3-[1-(2-chlorophenyl)ethoxy]-5-{6-[(2-hydroxyethyl)(methyl)amino]imidazo[1,2-a]pyridin-3-yl}thiophene-2-carboxyamide [100] (hereinafter, referred to as the compound [100])

19 mg of the compound [99] was dissolved in 3 mL of chloroform and 1 mL of methanol, then 31 μL of formaldehyde (37% aqueous solution) and 415 μL of a methanol solution containing 9 mg of zinc chloride and 8 mg of sodium cyanotrihydroborate were added, and the mixture was stirred overnight at room temperature. The solvent was concentrated under reduced pressure, and thus obtained residue was purified by preparative thin-layer chromatography, to obtain 13 mg of the target compound [100] as a pale yellow solid.

A spectral data of the compound [100] is presented below.
$^1$H-NMR (CDCl$_3$) δ: 7.59 (s, 1H), 7.55 (d, J=2.4 Hz, 1H), 7.49 (dd, J=8.0, 1.6 Hz, 1H), 7.45 (d, J=9.6 Hz, 1H), 7.39 (dd, J=8.0, 1.6 Hz, 1H), 7.32 (ddd, J=8.0, 8.0, 1.6 Hz, 1H), 7.28-7.24 (m, 1H), 7.11 (dd, J=9.6, 2.4 Hz, 1H), 6.67 (s, 1H), 6.86 (q, J=6.4 Hz, 1H), 5.81 (brs, 1H), 4.39 (s, 1H), 3.83 (t, J=5.2 Hz, 2H), 3.39 (t, J=5.2 Hz, 2H), 2.83 (s, 3H), 1.76 (d, J=6.4 Hz, 3H).
mass: 471, 473 (M+1)$^+$.

Example 101

Synthesis of 5-(6-aminoimidazo[1,2-a]pyridin-3-yl)-3-[(1R)-1-(2-chlorophenyl)ethoxy]thiophene-2-carboxyamide [101] (hereinafter, referred to as the compound [101])

(1) 1.0 g of methyl 5-(6-bromoimidazo[1,2-a]pyridin-3-yl)-3-hydroxythiophene-2-carboxylic acid [101-1] (hereinafter, referred to as the compound [101-1]) was obtained as a pale yellow solid from 2.0 g of 2-amino-5-bromopyridine according to the steps of Example 66-(1), (3), and (4), in that order.

(2) 1.1 g of methyl 5-(6-bromoimidazo[1,2-a]pyridin-3-yl)-3-[(1R)-1-(2-chlorophenyl)oxy-2-thiophenecarboxylic acid [101-2] (hereinafter, referred to as the compound [101-2]) was obtained as a pale yellow amorphous from the compound [101-1] and (S)-α-(2-chlorophenyl)ethyl alcohol according to the method of Example 1-(4).

(3) 33 mg of the compound [101-2] was dissolved in 2 mL of toluene, then 12.3 μL of benzophenoneimine, 29 mg of cesium carbonate, 14 mg of 4,5-bis(diphenylphosphino)-9,9-dimethylxanthene, and 7 mg of bis(dibenzylideneacetone)palladium were added, and the mixture was stirred overnight at 80° C. The reaction mixture was added with water and extracted with chloroform. The organic layer was washed with water and saturated brine, and dried over anhydrous sodium sulfate. The insolubles were filtered, the filtrate was concentrated under reduced pressure, and thus obtained residue was purified by preparative thin-layer chromatography, to obtain 25 mg of methyl 3-[1-(2-chlorophenyl)ethoxy]-5-{6-[(diphenylmethylene)amino]imidazo[1,2-a]pyridin-3-yl}thiophene-2-carboxylic acid [101-3] (hereinafter, referred to as the compound [101-3]) as a pale yellow amorphous.

(4)-3-[(1R) 1-(2-chlorophenyl)ethoxy]-5-{6-[(diphenylmethylene)amino]imidazo[1,2-a]pyridin-3-yl}thiophene-2-carboxyamide was obtained from 22 mg of the compound [101-3] according to the method of Example 10-(2), which was then dissolved in 4N hydrochloric acid-dioxane, and the mixture was stirred for 1 hour at room temperature. The solvent was removed by pouring and the residue was purified by preparative thin-layer chromatography to obtain 13 mg of the target compound [101] as a colorless solid.

A spectral data of the compound [101] is presented below.
$^1$H-NMR (DMSO-d$_6$) δ: 8.31 (s, 1H), 8.04 (d, J=2.4 Hz, 1H), 7.89 (brs, 1H), 7.75 (d, J=9.6 Hz, 1H), 7.68 (dd, J=8.0, 1.6 Hz, 1H), 7.50-7.47 (m, 2H), 7.42 (ddd, J=8.0, 7.6 Hz, 1.6 Hz, 1H), 7.36 (dd, J=7.6, 1.6 Hz, 1H), 7.34 (s, 1H), 7.18 (brs, 1H), 5.97 (q, J=6.4 Hz, 1H), 1.74 (d, J=6.4 Hz, 3H).
mass: 413, 415 (M+1)$^+$.

Example 102

Synthesis of 3-[(1R)-1-(2-chlorophenyl)ethoxy]-5-(6-piperazin-1-ylimidazo[1,2-a]pyridin-3-yl)thiophene-2-carboxyamide [102] (hereinafter, referred to as the compound [102])

(1) 30 mg of the compound [101-2] was dissolved in 2 mL of toluene, then 17 mg of 1-t-butoxycarbonylpiperazine, 29 mg of cesium carbonate, 16 mg of (R)-(+)-2,2'-bis(di-p-tolylphosphino)-1,1-binaphthyl, and 7 mg of bis(dibenzylideneacetone)palladium were added, and the mixture was stirred overnight at 100° C. The reaction mixture was added with water and extracted with chloroform. The organic layer was washed with water and saturated brine, and dried over anhydrous sodium sulfate. The insolubles were filtered, the filtrate was concentrated under reduced pressure, and thus obtained residue was purified by preparative thin-layer chromatography, to obtain 19 mg of t-butyl 4-{3-[4-[1-(2-chlorophenyl)ethoxy]-5-(methoxycarbonyl)-2-thienyl]imidazopyridine[1,2-a]pyridin-6-yl}piperazine-1-carboxylic acid [102-1] (hereinafter, referred to as the compound [102-1] as a light green oily product.

(2) 8.1 mg of t-butyl 4-(3-{5-(aminocarbonyl)-4-[1-(2-chlorophenyl)ethoxy]-2-thienyl}imidazopyridine[1,2-a]pyridin-6-yl)piperazine-1-carboxylic acid [102-2] (hereinafter, referred to as the compound [102-2]) was obtained as a pale yellow solid from 19 mg of the compound [102-1] according to the method of Example 10-(2).

(3) 5.4 mg of a hydrochloride salt of the target compound [102] was obtained as a pale yellow solid from 8.1 mg of the compound [102-2] according to the method of Example 68-(3).

A spectral data of the compound [102] is presented below.
$^1$H-NMR (DMSO-$d_6$) δ: 9.46 (brs, 2H), 8.31 (s, 1H), 7.91-7.85 (m, 4H), 7.67 (d, J=7.2 Hz, 1H), 7.51 (d, J=6.8 Hz, 1H), 7.44-7.36 (m, 2H), 7.33 (s, 1H), 7.18 (brs, 1H), 5.99 (q, J=6.4 Hz, 1H), 3.41-3.37 (m, 4H), 3.35-3.26 (m, 4H), 1.72 (d, J=6.4 Hz, 3H).
mass: 482, 484 (M+1)$^+$.

Example 103

Synthesis of 3-[(1R)-1-(2-chlorophenyl)ethoxy]-5-[6-(4-methylpiperazin-1-yl)imidazo[1,2-a]pyridin-3-yl]thiophene-2-carboxyamide [103] (hereinafter, referred to as the compound [103])

3.2 mg of the target compound [103] was obtained as a light blue solid from 4.6 mg of the compound [102] according to the method of Example 100.

A spectral data of the compound [103] is presented below.
$^1$H-NMR (CDCl$_3$) δ: 7.74 (d, J=2.4 Hz, 1H), 7.65 (s, 1H), 7.54 (d, J=9.6 Hz, 1H), 7.48 (dd, J=9.6, 2.0 Hz, 1H), 7.41 (dd, J=9.6, 2.0 Hz, 1H), 7.34-7.26 (m, 2H), 7.13 (dd, J=9.6, 2.4 Hz, 1H), 6.71 (s, 1H), 5.88 (q, J=6.4 Hz, 1H), 5.78 (brs, 1H), 3.18-3.11 (m, 4H), 2.67-2.64 (m, 4H), 2.43 (s, 3H), 1.76 (d, J=6.4 Hz, 3H).
mass: 496, 498 (M+1)$^+$.

Example 104

Synthesis of 3-[(1R)-1-(2-chlorophenyl)ethoxy]-5-[6-(dimethylamino)imidazo[1,2-a]pyridin-3-yl]thiophene-2-carboxyamide [104] (hereinafter, referred to as the compound [104])

7 mg of the target compound [104] was obtained as a pale yellow solid from the compound [101] according to the method of Example 100.

A spectral data of the compound [104] is presented below.
$^1$H-NMR (CDCl$_3$) δ: 7.64 (s, 1H), 7.57 (d, J=2.4 Hz, 1H), 7.52 (d, J=9.6 Hz, 1H), 7.48 (dd, J=7.6, 1.6 Hz, 1H), 7.40 (dd, J=7.2, 1.6 Hz, 1H), 7.33-7.24 (m, 2H), 7.09 (dd, J=9.6, 2.4 Hz, 1H), 6.71 (s, 1H), 5.88 (q, J=6.4 Hz, 1H), 5.86 (brs, 1H), 2.87 (s, 6H), 1.76 (d, J=6.4 Hz, 3H).
mass: 441, 443 (M+1)$^+$.

Example 105

Synthesis of 3-[(1R)-1-(2-chlorophenyl)ethoxy]-5-[6-(3-hydroxypiperidin-1-yl)imidazo[1,2-a]pyridin-3-yl]thiophene-2-carboxyamide [105] (hereinafter, referred to as the compound [105])

The target compound [105] was obtained as a colorless solid from the compound [101-2] and 3-hydroxypiperidine according to the methods of Example 102-(1) and (2).

A spectral data of the compound [105] is presented below.
$^1$H-NMR (CDCl$_3$) δ: 7.81-7.78 (m, 1H), 7.65 (s, 1H), 7.54 (d, J=9.6 Hz, 1H), 7.48 (d, J=7.6 Hz, 1H), 7.41 (d, J=8.0 Hz, 1H), 7.36-7.15 (m, 3H), 7.13 (dd, J=9.6, 2.4 Hz, 1H), 6.71 (s, 1H), 5.89 (q, J=6.4 Hz, 1H), 5.75 (brs, 1H), 4.05-3.95 (m, 1H), 3.20-3.15 (m, 1H), 3.05-2.85 (m, 3H), 2.05-1.97 (m, 2H), 1.85-1.75 (m, 2H), 1.76 (d, J=6.4 Hz, 3H).
mass: 497, 499 (M+1)$^+$.

Example 106

Synthesis of 3-[(1R)-1-(2-chlorophenyl)ethoxy]-5-[6-(3-hydroxypyrrolidin-1-yl)imidazo[1,2-a]pyridin-3-yl]thiophene-2-carboxyamide [106] (hereinafter, referred to as the compound [106])

The target compound [106] was obtained as a colorless solid from the compound [101-2] and 3-hydroxypyrrolidine according to the methods of Example 102-(1) and (2).

A spectral data of the compound [106] is presented below.
$^1$H-NMR (CDCl$_3$) δ: 7.62 (d, J=2.4 Hz, 1H), 7.52-7.45 (m, 2H), 7.43-7.20 (m, 4H), 6.89 (dd, J=9.6, 2.4 Hz, 1H), 6.68 (s, 1H), 5.90-5.84 (m, 1H), 5.72 (brs, 1H), 4.65-4.60 (m, 1H), 3.50-3.40 (m, 2H), 3.30-3.20 (m, 2H), 2.25-2.05 (m, 2H), 1.76 (d, J=6.4 Hz, 3H).
mass: 483, 485 (M+1)$^+$.

Example 107

Synthesis of 3-[(1R)-1-(2-chlorophenyl)ethoxy]-5-[6-(hydroxymethyl)imidazo[1,2-a]pyridin-3-yl]thiophene-2-carboxyamide [107] (hereinafter, referred to as the compound [107])

(1) To 150 mL of a tetrahydrofuran suspension solution containing 5.5 g of lithium aluminum hydride, 5.0 g of 6-amino-nicotinic acid was added in an ice bath, and the mixture was stirred overnight at 50° C. Thereto, sodium sulfate decahydrate was added until there are no bubbles, and stirred overnight at room temperature. The insolubles were filtered through celite, well washed with chloroform, and the filtrate was concentrated under reduced pressure. Thus obtained (6-amino-3-pyridinyl)methanol [107-1] (hereinafter, referred to as the compound [107-1]) was used in the subsequent reaction without further purification.

(2) Imidazo[1,2-a]pyridin-6-yl methanol [107-2] (hereinafter, referred to as the compound [107-2]) was obtained from 3.0 g of the compound [107-1] according to the method of Example 66-(1). The compound [107-2] was used in the subsequent reaction without further purification.

(3) 4.4 g of 6-([t-butyl(dimethyl)silyl]oxymethyl)imidazo[1,2-a]pyridine [107-3] (hereinafter, referred to as the compound [107-3]) was obtained as a colorless solid from the compound [107-2] according to the method of Example 54-(2). The compound [107-3] was used in the subsequent reaction without further purification.

(4) Methyl 5-[6-([t-butyl(dimethyl)silyl]oxymethyl)imidazo[1,2-a]pyridin-3-yl]-3-hydroxy-2-thiophenecarboxylic acid [107-4] (hereinafter, referred to as the compound [107-4]) was obtained as a pale yellow solid from the compound [107-3] according to the methods of Example 1-(1) to (3).

(5) 500 mg of the target compound [107] was obtained from 500 mg of the compound [107-4] and 180 μL of (S)-α-(2-chlorophenyl)ethyl alcohol according to the method of Example 20 as pale yellow amorphous.

A spectral data of the compound [107] is presented below.
$^1$H-NMR (CD$_3$OD) δ: 8.34 (s, 1H), 7.76 (s, 1H), 7.64-7.61 (m, 2H), 7.50 (dd, J=8.0, 1.5 Hz, 1H), 7.45 (dd, J=9.0, 1.5 Hz, 1H), 7.41 (dt, J=1.5, 8.0 Hz, 1H), 7.35 (dt, J=1.5, 8.0 Hz, 1H), 7.06 (s, 1H), 6.10 (q, J=6.5 Hz, 1H), 4.67 (s, 2H), 1.81 (d, J=6.5 Hz, 3H).
mass: 428, 430 (M+1)$^+$.

Example 108

Synthesis of 3-[1-(2-chlorophenyl)ethoxy]-5-(6-formylimidazo[1,2-a]pyridin-3-yl)thiophene-2-carboxyamide [108] (hereinafter, referred to as the compound [108])

(1) 500 mg of 3-[1-(2-chlorophenyl)ethoxy]-5-[6-(hydroxymethyl)imidazo[1,2-a]pyridin-3-yl]thiopene-2-carboxyamide [108-1] (hereinafter, referred to as the compound [108-1]) was obtained as pale yellow amorphous from the compound [107-4] and 2-chloro-α-methylbenzyl alcohol according to the method of Example 20.

(2) 163 mg of the compound [108-1] was dissolved in 2 mL of dimethylsulfoxide, then 0.85 mL of triethylamine and 485 mg of sulfur trioxide pyridine complex were added, and the mixture was stirred for 4 hours at room temperature. The reaction mixture was added with water and extracted with chloroform. The organic layer was washed with saturated brine, and dried over anhydrous sodium sulfate. The insolubles were filtered, the filtrate was concentrated under reduced pressure, and thus obtained residue was purified by silica gel column chromatography, to obtain 150 mg of the target compound [108] as a pale yellow solid.

A spectral data of the compound [108] is presented below.
$^1$H-NMR (CDCl$_3$) δ: 9.89 (s, 1H), 8.69 (s, 1H), 7.82 (s, 1H), 7.72 (s, 1H), 7.71 (s, 1H), 7.49 (dd, J=7.5, 2.0 Hz, 1H), 7.43 (dd, J=7.5, 2.0 Hz, 1H), 7.34 (dt, J=1.5, 7.5 Hz, 1H), 7.29 (dt, J=1.5, 7.5 Hz, 1H), 7.25 (br, 1H), 6.78 (s, 1H), 5.92 (br, 1H), 5.91 (q, J=6.5 Hz, 1H), 1.77 (d, J=6.5 Hz, 3H).
mass: 426, 428 (M+1)$^+$.

Example 109

Synthesis of 3-[1-(2-chlorophenyl)ethoxy]-5-[6-pyrrolidin-1-ylmethyl]imidazo[1,2-a]pyridin-3-yl]thiophene-2-carboxyamide [109] (hereinafter, referred to as the compound [109])

The compound [108] and pyrrolidine were dissolved in chloroform and methanol, a methanol solution of zinc chloride and sodium cyanotrihydroborate was added thereto, according to the method of Example 100, and the mixture was stirred overnight at room temperature. The solvent was concentrated under reduced pressure and thus obtained residue was purified by preparative thin-layer chromatography, to obtain the target compound [109] as a colorless solid.

A spectral data of the compound [109] is presented below.
$^1$H-NMR (CDCl$_3$) δ: 8.21 (s, 1H), 7.72 (s, 1H), 7.60 (d, J=9.0 Hz, 1H), 7.48 (dd, J=7.5, 1.5 Hz, 1H), 7.42 (dd, J=7.5, 1.5 Hz, 1H), 7.35-7.26 (m, 4H), 6.73 (s, 1H), 5.91 (q, J=6.5 Hz, 1H), 5.70 (br, 1H), 3.59 (m, 2H), 2.53-2.50 (m, 4H), 1.81-1.78 (m, 4H), 1.77 (d, J=6.5 Hz, 3H).
mass: 481, 483 (M+1)$^+$.

Example 110

Synthesis of 3-[1-(2-chlorophenyl)ethoxy]-5-[6-(morpholin-4-ylmethyl)imidazo[1,2-a]pyridin-3-yl]thiophene-2-carboxyamide [110] (hereinafter, referred to as the compound [110])

The target compound [110] was obtained as a colorless solid from the compound [108] and morpholine according to the method of Example 109.

A spectral data of the compound [110] is presented below.
$^1$H-NMR (CDCl$_3$) δ: 8.17 (s, 1H), 7.71 (s, 1H), 7.61 (d, J=9.0 Hz, 1H), 7.48 (dd, J=7.5, 1.5 Hz, 1H), 7.42 (dd, J=7.5, 1.5 Hz, 1H), 7.34-7.25 (m, 4H), 6.72 (s, 1H), 5.90 (br, 1H); 5.90 (q, J=6.5 Hz, 1H), 3.73-3.69 (m, 4H), 3.45 (dd, J=18.5, 17.5 Hz, 2H), 2.47-2.43 (m, 4H), 1.76 (d, J=6.5 Hz, 3H).
mass: 497, 499 (M+1)$^+$.

Example 111

Synthesis of 3-[1-(2-chlorophenyl)ethoxy]-5-[6-(piperidin-1-ylmethyl)imidazo[1,2-a]pyridin-3-yl]thiophene-2-carboxyamide [111] (hereinafter, referred to as the compound [111])

The target compound [111] was obtained as a colorless solid from the compound [108] and piperidine according to the method of Example 109.

A spectral data of the compound [111] is presented below.
$^1$H-NMR (CDCl$_3$) δ: 8.31 (s, 1H), 7.75 (s, 1H), 7.65 (d, J=9.0 Hz, 1H), 7.52 (dd, J=7.5, 1.5 Hz, 1H), 7.43 (dd, J=7.5, 1.5 Hz, 1H), 7.36-7.28 (m, 4H), 6.84 (s, 1H), 6.15-5.90 (m, 1H), 5.86 (br, 1H), 3.55 (s, 2H), 2.70-2.30 (m, 4H), 1.80-1.60 (m, 4H), 1.79 (d, J=6.5 Hz, 3H), 1.56-1.48 (m, 2H).
mass: 495, 497 (M+1)$^+$.

Example 112

Synthesis of 3-[1-(2-chlorophenyl)ethoxy]-5-{6-[(diethylamino)methyl]imidazo[1,2-a]pyridin-3-yl}thiophene-2-carboxyamide [112] (hereinafter, referred to as the compound [112])

The target compound [112] was obtained as a colorless solid from the compound [108] and diethylamine according to the method of Example 109.

A spectral data of the compound [112] is presented below.
$^1$H-NMR (CDCl$_3$) δ: 8.19 (s, 1H), 7.70 (s, 1H), 7.59 (d, J=9.0 Hz, 1H), 7.47 (dd, J=7.5, 1.5 Hz, 1H), 7.40 (dd, J=7.5, 1.5 Hz, 1H), 7.34-7.25 (m, 4H), 6.73 (s, 1H), 5.89 (q, J=6.5 Hz, 1H), 5.77 (br, 1H), 3.52 (dd, J=18.5, 14.0 Hz, 2H), 2.53

(q, J=7.0 Hz, 4H), 1.76 (d, J=6.5 Hz, 3H), 1.03 (t, J=7.0 Hz, 6H).
mass: 483, 485 (M+1)⁺.

Example 113

Synthesis of 3-[1-(2-chlorophenyl)ethoxy]-5-{6-[(4-methylpiperazin-1-yl)methyl]imidazo[1,2-a]pyridin-3-yl}thiophene-2-carboxyamide [113] (hereinafter, referred to as the compound [113])

The target compound [113] was obtained as a colorless solid from the compound [108] and N-methylpiperazine according to the method of Example 109.
A spectral data of the compound [113] is presented below.
¹H-NMR (CDCl₃) δ: 8.19 (s, 1H), 7.75 (s, 1H), 7.63 (d, J=9.0 Hz, 1H), 7.51-7.46 (m, 2H), 7.36-7.26 (m, 4H), 6.75 (s, 1H), 5.93 (br, 1H), 5.92 (q, J=6.5 Hz, 1H), 3.53 (dd, J=21.0, 13.5 Hz, 2H), 2.85-2.55 (m, 8H), 2.49 (s, 3H), 1.78 (d, J=6.5 Hz, 3H).
mass: 510, 512 (M+1)⁺.

Example 114

Synthesis of 3-[1-(2-chlorophenyl)ethoxy]-5-{6-[(dimethylamino)methyl]imidazo[1,2-a]pyridin-3-yl}thiophene-2-carboxyamide [114] (hereinafter, referred to as the compound [114])

The target compound [114] was obtained as a colorless solid from the compound [108] and dimethylamine according to the method of Example 109.
A spectral data of the compound [114] is presented below.
¹H-NMR (CD₃OD) δ: 8.36 (s, 1H), 7.78 (s, 1H), 7.65 (d, J=10.0 Hz, 1H), 7.62 (dd, J=7.5, 1.5 Hz, 1H), 7.51-7.46 (m, 2H), 7.41 (dt, J=1.5, 8.0, 1H), 7.35 (dt, J=1.5, 8.0 Hz, 1H), 7.07 (s, 1H), 6.12 (q, J=6.5, 1H), 4.88 (s, 1H), 3.68 (dd, J=23.0, 12.5 Hz, 2H), 2.41 (s, 6H), 1.81 (d, J=6.5 Hz, 3H).
mass: 455, 457 (M+1)⁺.

Example 115

Synthesis of 3-[1-(2-chlorophenyl)ethoxy]-5-{6-[(methylamino)methyl]imidazo[1,2-a]pyridin-3-yl}thiophene-2-carboxyamide [115] (hereinafter, referred to as the compound [115])

The target compound [115] was obtained as a colorless solid from the compound [108] and N-methylamine according to the method of Example 109.
A spectral data of the compound [115] is presented below.
¹H-NMR (CDCl₃) δ: 8.23 (s, 1H), 7.71 (s, 1H), 7.61 (d, J=9.5 Hz, 1H), 7.47 (dd, J=7.5, 1.5 Hz, 1H), 7.41 (dd, J=7.5, 1.5 Hz, 1H), 7.33-7.25 (m, 4H), 6.72 (s, 1H), 5.91 (br, 1H), 5.89 (q, J=6.5 Hz, 1H), 3.74 (s, 2H), 2.46 (s, 3H), 1.78 (br, 1H), 1.75 (d, J=6.5 Hz, 3H).
mass: 441, 443 (M+1)⁺.

Example 116

Synthesis of 3-[1-(2-chlorophenyl)ethoxy]-5-(6-{[(3R)-3-hydroxypiperidin-1-yl]methyl}imidazo[1,2-a]pyridin-3-yl)thiophene-2-carboxyamide [116] (hereinafter, referred to as the compound [116])

The target compound [116] was obtained as a colorless solid from the compound [108] and (R)-3-hydroxypiperidine according to the method of Example 109.
A spectral data of the compound [116] is presented below.
¹H-NMR (CDCl₃) δ: 8.18 (s, 1H), 7.71 (s, 1H), 7.60 (d, J=9.5 Hz, 1H), 7.47 (dd, J=7.5, 1.5 Hz, 1H), 7.41 (dd, J=7.5, 1.5 Hz, 1H), 7.33-7.20 (m, 4H), 6.73 (s, 1H), 5.93-5.87 (m, 1H), 5.80 (br, 1H), 3.85-3.78 (m, 1H), 3.47 (s, 2H), 2.54-2.39 (m, 3H), 2.38-2.26 (m, 1H), 1.85-1.53 (m, 4H), 1.76 (d, J=6.5 Hz, 3H).
mass: 511, 513 (M+1)⁺.

Example 117

Synthesis of 3-[1-(2-chlorophenyl)ethoxy]-5-(6-{[(3S)-3-hydroxypyrrolidin-1-yl]methyl}imidazo[1,2-a]pyridin-3-yl)thiophene-2-carboxyamide [117] (hereinafter, referred to as the compound [117])

The target compound [117] was obtained as a colorless solid from the compound [108] and (S)-3-hydroxypyrrolidine according to the method of Example 109;
A spectral data of the compound [117] is presented below.
¹H-NMR (CDCl₃) δ: 8.22 (s, 1H), 7.71 (s, 1H), 7.60 (d, J=9.5 Hz, 1H), 7.47 (d, J=7.5 Hz, 1H), 7.41 (d, J=7.5 Hz, 1H), 7.33-7.23 (m, 4H), 6.73 (s, 1H), 5.92-5.87 (m, 1H), 5.85 (br, 1H), 4.40-4.36 (m, 1H), 3.61 (s, 2H), 2.89-2.83 (m, 1H), 2.70-2.68 (m, 1H), 2.59-2.56 (m, 1H), 2.38-2.32 (m, 1H), 2.25-2.17 (m, 1H), 1.81-1.75 (m, 1H), 1.75 (d, J=6.5 Hz, 3H).
mass: 497, 499 (M+1)⁺.

Example 118

Synthesis of 3-[1-(2-chlorophenyl)ethoxy]-5-(6-{[(3R)-3-hydroxypyrrolidin-1-yl]methyl}imidazo[1,2-a]pyridin-3-yl)thiophene-2-carboxyamide [118] (hereinafter, referred to as the compound [118])

The target compound [118] was obtained as a colorless solid from the compound [108] and (R)-3-hydroxypyrrolidine according to the method of Example 109.
A spectral data of the compound [118] is presented below.
¹H-NMR (CDCl₃) δ: 8.23 (s, 1H), 7.71 (s, 1H), 7.60 (d, J=9.5 Hz, 1H), 7.47 (d, J=7.5 Hz, 1H), 7.41 (d, J=7.5 Hz, 1H), 7.32-7.29 (m, 4H), 6.73 (s, 1H), 5.92-5.87 (m, 1H), 5.85 (br, 1H), 4.39-4.36 (m, 1H), 3.61 (s, 2H), 2.89-2.84 (m, 1H), 2.70-2.68 (m, 1H), 2.60-2.57 (m, 1H), 2.38-2.32 (m, 1H), 2.26-2.17 (m, 1H), 1.82-1.71 (m, 1H), 1.75 (d, J=6.5 Hz, 3H).
mass: 497, 499 (M+1)⁺.

Example 119

Synthesis of 3-[(1R)-1-(2-chlorophenyl)ethoxy]-5-[6-(piperazin-1-ylmethyl)imidazo[1,2-a]pyridin-3-yl]thiophene-2-carboxyamide [119] (hereinafter, referred to as the compound [119])

(1) 3-[(1R)-1-(2-chlorophenyl)ethoxy]-5-(6-formylimidazo[1,2-a]pyridin-3-yl)thiophene-2-carboxyamide [119-1] (hereinafter, referred to as the compound [119-1]) was obtained as a pale yellow solid from the compound [107] according to the method of Example 108-(2).
(2) The target compound [119] was obtained as a colorless solid from the compound [119-1] and piperazine according to the method of Example 109.
A spectral data of the compound [119] is presented below.
¹H-NMR (CDCl₃) δ: 8.17 (s, 1H), 7.71 (s, 1H), 7.60 (d, J=9.5 Hz, 1H), 7.48 (d, J=7.5 Hz, 1H), 7.42 (d, J=7.5 Hz, 1H), 7.34-7.26 (m, 4H), 6.73 (s, 1H), 6.31 (br, 1H), 5.90 (q, J=6.5

Hz, 1H), 3.44 (dd, J=19, 5, 13.0 Hz, 2H), 2.90-2.87 (m, 4H), 2.42 (br, 4H), 1.96 (br, 1H), 1.76 (d, J=6.5 Hz, 3H).
mass: 496, 498 (M+1)$^+$.

Example 120

Synthesis of 3-[1-(2-chlorophenyl)ethoxy]-5-{6-[(4-hydroxypiperidin-1-yl)methyl]imidazo[1,2-a]pyridin-3-yl}thiophene-2-carboxyamide-[120] (hereinafter, referred to as the compound [120])

The target compound [120] was obtained as a colorless solid from the compound [108] and 4-hydroxypiperidine according to the method of Example 109.
A spectral data of the compound [120] is presented below.
$^1$H-NMR (CDCl$_3$) δ: 8.20 (s, 1H), 7.71 (s, 1H), 7.60 (d, J=9.5 Hz, 1H), 7.47 (dd, J=7.5, 1.5 Hz, 1H), 7.41 (dd, J=7.5, 1.5 Hz, 1H), 7.34-7.21 (m, 4H), 6.73 (s, 1H), 5.90 (q, J=6.5 Hz, 1H), 5.85 (br, 1H), 3.74-3.69 (m, 1H), 3.46 (s, 2H), 2.75-2.72 (m, 2H), 2.26-2.16 (m, 2H), 1.92-1.85 (m, 2H), 1.76 (d, J=6.5 Hz, 3H), 1.63-1.52 (m, 2H).
mass: 511, 513 (M+1)$^+$.

Example 121

Synthesis of 5-[6-(aminomethyl)imidazo[1,2-a]pyridin-3-yl]-3-[(1R)-1-(2-chlorophenyl)ethoxy]thiophene-2-carboxyamide [121] (hereinafter, referred to as the compound [121])

(1) 20 mg of the compound [107] was dissolved in 0.5 mL of chloroform, and 20 μL of triethylamine and 11 μL of methanesulfonyl chloride were added thereto. The mixture was stirred for 1 hour at room temperature, and the reaction mixture was added with water and extracted with chloroform. The organic layer was washed with saturated brine, and dried over anhydrous sodium sulfate. The insolubles were filtered and the filtrate was concentrated under reduced pressure. Thus obtained compound [3-(5-(aminocarbonyl)-4-[(1R)-1-(2-chlorophenyl)ethyl]oxy-2-thienyl)imidazo[1,2-a]pyridin-6-yl]methylmethanesulfonate [121-1] (hereinafter, referred to as the compound [121-1]) was used in the subsequent reaction without further purification.
(2) The compound [121-1] was dissolved in 0.5 mL of N,N-dimethylformamide, then 8 mg of sodium iodide and 17 mg of sodium azide were added, and the mixture was stirred for 1 hour at room temperature. The reaction mixture was added with water and extracted with chloroform. The organic layer was washed with saturated brine and dried over anhydrous sodium sulfate. The insolubles were filtered, the filtrate was concentrated under reduced pressure, and thus obtained residue was purified by preparative thin-layer chromatography, to obtain 12.3 mg of 5-[6-(azidomethyl)imidazo[1,2-a]pyridin-3-yl]-3-[(1R)-1-(2-chlorophenyl)ethyl]oxy-2-thiophenecarboxyamide [121-2] (hereinafter, referred to as the compound [121-2]) as a pale yellow solid.
(3) 12.3 mg of the compound [121-2] was dissolved in 0.5 mL of chloroform and 0.5 mL of methanol, then 30 mg of a 10% palladium carbon catalyst was added thereto, and the solution was stirred overnight at room temperature under a hydrogen atmosphere of 1 atmospheric pressure. The insolubles were filtered through celite, the filtrate was concentrated under reduced pressure, and thus obtained residue was purified by preparative thin-layer chromatography, to obtain 3.7 mg of the target compound [121] as a colorless solid.

A spectral data of the compound [121] is presented below.
$^1$H-NMR (CD$_3$OD) δ: 8.30 (s, 1H), 7.75 (s, 1H), 7.63 (d, J=9.0 Hz, 2H), 7.52-7.48 (m, 2H), 7.43-7.35 (m, 2H), 7.07 (s, 1H), 6.12 (q, J=6.0 Hz, 1H), 3.88 (s, 2H), 1.82 (d, J=6.0 Hz, 3H), 1.31 (br, 2H).
mass: 427, 429 (M+1)$^+$.

Example 122

Synthesis of t-butyl{(3S)-1-[(3-{5-(aminocarbonyl)-4-[(1R)-1-(2-chlorophenyl)ethoxy]-2-thienyl}imidazo[1,2-a]pyridin-6-yl)methyl]pyrrolidin-3-yl}carbamate [122] (hereinafter, referred to as the compound [122])

The target compound [122] was obtained as a colorless solid from the compound [119-1] and (3R)-(+)-3-(t-butoxycarbonylamino)pyrrolidine according to the method of Example 109.
A spectral data of the compound [122] is presented below.
$^1$H-NMR (CDCl$_3$) δ: 8.19 (s, 1H), 7.73 (s, 1H), 7.61 (d, J=9.5 Hz, 1H), 7.49 (d, J=7.5 Hz, 1H), 7.42 (d, J=7.5 Hz, 1H), 7.35-7.27 (m, 4H), 6.74 (s, 1H), 6.06 (br, 1H), 5.91 (q, J=6.5 Hz, 1H), 4.84 (br, 1H), 4.25-3.98 (m, 1H), 3.56 (dd, J=21.0, 13.0 Hz, 2H), 2.83-2.72 (m, 1H), 2.68-2.60 (m, 1H), 2.57-2.42 (m, 1H), 2.42-2.17 (m, 2H), 2.05-1.83 (m, 1H), 1.77 (d, J=6.5 Hz, 3H), 1.43 (s, 9H).
mass: 596, 598 (M+1)$^+$.

Example 123

Synthesis of t-butyl{(3R)-1-[(3-{5-(aminocarbonyl)-4-[(1R)-1-(2-chlorophenyl)ethoxy]-2-thienyl}imidazo[1,2-a]pyridin-6-yl)methyl]pyrrolidin-3-yl}carbamate [123] (hereinafter, referred to as the compound [123])

The target compound [123] was obtained as a colorless solid from the compound [119-1] and (3S)-(−)-3-(t-butoxycarbonylamino)pyrrolidine according to the method of Example 109.
A spectral data of the compound [123] is presented below.
$^1$H-NMR (CDCl$_3$) δ: 8.19 (s, 1H), 7.73 (s, 1H), 7.62 (d, J=9.5 Hz, 1H), 7.49 (d, J=7.5 Hz, 1H), 7.42 (d, J=7.5 Hz, 1H), 7.35-7.27 (m, 4H), 6.74 (s, 1H), 6.07 (br, 1H), 5.91 (q, J=6.5 Hz, 1H), 4.85 (br, 1H), 4.25-3.98 (m, 1H), 3.56 (s, 2H), 2.84-2.71 (m, 1H), 2.68-2.59 (m, 1H), 2.57-2.42 (m, 1H), 2.40-2.15 (m, 2H), 2.03-1.83 (m, 1H), 1.77 (d, J=6.5 Hz, 3H), 1.43 (s, 9H).
mass: 596, 598 (M+1)$^+$.

Example 124

Synthesis of 5-(6-{[(3S)-3-aminopyrrolidin-1-yl]methyl}imidazo[1,2-a]pyridin-3-yl)-3-[(1R)-1-(2-chlorophenyl)ethoxy]thiophene-2-carboxyamide [124] (hereinafter, referred to as the compound [124])

The target compound [124] was obtained as a colorless solid from the compound [122] according to the method of Example 68-(3).
A spectral data of the compound [124] is presented below.
$^1$H-NMR (CDCl$_3$) δ: 8.25 (s, 1H), 7.72 (s, 1H), 7.61 (d, J=9.5 Hz, 1H), 7.47 (dd, J=7.5, 1.5 Hz, 1H), 7.41 (dd, J=7.5, 1.5 Hz, 1H), 7.34-7.23 (m, 4H); 6.73 (s, 1H), 5.91 (br, 1H), 5.90 (q, J=6.5 Hz, 1H), 3.60 (s, 2H), 2.82-2.76 (m, 1H);

2.72-2.68 (m, 1H), 2.51-2.42 (m, 2H), 2.28-2.17 (m, 1H), 1.95 (br, 2H), 1.80-1.70 (m, 1H), 1.76 (d, J=6.5 Hz, 3H), 1.66-1.55 (m, 1H).

mass: 496, 498 (M+1)⁺.

Example 125

Synthesis of 5-(6-{[(3R)-3-aminopyrrolidin-1-yl] methyl}imidazo[1,2-a]pyridin-3-yl)-3-[(1R)-1-(2-chlorophenyl)ethoxy]thiophene-2-carboxamide [125] (hereinafter, referred to as the compound [125])

The target compound [125] was obtained as a colorless solid from the compound [123] according to the method of Example 68-(3).

A spectral data of the compound [125] is presented below.
$^1$H-NMR (CDCl$_3$) δ: 8.24 (s, 1H), 7.72 (s, 1H), 7.61 (d, J=9.5 Hz, 1H), 7.48 (dd, J=7.5, 1.5 Hz, 1H), 7.42 (dd, J=7.5, 1.5 Hz, 1H), 7.35-7.23 (m, 4H), 6.74 (s, 1H), 5.90 (q, J=6.5 Hz, 1H), 5.83 (br, 1H), 3.59 (dd, J=26.0, 13.0 Hz, 2H), 2.80-2.74 (m, 1H), 2.72-2.68 (m, 1H), 2.49-2.41 (m, 2H), 2.26-2.17 (m, 1H), 1.81 (br, 3H), 1.76 (d, J=6.5 Hz, 3H), 1.62-1.57 (m, 1H).

mass: 496, 498 (M+1)⁺.

Example 126

Synthesis of 5-(6-{[(2-aminoethyl)amino] methyl}imidazo[1,2-a]pyridin-3-yl)-3-[(1R)-1-(2-chlorophenyl)ethoxy]thiophene-2-carboxamide [126] (hereinafter, referred to as the compound [126])

A trifluoroacetate salt of the target compound [126] was obtained as a colorless solid from the compound [119-1] and ethylenediamine according to the method of Example 109.

A spectral data of the compound [126] is presented below.
$^1$H-NMR (CD$_3$OD) δ: 8.82 (s, 1H), 8.08 (s, 1H), 7.88 (d, J=3.0 Hz, 2H), 7.59 (d, J=8.0 Hz, 1H), 7.43 (d, J=8.0 Hz, 1H), 7.38-7.30 (m, 2H), 7.18 (s, 1H), 6.08 (q, J=6.0 Hz, 1H), 4.38 (dd, =23.0, 15.5 Hz, 2H), 3.40-3.25 (m, 4H), 1.79 (d, J=6.0 Hz, 3H).

mass: 470, 472 (M+1)⁺.

Example 127

Synthesis of 3-[(1R)-1-(2-chlorophenyl)ethoxy]-5-[6-({[2-(dimethylamino)ethyl]amino}methyl)imidazo[1,2-a]pyridin-3-yl]thiophene-2-carboxamide [127] (hereinafter, referred to as the compound [127])

The target compound [127] was obtained as a colorless solid from the compound [119-1] and N,N-dimethylethylenediamine according to the method of Example 109.

A spectral data of the compound [127] is presented below.
$^1$H-NMR (CDCl$_3$) δ: 8.25 (s, 1H), 7.72 (s, 1H), 7.62 (d, J=9.5 Hz, 1H), 7.48 (dd, J=7.5, 1.5 Hz, 1H), 7.42 (dd, J=7.5, 1.5 Hz, 1H), 7.34-7.24 (m, 4H), 6.74 (s, 1H), 5.91 (q, J=6.5 Hz, 1H), 5.85 (br, 1H), 3.80 (dd; J=15.0, 13.5 Hz, 2H), 2.67 (t, J=5.5 Hz, 2H), 2.48 (t, J=5.55H, 2H), 2.25 (s, 6H), 1.90-1.76 (m, 1H), 1.77 (d, J=6.5 Hz, 3H).

mass: 498, 500 (M+1)⁺.

Example 128

Synthesis of 3-[(1R)-1-(2-chlorophenyl)ethoxy]-5-{6-[(4-formylpiperazin-1-yl)methyl]imidazo[1,2-a]pyridin-3-yl}thiophene-2-carboxamide [128] (hereinafter, referred to as the compound [128])

The target compound [128] was obtained as a colorless solid from the compound [119-1] and 1-piperazinecarboxaldehyde according to the method of Example 109.

A spectral data of the compound [128] is presented below.
$^1$H-NMR (CDCl$_3$) δ: 8.22 (s, 1H), 8.05 (s, 1H), 7.74 (s, 1H), 7.64 (d, J=9.5 Hz, 1H), 7.49 (dd, J=7.5, 1.5 Hz, 1H), 7.41 (dd, J=7.5, 1.5 Hz, 1H), 7.35-7.23 (m, 4H), 6.74 (s, 1H), 5.90 (q, J=6.5 Hz, 1H), 5.73 (br, 1H), 3.59-3.57 (m, 2H), 3.51 (dd, J=16.5, 13.5 Hz, 2H), 3.39 (t, J=5.5 Hz, 2H), 2.48-2.44 (m, 4H), 1.77 (d, J=6.5 Hz, 3H).

mass: 524, 526 (M+1)⁺.

Example 129

Synthesis of 5-{6-[(4-acetylpiperazin-1-yl)methyl] imidazo[1,2-a]pyridin-3-yl}-3-[(1R)-1-(2-chlorophenyl)ethoxy]thiophene-2-carboxamide [129] (hereinafter, referred to as the compound [129])

The target compound [129] was obtained as a colorless solid from the compound [119-1] and 1-acetylpiperazine according to the method of Example 109.

A spectral data of the compound [129] is presented below.
$^1$H-NMR (CDCl$_3$) δ: 8.22 (s, 1H), 7.73 (s, 1H), 7.63 (d, J=9.5 Hz, 1H), 7.49 (dd, J=7.5, 1.5 Hz, 1H), 7.41 (dd, J=7.5, 1.5 Hz, 1H), 7.35-7.24 (m, 4H), 6.74 (s, 1H), 5.91 (br, 1H), 5.90 (q, J=6.5 Hz, 1H), 3.64-3.62 (m, 2H), 3.56-3.45 (m, 4H), 2.45-2.43 (m, 4H), 2.10 (s, 3H), 1.77 (d, J=6.5 Hz, 3H).

mass: 538, 540 (M+1)⁺.

Example 130

Synthesis of 3-[(1R)-1-(2-chlorophenyl)ethoxy]-5-(6-{[4-(2-hydroxyethyl)piperazin-1-yl] methyl}imidazo[1,2-a]pyridin-3-yl)thiophene-2-carboxamide [130] (hereinafter, referred to as the compound [130])

The target compound [130] was obtained as a colorless solid from the compound [119-1] and N-(2-hydroxyethyl)piperazine according to the method of Example 109.

A spectral data of the compound [130] is presented below.
$^1$H-NMR (CDCl$_3$) δ: 8.21 (s, 1H), 7.73 (s, 1H), 7.61 (d, J=9.5 Hz, 1H), 7.49 (dd, J=7.5, 1.5 Hz, 1H), 7.43 (dd, J=7.5, 1.5 Hz, 1H), 7.35-7.24 (m, 4H), 6.74 (s, 1H), 5.91 (q, J=6.5 Hz, 1H), 5.90 (br, 1H), 3.64 (t, J=5.0 Hz, 2H), 3.49 (dd, J=18.0, 13.5 Hz, 2H), 2.61-2.52 (m, 6H), 2.60 (t, J=5.0 Hz, 2H) 2.30-2.00 (m, 3H), 1.77 (d, J=6.5 Hz, 3H).

mass: 540, 542 (M+1)⁺.

Example 131

Synthesis of 3-[(1R)-1-(2-chlorophenyl)ethoxy]-5-(6-{[[2-(dimethylamino)ethyl](methyl)amino] methyl}imidazo[1,2-a]pyridin-3-yl)thiophene-2-carboxamide [131] (hereinafter, referred to as the compound [131])

The target compound [131] was obtained as a colorless solid from the compound [119-1] and N,N,N'-trimethylethylenediamine according to the method of Example 109.

A spectral data of the compound [131] is presented below.
$^1$H-NMR (CDCl$_3$) δ: 8.19 (s, 1H), 7.72 (s, 1H), 7.61 (d, J=9.5 Hz, 1H), 7.48 (dd, J=7.5, 1.5 Hz, 1H), 7.42 (dd, J=7.5, 1.5 Hz, 1H), 7.35-7.27 (m, 4H), 6.74 (s, 1H), 5.91 (q, J=6.5 Hz, 1H), 5.86 (br, 1H), 3.49 (dd, J=18.0, 13.5 Hz, 2H), 2.53-2.47 (m, 4H), 2.25 (s, 9H), 1.77 (d, J=6.5 Hz, 3H).

mass: 512, 514 (M+1)$^+$.

Example 132

Synthesis of 5-(6-{[(3R)-3-(acetylamino)pyrrolidin-1-yl]methyl}imidazo[1,2-a]pyridin-3-yl)-3-[(1R)-1-(2-chlorophenyl)ethoxy]thiophene-2-carboxyamide [132] (hereinafter, referred to as the compound [132])

8 mg of the compound [125] was dissolved in 0.3 mL of chloroform, then 9 μL of triethylamine and 5 μL of acetylchloride were added, and the mixture was stirred for 30 minutes at room temperature. The reaction mixture was added with water and extracted with chloroform. The organic layer was washed with saturated brine, and dried over anhydrous sodium sulfate. The insolubles were filtered and the filtrate was concentrated under reduced pressure. Thus obtained residue was purified by preparative thin-layer chromatography to obtain 2.4 mg of the target compound [132] as a colorless solid.

A spectral data of the compound [132] is presented below.
$^1$H-NMR (CDCl$_3$) δ: 8.31 (s, 1H), 7.74 (s, 1H), 7.62 (d, J=9.5 Hz, 1H), 7.48 (dd, J=7.5, 1.5 Hz, 1H), 7.42 (dd, J=7.5, 1.5 Hz, 1H), 7.34-7.24 (m, 4H), 6.75 (s, 1H), 5.91 (q, J=6.5 Hz, 1H), 5.88 (br, 1H), 5.75 (br, 1H), 3.59 (dd, J=18.0, 13.5 Hz, 2H), 2.92-2.89 (m, 1H), 2.65-2.63 (m, 1H), 2.56-2.52 (m, 1H), 2.34-2.28 (m, 2H), 1.95 (s, 3H), 1.78-1.60 (m, 2H), 1.77 (d, J=6.5 Hz, 3H).

mass: 538, 540 (M+1)$^+$.

Example 133

Synthesis of methyl{(3R)-1-[(3-{5-(aminocarbonyl)-4-[(1R)-1-(2-chlorophenyl)ethoxy]-2-thienyl}imidazo[1,2-a]pyridin-6-yl)methyl]pyrrolidin-3-yl}carbamate [133] (hereinafter, referred to as the compound [133])

The target compound [133] was obtained from the compound [125] and methylchloroformate according to the method of Example 132.

A spectral data of the compound [133] is presented below.
$^1$H-NMR (CDCl$_3$) δ: 8.21 (s, 1H), 7.23 (s, 1H), 7.62 (d, J=9.5 Hz, 1H), 7.48 (dd, J=7.5, 1.5 Hz, 1H), 7.42 (dd, J=7.5, 1.5 Hz, 1H), 7.34-7.24 (m, 4H), 6.73 (s, 1H), 5.91 (q, J=6.5 Hz, 1H), 5.86 (br, 1H), 4.98 (br, 1H), 3.64 (s, 3H), 3.57 (dd, J=18.0, 13.5 Hz, 2H), 2.86-2.76 (m, 1H), 2.65-2.53 (m, 2H), 2.39-2.25 (m, 2H), 1.77 (d, J=6.5 Hz, 3H), 1.70-1.58 (m, 2H).

mass: 554, 556 (M+1)$^+$.

Example 134

Synthesis of 3-[(1R)-1-(2-chlorophenyl)ethoxy]-5-{6-[(3-oxopiperazin-1-yl)methyl]imidazo[1,2-a]pyridin-3-yl}thiophene-2-carboxyamide [134] (hereinafter, referred to as the compound [134])

The target compound [134] was obtained as a colorless solid from the compound [107] and piperazin-2-one according to the method of Example 50.

A spectral data of the compound [134] is presented below.
$^1$H-NMR (CDCl$_3$) δ: 8.25 (s, 1H), 7.74 (s, 1H), 7.64 (d, J=9.5 Hz, 1H), 7.49 (dd, J=7.5, 1.5 Hz, 1H), 7.42 (dd, J=7.5, 1.5 Hz, 1H), 7.35-7.27 (m, 4H), 6.75 (s, 1H), 6.30 (s, 1H), 6.18 (s, 1H), 5.91 (q, J=6.5 Hz, 1H), 3.56 (s, 2H), 3.38 (m, 2H), 3.19 (s, 2H), 2.67 (t, J=5.5 Hz, 2H), 1.77 (d, J=6.5 Hz, 3H).

mass: 510, 512 (M+1)$^+$.

Example 135

Synthesis of methyl {4-[(3-{5-(aminocarbonyl)-4-[(1R)-1-(2-chlorophenyl)ethoxy]-2-thienyl}imidazo[1,2-a]pyridin-6-yl)methyl]piperazin-1-yl}acetate [135] (hereinafter, referred to as the compound [135])

10 mg of the compound [119] was dissolved in 1 mL of chloroform, then 10 μL of diisopropylethylamine and 6 μL of methylbromoacetate were added, and the mixture was stirred overnight at room temperature. The reaction mixture was added with water and then extracted with chloroform. The organic layer was washed with saturated brine and dried over anhydrous sodium sulfate. The insolubles were filtered and the filtrate was concentrated under reduced pressure. Thus obtained residue was purified by preparative thin-layer chromatography to obtain 2.4 mg of the target compound [135] as a colorless solid.

A spectral data of the compound [135] is presented below.
$^1$H-NMR (CDCl$_3$) δ: 8.16 (s, 1H), 7.72 (s, 1H), 7.61 (d, J=9.5 Hz, 1H), 7.49 (dd, J=7.5, 1.5 Hz, 1H), 7.43 (dd, J=7.5, 1.5 Hz, 1H), 7.35-7.26 (m, 4H), 6.73 (s, 1H), 5.92 (br, 1H), 5.91 (q, J=6.5 Hz, 1H), 3.73 (s, 3H), 3.48 (dd, J=23.0, 13.0 Hz, 2H), 3.24 (s, 2H), 2.62 (br, 4H), 2.55 (br, 4H), 1.77 (d, J=6.5 Hz, 3H).

mass: 568, 570 (M+1)$^+$.

Example 136

Synthesis of 3-[(1R)-1-(2-chlorophenyl)ethoxy]-5-(6-{[(3R)-3-(dimethylamino)pyrrolidin-1-yl]methyl}imidazo[1,2-a]pyridin-3-yl)thiophene-2-carboxyamide [136] (hereinafter, referred to as the compound [136])

The target compound [136] was obtained as a colorless solid from the compound [107] and (3R)-(+)-3-(dimethylamino)pyrrolidine according to the method of Example 50.

A spectral data of the compound [136] is presented below.
$^1$H-NMR (CDCl$_3$) δ: 8.20 (s, 1H), 7.22 (s, 1H), 7.60 (d, J=9.0 Hz, 1H), 7.47 (dd, J=7.5, 1.5 Hz, 1H), 7.42 (dd, J=7.5, 1.5 Hz, 1H), 7.34-7.23 (m, 4H), 6.73 (s, 1H), 5.91 (q, J=6.5 Hz, 1H), 5.81 (br, 1H), 3.57 (dd, J=53.0, 13.0 Hz, 2H), 2.83-2.77 (m, 2H), 2.70-2.65 (m, 1H), 2.57-2.51 (m, 1H), 2.41-2.38 (m, 1H), 2.23 (s, 6H), 2.06-1.97 (m, 1H), 1.80-1.70 (m, 1H), 1.77 (d, J=6.5 Hz, 3H).

mass: 524, 526 (M+1)$^+$.

Example 137

Synthesis of 5-[6-(acetidin-1-ylmethyl)imidazo[1,2-a]pyridin-3-yl]-3-[(1R)-1-(2-chlorophenyl)ethoxy]thiophene-2-carboxyamide [137] (hereinafter, referred to as the compound [137])

The target compound [137] was obtained as a colorless solid from the compound [107] and azetidine according to the method of Example 50.

A spectral data of the compound [137] is presented below.
$^1$H-NMR (CDCl$_3$) δ: 8.19 (s, 1H), 7.71 (s, 1H), 7.59 (d, J=9.0 Hz, 1H), 7.49 (dd, J=7.5, 1.5 Hz, 1H), 7.42 (dd, J=7.5, 1.5 Hz, 1H), 7.35-7.22 (m, 4H), 6.74 (s, 1H), 5.91 (q, J=6.5 Hz, 1H), 5.87 (br, 1H), 3.53 (s, 2H), 3.23 (t, J=6.5 Hz, 4H), 2.12 (quin, J=6.5 Hz, 2H), 1.77 (d, J=6.5 Hz, 3H).
mass: 467, 469 (M+1)$^+$.

Example 138

Synthesis of 3-[1-(2-chlorophenyl)-2-hydroxyethoxy]-5-[6-(hydroxymethyl)imidazo[1,2-a]pyridin-3-yl]thiophene-2-carboxyamide [138] (hereinafter, referred to as the compound [138])

The target compound [138] was obtained as a colorless solid from the compound [107-4] and the compound [54-2] according to the method of Example 20.
A spectral data of the compound [138] is presented below.
$^1$H-NMR (DMSO-d$_6$) δ: 8.32 (s, 1H), 7.81 (s, 1H), 7.77 (brs, 1H), 7.63 (d, J=9.3 Hz, 1H), 7.55 (dd, J=2.0, 6.3 Hz, 1H), 7.49 (dd, J=1.9, 7.3 Hz, 1H), 7.40-7.31 (m, 4H), 6.99 (s, 1H), 5.83 (q, J=3.4 Hz, 1H), 5.59 (t, J=5.9 Hz, 1H), 5.41 (t, J=5.8 Hz, 1H), 4.54 (d, J=5.9 Hz, 2H), 3.89-3.79 (m, 2H).
mass: 444, 446 (M+1)$^+$.

Example 139

Synthesis of 3-[(1R)-1-(2-bromophenyl)ethoxy]-5-[6-(hydroxymethyl)imidazo[1,2-a]pyridin-3-yl]thiophene-2-carboxyamide [139] (hereinafter, referred to as the compound [139])

The target compound [139] was obtained as a colorless solid from the compound [107-4] and (S)-2-bromo-α-methylbenzyl-alcohol according to the method of Example 20.
A spectral data of the compound [139] is presented below.
$^1$H-NMR (DMSO-d$_6$) δ: 8.37 (s, 1H), 7.82 (s, 1H), 7.73 (brs, 1H), 7.67-7.63 (m, 3H), 7.45 (t, J=6.8 Hz, 1H), 7.34 (dd, J=1.5, 9.2 Hz, 1H), 7.26 (m, 1H), 7.13 (brs, 1H), 7.10 (s, 1H), 5.93 (q, J=6.3 Hz, 1H), 5.42 (t, J=5.3 Hz, 1H), 4.56 (d, J=5.3 Hz, 2H), 1.70 (d, J=6.3 Hz, 3H).
mass: 472, 474 (M+1)$^+$.

Example 140

Synthesis of 3-[(1R)-1-(2-cyanophenyl)ethoxy]-5-[6-(hydroxymethyl)imidazo[1,2-a]pyridin-3-yl]thiophene-2-carboxyamide [140] (hereinafter, referred to as the compound [140])

The target compound [140] was obtained as a colorless solid from the compound [139] according to the method of Example 46.
A spectral data of the compound [140] is presented below.
$^1$H-NMR (DMSO-d$_6$) δ: 8.39 (s, 1H), 7.90-7.84 (m, 3H), 7.79-7.76 (m, 2H), 7.67-7.52 (m, 2H), 7.39-7.33 (m, 2H), 7.06 (brs, 1H), 5.97 (q, J=6.4 Hz, 1H), 5.41 (t, J=5.4 Hz, 1H), 4.56 (d, J=5.4 Hz, 2H), 1.80 (d, J=6.3 Hz, 3H).
mass: 419 (M+1)$^+$.

Example 141

Synthesis of 5-[6-(hydroxymethyl)imidazo[1,2-a]pyridin-3-yl]-3-[1-(2-nitrophenyl)ethoxy]thiophene-2-carboxyamide [141] (hereinafter, referred to as the compound [141])

The target compound [141] was obtained as a colorless solid from the compound [107-4] and the compound [5-1] according to the method of Example 20.
A spectral data of the compound [141] is presented below.
$^1$H-NMR (DMSO-d$_6$) δ: 8.32 (s, 1H), 8.01 (dd, J=1.5, 8.3 Hz, 1H), 7.86 (dd, J=1.5, 7.8 Hz, 1H), 7.82 (s, 1H), 7.79 (t, J=7.8 Hz, 1H), 7.74 (brs, 1H), 7.64 (d, J=9.2 Hz, 1H), 7.58 (m, 1H), 7.33 (dd, J=1.5, 9.2 Hz, 1H), 7.19 (s, 1H), 7.08 (brs, 1H), 6.15 (q, J=6.3 Hz, 1H), 5.39 (t, J=5.4 Hz, 1H), 4.54 (d, J=5.4 Hz, 2H), 1.80 (d, J=6.3 Hz, 3H).
mass: 439 (M+1)$^+$.

Example 142

Synthesis of 3-{5-(aminocarbonyl)-4-[(1R)-1-(2-chlorophenyl)ethoxy]-2-thienyl}imidazo[1,2-a]pyridine-6-carboxylic acid [142] (hereinafter, referred to as the compound [142])

10 mg of the compound [119-1], 12 μL of 2-methyl-2-butene, and 9 mg of sodium dihydrogenphosphate were dissolved in a mixed solvent of 0.1 mL of water and 0.4 mL of t-butanol, then 3 mg of sodium chlorite was added, and the mixture was stirred for 1 hour at room temperature. The reaction mixture was added with water and then extracted with chloroform. The organic layer was washed with saturated brine and dried over anhydrous sodium sulfate. The insolubles were filtered and the filtrate was concentrated under reduced pressure. Thus obtained residue was purified by preparative thin-layer chromatography to obtain 4 mg of the target compound [142] as a colorless solid;
A spectral data of the compound [142] is presented below.
$^1$H-NMR (CD$_3$OD) δ: 9.04 (s, 1H), 7.90 (d, J=9.0 Hz, 1H), 7.83 (s, 1H), 7.66 (d, J=9.0 Hz, 1H), 7.60 (d, J=8.0 Hz, 1H), 7.45 (d, J=8.0 Hz, 1H), 7.38-7.28 (m, 2H), 7.11 (s, 1H), 6.08 (q, J=6.0 Hz, 1H), 1.79 (d, J=6.0 Hz, 3H).
mass: 442, 444 (M+1)$^+$.

Example 143

Synthesis of methyl 3-[5-(aminocarbonyl)-4-{[2-(trifluoromethyl)benzyl]oxy}-2-thienyl]imidazo[1,2-a]pyridine-7-carboxylic acid [143] (hereinafter, referred to as the compound [143])

(1) 2.08 g of methyl imidazo[1,2-a]pyridine-7-carboxylic acid [143-1] (hereinafter, referred to as the compound [143-1]) was obtained as a colorless solid from 1.26 g of 2-aminopyridinecarboxylic acid methyl ester according to the method of Example 66-(1).
(2) Methyl 3-(3-methoxy-3-oxo-1-propynyl)imidazo[1,2-a]pyridine-7-carboxylic acid [143-2] (hereinafter, referred to as the compound [143-2]) was obtained as a pale yellow solid from the compound [143-1] according to the methods of Example 1-(1) and (2).
(3) 1.14 g of potassium thioacetate and 1.95 g of t-butyl-bromoacetate were dissolved in 10 mL of N,N-dimethylformamide, and the mixture was stirred for 3 hours at room temperature. The reaction mixture was added with water and then extracted with ethyl acetate. The organic layer was washed with saturated brine and dried over anhydrous sodium sulfate. The insolubles were filtered and the filtrate was concentrated under reduced pressure to obtain 2.16 g of t-butyl 2-(acetylthio)acetate [143-3] (hereinafter, referred to as the compound [143-3]) as a pale yellow oily product. The compound [143-3] was used in the subsequent reaction without further purification.

(4) 408 mg of the compound [143-3] was dissolved in 10 mL of methanol, then 2.4 mL of a 1N aqueous sodium hydroxide solution was added, and the mixture was stirred for 30 minutes at room temperature. The reaction solution was neutralized with 1N hydrochloric acid, and the solvent was concentrated under reduced pressure and extracted with ethyl acetate. The organic layer was washed with saturated brine and dried over anhydrous sodium sulfate. The insolubles were filtered and the filtrate was concentrated under reduced pressure to obtain 200 mg of t-butyl 2-mercaptoacetate [143-4] (hereinafter, referred to as the compound [143-4]) as a pale yellow oily product. The compound [143-4] was used in the subsequent reaction without further purification.

(5) Methyl 3-[5-(t-butoxycarbonyl)-4-hydroxy-2-thienyl]imidazo[1,2-a]pyridine-7-carboxylic acid [143-5] (hereinafter, referred to as the compound [143-5]) was obtained as a pale yellow solid from the compound [143-2] and the compound [143-4] according to the method of Example 1-(3).

(6) 104 mg of the compound [143-5] was dissolved in 3 mL of N,N-dimethylformamide, then 73 mg of 2-trifluoromethylbenzylbromide and 76 mg of potassium carbonate were added, and the mixture was stirred from 5 hours at room temperature. The reaction mixture was added with water and then extracted with ethyl acetate. The organic layer was washed with saturated brine and dried over anhydrous sodium sulfate. The insolubles were filtered, the filtrate was concentrated under reduced pressure, and the residue was purified by silica gel chromatography, to obtain 131 mg of methyl 3-[5-(t-butoxycarbonyl)-4-[(2-trifluoromethylbenzyl)oxy]-2-thienyl]imidazo[1,2-a]pyridine-7-carboxylic acid [143-6] (hereinafter, referred to as the compound [143-6]) as a pale yellow oily product.

(7) 30 mg of the compound [143-6] was dissolved in 3 mL of chloroform, and 2 mL of trifluoroacetic acid was added and stirred for 3 hours. A monocarboxylic acid substance of the target compound was confirmed by LC-MS, and the solvent was concentrated under reduced pressure. The residue was dissolved in N,N-dimethylformamide, then 500 mg of ammonium chloride, 300 mg of 1-hydroxybenzotriazole, 2 mL of triethylamine, and 300 mg of 1-(3-dimethylaminopropyl)-3-ethylcarbodiimide were added, and the mixture was stirred overnight at room temperature. The reaction mixture was added with water and then extracted with ethyl acetate. The organic layer was washed with saturated brine and dried over anhydrous sodium sulfate. The insolubles were filtered, the filtrate was concentrated under reduced pressure, and the residue was purified by silica gel chromatography, to obtain 15 mg of the target compound [143] as a colorless oily product.

A spectral data of the compound [143] is presented below.
$^1$H-NMR (CDCl$_3$) δ: 8.48 (d, J=7.6 Hz, 1H), 8.41 (s, 1H), 7.98 (brs, 1H), 7.77 (d, J=8.0 Hz, 1H), 7.68-7.63 (m, 2H), 7.60-7.50 (m, 2H), 7.07 (s, 1H), 7.00 (brs, 1H), 5.90 (brs, 1H), 5.51 (s, 2H), 3.98 (s, 3H).
mass: 476 (M+1)$^+$.

Example 144

Synthesis of 3-(5-(aminocarbonyl)-4-{[2-(trifluoromethyl)benzyl]oxy}-2-thienyl)imidazo[1,2-a]pyridine-7-carboxylic acid [144] (hereinafter, referred to as the compound [144])

14 mg of the compound [143] was dissolved in 1 mL of tetrahydrofuran and 1 mL of methanol, then 1 mL of a 1N aqueous sodium hydroxide solution was added, and the mixture was stirred for 2 hours at 60° C. After the reaction, the reaction solution was neutralized with 1N hydrochloric acid and concentrated under reduced pressure. Thus obtained residue was purified by preparative reverse-phase liquid chromatography to obtain 1.7 mg of a trifluoroacetate salt of the target compound [144] as a colorless oily product.

A spectral data of the compound [144] is presented below.
$^1$H-NMR (DMSO-d$_6$) δ: 8.86 (d, J=7.6 Hz, 1H), 8.25 (m, 2H), 7.90-7.86 (m, 2H), 7.85-7.78 (m, 2H), 7.68-7.66 (m, 1H), 7.54 (d, J=7.2 Hz, 1H), 5.60 (s, 2H).
mass: 462 (M+1)$^+$.

Example 145

Synthesis of 3-(5-(aminocarbonyl)-4-{[2-(trifluoromethyl)benzyl]oxy}-2-thienyl)-N-(2-morpholin-4-ylethyl)imidazo[1,2-a]pyridine-7-carboxyamide [145] (hereinafter, referred to as the compound [145])

A trifluoroacetate salt of the target compound [145] was obtained as a colorless solid from the compound [144] and N-(2-aminoethyl)morpholine according to the method of Example 8.

A spectral data of the compound [145] is presented below.
$^1$H-NMR (CD$_3$OD) δ: 8.91 (d, J=7.8 Hz, 1H), 8.37 (s, 1H), 8.32 (s, 1H), 7.86-7.72 (m, 4H), 7.68-7.60 (m, 2H), 5.65 (s, 2H), 4.20-4.00 (m, 2H), 3.90-3.82 (m, 2H), 3.80-3.70 (m, 2H), 3.55-3.45 (m, 2H), 3.42-3.35 (m, 4H).
mass: 534 (M+1)$^+$.

Example 146

Synthesis of 3-(5-(aminocarbonyl)-4-{[2-(trifluoromethyl)benzyl]oxy}-2-thienyl)imidazo[1,2-a]pyridine-7-carboxyamide [146] (hereinafter, referred to as the compound [146])

A trifluoroacetate salt of the target compound [146] was obtained as a colorless solid from the compound [145] according to the method of Example 8.

A spectral data of the compound [146] is presented below.
$^1$H-NMR (CD$_3$OD) δ: 8.91 (d, J=7.2 Hz, 1H), 8.39 (s, 1H), 8.34 (s, 1H), 7.81-7.78 (m, 3H), 7.76 (m, 1H), 7.68-7.64 (m, 2H), 5.65 (s, 2H).
mass: 461 (M+1)$^+$.

Example 147

Synthesis of 5-(7-aminoimidazo[1,2-a]pyridin-3-yl)-3-[1-(2-chlorophenyl)ethoxy]thiophene-2-carboxyamide [147] (hereinafter, referred to as the compound [147])

(1) Methyl 3-[5-(t-butoxycarbonyl)-4-[1-(2-chlorophenyl)ethoxy]-2-thienyl]imidazo[1,2-a]pyridine-7-carboxylic acid (target compound) [147-1] (hereinafter, referred to as the compound [147-1]) was obtained as a colorless oily product from the compound [143-5] and 2-chloro-α-methylbenzyl alcohol according to the method of Example 1-(4).

(2) Methyl 3-[5-(aminocarbonyl)-4-[1-(2-chlorophenyl)ethoxy]-2-thienyl]imidazo[1,2-a]pyridine-7-carboxylic acid [147-2] (hereinafter, referred to as the compound [147-2]) was obtained as a pale yellow solid from the compound [147-1] according to the method of Example 143-(7).

(3) 3-[5-(aminocarbonyl)-4-[1-(2-chlorophenyl)ethoxy]-2-thienyl]imidazo[1,2-a]pyridine-7-carboxylic acid [147-3] (hereinafter, referred to as the compound [147-3]) was obtained as a colorless solid from the compound [147-2] according to the method of Example 144.

(4) 66 mg of the compound [147-3] was dissolved in 3 mL of 1,4-dioxane and 2 mL of t-butanol, then 45 μL of triethylamine and 10 μL of diphenylphosphorylazide were added, and the mixture was stirred for 2 hours at 100° C. The reaction mixture was added with water and then extracted with chloroform. The organic layer was washed with saturated brine and dried over anhydrous sodium sulfate. The insolubles were filtered, the filtrate was concentrated under reduced pressure, and thus obtained residue was purified by preparative thin-layer chromatography, to obtain 24 mg of the target compound [147] as a colorless solid.

A spectral data of the compound [147] is presented below.
$^1$H-NMR (CDCl$_3$) δ: 8.04 (d, J=7.6 Hz, 1H), 7.53 (s, 1H), 7.46 (dd, J=2.0, 7.6 Hz, 1H), 7.41 (dd, J=2.0, 7.2 Hz, 1H), 7.38-7.24 (m, 3H), 7.21 (brs 1H), 6.71 (d, J=2.0 Hz, 1H), 6.62 (s, 1H), 6.36 (dd, J=2.0, 7.2 Hz, 1H), 5.88 (q, J=6.4 Hz, 1H), 4.07 (brs, 2H), 1.75 (d, J=6.4 Hz, 3H).
mass: 413, 415 (M+1)$^+$.

Example 148

Synthesis of 3-[1-(2-chlorophenyl)ethoxy]-5-[7-(hydroxymethyl)imidazo[1,2-a]pyridin-3-yl]thiophene-2-carboxyamide [148] (hereinafter, referred to as the compound [148])

The compound [147-3] was dissolved in tetrahydrofuran, and a borane-tetrahydrofuran complex (1.0M tetrahydrofuran solution) was slowly added dropwise. The mixture was stirred for 2 hours at room temperature, a saturated aqueous solution of sodium hydrogen carbonate was added thereto, and extracted with ethyl acetate. The organic layer was washed with saturated brine, and dried over anhydrous sodium sulfate. The insolubles were filtered, the filtrate was concentrated under reduced pressure, and thus obtained residue was purified by preparative reverse-phase liquid chromatography, to obtain a trifluoroacetate salt of the target compound [148] as a pale yellow solid.

A spectral data of the compound [148] is presented below.
$^1$H-NMR (CD$_3$OD) δ: 8.47 (d, J=6.8 Hz, 1H), 8.18 (s, 1H), 7.92 (s, 1H), 7.62 (d, J=7.6 Hz, 1H), 7.50 (d, J=6.4 Hz, 1H), 7.48-7.21 (m, 3H), 7.21 (s, 1H), 6.12 (q, J=6.4 Hz, 1H), 4.88 (s, 2H), 1.84 (d, J=6.4 Hz, 3H).
mass: 428, 430 (M+1)$^+$.

Example 149

Synthesis of 3-[1-(2-chlorophenyl)ethoxy]-5-[7-(morpholin-4-ylmethyl)imidazo[1,2-a]pyridin-3-yl]thiophene-2-carboxyamide [149] (hereinafter, referred to as the compound [149])

A trifluoroacetate salt of the target compound [149] was obtained as a colorless solid from the compound [148] and morpholine according to the method of Example 50.

A spectral data of the compound [149] is presented below.
$^1$H-NMR (CD$_3$OD) δ: 8.61 (d, J=7.2 Hz, 1H), 8.20 (s, 1H), 8.08 (s, 1H), 7.62 (d, J=7.2 Hz, 1H), 7.63-7.47 (m, 2H), 7.43-7.36 (m, 2H), 7.18 (s, 1H), 6.12 (q, J=6.4 Hz, 1H), 4.53 (s, 2H), 4.00-3.90 (m, 4H), 3.35-3.33 (m, 4H), 1.84 (d, J=6.4 Hz, 3H).
mass: 497, 499 (M+1)$^+$.

Example 150

Synthesis of 5-(2-aminoimidazo[1,2-a]pyridin-3-yl)-3-[1-(2-chlorophenyl)ethoxy]thiophene-2-carboxyamide [150] (hereinafter, referred to as the compound [150])

1) 7.5 g of 2-aminopyridine was dissolved in 180 mL of tetrahydrofuran, and 11.2 mL of ethylbromopyruvate was added thereto at room temperature. The reaction solution was heated to 90° C., and the solution was overheated overnight under reflux. The reaction solution was cooled back to room temperature, thus obtained solid was taken by filtration, and the solid was washed with tetrahydrofuran. Thus obtained solid was crystallized from ethanol, and the obtained crystals were taken by filtration and dried under reduced pressure. After further concentrating the filtrate, 5.6 g of ethyl imidazo[1,2-a]pyridine-2-carboxylic acid [150-1] (hereinafter, referred to as the compound [150-1]) was obtained by crystallizing from ethanol.

(2) Ethyl 3-(3-t-butoxy-3-oxoprop-1-in-1-yl)imidazo[1,2-a]pyridine-2-carboxylic acid was obtained from the compound [150-1] according to the methods of Example 1-(1) and (2). From the obtained compound and the compound [143-4], ethyl 3-[5-(t-butoxycarbonyl)-4-hydroxy-2-thienyl]imidazo[1,2-a]pyridine-2-carboxylic acid was obtained according to the method of Example 1-(3). Subsequently, from the obtained compound and 2-chloro-α-methylbenzyl alcohol, ethyl 3-[5-(t-butoxycarbonyl)-4-[1-(2-chlorophenyl)ethoxy]-2-thienyl]imidazo[1,2-a]pyridine-2-carboxylic acid [150-2] (hereinafter, referred to as the compound [150-2]) was obtained according to the method of Example 1-(4).

(3) The compound [150-2] was dissolved in methanol, then a 1N aqueous sodium hydroxide solution was added thereto and stirred overnight at room temperature. The reaction solvent was distilled off under reduced pressure, and thus obtained residue was added with 1N hydrochloric acid and concentrated under reduced pressure. Ethanol was added to the residue, and produced undesired substance was separated by filtration. The filtrate was concentrated to obtain 3-[5-(t-butoxycarbonyl)-4-[1-(2-chlorophenyl)ethoxy]-2-thienyl]imidazo[1,2-a]pyridine-2-carboxylic acid [150-3] (hereinafter, referred to as the compound [150-3]).

(4) t-butyl 5-[2-[(t-butoxycarbonyl)amino]imidazo[1,2-a]pyridin-3-yl]-3-(1-2-chlorophenylethoxy)-2-thiophenecarboxylic acid [150-4] (hereinafter, referred to as the compound [150-4]) was obtained from the compound [150-3] according to the method of Example 147-(4).

(5) The target compound [150] was obtained as a colorless solid from the compound [150-4] according to the method of Example 10-(2).

A spectral data of the compound [150] is presented below.
$^1$H-NMR (CDCl$_3$) δ: 8.15 (d, J=6.8 Hz, 1H), 7.47 (dd, J=2.0, 8.0 Hz, 1H), 7.43 (dd, J=2.0 Hz, 7.6 Hz, 1H), 7.35-7.29

(m, 3H), 7.20-7.15 (m, 1H), 6.77 (dt, J=1.0, 6.8 Hz, 1H), 6.59 (s, 1H), 5.89 (q, J=6.8 Hz, 1H), 1.77 (d, J=6.8 Hz, 3H).
mass: 413, 415 (M+1)$^+$.

Example 151

Synthesis of 3-[1-(2-chlorophenyl)ethoxy]-5-[2-(difluoromethyl)imidazo[1,2-a]pyridin-3-yl]thiophene-2-carboxyamide [151] (hereinafter, referred to as the compound [151])

(1) 214 mg of the compound [150-3] was dissolved in 10 mL of anhydrous tetrahydrofuran under a nitrogen atmosphere, and 348 mg of carbonyldiimidazole was added thereto and stirred overnight at room temperature. The reaction solution was cooled to 0° C., and 33 mg of an aqueous sodium boronhydride solution was added thereto and stirred for 7 hours at room temperature. The reaction solution was concentrated under reduced pressure, thus obtained residue was poured onto a saturated aqueous solution of ammonium chloride, and extracted with chloroform. The extract was dried over anhydrous sodium sulfate, and the solvent was distilled off under reduced pressure. The obtained residue was purified by silica gel chromatography to obtain 147 mg of t-butyl 3-[1-(2-1-chlorophenyl)ethoxy]-5-[2-(hydroxymethyl)imidazo[1,2-a]pyridin-3-yl]-2-thiophenecarboxylic acid [151-1] (hereinafter, referred to as the compound [151-1].

(2) 43 mg of the compound [151-1] was dissolved in 5 mL of chloroform, then 125 mg of manganese dioxide was added at room temperature, and the mixture was stirred for 1 hour. The reaction solution was filtered through celite and the filtrate was concentrated under reduced pressure to obtain 37 mg of t-butyl 3-[1-(2-chlorophenyl)ethoxy]-5-(2-formylimidazo[1,2-a]pyridin-3-yl]-2-thiophenecarboxylic acid [151-2] (hereinafter, referred to as the compound [151-2].

(3) 37 mg of the compound [151-2] was dissolved in 2 mL of methylene chloride, and 30 µL of (diethylamino)sulfurtrifluoride (DAST) was added and stirred for 1 hour. Methanol was added to the reaction solution, which was then poured onto a saturated aqueous solution of sodium hydrogen carbonate and extracted with chloroform. The extract was dried over anhydrous sodium sulfate, and then the solvent was distilled off under reduced pressure. The obtained residue was purified by preparative thin-layer silica gel chromatography to obtain 20 mg of t-butyl 3-[1-(2-chlorophenyl)ethoxy]-5-(2-(difluoromethyl)imidazo[1,2-a]pyridin-3-yl)-2-thiophenecarboxylic acid [151-3] (hereinafter, referred to as the compound [151-3].

(4) 15 mg of the target compound [151] was obtained as a colorless solid from 20 mg of the compound [151-3] according to the method of Example 10-(2).
A spectral data of the compound [151] is presented below.
$^1$H-NMR (CDCl$_3$) δ: 8.18 (d, J=7.0 Hz, 1H), 7.68 (d, J=9.2 Hz, 1H), 7.48-7.38 (m, 2H), 7.36-7.24 (m, 3H), 6.87 (t, J=7.0 Hz, 1H), 6.71 (s, 1H), 6.60 (t, J=54.0 Hz, 1H), 5.88 (q, J=6.4 Hz, 1H), 1.78 (d, J=6.4 Hz, 3H).
mass: 448, 450 (M+1)$^+$.

Example 152

Synthesis of 3-[(1R)-1-(2-chlorophenyl)ethoxy]-5-(8-methylimidazo[1,2-a]pyridin-3-yl)thiophene-2-carboxyamide [152] (hereinafter, referred to as the compound [152])

(1) The compound [143-4] was dissolved in dehydrated methanol under a nitrogen atmosphere, then 4.32 g of sodium methoxide was added under an ice-cold condition, and the mixture was stirred for 5 minutes at room temperature. To the obtained reaction solution, 50 mL of an anhydrous methanol solution containing 13.6 g of dimethyl acetylenedicarboxylate was added, and the mixture was stirred for 20 minutes at room temperature. The reaction solution was cooled to 0° C., 4.58 mL of acetic acid was added, and the reaction solution was distilled off under reduced pressure. The obtained residue was poured onto saturated brine, extracted with ethyl acetate, and the extract was washed with saturated brine and then dried over anhydrous sodium sulfate. The solvent was distilled off under reduced pressure and thus obtained residue was purified by silica gel chromatography to obtain 12.3 g of 2-(t-butyl)-5-methyl 3-hydroxy-2,5-thiophenedicarboxylic acid [152-1] (hereinafter, referred to as the compound [152-1]).

(2) 5.0 g of the compound [152-1] was dissolved in anhydrous tetrahydrofuran under a nitrogen atmosphere, and 4.5 g of (S)-α-(2-chlorophenyl)ethyl alcohol was added thereto. The mixture was cooled to 0° C. Thereto, 6.68 mL of tributylphosphine and 8.60 mL of diisopropyl azodicarboxylate were added, and the mixture was heated to room temperature. After stirring the reaction solution for 2 hours at room temperature, the solution was poured onto saturated brine in an ice bath, and extracted with ethyl acetate. The extract was washed with saturated brine, and then dried over anhydrous sodium sulfate. The solvent was distilled off under reduced pressure. The obtained residue was purified by silica gel column chromatography to obtain 7.6 g of 2-(t-butyl)-5-methyl 3-[(1R)-1-(2-chlorophenyl)ethyl]oxy-2,5-thiophenedicarboxylic acid [152-2] (hereinafter, referred to as the compound [152-2]).

(3) 7.6 g of the compound [152-2] was dissolved in 125 mL of mixed solvent of methanol/tetrahydrofuran (4:1), then 25 mL of a 1N aqueous sodium hydroxide solution was added under an ice-cold condition, and the mixture was stirred overnight at room temperature. The reaction solution was concentrated under reduced pressure, thus obtained residue was cooled to 0° C., and 1N hydrochloric acid was added to acidify the solution. The obtained aqueous solution was extracted with chloroform, dried over anhydrous sodium sulfate, and then the solvent was removed under reduced pressure, to obtain 6.8 g of 5-(t-butoxycarbonyl)-4-[(1R)-1-(2-chlorophenyl)ethyl]oxy-2-thiophenedicarboxylic acid [152-3] (hereinafter, referred to as the compound [152-3]).

(4) 6.8 g of the compound [152-3] was dissolved in 40 mL of anhydrous tetrahydroufuran under a nitrogen atmosphere, and then a tetrahydroufuran solution (62 mL) of 1M boranetetrahydroufuran complex was added thereto under an ice-cold condition. The mixture was heated to room temperature and stirred for 2 days at the same temperature. To the reaction solution, methanol was added under an ice-cold condition, and the solvent was removed under reduced pressure. Thus obtained residue was dissolved in ethyl acetate, which was then poured onto a saturated aqueous solution of sodium hydrogen carbonate and extracted with ethyl acetate. The extract was washed with a saturated aqueous solution of sodium hydrogen carbonate and saturated brine, and then dried over anhydrous sodium sulfate. The solvent was removed under reduced pressure and thus obtained residue was purified by silica gel chromatography to obtain 6.1 g of t-butyl t-butyl3-[(1R)-1-(2-chlorophenyl)ethyl]oxy-5-(hydroxymethyl)-2-thiophenecarboxylic acid [152-4] (hereinafter, referred to as the compound [152-4]).

(5) 6.1 g of the compound [152-4] was dissolved in 100 mL of chloroform, then 14.4 g of manganese dioxide was added at room temperature, and the mixture was stirred for 1 hour.

Thereto, 7.2 g of manganese dioxide was further added and stirred for 30 minutes. The reaction solution was filtered through celite, thoroughly washed with chloroform, and the filtrate was removed under reduced pressure, to obtain 6.1 g of t-butyl 3-[(1R)-1-(2-chlorophenyl)ethyl]oxy-5-formyl-2-thiophenecarboxylic acid [152-5] (hereinafter, referred to as the compound [152-5]). The compound [152-5] was used in the subsequent reaction without further purification.

(6) 6.1 g of methoxymethyltriphenylphosphonium chloride was added to 70 mL of tetrahydroufuran under a nitrogen atmosphere, and 10.9 mL of a cyclohexane solution of 1.5M lithium diisopropylamide was added under an ice-cold condition. The mixture was stirred for 1 hour at the same temperature. Thereto, 15 mL of a tetrahydrofuran solution containing 3.0 g of the compound [152-5] was added, and the mixed solution was heated to room temperature. After the overnight stirring at room temperature, the reaction solution was poured onto a saturated aqueous solution of ammonium chloride in an ice bath, and extracted with ethyl acetate. The extract was washed with saturated brine, and then dried over anhydrous sodium sulfate. The solvent was removed under reduced pressure. The obtained residue was purified by silica gel column chromatography to obtain 1.5 g of t-butyl 3-[(1R)-1-(2-chlorophenyl)ethyl]oxy-5-[(E)-2-methoxyethynyl]-2-thiophenecarboxylic acid [152-6E] (hereinafter, referred to as the compound [152-6E]) and 738 mg of t-butyl 3-[(1R)-1-(2-chlorophenyl)ethyl]oxy-5-[(Z)-2-methoxyethynyl]-2-thiophenecarboxylic acid [152-6Z] (hereinafter, referred to as the compound [152-6Z]).

(7) 30 mg of the compound [152-6E] was dissolved in 2 mL of a mixed solvent of dioxane and water (3:1), then 14 mg of N-bromosuccinimide was added under an ice-cold condition, and the mixture was stirred for 30 minutes at the same temperature. Thereto, 12 mg of 3-methyl-2-aminopyridine was added, heated to room temperature, and stirred for 1 hour. The reaction solution was heated to 50° C., and subjected to further overnight stirring. The reaction solution was poured onto a saturated aqueous solution of sodium hydrogen carbonate, and extracted with chloroform. The extract was dried over anhydrous sodium sulfate, the solvent was concentrated under reduced pressure, and thus obtained residue was purified by preparative thin-layer silica gel chromatography, to obtain 11 mg of t-butyl 3-[(1R)-1-(2-chlorophenyl)ethyl] oxy-5-(8-methylimidazo[1,2-a]pyridin-3-yl)-2-thiophenecarboxylic acid [152-7] (hereinafter, referred to as the compound [152-7]).

(8) 11 mg of the compound [152-7] was dissolved in 2 mL of methanol, 1 mL of a 1N aqueous sodium hydroxide solution was added, and the mixture was stirred overnight at 80° C. The reaction solution was cooled to 0° C., 1 mL of 1N hydrochloric acid was added thereto, and the solvent was concentrated under reduced pressure to dry completely. Thereto, 2 mL of N,N-dimethylformamide was added, and 12 mg of ammonium chloride, 63 μL of triethylamine, 35 mg of hydroxybenzotriazole, and 44 mg of 1-(3-dimethylaminopropyl)-3-ethylcarbodiimide were added to the obtained solution at room temperature. The mixture was stirred for 5 hours at the same temperature. The reaction solution was poured onto saturated brine and extracted with ethyl acetate. The extract was washed with water and saturated brine, and dried over anhydrous sodium sulfate. The solvent was concentrated under reduced pressure and thus obtained residue was purified by preparative thin-layer silica gel chromatography to obtain 7.0 mg of the target compound [152] as a colorless solid.

A spectral data of the compound [152] is presented below.
$^1$H-NMR (CDCl$_3$) δ: 8.11 (d, J=7.0 Hz, 1H), 7.72 (s; 1H), 7.47 (dd; J=2.0, 8.0 Hz, 1H), 7.41 (dd, J=1.6, 8.0 Hz, 1H), 7.32-7.25 (m, 2H), 7.23 (brs, 1H), 7.04 (d, J=7.0 Hz, 1H), 6.78 (t, J=7.0 Hz, 1H), 6.72 (s, 1H), 5.90 (q, J=6.4 Hz, 1H), 5.70 (brs, 1H), 2.62 (s, 3H), 1.77 (d, J=6.4 Hz, 3H).
mass: 412, 414 (M+1)$^+$.

Example 153

Synthesis of methyl 3-{5-(aminocarbonyl)-4-[1-(2-chlorophenyl)ethoxy]-2-thienyl}imidazo[1,2-a]pyridine-5-carboxylic acid [153] (hereinafter, referred to as the compound [153])

(1) Methyl 3-[5-(t-butoxycarbonyl)-4-hydroxy-2-thienyl]imidazo[1,2-a]pyridine-5-carboxylic acid [153-1] (hereinafter, referred to as the compound [153-1]) was obtained from 6-amino-2-pyridinecarboxylic acid methyl ester according to the methods of Example 143-(1) to (5).

(2) Methyl 3-{5-(t-butoxycarbonyl)-4-[1-(2-chlorophenyl)ethoxy]-2-thienyl}imidazo[1,2-a]pyridine-5-carboxylic acid [153-2] (hereinafter, referred to as the compound [153-2]) was obtained from the compound [153-1] and 2-chloro-α-methylbenzyl alcohol according to the method of Example 1-(4).

(3) The target compound [153] was obtained as a colorless solid from the compound [153-2] according to the method of Example 143-(7).

A spectral data of the compound [153] is presented below.
$^1$H-NMR (CDCl$_3$) δ: 7.80 (dd, J=1.2, 8.8 Hz, 1H), 7.66 (s, 1H), 7.46 (dd, J=2.0, 7.2 Hz, 1H), 7.40 (dd, J=2.0, 7.2 Hz, 1H), 7.34 (dd, J=1.6, 7.2 Hz, 1H), 7.31-7.24 (m, 3H), 6.52 (s, 1H), 5.81 (q, J=6.4 Hz, 1H), 3.41 (s, 3H), 1.74 (d, J=6.4 Hz, 3H).
mass: 456, 458 (M+1)$^+$.

Example 154

Synthesis of 3-{5-(aminocarbonyl)-4-[1-(2-chlorophenyl)ethoxy]-2-thienyl}imidazo[1,2-a]pyridine-5-carboxylic acid [154] (hereinafter, referred to as the compound [154])

A trifluoroacetate salt of the target compound [154] was obtained as a colorless solid from the compound [153] according to the method of Example 144.

A spectral data of the compound [154] is presented below.
$^1$H-NMR (CD$_3$OD) δ: 8.14 (s, 1H), 8.03 (dd, J=1.6, 8.8 Hz, 1H), 7.97 (d, J=7.2 Hz, 1H), 7.79 (dd, J=1.2, 7.2 Hz, 1H), 7.58 (dd, J=2.0, 7.6 Hz, 1H), 7.42-7.30 (m, 3H), 6.91 (s, 1H), 5.93 (q, J=6.4 Hz, 1H), 1.79 (d, J=6.4 Hz, 3H).
mass: 442, 444 (M+1)+

Example 155

Synthesis of 5-(5-aminoimidazo[1,2-a]pyridin-3-yl)-3-[1-(2-chlorophenyl)ethoxy]thiophene-2-carboxyamide [155] (hereinafter, referred to as the compound [155])

The target compound [155] was obtained as a pale yellow oily product from the compound [154] according to the method of Example 147-(4).

A spectral data of the compound [155] is presented below.
$^1$H-NMR (CDCl$_3$) δ: 7.55 (s, 1H), 7.51-7.39 (m, 2H), 7.33-7.25 (m, 3H), 7.18-7.12 (m, 2H), 6.51 (s, 1H), 6.20 (brs, 1H), 5.97 (dd, J=2.0, 6.4 Hz, 1H), 5.85 (q, J=6.4 Hz, 1H), 4.17 (s, 2H), 1.75 (d, J=6.4 Hz, 311).

mass: 413, 415 (M+1)$^+$.

Example 156

Synthesis of 3-[1-(2-chlorophenyl)ethoxy]-5-[5-(hydroxymethyl)imidazo[1,2-a]pyridin-3-yl]thiophene-2-carboxyamide [156] (hereinafter, referred to as the compound [156])

The target compound [156] was obtained as a pale yellow oily product from the compound [154] according to the method of Example 148.

A spectral data of the compound [156] is presented below.
$^1$H-NMR (CDCl$_3$) δ: 7.62 (d, J=8.8 Hz, 1H), 7.57 (s, 1H), 7.46 (d, J=7.6 Hz, 1H), 7.40 (d, J=7.6 Hz, 1H), 7.35-7.26 (m, 5H), 6.93 (d, J=7.2 Hz, 1H), 6.59 (s, 1H), 5.84 (q, J=6.4 Hz, 1H), 5.72 (brs, 1H), 4.32 (d, J=12.5 Hz, 1H), 4.26 (d, J=12.5 Hz, 1H), 1.77 (d, J=6.4 Hz, 3H).

mass: 428, 430 (M+1)$^+$.

Example 157

Synthesis of 2-imidazo[1,2-a]pyridin-3-yl-4-{[2-(trifluoromethyl)benzyl]oxy}-1,3-thiazole-5-carboxylic acid [157] (hereinafter, referred to as the compound [157])

(1) 650 mg of methyl imidazo[1,2-a]pyridine-3-carboxylic acid target compound [157-1] (hereinafter, referred to as the compound [157-1]) was obtained as a pale yellow oily product from 1.81 g of the compound [1-1] according to the method of Example 45.

(2) 536 mg of imidazo[1,2-a]pyridine-3-carboxyamide [157-2] (hereinafter, referred to as the compound [157-2]) was obtained as a pale yellow oily product from 650 mg of the compound [157-1] according to the method of Example 10-(2).

(3) 536 mg of the compound [157-2] was dissolved in 20 mL of toluene, then 790 mg of Lawesson's Reagent was added thereto, and the mixture was heated overnight under reflux. The insolubles were filtered and the filtrate was concentrated under reduced pressure. The residue was dissolved in 20 mL of ethanol, 672 μL of bromomalonic acid diethyl ester was added thereto, and the mixture was heated for 4 hours under reflux. The solvent was concentrated under reduced pressure and the residue was purified by silica gel chromatography to obtain 536 mg of ethyl 4-hydroxy-2-imidazo[1,2-a]pyridin-3-yl-1,3-thiazole-5-carboxylic acid [157-3] (hereinafter, referred to as the compound [157-3]) as a pale yellow oily product.

(4) 66 mg of ethyl 2-imidazo[1,2-a]pyridin-3-yl-4-{[2-(trifluoromethyl)benzyl]oxy}-1,3-thiazole-5-carboxylic acid [157-4] (hereinafter, referred to as the compound [157-4]) was obtained as a pale yellow oily product from 83 mg of the compound [157-3] and 2-trifluoromethylbenzylbromide according to the method of Example 10-(1).

(5) The target compound [157] was obtained as a colorless solid from the compound [157-4] according to the method of Example 1-(5).

A spectral data of the compound [157] is presented below.
$^1$H-NMR (CDCl$_3$) δ: 9.24 (d, J=7.2 Hz, 1H), 8.28 (s, 1H), 7.80-7.70 (m, 5H), 7.45-7.40 (m, 1H), 6.96 (d, J=3.6 Hz, 1H), 5.94 (s, 2H).

mass: 420 (M+1)$^+$.

Example 158

Synthesis of 2-imidazo[1,2-a]pyridin-3-yl-4-{[2-(trifluoromethyl)benzyl]oxy}-1,3-thiazole-5-carboxyamide [158] (hereinafter, referred to as the compound [158])

The target compound [158] was obtained as a colorless solid from the compound [157] according to the method of Example 8.

A spectral data of the compound [158] is presented below.
$^1$H-NMR (DMSO-d$_6$) δ: 9.24 (d, J=7.2 Hz, 1H), 8.57 (s, 1H), 7.90-7.75 (m, 5H), 7.64-7.60 (m, 2H), 7.22-7.21 (m, 1H), 7.00 (brs, 1H), 5.89 (s, 2H).

mass: 419 (M+1)$^+$.

Example 159

Synthesis of 4-[(2-trifluorobenzyl)oxy]-2-imidazo[1,2-a]pyridin-3-yl-1,3-thiazole-5-carboxyamide [159] (hereinafter, referred to as the compound [159])

The target compound [159] was obtained as a colorless solid from the compound [157-3] and 2-fluorobenzylbromide according to the method of Example 10. The target compound was confirmed by LC-MS.

mass: 369 (M+1)$^+$.

Example 160

Synthesis of 4-[(2-chloropyridin-3-yl)methoxy]-2-imidazo[1,2-a]pyridin-3-yl-1,3-thiazole-5-carboxyamide [160] (hereinafter, referred to as the compound [160])

(1) (2-chloro-3-pyridinyl)methanol [160-1] (hereinafter, referred to as the compound [160-1]) was obtained as a pale yellow oily product from 2-chloronicotinyl chloride according to the method of Example 5-(1).

(2) The target compound [160] was obtained from the compound [160-1] and the compound [157-3] according to the method of Example 20.

A spectral data of the compound [160] is presented below.
$^1$H-NMR (CDCl$_3$) δ: 9.24 (d, J=6.8 Hz, 1H), 8.42 (dd, J=2.0, 4.8 Hz, 1H), 8.23 (s, 1H), 8.01 (brs, 2H), 7.84 (d, J=2.0, 7.6 Hz, 1H), 7.75 (dd, J=2.0, 7.2 Hz, 1H), 7.43-7.38 (m, 1H), 7.32 (dd, J=4.8, 7.6 Hz, 1H), 7.06-7.03 (m, 1H), 5.78 (s, 2H).

mass: 386, 388 (M+1)$^+$.

Example 161

Synthesis of 4-[1-(2-chlorophenyl)ethoxy]-2-imidazo[1,2-a]pyridin-3-yl-1,3-thiazole-5-carboxyamide [161] (hereinafter, referred to as the compound [161])

A trifluoroacetate salt of the target compound [161] was obtained as a colorless solid from 2-chloro-α-methylbenzyl alcohol and the compound [157-3] according to the method of Example 20.

A spectral data of the compound [161] is presented below.
$^1$H-NMR (CD$_3$OD) δ: 9.29 (d, J=6.8 Hz, 1H), 8.58 (s, 1H), 7.88-7.86 (m, 2H), 7.61 (d, J=7.6 Hz, 1H), 7.55 (d, J=6.4 Hz, 1H), 7.40-7.32 (m, 3H), 6.57 (q, J=6.4 Hz, 1H), 1.85 (d, J=6.4 Hz, 3H).

mass: 399, 401 (M+1)$^+$.

Example 162

Synthesis of 5-[1-(2-chlorophenyl)ethoxy]-2-imidazo[1,2-a]pyridin-3-yl-1,3-oxazole-4-carboxyamide [162] (hereinafter, referred to as the compound [162])

(1) 660 mg of diethyl 2-[(imidazo[1,2-a]pyridin-3-ylcarbonyl)amino]malonic acid [162-1] (hereinafter, referred to as the compound [162-1]) was obtained as a light brown solid from 670 mg of the compound [157-1] and diethyl aminomalonate according to the method of Example 10-(2).

(2) 300 mg of the compound [162-1] was dissolved in 2-chloro-α-methylbenzyl alcohol and stirred overnight at 190° C. After cooling back to room temperature, the reaction mixture was purified by preparative reverse-phase liquid chromatography to obtain 54 mg of bis(1-chlorophenylethyl)-2-[(imidazo[1,2-a]pyridin-3-ylcarbonyl)amino]malonic acid [162-2] (hereinafter, referred to as the compound [162-2]) as a pale yellow oily product.

(3) 54 mg of the compound [162-2] was dissolved in 6 mL of methylene chloride, then 60 μL of triethylamine, 53 mg of iodine, and 55 mg of triphenylphosphine were added thereto, and the mixture was stirred for 1 hour at room temperature. The solvent was concentrated under reduced pressure and the residue was purified by preparative thin-layer chromatography to obtain 31 mg of 1-chlorophenylethyl 2-imidazo[1,2-a]pyridin-3-yl-5-(1-chlorophenylethoxy)1,3-oxazole-4-carboxylic acid compound [162-3] (hereinafter, referred to as the compound [162-3]) as a yellow oily product.

(4) The target compound [162] was obtained as a colorless solid from the compound [162-3] according to the method of Example 10-(2).

A spectral data of the compound [162] is presented below.
$^1$H-NMR (CDCl$_3$) δ: 9.22 (d, J=6.0 Hz, 1H), 8.12 (s, 1H), 7.75-7.70 (m, 2H), 7.40-7.30 (m, 3H), 7.28-7.25 (m, 1H), 7.03 (dd, J=6.0, 6.0 Hz, 1H), 6.60 (brs, 1H), 6.43 (q, J=6.4 Hz, 1H), 1.81 (d, J=6.4 Hz, 3H).
mass: 383, 385 (M+1)$^+$.

Example 163

Synthesis of 3-[1-(2-chlorophenyl)ethoxy]-5-imidazo[1,2-a]pyrazin-3-ylthiophene-2-carboxyamide [163] (hereinafter, referred to as the compound [163])

4.7 mg of the target compound [163] was obtained as a colorless solid from 30 mg of the compound [152-6Z] and 11 mg of 2-aminopyrazine according to the methods of Example 152-(7) and (8).

A spectral data of the compound [163] is presented below.
$^1$H-NMR (CDCl$_3$) δ: 9.14 (d, J=1.2 Hz, 1H), 8.13 (dd, J=1.6, 4.8 Hz, 1H), 7.95 (d, J=4.8 Hz, 1H), 7.88 (s, 1H), 7.48-7.43 (m, 2H), 7.36-7.26 (m, 2H), 6.79 (s, 1H), 5.91 (q, J=6.4 Hz, 1H), 1.78 (d, J=6.4 Hz, 3H).
mass: 399, 401 (M+1)$^+$.

Example 164

Synthesis of 3-[1-(2-chlorophenyl)ethoxy]-5-(6-ethoxyimidazo[1,2-b]pyridazin-3-yl)thiophene-2-carboxyamide [164] (hereinafter, referred to as the compound [164])

4.8 mg of the target compound [164] was obtained as a colorless solid from 36 mg of the compound [152-6Z] and 18 mg of 2-amino-6-chloropyridazine according to the methods of Example 152-(7) and (8).

A spectral data of the compound [164] is presented below.
$^1$H-NMR (CDCl$_3$) δ: 7.86 (s, 1H), 7.81 (d, J=9.6 Hz, 1H), 7.47-7.40 (m, 2H), 7.33-7.22 (m, 2H), 7.08 (s, 1H), 6.73 (d, J=9.6 Hz, 1H), 5.90 (q, J=6.4 Hz, 1H), 4.48 (q, J=7.2 Hz, 2H), 1.76 (d, J=6.4 Hz, 3H), 1.50 (t, J=7.2 Hz, 3H).
mass: 443, 445 (M+1)$^+$.

Example 165

Synthesis of 3-{1-[(2-chloro-5-hydroxymethyl)phenyl]ethoxy}-5-imidazo[1,2-a]pyridin-3-ylthiophene-2-carboxyamide [165] (hereinafter, referred to as the compound [165])

(1) 1.65 g of 1-(5-bromo-2-chlorophenyl)-1-ethanone [165-1] (hereinafter, referred to as the compound [165-1]) was obtained as a colorless oily product from 2.0 g of 5-bromo-2-chlorobenzoic acid according to the methods of Example 55-(1) and (2).

(2) 90 mg of 1-[5-([t-butyl(dimethyl)silyl]oxymethyl)-2-chlorophenyl]-1-ethanol [165-2] (hereinafter, referred to as the compound [165-2]) was obtained as a light brown oily product from 700 mg of the compound [165-1] according to the methods of Example 55-(3) to (5).

(3) The target compound [165] was obtained as a colorless oily product from the compound [165-2] and the compound [1-3] according to the method of Example 20.

A spectral data of the compound [165] is presented below.
$^1$H-NMR (CDCl$_3$) δ: 8.87 (d, J=5.8 Hz, 1H), 8.26 (s, 1H), 8.11 (brs, 1H), 8.08 (dd, J=1.0, 10.2 Hz, 1H), 8.01 (d, J=2.4 Hz, 1H), 7.83 (d, J=5.8 Hz, 1H), 7.76 (m, 1H), 7.68 (m, 1H), 7.58 (s, 1H), 7.50-7.46 (m, 2H), 6.41 (q, J=6.3 Hz, 1H), 5.70 (brs, 1H), 4.86 (d, J=4.4 Hz, 2H), 2.11 (d, J=6.3 Hz, 3H).
mass: 428, 430 (M+1)$^+$.

Examples 166 and 167

Synthesis of 3-{1-[2-chloro-4-(hydroxymethyl)phenyl]ethoxy}-5-imidazo[1,2-a]pyridin-3-ylthiophene-2-carboxyamide (any one of R-form and S-form enantiomers)[166] (hereinafter, referred to as the compound [166]) and 3-{1-[2-chloro-4-(hydroxymethyl)phenyl]ethoxyl}-5-imidazo[1,2-a]pyridin-3-ylthiophene-2-carboxyamide [167] (enantiomer different from the compound [166]) (hereinafter, referred to as the compound [167])

40 mg of the compound [55] (racemic mixture) was optically resolved using Chiralpack AD-H, Daicel Chemical Industries Ltd.) and hexane/ethanol as an eluent. The assay conditions were as follows.

Assay Conditions:
column: Chiralpack AD-H (Daicel Chemical Industries Ltd.), diameter of 0.46 mm, length of 250 mm;
eluent: hexane/ethanol (65:35);
flow rate: 1.0 mL/min.

Thus obtained solution was concentrated under reduced pressure to obtain 10.5 mg of the target compound [166] (RT=15.9 min) as a white solid and 10.1 mg of the target compound [167] (RT=21.1 min) as a white solid.

A spectral data of the compound [166] is presented below.
$^1$H-NMR (DMSO-d$_6$) δ: 8.46 (dd, J=1.0, 5.9 Hz, 1H), 7.86 (s, 1H), 7.71 (brs, 1H), 7.68 (dd, J=1.0, 7.7 Hz, 1H), 7.61 (d, J=7.8 Hz, 1H), 7.40-7.31 (m, 3H), 7.18 (s, 1H), 7.10-7.06 (m, 2H), 6.01 (q, J=6.4 Hz, 1H), 5.29 (t, J=5.8 Hz, 1H), 4.46 (d, J=5.4 Hz, 2H), 1.71 (d, J=6.4 Hz, 3H).
mass: 428, 430 (M+1)$^+$.

A spectral data of the compound [167] is presented below.
$^1$H-NMR (DMSO-d$_6$) δ: 8.46 (dd, J=1.0, 5.9 Hz, 1H), 7.86 (s, 1H), 7.71 (brs, 1H), 7.68 (dd, J=1.0, 7.7 Hz, 1H), 7.61 (d, J=7.8 Hz, 1H), 7.40-7.31 (m, 3H), 7.18 (s, 1H), 7.10-7.06 (m, 2H), 6.01 (q, J=6.4 Hz, 1H), 5.29 (t, J=5.8 Hz, 1H), 4.46 (d, J=5.4 Hz, 2H), 1.71 (d, J=6.4 Hz, 3H).
mass: 428, 430 (M+1)$^+$.

Example 168

Synthesis of 3-{(1R)-1-[2-(difluoromethoxy)-4-(hydroxymethyl)phenyl]ethoxy}-5-imidazo[1,2-a]pyridin-3-ylthiophene-2-carboxyamide [168] (hereinafter, referred to as the compound [168])

(1) 22.0 g of methyl 3-hydroxy-4-methyl-benzoic acid was dissolved in 500 mL of N,N-dimethylformamide, 36.7 g of potassium carbonate was added, and a solution prepared by dissolving 23 g of methyl chlorodifluoroacetate to 200 mL of N,N-dimethylformamide was slowly added dropwise at 100° C. After heating for 2 hours at 100° C., the insolubles were filtered and the reaction solution was distilled off under reduced pressure. The residue was added with ethyl acetate, washed with water and saturated brine in that order, and dried over anhydrous sodium sulfate. The insolubles were filtered and the filtrate was concentrated under reduced pressure to obtain 16.6 g of methyl 3-difluoromethoxy-4-methylbenozoic acid [168-1] (hereinafter, referred to as the compound [168-1]) as a colorless oily product.

(2) 16.6 g of the compound [168-1] was dissolved in 300 mL of carbon tetrachloride, 34.2 g of N-bromosuccinimide and 745 mg of benzoyl peroxide were added, and the mixture was stirred overnight at 70° C. under a nitrogen atmosphere. After cooling the reaction solution to room temperature, ethyl acetate was added, washed with water and saturated brine in that order, and dried over anhydrous sodium sulfate. The insolubles were filtered and the filtrate was concentrated under reduced pressure. The residue was dissolved in 250 mL of acetonitrile, then 30.2 g of potassium acetate and 4.0 g of 18-crown-6 were added, and the mixture was stirred overnight at 90° C. The insolubles were filtered and the filtrate was concentrated under reduced pressure. The residue was added with ethyl acetate, washed with water and saturated brine in that order, and dried over anhydrous sodium sulfate. The insolubles were filtered, the filtrate was concentrated under reduced pressure, and thus obtained residue was dissolved in 300 mL of methanol. Thereto, 8.3 g of sodium methoxide was added under an ice-cold condition and the mixture was stirred for 3 hours at room temperature. The reaction solution was concentrated under reduced pressure, ethyl acetate was added, washed with water and saturated brine in that order, and dried over anhydrous sodium sulfate. The insolubles were filtered, the filtrate was concentrated under reduced pressure, and thus obtained residue was purified by silica gel chromatography, to obtain 14.4 g of methyl 3-difluoromethoxy-4-formylbenzoic acid [168-2] (hereinafter, referred to as the compound [168-2]) as a white solid.

(3) 14.4 g of the compound [168-2] was dissolved in 200 mL of tetrahydrofuran, and 23 mL of methylmagnesium bromide (3.0M tetrahydrofuran solution) was added at 78° C. under a nitrogen atmosphere. After the 4 hours stirring at −78° C., a saturated aqueous solution of ammonium chloride was added, 15 mL of 5N hydrochloric acid was then added, and extracted with ethyl acetate. The organic layer was washed with saturated brine and dried over anhydrous sodium sulfate. The insolubles were filtered, the filtrate was concentrated under reduced pressure, thus obtained residue was dissolved in 300 mL of tetrahydrofuran, and lithium tetrahydroborate was added and stirred for 4 hours at 60° C. Thereto, water was added, 30 mL of 5N hydrochloric acid was then added, and the resultant was extracted with ethyl acetate. The organic layer was washed with saturated brine and dried over anhydrous sodium sulfate. The insolubles were filtered, the filtrate was concentrated under reduced pressure, thus obtained residue was dissolved in 200 mL of N,N-dimethylformamide, and 7.32 g of imidazole and 8.35 g of t-butyldimethylsilylchloride were added at 0° C. The mixture was stirred for 3 hours. The reaction mixture was added with ethyl acetate, washed with water and saturated brine, and dried over anhydrous sodium sulfate. The insolubles were filtered, the filtrate was concentrated under reduced pressure, and thus obtained residue was purified by silica gel column chromatography, to obtain 15.5 g of 1-[4-(t-butyldimethylsilyloxy)methyl-2-(difluoromethoxy)phenyl]ethanol [168-3] (hereinafter, referred to as the compound [168-3]) as a pale yellow oily product.

(4) 15.4 g of the compound [168-3] was dissolved in 700 mL of chloroform, then 40.2 g of manganese dioxide was added at room temperature, and the mixture was stirred overnight at 60° C. The reaction solution was filtered through celite and the filtrate was concentrated under reduced pressure to obtain 13.4 g of 1-[4-(t butyldimethylsilyloxy)methyl-2-(difluoromethoxy)phenyl]ethanone [168-4] (hereinafter, referred to as the compound [168-4]) as a pale yellow oily product.

(5) 1.13 g of R-5,5-diphenyl-2-methyl-3,4-propano-1,3,2-oxazaborolidine was dissolved in 130 µL of tetrahydrofuran in accordance with the method disclosed in the literature (J. Am. Chem. Soc., 109, 7925, (1987)), and 2.43 mL of borane-dimethylsulfide complex (10M dimethylsulfide solution) was added at 0° C. under a nitrogen atmosphere. The mixture was stirred for 20 minutes at the same temperature. Thereto, a solution prepared by dissolving 13.4 g of the compound [168-4] to 300 mL of tetrahydrofuran was slowly added dropwise at 0° C. After the overnight stirring at 0° C., methanol was added, and the reaction solution was concentrated under reduced pressure. The residue was added with ethyl acetate, washed with water and saturated brine in that order, and dried over anhydrous sodium sulfate. The insolubles were filtered, the filtrate was concentrated under reduced pressure, and thus obtained residue was purified by silica gel chromatography, to obtain 11.4 g of (1S)-1-[4-(t-butyldimethylsilyloxy)methyl-2-(difluoromethoxy)phenyl]ethanol [168-5] (hereinafter, referred to as the compound [168-5]) as a yellow oily product. The stereostructure of the compound [168-5] was determined by the method disclosed in the literature (J. Am. Chem. Soc., 113, 4092 (1991)).

(6) In accordance with the method disclosed in the literature (Bull. Chem. Soc. Jpn., 69, 1079 (1996)), the compound [168-5] was dissolved in a solvent of 100 mL of hexane and 100 mL of vinyl acetate, 15 g of lipase PS-C was added, and the mixture was stirred overnight at 37° C. The insolubles were filtered through celite and the filtrate was purified by silica gel chromatography to obtain 10.6 g of the compound [168-5] as a yellow oily product.

(7) 1.2 g of the compound [1-3] was dissolved in 60 mL of tetrahydrofuran, 1.45 g of the compound [168-5], 2.12 mL of tributylphosphine, and 1.72 mL of diisopropyl azodicarboxylate were added, and the mixture was stirred for 2 hours at 60° C. Thereto, methanol was added, the solvent was concentrated under reduced pressure, and thus obtained residue was purified by silica gel chromatography, to obtain 2.95 g of methyl 3-{(1R)-1-[4-({[t-butoxy(dimethyl)silyl]oxyl}methyl)-2-(difluoromethoxy)phenyl]ethoxy}-5-imidazo[1,2-a]pyridin-3-ylthiophene-2-carboxylic acid [168-6]

(including impurities) (hereinafter, referred to as the compound [168-6]) as a pale yellow oily product.

(8) 2.95 g of the compound [168-6] was added to 40 mL of ammonia (methanol solution, 7M), and the mixture was stirred in a sealed tube for 4 days at 90° C. After concentrating the reaction mixture, the obtained residue was purified by preparative reverse-phase liquid chromatography to obtain 2.0 g of the target compound [168] as a colorless oily product.

A spectral data of the compound [168] is presented below.
$^1$H-NMR (CDCl$_3$) δ: 8.33 (d, J=6.8 Hz, 1H), 7.74 (s, 1H), 7.66 (d, J=9.3 Hz, 1H), 7.46 (d, J=8.3 Hz, 1H), 7.25-7.22 (m, 3H), 6.90 (t, J=6.8 Hz, 1H), 6.83 (s, 1H), 6.68 (t, J=73.6 Hz, 1H), 5.85 (q, J=6.3 Hz, 1H), 5.76 (brs, 1H), 4.72 (s, 2H), 1.76 (d, J=6.8 Hz, 3H).
mass: 460 (M+1)$^+$.

Example 169

Synthesis of 3-{(1R)-1-[2-(difluoromethoxy)-4-formylphenyl]ethoxy}-5-imidazo[1,2-a]pyridin-3-ylthiophene-2-carboxyamide [169] (hereinafter, referred to as the compound [169])

99 mg of the target compound [169] was obtained as a colorless oily product from 114 mg of the compound [168] according to the method of Example 108-(2).

A spectral data of the compound [169] is presented below.
$^1$H-NMR (CDCl$_3$) δ: 9.99 (s, 1H), 8.33 (d, J=6.8 Hz, 1H), 7.79-7.66 (m, 5H), 7.26 (m, 1H), 7.19 (brs, 1H), 6.89 (t, J=6.8 Hz, 1H), 6.77 (t, J=72.7 Hz, 1H), 6.76 (s, 1H), 5.89 (m, 2H), 1.79 (d, J=6.3 Hz, 3H).
mass: 458 (M+1)$^+$.

Example 170

Synthesis of 4-((1R)-1-{[2-(aminocarbonyl)-5-imidazo[1,2-a]pyridin-3-yl-3-thienyl]oxy}ethyl-3-(difluoro)methoxybenzoic acid [170] (hereinafter, referred to as the compound [170])

11 mg of the target compound [170] was obtained as a white solid from 94 mg of the compound [169] according to the method of Example 142.

A spectral data of the compound [170] is presented below.
$^1$H-NMR (DMSO-d$_6$) δ: 8.52 (d, J=6.8 Hz, 1H), 7.86-7.82 (m, 2H), 7.78-7.63 (m, 4H), 7.38 (m, 1H), 7.27 (m, 1H), 7.27 (t, J=84.4 Hz, 1H), 7.10 (brs, 1H), 7.05 (m, 1H), 6.20 (q, J=6.3 Hz, 1H), 1.71 (d, J=6.8 Hz, 3H).
mass: 474 (M+1)$^+$.

Example 171

Synthesis of 3-((1R)-1-{2-chloro-4-[2-(methylamino)ethoxy]phenyl}ethoxy)-5-imidazo[1,2-a]pyridin-3-ylthiophene-2-carboxyamide [171] (hereinafter, referred to as the compound [171])

(1) 438 mg of (1S)-1-(4-bromo-2-chlorophenyl)ethanol was dissolved in 5 mL of dimethylformamide, and 250 mg of imidazole and 340 mg of t-butylchlorodimethylsilane were added thereto. After the 3 hours stirring at room temperature, the reaction mixture was added with ethyl acetate, washed with water and saturated brine, and dried over anhydrous sodium sulfate. The insolubles were filtered and the filtrate was concentrated under reduced pressure to obtain 633 mg of [(1S)-1-(4-bromo-2-chlorophenyl)ethoxy](t-butyl)dimethylsilane [171-1] (hereinafter, referred to as the compound [171-1] as a colorless oily product.

(2) 300 mg of the compound [171-1], 70 mg of [1,1'-bis(diphenylphosphino)ferrocene]dichloropalladium (II) dichloromethane adduct, 250 mg of potassium acetate, and 300 mg of bis(pinacolate)diboron were dissolved in 4 mL of dimethylsulfoxide, and the mixture was stirred for 1.5 hours at 80° C. under a nitrogen atmosphere. The reaction mixture was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography, to obtain 273 mg of t-butyl {(1S)-1-[2-chloro-4-(4,4,5,5-tetramethyl-1,3,2-dioxaborolan-2-yl)phenyl]ethoxy}dimethylsilane [171-2] (hereinafter, referred to as the compound [171-2]) as a colorless oily product.

(3) 272 mg of the compound [171-2] was dissolved in 8 mL of chloroform, and 160 mg of sodium hydrogen carbonate and 155 mg of metachloroperbenzoic acid were added at 0° C. After the 2 hours stirring at the same temperature, the reaction mixture was further added with 40 mg of metachloroperbenzoic acid and stirred for 1 hour. The reaction solution was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography, to obtain 185 mg of 4-((1S)-1-{[t-butyl(dimethyl)silyl]oxy}ethyl)-3-chlorophenol [171-3] (hereinafter, referred to as the compound [171-3]) as a colorless oily product.

(4) 145 mg of the compound [171-3] was dissolved in 5 mL of acetonitrile, 250 mg of potassium carbonate and 100 μL of 2-(2-bromoethoxy)tetrahydro-2H-pyran were added, and the mixture was heated for 4 hours under reflux. The reaction mixture was cooled back to room temperature, ethyl acetate was then added, washed with water and saturated brine in that order, and dried over anhydrous sodium sulfate. The insolubles were filtered, the filtrate was concentrated under reduced pressure, and thus obtained residue was purified by silica gel column chromatography, to obtain 180 mg of t-butyl (1S)-1-{2-chloro-4-[2-(tetrahydro-2H-pyran-2-yloxy)ethoxy]phenyl}ethoxy)dimethylsilane [171-4] (hereinafter, referred to as the compound [171-4]) as a colorless oily product.

(5) 180 mg of the compound [171-4] was dissolved in tetrahydrofuran, 0.85 mL of tetrabutylammonium fluoride (tetrahydrofuran solution, 1M) was added thereto, and the mixture was stirred for 6 hours at room temperature. The reaction mixture was concentrated and the residue was purified by chromatography to obtain 134 mg of (1S)-1-{2-chloro-4-[2-(tetrahydro-2H-pyran-2-yloxy)ethoxy]phenyl}ethanol [171-5] (hereinafter, referred to as the compound [171-5]) as a colorless oily product.

(6) 134 mg of the compound [171-5] and 160 mg of the compound [1-3] were dissolved in 4 mL of tetrahydrofuran, then 200 μL of tributylphosphine and 160 μL of diisopropyl azodicarboxylate were added, and the mixture was stirred for 1 hour at room temperature. The reaction mixture was concentrated and then purified by chromatography to obtain 418 mg of methyl 3-((1R)-1-{2-chloro-4-[2-(tetrahydro-2H-pyran-2-yloxy)ethoxy]phenyl}ethoxy)-5-imidazo[1,2-a]pyridin-3-ylthiophene-2-carboxylate [171-6] (hereinafter, referred to as the compound [171-6]) as a reddish brown amorphous substance.

(7) 418 mg of the compound [171-6] was added to 8 mL of ammonia (methanol solution, 7M), and the mixture was stirred in a sealed tube for 3 days at 70° C. After concentrating the reaction mixture, the obtained residue was purified by preparative reverse-phase liquid chromatography to obtain 126 mg of 3-((1R)-{2-chloro-4-[2-(tetrahydro-2H-pyran-2-yloxy)ethoxy]phenyl}ethoxy)-5-imidazo[1,2-a]pyridin-3-ylthiophene-2-carboxyamide [171-7] (hereinafter, referred to as the compound [171-7]) as a light brown amorphous substance.

(8) 126 mg of the compound [171-7] was dissolved in 0.5 mL of tetrahydrofuran, then 0.5 mL of water and 2 mL of acetic acid were added, and the mixture was stirred overnight at room temperature. After concentrating the reaction mixture, the obtained residue was purified by chromatography to obtain 79 mg of 3-{(1R)-1-[2-chloro-4-(2-hydroxyethoxy)phenyl]ethoxy}-5-imidazo[1,2-a]pyridin-3-ylthiophene-2-carboxyamide [171-8] (hereinafter, referred to as the compound [171-8]) as a white solid.

(9) 30 mg of the compound [171-8] was dissolved in 2 mL of chloroform, then 32 mg of carbon tetrabromide and 20 mg of triphenylphosphine were added, and the mixture was stirred overnight at room temperature. After concentrating the reaction mixture, the obtained residue was dissolved in 2 mL of dimethylsulfoxide. Thereto, 160 µL of methylamine (40% aqueous solution) was added, and the mixture was stirred for 4 hours at room temperature. The reaction mixture was directly purified by preparative reverse-phase liquid chromatography to obtain 2.8 mg of the target compound [171] as a white solid.

A spectral data of the compound [171] is presented below.
$^1$H-NMR (DMSO-d$_6$) δ: 8.51 (d, J=6.8 Hz, 1H), 7.88 (s, 1H), 7.68-7.71 (m, 2H), 7.57 (d, J=8.8 Hz, 1H), 7.36-7.40 (m, 1H), 7.22 (s, 1H), 7.05-7.11 (m, 3H), 6.98 (dd, J=2.2, 8.8 Hz, 1H), 5.97 (q, J=6.8 Hz, 1H), 4.00 (t, J=6.0 Hz, 2H), 2.76 (t, J=6.0 Hz, 2H), 2.28 (s, 3H), 1.69 (d, J=6.8 Hz, 3H).
mass: 471, 473 (M+1)$^+$.

Example 172

Synthesis of 3-((1R)-1-{2-chloro-4-[(dimethylamino)methyl]phenyl}ethoxy)-5-imidazo[1,2-a]pyridin-3-ylthiophene-2-carboxyamide [172] (hereinafter, referred to as the compound [172])

(1) 1.58 g of R-5,5-diphenyl-2-methyl-3,4-propano-1,3,2-oxazaborolidine was dissolved in 250 mL of tetrahydrofuran in accordance with the method disclosed in the literature (J. Am. Chem. Soc., 109, 7925, (1987)), and 3.42 mL of borane-dimethylsulfide complex (10M dimethylsulfide solution) was added at 0° C. under a nitrogen atmosphere. The mixture was stirred for 10 minutes at the same temperature. Thereto, a solution prepared by dissolving 13.3 g of the compound [55-2] to 100 mL of tetrahydrofuran was slowly added dropwise at 0° C. After the 6 hours stirring at 0° C., water and ethyl acetate were added in that order, and the organic layer was washed with water and saturated brine in that order and dried over anhydrous sodium sulfate. The insolubles were filtered, the filtrate was concentrated under reduced pressure, and thus obtained residue was purified by silica gel chromatography, to obtain 14.3 g of (1S)-1-(4-bromo-2-chlorophenyl)ethanol [172-1] (hereinafter, referred to as the compound [172-1]) as a pale yellow oily product. In accordance with the method disclosed in the literature (Bull. Chem. Soc. Jpn., 69, 1079 (1996)), 14.3 g of the compound [172-1] was dissolved in a solvent of 100 mL of hexane and 100 mL of vinyl acetate, 8.0 g of lipase PS-C was added, and the mixture was stirred overnight at 37° C. The insolubles were filtered through celite and the filtrate was purified by silica gel chromatography to obtain 13.8 g of the compound [172-1] as a yellow oily product.

(2) 13.8 g of the compound [172-1] was dissolved in a solvent of 150 mL of N,N-dimethylformamide and 150 mL of methanol, then 4.8 g of 1,1'-bis(diphenylphosphino)ferrocenedichloropalladium (II) and 20.6 mL of diisopropylethylamine were added under a carbon monoxide atmosphere (1 atmospheric pressure), and the mixture was stirred overnight at 90° C. After cooling back to room temperature, the insolubles were separated by filtration, and ethyl acetate was added thereto. The organic layer was washed with saturated brine and dried over anhydrous sodium sulfate. The insolubles were filtered, the filtrate was concentrated under reduced pressure, and thus obtained residue was purified by silica gel column chromatography, to obtain 10.8 g of methyl 3-chloro-4-[(1S)-1-hydroxyethyl]benzoic acid [172-2] (hereinafter, referred to as the compound [172-2]) as a pale yellow oily product.

(3) 10.8 g of the compound [172-2] was dissolved in 300 mL of tetrahydrofuran, then 2.18 g of lithium tetrahydroborate was added, and the mixture was stirred for 4 hours at 60° C. Thereto, water was added, 30 mL of 5N hydrochloric acid was then added, and the resultant was extracted with ethyl acetate. The organic layer was washed with saturated brine and dried over anhydrous sodium sulfate. The insolubles were filtered and the filtrate was concentrated under reduced pressure to obtain 9.97 g of (1S)-1-[2-chloro-4-(hydroxymethyl)phenyl]ethanol [172-3] (hereinafter, referred to as the compound [172-3] as a pale yellow oily product.

(4) 7.1 g of the compound [172-3] was dissolved in 100 mL of N,N-dimethylformamide, then 5.45 g of imidazole and 5.66 g of t-butyldimethylsilylchloride were added at 0° C., and the mixture was stirred for 10 hours at room temperature. The reaction mixture was added with ethyl acetate, washed with saturated brine, and dried over anhydrous sodium sulfate. The insolubles were filtered and the filtrate was concentrated under reduced pressure to obtain 9.5 g of (1S)-1-[4-(t-butyldimethylsilyloxy)methyl-2-chlorophenyl]ethanol [172-4] (hereinafter, referred to as the compound [172-4]) as a pale yellow oily product. The stereostructure of the compound [172-4] was determined by the method disclosed in the literature (J. Am. Chem. Soc., 113, 4092 (1991)).

(5) 120 mg of the compound [172-4] and 109 mg of the compound [1-3] were dissolved in 4 mL of tetrahydrofuran, then 250 µL of tributylphosphine and 197 µL of diisopropyl azodicarboxylate were added, and the mixture was stirred for 4 hours at 60° C. Thereto, methanol was added, the solvent was concentrated under reduced pressure, and thus obtained residue was purified by silica gel chromatography, to obtain 190 mg of methyl 3-{(1R)-1-[4-({[t-butyl(dimethyl)silyl]oxy}methyl)-2-chlorophenyl]ethoxy}-5-imidazo[1,2-a]pyridin-3-ylthiophene-2-carboxylic acid [172-5] (hereinafter, referred to as the compound [172-5]).

(6) 190 mg of the compound [172-5] was dissolved in a solvent of 2 mL of tetrahydrofuran and 2 mL of methanol, then 1 mL of a 2N aqueous sodium hydroxide solution was added, and the mixture was stirred overnight at room temperature. 2N hydrochloric acid was added to the reaction solution and the mixture was concentrated. The residue was dissolved in 4 mL of N,N-dimethylformamide, then 150 mg of ammonium chloride, 170 mg of 1-hydroxybenzotriazole, 220 µL of diisopropylethylamine, and 240 mg of 1-(3-dimethylaminopropyl)-3-ethylcarbodiimide were added, and the mixture was stirred overnight at room temperature. The reaction solution was added with ethyl acetate, washed with saturated brine, and dried over anhydrous sodium sulfate. The insolubles were filtered, the filtrate was concentrated under reduced pressure, and thus obtained residue was purified by silica gel column chromatography, to obtain 3-{(1R)-1-[2-chloro-4-(hydroxymethyl)phenyl]ethoxy}-5-imidazo[1,2-a]pyridin-3-ylthiophene-2-carboxyamide [172-6] (hereinafter, referred to as the compound [172-6]) as a white solid.

(7) 8 mg of the compound [172-6] was dissolved in 2 mL of chloroform, and 10 μL of diisopropylethylamine and 3 μL of methanesulfonyl chloride were added at 0° C. The mixture was stirred for 1 hour at the same temperature, and the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.3 mL of dimethylsulfoxide, 80 μL of dimethylamine was added, and the mixture was stirred overnight at room temperature. The reaction mixture was purified by preparative reverse-phase liquid chromatography to obtain a trifluoroacetate salt of the target compound [172] as a colorless oily product.

A spectral data of the compound [172] is presented below.
$^1$H-NMR (CD$_3$OD) δ: 8.73 (d, J=6.8 Hz, 1H), 8.19 (s, 1H), 7.95 (m, 2H), 7.79 (d, J=8.0 Hz, 1H), 7.69 (d, J=1.8 Hz, 1H), 7.56 (d, J=8.2 Hz, 1H), 7.49 (m, 1H), 7.30 (s, 1H), 6.18 (q, J=6.6 Hz, 1H), 4.33 (s, 2H), 2.88 (s, 6H), 1.85 (d, J=6.4 Hz, 3H).
mass: 455, 457 (M+1)$^+$.

Example 173

Synthesis of 3-((1R)-1-{2-chloro-4-[(ethylamino)methyl]phenyl}ethoxy)-5-imidazo[1,2-a]pyridin-3-ylthiophene-2-carboxyamide [173] (hereinafter, referred to as the compound [173])

A trifluoroacetate salt of the target compound [173] was obtained as a colorless oily product from 8 mg of the compound [172-6] and ethylamine according to the method of Example 172-(7).

A spectral data of the compound [173] is presented below.
$^1$H-NMR (DMSO-d$_6$) δ: 8.74 (brs, 2H), 8.70 (d, J=6.8 Hz, 1H), 8.14 (s, 1H), 7.85 (m, 2H), 7.75 (d, J=7.8 Hz, 1H), 7.67-7.63 (m, 2H), 7.49 (dd, J=1.4, 8.3 Hz, 1H), 7.32-7.28 (m, 2H), 7.16 (brs, 1H), 6.06 (q, J=6.3 Hz, 1H), 4.10 (m, 2H), 2.95 (q, J=6.3 Hz, 2H), 1.72 (d, J=6.3 Hz, 3H), 1.15 (t, J=6.8 Hz, 3H).
mass: 455, 457 (M+1)$^+$.

Example 174

Synthesis of 3-[(1R)-1-(2-chloro-4-{[(2-hydroxy-1,1-dimethylethyl)amino]methyl}phenyl)ethoxy]-5-imidazo[1,2-a]pyridin-3-ylthiophene-2-carboxyamide [174] (hereinafter, referred to as the compound [174])

A trifluoroacetate salt of the target compound [174] was obtained as a colorless oily product from 8 mg of the target compound [172-6] and 2-amino-2-methyl-1-propanol according to the method of Example 172-(7).

A spectral data of the compound [174] is presented below.
$^1$H-NMR (CDCl$_3$) δ: 8.32 (d, J=6.8 Hz, 1H), 7.74 (s, 1H), 7.66 (d, J=9.0 Hz, 1H), 7.45 (s, 1H), 7.41 (d, J=8.0 Hz, 1H), 7.31-7.23 (m, 3H), 6.90 (t, J=6.7 Hz, 1H), 6.74 (s, 1H), 5.87 (q, J=6.3 Hz, 1H), 5.73 (brs, 1H), 3.69 (s, 2H), 3.38 (s, 2H), 1.75 (d, J=6.3 Hz, 3H), 1.14 (s, 6H).
mass: 499, 501 (M+1)$^+$.

Example 175

Synthesis of 3-{(1R)-1-[2-chloro-4-({[(1S)-2-hydroxy-1-methylethyl]amino}methyl)phenyl]ethoxy}-5-imidazo[1,2-a]pyridin-3-ylthiophene-2-carboxyamide [175] (hereinafter, referred to as the compound [175])

50 mg of the compound [172-6] was dissolved in 3 mL of chloroform, and 42 μL of diisopropylethylamine and 12 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.3 mL of dimethylsulfoxide, 100 μL of L-alaninol was added thereto, and the mixture was stirred overnight at room temperature. The reaction mixture was purified by preparative reverse-phase liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure to obtain 7.0 mg of the target compound [175] as a colorless oily product.

A spectral data of the compound [175] is presented below.
$^1$H-NMR (DMSO-d$_6$) δ: 8.47 (d, J=6.8 Hz, 1H), 7.86 (s, 1H), 7.73-7.69 (m, 2H), 7.59 (d, J=7.8 Hz, 1H), 7.45 (s, 1H), 7.39-7.33 (m, 2H), 7.19 (s, 1H), 7.09 (m, 2H), 6.00 (q, J=6.3 Hz, 1H), 4.48 (t, J=5.4 Hz, 1H), 3.68 (q, J=14.6 Hz, 2H), 3.22 (t, J=5.9 Hz, 2H), 2.56 (m, 1H), 1.71 (d, J=6.3 Hz, 3H), 0.88 (d, J=6.3 Hz, 3H).
mass: 485, 487 (M+1)$^+$.

Example 176

Synthesis of 3-((1R)-1-{2-chloro-4-[(cyclopentylamino)methyl]phenyl}ethoxy)-5-imidazo[1,2-a]pyridin-3-ylthiophene-2-carboxyamide [176] (hereinafter, referred to as the compound [176])

15 mg of the compound [172-6] was dissolved in 2 mL of chloroform, and 13 μL of diisopropylethylamine and 3 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.3 mL of dimethylsulfoxide, 80 μL of cyclopentylamine was added thereto, and the mixture was stirred overnight at room temperature. The reaction mixture was purified by preparative reverse-phase liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure to obtain 14.0 mg of the target compound [176] as a colorless oily product.

A spectral data of the compound [176] is presented below.
$^1$H-NMR (DMSO-d$_6$) δ: 8.47 (d, J=6.8 Hz, 1H), 7.86 (s, 1H), 7.74 (brs, 1H), 7.68 (d, J=9.3 Hz, 1H), 7.57 (d, J=8.3 Hz, 1H), 7.43 (d, J=1.5 Hz, 1H), 7.39-7.31 (m, 2H), 7.17 (s, 1H), 7.10-7.07 (m, 2H), 6.00 (q, J=6.3 Hz, 1H), 3.60 (s, 2H), 2.89 (m, 1H), 1.71 (d, J=6.3 Hz, 3H), 1.60-1.52 (m, 4H), 1.39-1.20 (m, 4H).

mass: 495, 497 (M+1)[+].

Example 177

Synthesis of 3-((1R)-1-{4-[(t-butylamino)methyl]-2-chlorophenyl}ethoxy)-5-imidazo[1,2-a]pyridin-3-ylthiophene-2-carboxyamide [177] (hereinafter, referred to as the compound [177])

15 mg of the compound [172-6] was dissolved in 2 mL of chloroform, and 13 μL of diisopropylethylamine and 3 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.3 mL of dimethylsulfoxide, 80 μL of t-butylamine was added thereto, and the mixture was stirred overnight at room temperature. The reaction mixture was purified by preparative reverse-phase liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure to obtain 13 mg of the target compound [177] as a colorless oily product.

A spectral data of the compound [177] is presented below.
$^1$H-NMR (DMSO-d$_6$) δ: 8.47 (d, J=6.8 Hz, 1H), 7.86 (s, 1H), 7.74 (brs, 1H), 7.69 (d, J=8.8 Hz, 1H), 7.56 (d, J=7.8 Hz, 1H), 7.44 (s, 1H), 7.39-7.32 (m, 2H), 7.17 (s, 1H), 7.10 (m, 2H), 5.99 (q, J=6.3 Hz, 1H), 3.59 (s, 2H), 1.70 (d, J=6.3 Hz, 3H), 1.02 (s, 9H).

mass: 483, 485 (M+1)[+].

Example 178

Synthesis of 5-imidazo[1,2-a]pyridin-3-yl-3-{1-[4-[(methylamino)methyl]-2(trifluoromethyl)phenyl]ethoxy}thiophene-2-carboxyamide [178] (hereinafter, referred to as the compound [178])

(1) 1.02 g of 4-methyl-2-(trifluoromethyl)benzoic acid was dissolved in 30 mL of methanol, and 1.0 mL of thionyl chloride was added thereto. After the overnight stirring at 70° C., the reaction solution was added with ethyl acetate, washed with water and saturated brine in that order, and dried over anhydrous sodium sulfate. The insolubles were filtered, the filtrate was concentrated under reduced pressure, and thus obtained residue was purified by silica gel chromatography to obtain 1.06 g of methyl (4-methyl-2-(trifluoromethyl)benzoic acid [178-1] (hereinafter, referred to as the compound [178-1]) as a yellow oily product.

(2) 1.06 g of the compound [178-1] was dissolved in 25 mL of carbon tetrachloride, then 865 mg of N-bromosuccinimide and 47 mg of benzoyl peroxide were added, and the mixture was stirred overnight at 70° C. under a nitrogen atmosphere. The insolubles were filtered through celite and the filtrate was concentrated under reduced pressure. The obtained residue was dissolved in 10 mL of N,N-dimethylformamide, 500 mg of potassium acetate was added, and the mixture was stirred overnight at room temperature. The reaction solution was added with ethyl acetate, washed with water and saturated brine in that order, and dried over anhydrous sodium sulfate. The insolubles were filtered, the filtrate was concentrated under reduced pressure, and thus obtained residue was purified by silica gel chromatography, to obtain 700 mg of methyl 4-acetoxymethyl-2-(trifluoromethyl)benzoic acid [178-2] (hereinafter, referred to as the compound [178-2]) as a yellow oily product.

(3) In accordance with the method disclosed in the literature (Tetrahedron Lett., 1995, 36, 5461), 700 mg of the compound [178-2] was dissolved in 20 mL of tetrahydrofuran, 617 mg of N,O-dimethylhydroxylamine hydrochloride was added thereto, and 6.3 mL of isopropylmagnesium bromide was then added at 0° C. The mixture was stirred overnight at room temperature, water was added thereto, 30 mL of 5N hydrochloric acid was then added, and the resultant was extracted with ethyl acetate. The organic layer was washed with saturated brine and dried over anhydrous sodium sulfate. The insolubles were filtered, the filtrate was concentrated under reduced pressure, and purified by silica gel chromatography, to obtain 346 mg of 4-(hydroxymethyl)-N-methoxy-N-methyl-2-(trifluoromethyl)benzamide [178-3] (hereinafter, referred to as the compound [178-3]) as a yellow oily product.

(4) 346 g of the compound [178-3] was dissolved in 5 mL of tetrahydrofuran, and 1.14 mL of methylmagnesium chloride (3M tetrahydrofuran solution) was added at −20° C. under a nitrogen atmosphere. After cooling back to room temperature, the mixture was stirred overnight, 1N hydrochloric acid was added thereto, and extracted with ethyl acetate. The organic layer was washed with saturated brine and dried over anhydrous sodium sulfate. The insolubles were filtered and the filtrate was concentrated under reduced pressure. The obtained residue was dissolved in 5 mL of tetrahydrofuran, 50 mg of sodium borohydride was added, and the mixture was stirred overnight at room temperature. Thereto, ethyl acetate was added, washed with saturated brine, and dried over anhydrous sodium sulfate. The insolubles were filtered and the filtrate was concentrated under reduced pressure. The residue was dissolved in 2 mL of N,N-dimethylformamide, 122 mg of imidazole and 135 mg of t-butyldimethylsilylchloride were added, and the mixture was stirred for 4 hours at room temperature. The reaction solution was added with ethyl acetate, washed with saturated brine, and dried over anhydrous sodium sulfate. The insolubles were filtered, the filtrate was concentrated under reduced pressure, and the residue was purified by silica gel column chromatography, to obtain 100 mg of 1-[4-(t-butyldimethylsilyloxy)methyl-2-trifluoromethylphenyl]ethanol [178-4] (hereinafter, referred to as the compound [178-4]) as a yellow oily product.

(5) 164 mg of 3-{1-[4-(hydroxymethyl)-2-(trifluoromethyl)phenyl]ethoxy}-5-imidazo[1,2-a]pyridin-3-ylthiophene-2-carboxyamide [178-5] (hereinafter, referred to as the compound [178-5]) was obtained as a yellow oily product from 120 mg of the compound [178-4] and 99 mg of the compound [1-3] according to the method of Example 20.

(6) The target compound [178] was obtained as a colorless oily product from the compound [178-5] and methylamine according to the method of Example 50.

A spectral data of the compound [178] is presented below.
$^1$H-NMR (DMSO-d$_6$) δ: 8.44 (d, J=7.3 Hz, 1H), 7.81 (m, 2H), 7.76 (brs, 1H), 7.69-7.64 (m, 3H), 7.36 (m, 1H), 7.13-7.05 (m, 3H), 5.97 (q, J=5.8 Hz, 1H), 3.65 (s, 2H), 2.21 (s, 3H), 1.73 (d, J=6.3 Hz, 3H).
mass: 475 (M+1)$^+$.

Example 179

Synthesis of 3-((1R)-1-{2-(difluoromethoxy)-4-[(methylamino)methyl]phenyl}ethoxy)-5-imidazo[1,2-a]pyridin-3-ylthiophene-2-carboxamide [179] (hereinafter, referred to as the compound [179])

17 mg of the compound [168] was dissolved in 2 mL of chloroform, and 13 μL of diisopropylethylamine and 3 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.3 mL of dimethylsulfoxide, 80 μL of methylamine was added thereto, and the mixture was stirred overnight at room temperature. The reaction mixture was purified by preparative reverse-phase-liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure. The residue dissolved in 10% hydrochloric acid-methanol was stirred for 1 hour and the solvent was concentrated to obtain 7.0 mg of a hydrochloride salt of the target compound [179] as a colorless oily product.

A spectral data of the compound [179] is presented below.
$^1$H-NMR (DMSO-d$_6$) δ: 8.51 (d, J=7.3 Hz, 1H), 7.86 (s, 1H), 7.69 (m, 2H), 7.57 (d, J=7.8 Hz, 1H), 7.38 (m, 1H), 7.30 (t, J=73.6 Hz, 1H), 7.27 (s, 1H), 7.21 (m, 2H), 7.07 (m, 2H), 5.95 (q, J=6.3 Hz, 1H), 3.60 (s, 2H), 2.22 (s, 3H), 1.69 (d, J=6.3 Hz, 3H).
mass: 473 (M+1)$^+$.

Example 180

Synthesis of 3-{(1R)-1-[4-[(t-butylamino)methyl]-2-(difluoromethoxy)phenyl]ethoxy}-5-imidazo[1,2-a]pyridin-3-ylthiophene-2-carboxamide [180] (hereinafter, referred to as the compound [180])

17 mg of the compound [168] was dissolved in 2 mL of chloroform, and 13 μL of diisopropylethylamine and 3 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.2 mL of dimethylsulfoxide, 0.1 mL of t-butylamine was added thereto, and the mixture was stirred overnight at room temperature. The reaction mixture was purified by preparative reverse-phase liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure to obtain 7.9 mg of the target compound [180] as a colorless solid.

A spectral data of the compound [180] is presented below.
$^1$H-NMR (DMSO-d$_6$) δ: 8.51 (d, J=6.8 Hz, 1H), 7.86 (s, 1H), 7.69 (m, 2H), 7.54 (d, J=7.8 Hz, 1H), 7.38 (m, 1H), 7.30 (t, J=73.6 Hz, 1H), 7.26 (s, 1H), 7.23 (m, 2H), 7.08 (m, 2H), 5.95 (q, J=6.3 Hz, 1H), 3.62 (s, 2H), 1.69 (d, J=6.3 Hz, 3H), 1.03 (s, 9H).
mass: 515 (M+1)$^+$.

Example 181

Synthesis of 3-[(1R)-1-(2-(difluoromethoxy)-4-{[(2-hydroxy-1,1-dimethylethyl)amino]methyl}phenyl)ethoxy]-5-imidazo[1,2-a]pyridin-3-ylthiophene-2-carboxamide [181] (hereinafter, referred to as the compound [181])

17 mg of the compound [168] was dissolved in 2 mL of chloroform, and 13 μL of diisopropylethylamine and 3 μL of methanesulfonyl chloride were added thereto. After the 1 hour stirring at 0° C., the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 0.2 mL of dimethylsulfoxide, 0.1 mL of 2-amino-2-methyl-1-propanol was added thereto, and the mixture was stirred overnight at room temperature. The reaction mixture was purified by preparative reverse-phase liquid chromatography, and thus obtained fractions were neutralized with a saturated aqueous solution of sodium hydrogen carbonate and extracted with chloroform. The organic layer was washed with saturated brine and dried over anhydrous sodium sulfate. The insolubles were filtered and the filtrate was concentrated under reduced pressure to obtain 9 mg of the target compound [181] as a colorless solid.

A spectral data of the compound [181] is presented below.
$^1$H-NMR (DMSO-d$_6$) δ: 8.50 (d, J=6.8 Hz, 1H), 7.86 (s, 1H), 7.69 (m, 2H), 7.55 (d, J=8.3 Hz, 1H), 7.37 (m, 1H), 7.30 (t, J=73.6 Hz, 1H), 7.23 (m, 3H), 7.07 (m, 2H), 5.95 (q, J=6.3 Hz, 1H), 4.51 (t, J=5.4 Hz, 1H), 3.61 (s, 2H), 3.19 (d, J=5.4 Hz, 2H), 1.69 (d, J=6.3 Hz, 3H), 0.94 (s, 6H).
mass: 531 (M+1)$^+$.

Example 182

Synthesis of 3-((1R)-1-{2-chloro-4-[(methylamino)methyl]phenyl}ethoxy)-5-(6-cyanoimidazo[1,2-a]pyridin-3-yl)thiophene-2-carboxamide [182] (hereinafter, referred to as the compound [182])

(1) 4.0 g of 2-amino-5-bromopyridine was dissolved in 40 mL of chloroform, and 19 mL of chloroacetaldehyde (40% aqueous solution) and 3.8 g of sodium hydrogen carbonate were added at room temperature. The mixture was stirred overnight at room temperature, and the reaction mixture was added with water and extracted with chloroform. The organic layer was washed with water and saturated brine, and dried over anhydrous sodium sulfate. The insolubles were filtered, the filtrate was concentrated, and thus obtained residue was purified by silica gel column chromatography, to obtain 2.92 g of 6-bromoimidazo[1,2-a]pyridine [182-1] (hereinafter, referred to as the compound [182-1]) as a light brown solid.

(2) 2.92 g of the compound [182-1] was dissolved in 60 mL of acetonitrile, and 3.33 g of N-iodosuccinimide was added at room temperature. After the 2 hours stirring at room temperature, the precipitated powders were taken by filtration and washed with ether to obtain 4.25 g of 6-bromo-3-iodoimidazo

[1,2-a]pyridine [182-2] (hereinafter, referred to as the compound [182-2]) as a light brown oily product.

(3) 4.25 g of the compound [182-2] was dissolved in 240 mL of tetrahydrofuran, then 3.63 g of potassium carbonate, 1.84 g of bis(triphenylphosphine)palladium(II) dichloride, 501 mg of copper iodide, and 1.64 mL of methyl propiolic acid were added, and the mixture was stirred for 4 hours at room temperature under a nitrogen atmosphere. The insolubles were filtered through celite, the filtrate was concentrated under reduced pressure, and thus obtained residue was purified by silica gel column chromatography, to obtain 1.82 g of 3-(6-bromoimidazo[1,2-a]pyridin-3-yl)propi-2-noate [182-3] (hereinafter, referred to as the compound [182-3]). Subsequently, 352 mg of sodium methoxide was dissolved in 140 mL of methanol, 612 µL of methyl thioglycolate was added thereto, and the mixture was stirred for 10 minutes at room temperature. Next, 60 mL of methanol solution containing 1.82 g of the compound [182-3] was added to the reaction mixture, and stirred for 6 hours at the same temperature. Thereto, 561 µL of trifluoroacetic acid was added and neutralized, and the solution was under reduced pressure. The residue was added with water, and extracted with chloroform. The organic layer was washed with saturated brine and dried over anhydrous sodium sulfate. The insolubles were filtered, the filtrate was concentrated under reduced pressure, and thus obtained residue was purified by silica gel column chromatography, to obtain 1.64 g of methyl 5-(6-bromoimidazo[1,2-a]pyridin-3-yl)-3-hydroxythiophene-2-carboxylic acid [101-1] (hereinafter, referred to as the compound [101-1] as a colorless solid.

(4) 200 mg of the compound [101-1] was dissolved in 10 mL of tetrahydrofuran, then 255 mg of the compound [172-4], 211 µL of tributylphosphine, and 167 µL of diisopropyl azodicarboxylate were added thereto, and the mixture was stirred for 2 hours at room temperature. The solvent was concentrated under reduced pressure, and thus obtained residue was purified by silica gel column chromatography, to obtain 537 mg of methyl 5-(6-bromoimidazo[1,2-a]pyridin-3-yl)-3-{(1R)-1-[4-(t-butyldimethylsiloxy)methyl-2-chlorophenyl]ethoxy}thiophene-2-carboxylic acid [182-4] (hereinafter, referred to as the compound [182-4]) as pale yellow amorphous.

(5) 537 mg of the compound [182-4] was added to 20 mL of ammonia (methanol solution, 7M), and the mixture was stirred in a sealed tube for 2 days at 70° C. After concentrating the reaction mixture, the obtained residue was purified by silica gel column chromatography to obtain 252 mg of 5-(6-bromoimidazo[1,2-a]pyridin-3-yl)-3-{(1R)-1-[4-(t-butyldimethylsiloxy)methyl-2-chlorophenyl]ethoxy}thiophene-2-carboxyamide [182-5] (hereinafter, referred to as the compound [182-5]) as a light brown solid.

(6) 50 mg of the compound [182-5] was dissolved in 3 mL of N,N-dimethylformamide, then 38 mg of zinc cyanide and 93 mg of tetrakis(triphenylphosphine)palladium (0) were added thereto, and the mixture was stirred overnight at 100° C. under a nitrogen atmosphere. The reaction mixture was added with chloroform, washed with water and saturated brine, and dried over anhydrous sodium sulfate. The insolubles were filtered, the filtrate was concentrated under reduced pressure, and formed an azeotrope with toluene. The residue was dissolved in 4 mL of tetrahydrofuran, and 0.11 mL of tetrabutylammonium fluoride (tetrahydrofuran solution, 1M) was added. After the 1 hour stirring at room temperature, the reaction mixture was added with chloroform, washed with water and saturated brine, and dried over anhydrous sodium sulfate. The insolubles were filtered, the filtrate was concentrated under reduced pressure, and the residue was purified by preparative thin-layer chromatography, to obtain 24 mg of 3-{(1R)-1-[2-chloro-4-(hydroxymethyl)phenyl]ethoxy}-5-(6-cyanoimidazo[1,2-a]pyridin-3-yl)thiophene-2-carboxyamide [182-6] (hereinafter, referred to as the compound [182-6])
as a milky yellow solid.

(7) 5 mg of the compound [182-6] was dissolved in 3 mL of chloroform, and 4 µL of diisopropylethylamine and 1.3 µL of methanesulfonyl chloride were added thereto. The mixture was stirred overnight at 0° C., and the reaction mixture was added with water and extracted with chloroform. The organic layer was washed with saturated brine and dried over anhydrous sodium sulfate. The insolubles were filtered, the filtrate was concentrated under reduced pressure, and thus obtained residue was dissolved in 0.3 mL of tetrahydrofuran. Thereto, 1 mL of methylamine (2M tetrahydrofuran solution) was added and stirred overnight at room temperature. The reaction mixture was added with chloroform, washed with water and saturated brine, dried over anhydrous sodium sulfate. The insolubles were filtered and the filtrate was concentrated under reduced pressure. The residue was purified by preparative thin-layer chromatography, to obtain 4.5 mg of the target compound [182] as a colorless solid.

A spectral data of the compound [182] is presented below.
$^1$H-NMR (CDCl$_3$) δ: 8.49 (d, J=1.6 Hz, 1H), 7.85 (s, 1H), 7.74 (d, J=9.6 Hz, 1H), 7.52-7.50 (m, 1H), 7.42 (d, J=8.4 Hz, 1H), 7.33 (dd, J=9.6, 1.6 Hz, 1H), 7.32-7.30 (m, 1H), 7.24 (brs, 1H), 6.79 (s, 1H), 5.90 (q, J=6.4 Hz, 1H), 5.89 (brs, 1H), 3.75 (s, 2H), 2.45 (s, 3H), 1.77 (d, J=6.4 Hz, 3H).
mass: 466, 468 (M+1)$^+$.

Example 183

Synthesis of ((1R)-1-{2-chloro-4-[(dimethylamino)methyl]phenyl}ethoxy)-5-(6-cyanoimidazo[1,2-a]pyridin-3-yl)thiophene-2-carboxyamide [183] (hereinafter, referred to as the compound [183])

5 mg of the target compound [183] was obtained as colorless solid from 5 mg of the compound [182-6] and dimethylamine according to the method of Example 182-(7).

A spectral data of the compound [183] is presented below.
$^1$H-NMR (CDCl$_3$) δ: 8.56 (d, J=1.6 Hz, 1H), 7.84 (s, 1H), 7.75 (d, J=9.6 Hz, 1H), 7.49 (d, J=1.6 Hz, 1H), 7.41 (d, J=8.0 Hz, 1H), 7.34 (dd, J=9.6, 1.6 Hz, 1H), 7.29 (dd, J=8.0, 1.6 Hz, 1H), 7.25 (brs, 1H), 6.80 (s, 1H), 5.91 (brs, 1H), 5.90 (q, J=6.4 Hz, 1H), 3.41 (s, 2H), 2.23 (s, 6H), 1.77 (d, J=6.4 Hz, 3H).
mass: 480, 482 (M+1)$^+$.

Example 184

Synthesis of 3-[(1R)-1-(2-chloro-4-{[(2-hydroxy-1,1-dimethylethyl)amino]methyl}phenyl)ethoxy]-5-(6-cyanoimidazo[1,2-a]pyridin-3-yl)thiophene-2-carboxyamide [184] (hereinafter, referred to as the compound [184])

3.3 mg of the target compound [184] was obtained as a colorless solid from 5 mg of the compound [182-6] and 2-amino-2-methyl-1-propanol according to the method of Example 182-(7).

A spectral data of the compound [184] is presented below.
$^1$H-NMR (CDCl$_3$) δ: 8.40 (d, J=1.6 Hz, 1H), 7.85 (s, 1H), 7.74 (d, J=9.6 Hz, 1H), 7.59 (d, J=1.6 Hz, 1H), 7.42 (d, J=8.0 Hz, 1H), 7.32 (dd, J=9.6, 1.6 Hz, 1H), 7.31 (dd, J=8.0, 1.6 Hz, 1H), 7.24 (brs, 1H), 6.79 (s, 1H), 5.90 (brs, 1H), 5.89 (q, J=6.4 Hz, 1H), 3.71 (s, 2H), 3.37 (s, 2H), 1.76 (d, J=6.4 Hz, 3H), 1.14 (s, 6H).

mass: 524, 526 (M+1)$^+$.

Example 185

Synthesis of 3-((1R)-1-{2-chloro-4-[(4-methylpiperazin-1-yl)methyl]phenyl}ethoxy)-5-(6-cyanoimidazo[1,2-a]pyridin-3-yl)thiophene-2-carboxyamide [185] (hereinafter, referred to as the compound [185])

5 mg of the compound [182-6] was dissolved in 3 mL of chloroform, and 9 µL of diisopropylethylamine and 3 µL of methanesulfonyl chloride were added thereto. After the 1 hour stirring at room temperature, the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 1 mL of tetrahydrofuran, 24 µL of N-methylpiperazine was added thereto, and the mixture was stirred overnight at room temperature. The reaction mixture was added with chloroform, washed with water and saturated brine, and dried over anhydrous sodium sulfate. The insolubles were filtered and the filtrate was concentrated under reduced pressure. The residue was purified by preparative thin-layer chromatography to obtain 5.4 mg of the target compound [185] as a colorless solid.

A spectral data of the compound [185] is presented below.
$^1$H-NMR (CDCl$_3$) δ: 8.58 (d, J=1.6 Hz, 1H), 7.85 (s, 1H), 7.75 (d, J=9.6 Hz, 1H), 7.49 (d, J=1.6 Hz, 1H), 7.40 (d, J=8.0 Hz, 1H), 7.34 (dd, J=9.6, 1.6 Hz, 1H), 7.29 (dd, J=8.0, 1.6 Hz, 1H), 7.24 (brs, 1H), 6.81 (s, 1H), 5.98 (brs, 1H), 5.90 (q, J=6.4 Hz, 1H), 3.55-3.45 (m, 2H), 2.55-2.35 (m, 8H), 2.28 (s, 3H), 1.77 (d, J=6.4 Hz, 3H).

mass: 535, 537 (M+1)$^+$.

Example 186

Synthesis of 3-((1R)-1-{4-[(t-butylamino)methyl]-2-chlorophenyl}ethoxy)-5-(6-cyanoimidazo[1,2-a]pyridin-3-yl)thiophene-2-carboxyamide [186] (hereinafter, referred to as the compound [186])

10 mg of the compound [182-6] was dissolved in 2 mL of chloroform, and 19 µL of diisopropylethylamine and 6 µL of methanesulfonyl chloride were added thereto at 0° C. After the 1 hour stirring at room temperature, the reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 2 mL of tetrahydrofuran, 194 µL of t-butylamine was added thereto, and the mixture was stirred overnight at room temperature. The reaction mixture was added with chloroform, washed with water and saturated brine, and dried over anhydrous sodium sulfate; The insolubles were filtered and the filtrate was concentrated under reduced pressure. The residue was purified by preparative thin-layer chromatography to obtain 6.1 mg of the target compound [186] as a colorless solid.

A spectral data of the compound [186] is presented below.
$^1$H-NMR (CDCl$_3$) δ: 8.54-8.50 (m, 1H), 7.85 (s, 1H), 7.75 (d, J=9.6 Hz, 1H), 7.54-7.52 (m, 1H), 7.40 (d, J=8.0 Hz, 1H), 7.36-7.31 (m, 2H), 7.26 (brs, 1H), 6.79 (s, 1H), 6.03 (brs, 1H), 5.89 (q, J=6.4 Hz, 1H), 3.72 (s, 2H), 1.76 (d, J=6.4 Hz, 3H), 1.15 (s, 9H).

mass: 508, 510 (M+1)$^+$.

Example 187

Synthesis of 3-{(1R)-1-[4-[(t-butylamino)methyl]-2-(difluoromethoxy)phenyl]ethoxy}-5-(6-cyanoimidazo[1,2-a]pyridin-3-yl)thiophene-2-carboxyamide [187] (hereinafter, referred to as the compound [187])

(1) 1.09 g of methyl 5-(6-bromodimidazo[1,2-a]pyridin-3-yl)-3-{(1R)-1-[4-(t-butyldimethylsiloxy)methyl-2-(difluoromethoxy)phenyl]ethoxy}thiophene-2-carboxylic acid [187-1] (including impurities) (hereinafter, referred to as the compound [187-1]) was obtained as a colorless oily product from 418 mg of the compound [101-1] and 230 mg of the compound [168-5] according to the method of Example 1-(4).

(2) 505 mg of 5-(6-cyanoimidazo[1,2-a]pyridin-3-yl)-3-{(1R)-1-[2-(difluoromethoxy)-4-(hydroxymethyl)phenyl]ethoxy}thiophene-2-carboxyamide [187-2] (hereinafter, referred to as the compound [187-2]) was obtained as a colorless oily product from 1.09 g of the compound [187-1] according to the methods of Example 182-(5) and (6).

(3) The target compound [187] was obtained as a white solid from the compound [187-2] and t-butylamine according to the method of Example 186.

A spectral data of the compound [187] is presented below.
$^1$H-NMR (DMSO-d$_6$) δ: 9.27 (s, 1H), 9.13 (brs, 1H), 8.07 (s, 1H), 7.87 (d, J=8.0 Hz, 1H), 7.80 (brs, 1H), 7.67-7.74 (m, 2H), 7.60 (s, 1H), 7.52 (m, 1H), 7.43 (s, 1H), 7.34 (t, J=72 Hz, 1H), 7.16 (brs, 1H), 6.06 (q, J=6.7 Hz, 1H), 4.05-4.07 (m, 2H), 1.72 (d, J=6.7 Hz, 3H), 1.34 (s, 9H).

mass: 540 (M+1)$^+$.

Example 188

Synthesis of 5-(6-cyanoimidazo[1,2-a]pyridin-3-yl)-3-[(1R)-1-(2-(difluoromethoxy)-4-{[(2-hydroxy-1,1-dimethylethyl)amino]methyl}phenyl)ethoxy]thiophene-2-carboxyamide [188] (hereinafter, referred to as the compound [188])

The target compound [188] was obtained as a white solid from the compound [187-2] and 2-amino-2-methyl-1-propanol according to the method of Example 186.

A spectral data of the compound [188] is presented below.
$^1$H-NMR (DMSO-d$_6$) δ: 9.25 (s, 1H), 8.55 (brs, 1H), 8.01 (s, 1H), 7.85 (d, J=8.0 Hz, 1H), 7.80 (brs, 1H), 7.74 (d, J=8.0 Hz, 1H), 7.64 (d, J=8.0 Hz, 1H), 7.40-7.42 (m, 3H), 7.23 (t, J=72 Hz, 1H), 7.15 (brs, 1H), 6.07 (q, J=6.7 Hz, 1H), 4.04-4.07 (m, 2H), 3.46 (s, 2H), 1.72 (d, J=6.7 Hz, 3H), 1.23 (s, 6H).

mass: 556 (M+1)$^+$.

Example 189

Synthesis of 3-[(1R)-1-(2-chlorophenyl)ethoxy]-5-{6-[(N,N-dimethylglycyl)amino]imidazo[1,2-a]pyridin-3-yl}thiophene-2-carboxyamide [189] (hereinafter, referred to as the compound [189])

(1) 10 mg of t-butyl{[(3-{5-(aminocarbonyl)-4-[(1R)-1-(2-chlorophenyl)ethoxy]-2-thienyl}imidazo[1,2-a]pyridin-6-yl)amino]-2-oxoethyl}carbamate [189-1] (hereinafter, referred to as the compound [189-1]) was obtained as a pale yellow solid from 10 mg of the compound [101] and (t-butoxycarbonyl)amino acetic acid according to the method of Example 8.

(2) 10 mg of the compound [189-1] was dissolved in 4N hydrochloric acid-dioxane, and the mixture was stirred for 2 hours at room temperature. The reaction solution was concentrated under reduced pressure, the residue was dissolved in a solvent of 1 mL of chloroform and 1 mL of methanol, and 12 µL of formaldehyde (37% aqueous solution) and 153 µL of a methanol solution containing 4 mg of zinc chloride and 3 mg of sodium cyanotrihydroborate were added. The mixture was stirred overnight at room temperature, added with chloroform, and washed with water, a saturated aqueous solution of sodium hydrogen carbonate, and saturated brine. The organic layer was dried over anhydrous sodium sulfate. The insolubles were filtered, the filtrate was concentrated under reduced pressure, and the residue was purified by preparative thin-layer chromatography, to obtain 5.7 mg of the target compound [189] as a pale yellow solid.

A spectral data of the compound [189] is presented below.
$^1$H-NMR (CDCl$_3$) δ: 9.17 (d, J=1.6 Hz, 1H), 9.15 (brs, 1H), 7.71 (s, 1H), 7.62 (d, J=9.6 Hz, 1H), 7.47 (dd, J=8.0, 1.6 Hz, 1H), 7.38 (dd, J=8.0, 1.6 Hz, 1H), 7.33-7.23 (m, 3H), 6.80 (s, 1H), 5.93 (q, J=6.4 Hz, 1H), 5.84 (brs, 1H), 3.14 (s, 2H), 2.43 (s, 6H), 1.77 (d, J=6.4 Hz, 3H).
mass: 498, 500 (M+1)$^+$.

Example 190

Synthesis of 3-[(1R)-1-(2-chlorophenyl)ethoxy]-5-[6-(1-hydroxyethyl)imidazo[1,2-a]pyridin-3-yl]thiophene-2-carboxamide [190] (hereinafter, referred to as the compound [190])

2.5 mg of the target compound [190] was obtained as a light brown oily product from 7.7 mg of the compound [119-1] according to the method of Example 39-(2).

A spectral data of the compound [190] is presented below.
$^1$H-NMR (CDCl$_3$) δ: 8.20 (s, 1H), 8.01 (s, 1H), 7.69-7.29 (m, 16H), 6.67 (s, 1H), 6.64 (s, 1H), 5.89-5.83 (m, 4H), 4.89 (q, J=8.0 Hz, 1H), 4.78 (q, J=8.0 Hz, 1H), 1.77-1.75 (m, 6H), 1.53 (d, J=8.0 Hz, 6H).
mass: 442, 444 (M+1)$^+$.

Example 191

Synthesis of 3-[(1R)-1-(2-chlorophenyl)ethoxy]-5-[6-(2,2,2-trifluoro-1-hydroxyethyl)imidazo[1,2-a]pyridin-3-yl]thiophene-2-carboxamide [191] (hereinafter, referred to as the compound [191])

5 mg of the compound [119-1] was dissolved in 0.5 mL of tetrahydrofuran, 0.01 mL of (trifluoromethyl)trimethylsilane was added thereto, and 0.01 mL of tetrabutylammonium fluoride (tetrahydrofuran solution, 1M) was then added under an ice-cold condition. After stirring at room temperature for 1 hour and further stirring overnight at 40° C., the reaction solution was concentrated under reduced pressure and thus obtained residue was purified by silica gel column chromatography, to obtain 1.4 mg of the target compound [191] as a colorless solid.

A spectral data of the compound [191] is presented below.
$^1$H-NMR (CDCl$_3$) δ: 8.33 (s, 1H), 8.23 (s, 1H), 7.68-7.29 (m, 16H), 6.67 (s, 1H), 6.64 (s, 1H), 5.87-5.80 (m, 4H), 5.05 (q, 1H), 4.95 (q, 1H), 1.76 (d, J=8.0 Hz, 6H).
mass: 496, 498 (M+1)$^+$.

Example 192

Synthesis of 3-[(1R)-1-(2-chlorophenyl)ethoxy]-5-(6-{[(2-hydroxyethyl)(methyl)amino]methyl}imidazo[1,2-a]pyridin-3-yl)thiophene-2-carboxyamide [192] (hereinafter, referred to as the compound [192])

3.7 mg of the target compound [192] was obtained as a pale yellow solid from 5 mg of the compound [107] and 2-(methylamino)ethanol according to the method of Example 50.

A spectral data of the compound [192] is presented below.
$^1$H-NMR (CD$_3$OD) δ: 8.25 (s, 1H), 7.72 (s, 1H), 7.59 (d, J=8.0 Hz, 1H), 7.59 (dd, J=1.0, 8.0 Hz, 1H), 7.47 (dd, J=1.0, 8.0 Hz, 1H), 7.49 (dd, J=1.0, 8.0 Hz, 1H), 7.38 (ddd, J=1.0, 8.0, 8.0 Hz, 1H), 7.33 (ddd, J=1.0, 8.0, 8.0 Hz, 1H), 7.01 (s, 1H), 6.09 (q, J=8.0 Hz, 1H), 3.69 (t, J=8.0 Hz, 2H), 3.61 (dd, J=16, 24 Hz, 2H), 2.60 (t, J=8.0 Hz, 2H), 2.29 (s, 3H), 1.78 (d, J=8.0 Hz, 3H).
mass: 485, 487 (M+1)$^+$.

Example 193

Synthesis of 3-[(1R)-1-(2-chlorophenyl)ethoxy]-5-(6-{[(2-fluoroethyl)(methyl)amino]methyl}imidazo[1,2-a]pyridin-3-yl)thiophene-2-carboxamide [193] (hereinafter, referred to as the compound [193])

(1) 30 mg of 3-[(1R)-1-(2-chlorophenyl)ethoxy]-5-{6-[(methylamino)methyl]imidazo[1,2-a]pyridin-3-yl}thiophene-2-carboxyamide [193-1] (hereinafter, referred to as the compound [193-1]) was obtained as a pale yellow oily product from 60 mg of the compound [107] and methylamine according to the method of Example 50.

(2) 3.4 mg of the compound [193-1] was dissolved in 0.4 mL of dichloromethane, then 1.7 mg of 2-fluoroethyl 4-methylbenzenesulfonate and 6 µL of diisopropylethylamine were added, and the mixture was stirred overnight at room temperature. The reaction solution was concentrated under reduced pressure and thus obtained residue was purified by silica gel column chromatography, to obtain 1.4 mg of the target compound [193] as a pale yellow solid.

A spectral data of the compound [193] is presented below.
$^1$H-NMR (CDCl$_3$) δ: 8.20 (s, 1H), 7.73 (s, 1H), 7.62 (d, J=8.0 Hz, 1H), 7.48 (d, J=8.0 Hz, 1H), 7.42 (d, J=8.0 Hz, 1H), 7.34-7.24 (m, 4H), 6.74 (s, 1H), 5.91 (q, J=8.0 Hz, 1H), 5.70 (brs, 1H), 4.58 (dt, 5.0, 48 Hz, 2H), 3.57 (dd, J=13, 16 Hz, 2H), 2.78 (dt, J=5.0, 20 Hz, 2H), 2.32 (s, 3H), 1.77 (d, J=8.0 Hz, 3H).
mass: 487, 489 (M+1)$^+$.

Example 194

Synthesis of 3-[(1R)-1-(2-chlorophenyl)ethoxy]-5-(6-{[methyl(pyridin-2-yl)amino]methyl}imidazo[1,2-a]pyridin-3-yl)thiophene-2-carboxamide [194] (hereinafter, referred to as the compound [194])

1.0 mg of the target compound [194] was obtained as a colorless oily product from 5 mg of the compound [107] and 2-(methylamino)pyridine according to the method of Example 50.

A spectral data of the compound [194] is presented below.
¹H-NMR (CDCl₃) δ: 8.24 (s, 1H), 8.22 (d, J=5.0 Hz, 1H), 7.72 (s, 1H), 7.57 (d, J=8.0 Hz, 1H), 7.53-7.47 (m, 2H), 7.41 (dd, J=1.0, 8.0 Hz, 1H), 7.35-7.20 (m, 4H), 6.73 (s, 1H), 6.64 (dd, J=5.0, 7.0 Hz, 1H), 6.66 (d, J=8.0 Hz, 1H), 5.88 (q, J=8.0 Hz, 1H), 5.74 (brs, 1H), 4.85 (dd, J=12, 16 Hz, 2H), 2.98 (s, 3H), 1.76 (d, J=8.0 Hz, 3H).
mass: 518, 520 (M+1)⁺.

Example 195

Synthesis of 3-[(1R)-1-(2-chlorophenyl)ethoxy]-5-(6-{[(1H-imidazol-2-ylmethyl)(methyl)amino]methyl}imidazo[1,2-a]pyridin-3-yl)thiophene-2-carboxyamide [195] (hereinafter, referred to as the compound [195])

8.0 mg of the target compound [195] was obtained as a colorless oily product from 10 mg of the compound [193-1] and 7 mg of 2-imidazolcarboxyaldehyde according to the method of Example 109.
A spectral data of the compound [195] is presented below.
¹H-NMR (CDCl₃) δ: 8.25 (s, 1H), 7.72 (s, 1H), 7.59 (d, J=9.0 Hz, 1H), 7.47 (dd, J=2.0, 8.0 Hz, 1H), 7.41 (dd, J=2.0, 8.0 Hz, 1H), 7.34-7.24 (m, 5H), 7.04 (s, 2H), 6.74 (s, 1H), 6.08 (brs, 1H), 5.91 (q, J=8.0 Hz, 1H), 3.75 (s, 2H), 3.55 (s, 2H), 2.26 (s, 3H), 1.76 (d, J=8.0 Hz, 3H).
mass: 521, 523 (M+1)⁺.

Example 196

Synthesis of 3-{1-[2-(difluoromethoxy)phenyl]ethoxy}-5-{6-[(4-methylpiperazin-1-yl)methyl]imidazo[1,2-a]pyridin-3-yl}thiophene-2-carboxyamide [196] (hereinafter, referred to as the compound [196])

(1) 2.98 g of 1-[2-(difluoromethoxy)phenyl]ethanol [196-1] (hereinafter, referred to as the compound [196-1]) was obtained as a colorless oily product from 2.58 g of 2-(difluoromethoxy)benzaldehyde according to the method of Example 39-(2).
(2) 99 mg of 3-[1-(2-difluoromethoxy)ethoxy]-5-[6-(hydroxymethyl)imidazo[1,2-a]pyridin-3-yl]thiopene-2-carboxyamide [196-2] (hereinafter, referred to as the compound [196-2]) was obtained as a pale yellow oily product from 135 mg of the compound [196-1] and 250 mg of the compound [107-4] according to the method of Example 20.
(3) 5.0 mg of a trifluoroacetate salt of the target compound [196] was obtained from 10 mg of the compound [196-2] and N-methylpiperazine according to the method of Example 50.
A spectral data of the compound [196] is presented below.
¹H-NMR (DMSO-d₆) δ: 8.55 (s, 1H), 8.20 (s, 1H), 7.88-7.85 (m, 2H), 7.68 (d, J=9.2 Hz, 1H), 7.64 (dd, J=1.9, 7.8 Hz, 1H), 7.40 (m, 1H), 7.32 (m, 2H), 7.30 (t, J=73.6 Hz, 1H), 7.23 (d, J=7.8 Hz, 1H), 7.17 (brs, 1H), 5.94 (q, J=6.3 Hz, 1H), 3.75 (brs, 2H), 3.40 (brs, 2H), 3.00 (brs, 4H), 2.78 (s, 3H), 2.5 (brs, 2H), 1.71 (d, J=6.8 Hz, 3H).
mass: 542, 544 (M+1)⁺.

Example 197

Synthesis of 3-((1R)-1-{2-chloro-4-[(methylamino)methyl]phenyl}ethoxy)-5-[6-(hydroxymethyl)imidazo[1,2-a]pyridin-3-yl]thiophene-2-carboxyamide [197] (hereinafter, referred to as the compound [197])

(1) 1.0 g of the compound [172-4] was dissolved in 10 mL of tetrahydrofuran, and 0.5 mL of tetrabutylammonium fluoride (tetrahydrofuran solution, 1M) was added thereto under an ice-cold condition. After the 1 hour stirring at room temperature, the reaction solution was added with ethyl acetate, washed with water and saturated brine in that order, and dried over anhydrous sodium sulfate. The insolubles were filtered and the filtrate was concentrated under reduced pressure. The residue was dissolved in 10 mL of dichloromethane, 0.24 mL of 2,4,6-collidine and 0.1 mL of acetyl chloride were added under an ice-cold condition, and the mixture was stirred overnight at room temperature. The reaction solution was concentrated under reduced pressure and thus obtained residue was purified by silica gel column chromatography to obtain 284 mg of 3-chloro-4-[(1S)-1-hydroxyethyl]benzoylacetate [197-1] (hereinafter, referred to as the compound [197-1]) as a colorless oily product.
(2) 527 mg of the compound [107-4] was dissolved in 10 mL of tetrahydrofuran, 288 mg of the compound [197-1], 627 μL of tributylphosphine, and 497 μL of diisopropyl azodicarboxylate were added, and the mixture was stirred for 4 hours at 70° C. The solvent was concentrated under reduced pressure, thus obtained residue was dissolved in 10 mL of tetrahydrofuran, and 1.2 mL of tetrabutylammonium fluoride (tetrahydrofuran solution, 1M) was added thereto under an ice-cold condition. After the 1 hour stirring at room temperature, the reaction solution was concentrated under reduced pressure and the residue was purified by silica gel column chromatography to obtain 470 mg of methyl 3-((1R)-1-{4-[(acetyloxy)methyl]-2-chorophenyl}ethoxy)-5-[6-hydroxymethylimidazo[1,2-a]pyridin-3-yl]thiophene-2-carboxylic acid [197-2] (hereinafter, referred to as the compound [197-2]) as a colorless oily product.
(3) 110 mg of the compound [197-2] was dissolved in 3 mL of N,N-dimethylformaide, then 29 mg of imidazole and 54 μL of 1,3-dichloro-1,1,3,3-tetraisopropyldisiloxane were added, and the mixture was stirred overnight at room temperature. The reaction solution was added with ethyl acetate, washed with water and saturated brine in that order, and dried over anhydrous sodium sulfate. The insolubles were filtered and the filtrate was concentrated under reduced pressure. The residue was dissolved in a 7N ammonia/methanol solution and overheated overnight in a sealed tube at 70° C. The solvent was concentrated under reduced pressure and thus obtained residue was purified by silica gel column chromatography to obtain 106 mg of 3-{(1R)-1-[2-chloro-4-(hydroxymethyl)phenyl]ethoxy}-5-(6-{[(triisopropylsilyl)oxy]methyl}imidazo[1,2-a]pyridin-3-yl)thiophene-2-carboxyamide [197-3] (hereinafter, referred to as the compound [197-3]) as a colorless oily product.
(4) After the reaction of the compound [197-3] with monomethylamine in accordance with the method of Example 50, tetrabutylammonium fluoride (tetrahydrofuran solution, 1M) was added thereto. The mixture was stirred overnight at room temperature, and then the reaction solution was concentrated under reduced pressure. The residue was purified by preparative reverse-phase liquid chromatography to obtain the target compound [197] as a colorless oily product.
A spectral data of the compound [197] is presented below.
¹H-NMR (DMSO-d₆) δ: 8.37 (brs, 1H), 7.84 (s, 1H), 7.74 (brs, 1H), 7.65 (d, J=9.8 Hz, 1H), 7.60 (d, J=8.3 Hz, 1H), 7.41 (d, J=1.4 Hz, 1H), 7.32 (m, 2H), 7.17 (s, 1H), 7.11 (brs, 1H), 5.99 (q, J=6.3 Hz, 1H), 4.55 (s, 2H), 3.58 (s, 2H), 2.20 (s, 3H), 1.71 (d, J=6.3 Hz, 3H).
mass: 471, 473 (M+1)⁺.

Example 198

Synthesis of 3-((1R)-1-{2-chloro-4-[(isopropy-lamino)methyl]phenyl}ethoxy)-5-[6-(hydroxymethyl)imidazo[1,2-a]pyridin-3-yl]thiophene-2-carboxyamide [198](hereinafter, referred to as the compound [198])

5.8 mg of the target compound [198] was obtained as a colorless oily product from 10 mg of the compound [197-3] and isopropylamine according to the method of Example 197-(4).
A spectral data of the compound [198] is presented below.
$^1$H-NMR (DMSO-$d_6$) δ: 8.37 (brs, 1H), 7.84 (s, 1H), 7.74 (brs, 1H), 7.65 (d, J=9.8 Hz, 1H), 7.59 (d, J=7.8 Hz, 1H), 7.44 (d, J=1.4 Hz, 1H), 7.34 (m, 2H), 7.16 (s, 1H), 7.11 (brs, 1H), 5.98 (q, J=6.3 Hz, 1H), 4.55 (s, 2H), 3.64 (s, 2H), 2.49 (m, 1H), 1.70 (d, J=6.3 Hz, 3H), 0.95 (dd, J=1.0, 6.3 Hz, 6H).
mass: 499, 501 (M+1)$^+$.

Example 1-99

Synthesis of 3-{(1R)-1-[2-chloro-4-(pyrrolidin-1-ylmethyl)phenyl]ethoxy}-5-[6-(hydroxymethyl)imidazo[1,2-a]pyridin-3-yl]thiophene-2-carboxyamide [199] (hereinafter, referred to as the compound [199])

4.5 mg of the target compound [199] was obtained as a colorless oily product from 10 mg of the compound [197-3] and pyrrolidine according to the method of Example 197-(4).
A spectral data of the compound [199] is presented below.
$^1$H-NMR (DMSO-$d_6$) δ: 8.38 (s, 1H), 7.84 (s, 1H), 7.74 (brs, 1H), 7.66 (d, J=9.8 Hz, 1H), 7.60 (d, J=7.8 Hz, 1H), 7.38 (d, J=1.4 Hz, 1H), 0.32 (m, 2H), 7.17 (s, 1H), 7.10 (brs, 1H), 5.98 (q, J=6.3 Hz, 1H), 5.44 (brs, 1H), 4.55 (s, 2H), 3.52 (s, 2H), 2.36 (m, 4H), 1.71 (d, J=6.3 Hz, 3H), 1.64 (m, 4H).
mass: 511, 513 (M+1)$^+$.

Example 200

Synthesis of 3-((1R)-1-{2-chloro-4-[(dimethylamino)methyl]phenyl}ethoxy)-5-[6-(hydroxymethyl)imidazo[1,2-a]pyridin-3-yl]thiophene-2-carboxyamide [200] (hereinafter, referred to as the compound [200])

4.8 mg of the target compound [200] was obtained as a colorless oily product from 10 mg of the compound [197-3] and dimethylamine according to the method of Example 197-(4).
A spectral data of the compound [200] is presented below.
$^1$H-NMR (DMSO-$d_6$) δ: 8.38 (s, 1H), 7.84 (s, 1H), 7.74 (brs, 1H), 7.65 (d, J=8.3 Hz, 1H), 7.62 (d, J=7.8 Hz, 1H), 7.37 (d, J=1.5 Hz, 1H), 7.35-7.29 (m, 2H), 7.18 (s, 1H), 7.10 (brs, 1H), 5.99 (q, J=6.3 Hz, 1H), 5.43 (brs, 1H), 4.55 (s, 2H), 3.34 (s, 2H), 2.09 (s, 6H), 1.71 (d, J=6.3 Hz, 3H).
mass: 485, 487 (M+1)$^+$.

Example 201

Synthesis of 3-((1R)-1-{4-[(t-butylamino)methyl]-2-chlorophenyl}ethoxy)-5-[6-(hydroxymethyl)imidazo[1,2-a]pyridin-3-yl]thiophene-2-carboxyamide [201] (hereinafter, referred to as the compound [201])

2.8 mg of the target compound [201] was obtained as a colorless oily product from 10 mg of the compound [197-3] and t-butylamine according to the method of Example 197-(4).
A spectral data of the compound [201] is presented below.
$^1$H-NMR (CDCl$_3$) δ: 7.77 (brs, 1H), 7.72 (s, 1H), 7.56 (d, J=9.3 Hz, 1H), 7.47 (s, 1H), 7.44 (d, J=7.8 Hz, 1H), 7.25 (m, 2H), 7.12 (m, 1H), 6.57 (s, 1H), 5.79 (m, 2H), 4.61 (AB-q, J=13.17, 14.63 Hz, 2H), 3.72 (s, 2H), 1.76 (d, J=6.3 Hz, 3H), 1.22 (s, 9H).
mass: 513 (M+1)$^+$.

Example 202

Synthesis of 3-{(1R)-1-[4-[(t-butylamino)methyl]-2-(difluoromethoxy)phenyl]ethoxy}-5-[6-(hydroxymethyl)imidazo[1,2-a]pyridin-3-yl]thiophene-2-carboxyamide [202] (hereinafter, referred to as the compound [202])

(1) 660 mg of the compound [168-5] was dissolved in 20 mL of tetrahydrofuran, and 2.2 mL of tetrabutylammonium fluoride (tetrahydrofuran solution, 1M) was added thereto under an ice-cold condition. After the 1 hour stirring at room temperature, the reaction solution was concentrated under reduced pressure, the residue was dissolved in 20 mL of chloroform, 0.53 mL of 2,4,6-collidine and 0.25 mL of benzoyl chloride were added under an ice-cold condition, and the mixture was stirred overnight at room temperature. The reaction solution was concentrated under reduced pressure and thus obtained residue was purified by silica gel column chromatography to obtain 520 mg of 3-difluoromethoxy-4-[(1S)-1-hydroxyethyl]benzylbenzoate [202-1] (hereinafter, referred to as the compound [202-1]) as a colorless oily product.

(2) 613 mg of methyl 3-{(1R)-1-[4-(benzoyloxymethyl)-2-(difluoromethoxy)phenyl]ethoxy}-5-[6-(hydroxymethyl)imidazo[1,2-a]pyridin-3-yl]thiophene-2-carboxylic acid [202-2] (hereinafter, referred to as the compound [202-2]) was obtained as a colorless oily product from 527 mg of the compound [107-4] and 288 mg of the compound [202-1] according to the method of Example 197-(2).

(3) 3-{(1R)-1-[2-(difluoromethoxy)-4-(hydroxymethyl)phenyl]ethoxy}-5-(6-{[(triisopropylsilyl)oxy]methyl}imidazo[1,2-a]pyridin-3-yl)thiophene-2-carboxyamide [202-3] (hereinafter, referred to as the compound [202-3]) was obtained from 150 mg of the compound [202-2] according to the method of Example 197-(3).

(4) 24 mg of the target compound [202] was obtained as a colorless oily product from the compound [202-3] and t-butylamine according to the method of Example 197-(4).
A spectral data of the compound [202] is presented below.
$^1$H-NMR (CD$_3$OD) δ: 8.65 (s, 1H), 8.32 (s, 1H), 8.07-8.00 (m, 2H), 7.77 (d, J=8.0 Hz, 1H), 7.55 (s, 1H), 7.51 (d, J=8.0 Hz, 1H), 7.46 (s, 1H), 7.15 (t, J=73.2 Hz, 1H), 6.11 (q, J=6.3 Hz, 1H), 4.84 (s, 2H), 4.25 (s, 2H), 1.84 (d, J=6.3 Hz, 3H), 1.49 (s, 9H).
mass: 545, 547 (M+1)$^+$.

Example 203

Synthesis of 3-[(1R)-1-(2-chlorophenyl)ethoxy]-5-{6-[(ethylsulfonyl)methyl]imidazo[1,2-a]pyridin-3-yl}thiophene-2-carboxyamide [203] (hereinafter, referred to as the compound [203])

(1) 419 mg of the compound [107-4] was dissolved in 20 mL of N,N-dimethylformaide, and 276 mg of calcium carbonate and 0.083 mL of methoxymethyl chloride were added thereto under an ice-cold condition. After the overnight stirring at room temperature, the reaction mixture was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography. Next, the resultant residue was dissolved in 10 mL of tetrahydrofuran, and 1.0 mL of tetrabutylammonium fluoride (tetrahydrofuran solution, 1M) was added under an ice-cold condition. After the 3 hours stirring at room temperature, the reaction mixture was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography. The obtained compound was dissolved in 15 mL of chloroform, then 0.35 mL of diisopropylethylamine and 0.12 mL of methanesulfonyl chloride were added, and the mixture was stirred overnight at room temperature. The reaction mixture was added with ethyl acetate, washed with water and saturated brine in that order, and dried over anhydrous, sodium sulfate. The insolubles were filtered and the filtrate was concentrated under reduced pressure. The obtained residue was dissolved in 10 mL of N,N-dimethylformamide, then 408 mg of sodium methanesulfinate was added, and the mixture was stirred for 3 hours at 60° C. The reaction mixture was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography. The obtained compound was dissolved in 5 mL of methanol, 1 mL of 4N hydrochloric acid-methanol was added thereto, and the mixture was stirred for 6 hours at room temperature. The reaction solution was neutralized with a saturated sodium hydrogen carbonate solution, then extracted with chloroform, washed with saturated brine, and dried over anhydrous sodium sulfate. The insolubles were filtered and the filtrate was concentrated under reduced pressure to obtain 198 mg of methyl 3-hydroxy-5-{6-[(methylsulfonyl)methyl] imidazo[1,2-a]pyridin-3-yl]thiophene-2-carboxylic acid [203-1] (hereinafter, referred to as the compound [203-1]) as a colorless solid.

(2) 8 mg of the target compound [203] was obtained as a colorless solid from 13 mg of the compound [203-1] and 20 µL of (S)-α-(2-chlorophenyl)ethyl alcohol according to the method of Example 20.

A spectral data of the compound [203] is presented below.
$^1$H-NMR (CDCl$_3$) δ: 8.36 (s, 1H), 7.79 (s, 1H), 7.71 (d, J=8.0 Hz, 1H), 7.49-7.20 (m, 6H), 6.76 (s, 1H), 5.91 (q, J=8.0 Hz, 1H), 5.81-5.68 (bs, 1H), 4.26 (s, 2H), 2.89 (s, 3H), 1.78 (d, J=8.0 Hz, 3H).
mass: 490, 492 (M+1)$^+$.

Example 204

Synthesis of 5-{6-[(methylsulfonyl)methyl]imidazo [1,2-a]pyridin-3-yl}-3-{1-[2-(trifluoromethyl)phenyl]ethoxy}thiophene-2-carboxyamide [204] (hereinafter, referred to as the compound [204])

6.8 mg of the target compound [204] was obtained as a colorless oily product from 13 mg of the compound [203-1] and 20 µL of α-(2-trifluoromethylphenyl)ethyl alcohol according to the method of Example 20.

A spectral data of the compound [204] is presented below.
$^1$H-NMR (DMSO-d$_6$) δ: 8.63 (s, 1H), 7.90 (d, J=7.3 Hz, 1H), 7.83 (s, 1H), 7.70-7.80 (m, 4H), 7.52 (t, J=7.3 Hz, 1H), 7.38 (dd, J=1.5, 9.3 Hz, 1H), 7.15 (brs, 1H), 7.12 (s, 1H), 5.96 (q, J=6.3 Hz, 1H), 4.59 (s, 2H), 2.97 (s, 3H), 1.74 (d, J=6.3 Hz, 3H).
mass: 524, 526 (M+1)$^+$.

Examples 205 and 206

Synthesis of 3-{1-[2-(difluoromethoxy)phenyl] ethoxy}-5-{6-[(methylsulfonyl)methyl]imidazo[1,2-a]pyridin-3-yl}thiophene-2-carboxyamide (any one of R-form and S-form enantiomers)[205] (hereinafter, referred to as the compound [205]) and 3-{1-[2-(difluoromethoxy)phenyl]ethoxy}-5-{6-[(methylsulfonyl)methyl]imidazo[1,2-a]pyridin-3-yl}thiophene-2-carboxyamide [206] (enantiomer different from the compound [205]) (hereinafter, referred to as the compound [206])

(1) 10 mg of the compound [196-2] was dissolved in 4 mL of chloroform, then 8 µL of diisopropylethylamine and 3 µL of methanesulfonyl chloride were added, and the mixture was stirred for 2 hours at room temperature. The reaction mixture was added with chloroform, washed with water and saturated brine in that order, and dried over anhydrous sodium sulfate. The insolubles were filtered and the filtrate was concentrated under reduced pressure. The residue was dissolved in 10 mL of N,N-dimethylformamide, then 70 mg of sodium methanesulfinate was added, and the mixture was stirred for 5 hours at 70° C. The reaction mixture was added with chloroform, washed with water and saturated brine in that order, and dried over anhydrous sodium sulfate. The insolubles were filtered and the filtrate was concentrated under reduced pressure to obtain a racemic mixture of the compound [205] and the compound [206].

(2) The racemic mixture obtained in (1) was optically resolved using Chiralcel AS (Daicel Chemical Industries Ltd.) and hexane/ethanol+0.1% diethylamine as an eluent. The assay conditions were as follows.

Assay Conditions:
column: Chiralcel AS (Daicel Chemical Industries Ltd.), diameter of 0.46 mm, length of 250 mm;
eluent: hexane/ethanol (60:40)+0.1% diethylamine;
flow rate: 1.0 mL/min.

The obtained solution was concentrated under reduced pressure to obtain 4.5 mg of the target compound [206] (RT=9.96 min) as a colorless oily product and 5.0 mg of the target compound [205] (RT=12.0 min) as a colorless oily product.

A spectral data of the compound [205] is presented below.
$^1$H-NMR (DMSO-d$_6$) δ: 8.66 (s, 1H), 7.88 (s, 1H), 7.75 (brs, 1H), 7.72 (d, J=9.3 Hz, 1H), 7.62 (m, 1H), 7.12-7.49 (m, 7H), 5.95 (q, J=5.9 Hz, 1H), 4.61 (s, 2H), 2.97 (s, 3H), 1.70 (d, J=5.9 Hz, 3H).
mass: 522, 524 (M+1)$^+$.

A spectral data of the compound. [206] is presented below.
$^1$H-NMR (DMSO-d$_6$) δ: 8.66 (s, 1H)—, 7.88 (s, 1H), 7.75 (brs, 1H), 7.72 (d, J=−9.3 Hz, 1H), 7.62 (m, 1H), 7.12-7.49 (m, 7H), 5.95 (q, J=5.9 Hz, 1H), 4.61 (s, 2H), 2.97 (s, 3H), 1.70 (d, J=5.9 Hz, 3H).
mass: 522, 524 (M+1)$^+$.

Example 207

Synthesis of 3-((1R)-1-{2-chloro-4-[(dimethylamino)methyl]phenyl}ethoxy)-5-{6-[(methylsulfonyl)methyl]imidazo[1,2-a]pyridin-3-yl}thiophene-2-carboxyamide [207] (hereinafter, referred to as the compound [207])

(1) 248 mg of methyl 3-{(1R)-1-[2-chloro-4-(hydroxymethyl)phenyl]ethoxy}-5-{6-[(methylsulfonyl)methyl]imidazo[1,2-a]pyridin-3-yl}thiophene-2-carboxylic acid [207-1] (hereinafter, referred to as the compound [207-1]) was obtained as a pale yellow solid from 104 mg of the compound [203-1] and 86 mg of the compound [172-4] according to the method of Example 197-(2).

(2) 69 mg of 3-{(1R)-1-[2-chloro-4-(hydroxymethyl)phenyl]ethoxy}-5-{6-[(methylsulfonyl)methyl]imidazo[1,2-a]pyridin-3-yl]thiophene-2-carboxamide [207-2] (hereinafter, referred to as the compound [207-2]) was obtained as a pale yellow solid from 248 mg of the compound [207-1] according to the method of Example 171-(7).

(3) 2.6 mg of the target compound [207] was obtained as a white solid from 9 mg of the compound [207-2] and dimethylamine according to the method of Example 50.

A spectral data of the compound [207] is presented below.
$^1$H-NMR (DMSO-d$_6$) δ: 8.66 (s, 1H), 7.88 (s, 1H), 7.75 (brs, 1H), 7.72 (d, J=9.3 Hz, 1H), 7.60 (d, J=7.8 Hz, 1H), 7.39 (dd, J=9.3, 1.5 Hz, 1H), 7.35 (d, J=1.5 Hz, 1H), 7.29 (dd, J=7.8, 1.5 Hz, 1H), 7.22 (s, 1H), 7.11 (brs, 1H), 5.98 (q, J=6.3 Hz, 1H), 4.62 (s, 2H), 3.33 (s, 2H), 2.99 (s, 3H), 2.09 (s, 6H), 1.72 (d, J=6.3 Hz, 3H).
mass: 547, 549 (M+1)$^+$.

Example 208

Synthesis of 3-((1R)-1-{4-[(t-butylamino)methyl]-2-chlorophenyl}ethoxy)-5-{6-[(methylsulfonyl)methyl]imidazo[1,2-a]pyridin-3-yl}thiophene-2-carboxyamide [208] (hereinafter, referred to as the compound [208])

2.4 mg of the target compound [208] was obtained as a pale yellow solid from 9 mg of the compound [207-2] and t-butylamine according to the method of Example 50.

A spectral data of the compound [208] is presented below.
$^1$H-NMR (DMSO-d$_6$) δ: 8.67 (s, 1H), 7.89 (s, 1H), 7.77 (brs, 1H), 7.73 (d, J=9.3 Hz, 1H), 7.56 (d, J=8.1 Hz, 1H), 7.41 (s, 1H), 7.39 (dd, J=9.3, 1.5 Hz, 1H), 7.32 (d, J=8.1 Hz, 1H), 7.20 (s, 1H), 7.12 (brs, 1H), 5.98 (q, J=6.7 Hz, 1H), 4.62 (s, 2H), 3.59 (s, 2H), 2.99 (s, 3H), 1.71 (d, J=6.7 Hz, 3H), 1.03 (s, 9H).
mass: 575, 577 (M+1)$^+$.

Example 209

Synthesis of 3-{(1R)-1-[2-chloro-4-(hydroxymethyl)phenyl]ethoxy}-5-{6-[(dimethylamino)methyl]imidazo[1,2-a]pyridin-3-yl}thiophene-2-carboxyamide [209] (hereinafter, referred to as the compound [209])

(1) 5.3 mg of methyl 3-{(1R)-1-[4-(acetyloxymethyl)-2-chlorophenyl]ethoxy}-5-{6-[(dimethylamino)methyl]imidazo[1,2-a]pyridin-3-yl}thiophene-2-carboxylic acid [209-1] (hereinafter, referred to as the compound [209-1]) was obtained as a pale yellow oily product from 6 mg of the compound [197-2] and dimethylamine according to the method of Example 50.

(2) 4.2 mg of the target compound [209] was obtained as a colorless solid from 5.3 mg of the compound [209-1] according to the method of Example 171-(7).

A spectral data of the compound [209] is presented below.
$^1$H-NMR (CDCl$_3$) δ: 8.15 (d, J=1.6 Hz, 1H), 7.72 (s, 1H), 7.60 (d, J=9.6 Hz, 1H), 7.48 (d, J=1.6 Hz, 1H), 7.45 (d, J=8.0 Hz, 1H), 7.29-7.25 (m, 2H), 7.24 (brs, 1H), 6.73 (s, 1H), 5.89 (q, J=6.4 Hz, 1H), 5.87 (brs, 1H), 4.68 (s, 2H), 3.45-3.37 (m, 2H), 2.25 (s, 6H), 1.76 (d, J=6.4 Hz, 3H).
mass: 485, 487 (M+1)$^+$.

Example 210

Synthesis of 3-((1R)-1-{2-chloro-4-[(methylsulfonyl)methyl]phenyl}ethoxy)-5-(6-{[(2-hydroxyethyl)(methyl)amino]methyl}imidazo[1,2-a]pyridin-3-yl)thiophene-2-carboxyamide [210] (hereinafter, referred to as the compound [210])

(1) Methyl 3-{(1R)-1-[4-(acetyloxymethyl)-2-chlorophenyl]ethoxy}-5-{6-[(methylamino)methyl]imidazo[1,2-a]pyridin-3-yl}thiophene-2-carboxylic acid [210-1] (hereinafter, referred to as the compound [210-1]) was obtained as yellowish brown amorphous from 15 mg of the compound [197-2] and methylamine according to the method of Example 50.

(2) 12.3 mg of methyl 3-{(1R)-1-[4-(acetyloxymethyl)-2-chlorophenyl]ethoxy}-5-(6-{[(t-butoxycarbonyl)(methyl)amino]methyl}imidazo[1,2-a]pyridin-3-yl)thiophene-2-carboxylic acid [210-2] (hereinafter, referred to as the compound [210-2]) was obtained as yellowish brown amorphous from the compound [210-1] according to the method of Example 68-(1).

(3) 10.3 mg of t-butyl{[3-(5-(aminocarbonyl)-4-{(1R)-1-[2-chloro-4-(hydroxymethyl)phenyl]ethoxy}-2-thienyl)imidazo[1,2-a]pyridin-6-yl]methyl}methylcarbamate [210-3] (hereinafter, referred to as the compound [210-3]) was obtained as a colorless solid from the compound [210-2] according to the method of Example 171-(7).

(4) 7.9 mg of t-butyl({3-[5-(aminocarbonyl)-4-((1R)-1-{2-chloro-4-[(methylsulfonylmethyl)methyl]phenyl}ethoxy)-2-thienyl]imidazo[1,2-a]pyridin-6-yl}methyl)methylcarbamate [210-4] (hereinafter, referred to as the compound [210-4]) was obtained as a colorless solid from 10 mg of the compound [210-3] according to the method of Example 205-(1).

(5) 1.8 mg of the target compound [210] was obtained as a colorless solid from 4.0 mg of the compound [210-4] according to the method of Example 189-(2).

A spectral data of the compound [210] is presented below.
$^1$H-NMR (CDCl$_3$) δ: 8.33-8.31 (m, 1H), 7.74 (s, 1H), 7.64 (d, J=−8.0 Hz, 1H), 7.55-7.48 (m, 2H), 7.38-7.28 (m, 2H), 7.20 (brs, 1H), 6.75 (s, 1H), 5.94-5.86 (m, 1H), 5.74 (brs, 1H), 4.20 (s, 2H), 3.70-3.64 (m, 2H), 3.61 (s, 2H), 2.85 (s, 3H), 2.68-2.64 (m, 2H), 2.30 (s, 3H), 1.77 (d, J=6.4 Hz, 3H).
mass: 577, 579 (M+1)$^+$.

Example 211

Synthesis of 4-[(1R)-1-(2-chlorophenyl)ethoxy]-2-(6-{[[2-(dimethylamino)ethyl](methyl)amino]methyl}imidazo[1,2-a]pyridin-3-yl)-1,3-thiazole-5-carboxyamide [211] (hereinafter, referred to as the compound [211])

(1) 1.52 g of 6-iodoimidazo[1,2-a]pyridine-3-carbonitrile [211-1] (hereinafter, referred to as the compound [211-1]) was obtained as a pale yellow solid from 1.66 mL of 3-methoxyacronitrile and 2.2 g of 2-amino-5-iodopyridine according to the method of Example 152-(7).

(2) 1.52 g of the compound [211-1] was dissolved in 10 mL of N-methylpyrrolidone in accordance with the method disclosed in the literature (Synthesis, 1992 (12), 1219), then 2.83 mL of bis(trimethylsilyl)sulfide and 706 mg of sodium methoxide were added, and the mixture was stirred for 30 minutes at room temperature. The reaction mixture was added with 10 mL of water, and the precipitated solid was taken by filtration, washed with methanol and diethylether, and dried under reduced pressure, to obtain 1.38 g of 6-iodoimidazo[1,2-a]pyridine-3-carbothioamide [211-2] (hereinafter, referred to as the compound [211-2]) as a pale yellow solid.

(3) 538 mg of the compound [211-2] was dissolved in 10 mL of N,N-dimethylformaide, then 0.84 mL of bromomalonic acid diethyl ester was added, and the mixture was heated for 16 hours at 60° C. and stirred overnight at room temperature. The precipitated solid was taken by filtration, washed with methanol and diethylether, and dried under reduced pressure, to obtain 469 mg of ethyl 4-hydroxy-2-(6-iodoimidazo[1,2-a]pyridin-3-yl)-1,3-thiazole-5-carboxylic acid [211-3] (hereinafter, referred to as the compound [211-3]) as a colorless solid.

(4) 470 mg of ethyl 4-[(1R)-1-(2-chlorophenyl)ethoxy]-2-(6-iodoimidazo[1,2-a]pyridin-3-yl)-1,3-thiazole-5-carboxylic acid [211-4] (hereinafter, referred to as the compound [211-4]) was obtained as a colorless solid from 469 mg of the compound [211-3] and (S)-α-(2-chlorophenyl)ethyl alcohol according to the method of Example 1-(4).

(5) 340 mg of the compound [211-4] was dissolved in a solvent of 4 mL of tetrahydrofuran and 4 mL of methanol, then 117 mg of potassium vinyltrifluoroborate, 87 mg of bis(triphenylphosphine)palladium (II) dichloride, and 0.1 mL of triethylamine were added, and the mixture was heated for 2 hours under reflux. The insolubles were filtered through celite and the filtrate was concentrated under reduced pressure. The residue was purified by silica gel column chromatography, and 100 mg of thus obtained compound was dissolved in 5 mL of tetrahydrofuran. Thereto, 39 mg of 4-methylmorpholine N-oxide and 0.132 mL of osmium tetroxide (0.05M aqueous solution) were added, and the mixture was stirred overnight at room temperature. The reaction mixture was added with chloroform, washed with water and saturated brine in that order, and dried over anhydrous sodium sulfate. The insolubles were filtered and the filtrate was concentrated under reduced pressure. The obtained residue was dissolved in a solvent of 2 mL of tetrahydrofuran and 1 mL of water, then 160 mg of sodium periodate was added thereto, and the mixture was stirred for 1 hour at room temperature. To the reaction system, 17 mg of sodium borohydride was added, and the mixture was stirred for 1 hour. The reaction mixture was added with ethyl acetate, washed with water and saturated brine in that order, and dried over anhydrous sodium sulfate. The insolubles were filtered, the filtrate was concentrated under reduced pressure, and thus obtained residue was purified by silica gel column chromatography, to obtain 43 mg of ethyl 4-[(1R)-1-(2-chlorophenyl)ethoxy]-2-(6-hydroxymethylimidazo[1,2-a]pyridin-3-yl)-1,3-thiazole-5-carboxylic acid [211-5] (hereinafter, referred to as the compound [211-5]) as a colorless solid.

(6) 2.5 mg of the target compound [211] was obtained as a colorless solid from 10 mg of the compound [211-5] and N,N,N'-trimethylethylenediamine according to the methods of Example 209-(1) and (2).

A spectral data of the compound [211] is presented below.
$^1$H-NMR (CDCl$_3$) δ: 9.04 (s, 1H), 8.16 (s, 1H), 7.67 (d, J=8.0 Hz, 1H), 7.54-7.47 (m, 3H), 7.41-7.24 (m, 2H), 7.08 (brs, 1H), 6.58 (q, J=6.8 Hz, 1H), 5.76 (brs, 1H), 3.60 (dd, J=16.0, 20.0 Hz, 2H), 2.69 (brs, 3H), 2.42 (m, 5H), 2.27 (s, 3H), 1.80 (d, J=6.8 Hz, 3H).
mass: 513, 515 (M+1)$^+$.

Example 212

Synthesis of 4-[(1R)-1-(2-chlorophenyl)ethoxy]-2-{6-[(methylsulfonyl)methyl]imidazo[1,2-a]pyridin-3-yl}-1,3-thiazole-5-carboxyamide [212] (Hereinafter, referred to as the compound [212])

2.1 mg of the target compound [212] was obtained as a colorless solid from 10 mg of the compound [211-5] according to the method of Example 205-(1).

A spectral data of the compound [212] is presented below.
$^1$H-NMR (CDCl$_3$) δ: 9.17 (s, 1H), 8.21 (s, 1H), 7.75 (d, J=8.0 Hz, 1H), 7.52-7.47 (m, 2H), 7.34-7.26 (m, 3H), 7.10 (brs, 1H), 6.51 (q, J=6.8 Hz, 1H), 5.78 (brs, 1H), 4.33 (s, 2H), 2.79 (brs, 3H), 1.80 (d, J=6.8 Hz, 3H).
mass: 491, 493 (M+1)$^+$.

Example 213

Synthesis of 2-(6-aminoimidazo[1,2-a]pyridin-3-yl)-4-[(1R)-1-(2-chlorophenyl)ethoxy]-1,3-thiazole-5-carboxyamide [213] (hereinafter, referred to as the compound [213])

17 mg of the target compound [213] was obtained as a green solid from 60 mg of the compound [211-4] according to the methods of Example 101-(3) and (4).

A spectral data of the compound [213] is presented below.
$^1$H-NMR (CDCl$_3$) δ: 8.59 (d, J=1.6 Hz, 1H), 8.04 (s, 1H), 7.50 (d, J=9.6 Hz, 1H), 7.46 (dd, J=8.0, 1.2 Hz, 1H), 7.43 (dd, J=8.0, 1.2 Hz, 1H), 7.33-7.22 (m, 2H), 7.08 (brs, 1H), 6.93 (dd, J=9.6, 1.6 Hz, 1H), 6.52 (q, J=6.4 Hz, 1H), 5.86 (brs, 1H), 3.72 (brs, 2H), 1.78 (d, J=6.4 Hz, 3H).
mass: 414, 416 (M+1)$^+$.

Example 214

Synthesis of 2-[6-(azetidin-3-yloxy)imidazo[1,2-a]pyridin-3-yl]-4-[(1R)-1-(2-chlorophenyl)ethoxy]-1,3-thiazole-5-carboxyamide [214] (hereinafter, referred to as the compound [214])

(1) 18 mg of methyl 2-(6-{[1-(t-butoxycarbonyl)azetidin-3-yl]oxy}imidazo[1,2-a]pyridin-3-yl)-4-[(1R)-1-(2-chlorophenyl)ethoxy]-1,3-thiazole-5-carboxylic acid [214-1] (hereinafter, referred to as the compound [214-1]) was obtained as pale yellow amorphous from 150 mg of the compound [211-4] and t-butyl 3-hydroxyazetidine-1-carboxylate according to the method of Example 66-(2).

(2) 4.6 mg of the target compound [214] was obtained as a pale yellow solid from 18 mg of the compound [214-1] according to the method of Example 101-(4).

A spectral data of the compound [214] is presented below.
$^1$H-NMR (CDCl$_3$) δ: 9.27 (d, J=2.0 Hz, 1H), 8.81 (s, 1H), 8.04 (d, J=9.6 Hz, 1H), 7.91 (dd, J=9.6, 2.0 Hz, 1H), 7.66 (dd, J=8.0, 1.6 Hz, 1H), 7.49 (dd, J=8.0, 1.6 Hz, 1H), 7.40 (ddd, J=8.0, 8.0, 1.6 Hz, 1H), 7.33 (ddd, J=8.0, 8.0, 1.6 Hz, 1H), 6.70 (q, J=6.4 Hz, 1H), 5.47-5.40 (m, 1H), 4.75-4.65 (m, 2H), 4.45-4.35 (m, 2H), 1.89 (d, J=6.4 Hz, 3H).
mass: 470, 472 (M+1)$^+$.

Example 215

Synthesis of 4-{(1R)-1-[2-chloro-4-(hydroxymethyl)phenyl]ethoxy}-2-(6-{[(2-fluoroethyl)(methyl)amino]methyl}imidazo[1,2-a]pyridin-3-yl)-1,3-thiazole-5-carboxyamide [215] (hereinafter, referred to as the compound [215])

(1) 1.03 g of ethyl 4-{(1R)-1-[4-({[t-butyl(dimethyl)silyl]oxy}methyl)-2-chlorophenyl]ethoxy}-2-(6-iodoimidazo[1,2-a]pyridin-3-yl)-1,3-thiazole-5-carboxylic acid [215-1] (including impurities) (hereinafter, referred to as the compound [215-1]) was obtained as a pale yellow oily product from 452 mg of the compound [211-3] and the compound [172-4] according to the method of Example 1-(4).

(2) 97 mg of ethyl 4-{(1R)-1-[4-({[t-butyl(dimethyl)silyl]oxy}methyl)-2-chlorophenyl]ethoxy}-2-[6-(hydroxymethyl)imidazo[1,2-a]pyridin-3-yl]-1,3-thiazole-5-carboxylic acid [215-2] (hereinafter, referred to as the compound [215-2]) was obtained as a pale yellow oily product from 1.03 g of the compound [215-1] according to the method of Example 211-(5).

(3) ethyl 4-{(1R)-1-[4-({[t-butyl(dimethyl)silyl]oxy}methyl)-2-chlorophenyl]ethoxy}-2-(6-{[(2-fluoroethyl)amino]methyl}imidazo[1,2-a]pyridin-3-yl)-1,3-thiazole-5-carboxylic acid [215-3] (hereinafter, referred to as the compound [215-3]) was obtained as a pale yellow oily product from 12 mg of the compound [215-2] and 2-fluoroethylamine according to the method of Example 50.

(4) Ethyl 4-{(1R)-1-[4-({[t-butyl(dimethyl)silyl]oxy}methyl)-2-chlorophenyl]ethoxy}-2-(6-{[(2-fluoroethyl)(methyl)amino]methyl}imidazo[1,2-a]pyridin-3-yl)-1,3-thiazole-5-carboxylic acid [215-4] (hereinafter, referred to as the compound [215-4]) was obtained as a pale yellow oily product from the compound [215-3] according to the method of Example 100.

(5) 1.23 mg of the target compound [215] was obtained as a pale yellow oily product from the compound [215-4] according to the method of Example 10-(2).

A spectral data of the compound [215] is presented below.

$^1$H-NMR (CDCl$_3$) δ: 9.04 (s, 1H), 8.15 (s, 1H), 7.66 (d, J=8.0 Hz, 1H), 7.52-7.46 (m, 3H), 7.30-7.24 (m, 1H), 7.05 (brs, 1H), 6.54 (q, J=6.8 Hz, 1H), 5.60 (brs, 1H), 4.67-4.52 (m, 4H), 3.66 (dd, J=12.0, 16.0 Hz, 2H), 2.85-2.76 (m, 2H), 2.62 (s, 3H), 1.80 (d, J=6.8 Hz, 3H).

mass: 518, 520 (M+1)$^+$.

Example 216

Synthesis of 4-{(1R)-1-[2-chloro-4-(hydroxymethyl)phenyl]ethoxy}-2-{6-[(dimethylamino)methyl]imidazo[1,2-a]pyridin-3-yl}-1,3-thiazole-5-carboxyamide [216] (hereinafter, referred to as the compound [216])

0.4 mg of the target compound [216] was obtained as a pale yellow oily product from 9 mg of the compound [215-2] and dimethylamine according to the steps of Example 215-(3) and (5) in that order.

A spectral data of the compound [216] is presented below.

$^1$H-NMR (CDCl$_3$) δ: 8.99 (s, 1H), 8.15 (s, 1H), 7.70 (d, J=8.0 Hz, 1H), 7.50-7.40 (m, 3H), 7.30-7.24 (m, 1H), 7.10 (brs, 1H), 6.52 (q, J=6.8 Hz, 1H), 5.35 (brs, 1H), 4.68 (d, J=4.0 Hz, 2H), 3.50-3.40 (m, 2H), 2.60 (s, 6H), 1.80 (d, J=6.8 Hz, 3H).

mass: 486, 488 (M+1)$^+$.

Example 217

Synthesis of 4-((1R)-1-{2-chloro-4-[(methylamino)methyl]phenyl}ethoxy)-2-imidazo[1,2-a]pyridin-3-yl-1,3-thiazole-5-carboxyamide [217] (hereinafter, referred to as the compound [217])

(1) 141 mg of 4-{(1R)-1-[2-chloro-4-(hydroxymethyl)phenyl]ethoxy}-2-imidazo[1,2-a]pyridin-3-yl-1,3-thiazole-5-carboxyamide [217-1] (hereinafter, referred to as the compound [217-1]) was obtained as a pale yellow oily product from 289 mg of the compound [157-3] and 301 mg of the compound [172-4] according to the methods of Example 207-(1) and (2).

(2) 5.5 mg of the target compound [217] was obtained as a pale yellow oily product from 10 mg of the compound [217-1] and methylamine according to the method of Example 50.

A spectral data of the compound [217] is presented below.

$^1$H-NMR (DMSO-d$_6$) δ: 9.15 (d, J=6.8 Hz, 1H), 8.68 (brs, 2H), 8.39 (s, 1H), 7.82 (brs, 1H), 7.75 (d, J=8.8 Hz, 1H), 7.68 (d, J=8.3 Hz, 1H), 7.61 (d, J=2.0 Hz, 1H), 7.52-7.39 (m, 2H), 7.18-7.13 (m, 2H), 6.42 (q, J=6.3 Hz, 1H), 4.02 (m, 5H), 1.68 (d, J=6.3 Hz, 3H).

mass: 442, 444 (M+1)$^+$.

Example 218

Synthesis of 4-((1R)-1-{2-chloro-4-[(isopropylamino)methyl]phenyl}ethoxy)-2-imidazo[1,2-a]pyridin-3-yl-1,3-thiazole-5-carboxyamide [218] (hereinafter, referred to as the compound [218])

9.4 mg of the target compound [218] was obtained as a pale yellow oily product from 10 mg of the compound [217-1] and isopropylamine according to the method of Example 50.

A spectral data of the compound [218] is presented below.

$^1$H-NMR (DMSO-d$_6$) δ: 9.20 (d, J=6.8 Hz, 1H), 8.61 (brs, 2H), 8.47 (s, 1H), 7.84 (brs, 1H), 7.79 (d, J=9.3 Hz, 1H), 7.68 (m, 2H), 7.57 (m, 1H), 7.45 (m, 1H), 7.23 (dd, J=6.8, 8.3 Hz, 1H), 7.15 (brs, 1H), 6.44 (q, J=6.3 Hz, 1H), 4.05 (m, 2H), 3.22 (m, 1H), 1.69 (d, J=6.8 Hz, 3H), 1.16 (d, J=6.3 Hz, 6H).

mass: 470, 472 (M+1)$^+$.

Example 219

Synthesis of 4-[(1R)-1-(2-chloro-4-{[(2-hydroxy-1,1-dimethylethyl)amino]methyl}phenyl)ethoxy]-2-imidazo[1,2-a]pyridin-3-yl-1,3-thiazole-5-carboxyamide [219] (hereinafter, referred to as the compound [219])

4.3 mg of the target compound [219] was obtained as a pale yellow oily product from 10 mg of the compound [217-1] and 2-amino-2-methyl-1-propanol according to the method of Example 50.

A spectral data of the compound [219] is presented below.

$^1$H-NMR (DMSO-d$_6$) δ: 9.08 (d, J=6.8 Hz, 1H), 8.34 (s, 1H), 7.77 (brs, 1H), 7.72 (dd, J=1.0, 6.8 Hz, 1H), 7.50-7.43

(m, 3H), 7.26 (d, J=8.3 Hz, 1H), 7.14-7.09 (m, 2H), 6.37 (q, J=6.3 Hz, 1H), 4.49 (brs, 1H), 3.53 (s, 2H), 3.12 (s, 2H), 1.67 (d, J=6.8 Hz, 3H), 0.88 (s, 6H).
mass: 500, 502 (M+1)$^+$.

Example 220

Synthesis of 4-{(1R)-1-[4-[(t-butylamino)methyl]-2-(difluoromethoxy)phenyl]ethoxy}-2-imidazo[1,2-a]pyridin-3-yl-1,3-thiazole-5-carboxyamide [220] (hereinafter, referred to as the compound [220])

(1) 13 mg of 4-{(1R)-1-[2-(difluoromethoxy)-4-(hydroxymethyl)phenyl]ethoxy}-2-imidazo[1,2-a]pyridin-3-yl-1,3-thiazole-5-carboxyamide [220-1] (hereinafter, referred to as the compound [220-1]) was obtained as a pale yellow solid from 100 mg of the compound [157-3] and 125 mg of the compound [168-5] according to the methods of Example 207-(1) and (2).

(2) the target compound [220] was obtained as a pale yellow solid from 6 mg of the compound [220-1] and t-butylamine according to the method of Example 50.

A spectral data of the compound [220] is presented below.
$^1$H-NMR (DMSO-d$_6$) δ: 9.33 (d, J=7.3 Hz, 1H), 8.64-8.60 (m, 2H), 8.44 (s, 1H), 7.83 (brs, 1H), 7.81 (d, J=8.8 Hz, 1H), 7.78 (d, J=8.8 Hz, 1H), 7.60-7.56 (m, 1H), 7.43-7.40 (m, 2H), 7.31 (s, 1H), 7.20 (dt, J=1.2, 6.8 Hz, 1H), 7.13 (brs, 1H), 7.11 (t, J=73 Hz, 1H), 6.51 (q, J=6.3 Hz, 1H), 4.9-4.08 (m, 2H), 1.73 (d, J=6.3 Hz, 3H), 1.30 (s, 9H).
mass: 516 (M+1)$^+$.

Example 221

Synthesis of 4-((1R)-1-{2-chloro-4-[(dimethylamino)methyl]phenyl}ethoxy)-2-[6-(hydroxymethyl)imidazo[1,2-a]pyridin-3-yl]-1,3-thiazole-5-carboxyamide [221] (hereinafter, referred to as the compound [221])

(1) 106 mg of the compound [215-2] was dissolved in 0.5 mL of pyridine, then 0.5 mL of acetic anhydride was added under an ice-cold condition, and the mixture was stirred for 4 hours at room temperature. The reaction mixture was added with ethyl acetate, washed with water and saturated brine in that order, and dried over anhydrous sodium sulfate. The insolubles were filtered and the filtrate was concentrated under reduced pressure. The obtained residue was dissolved in 3 mL of tetrahydrofuran, and 1.0 mL of tetrabutylammonium fluoride (tetrahydrofuran solution, 1M) was added under an ice-cold condition. After the overnight stirring at room temperature, the reaction solution was added with ethyl acetate, washed with water and saturated brine in that order, and dried over anhydrous sodium sulfate. The insolubles were filtered, the filtrate was concentrated under reduced pressure, and thus obtained residue was purified by preparative thin-layer chromatography, to obtain 39 mg of ethyl 2-{6-[(acetoxy)methyl]imidazo[1,2-a]pyridin-3-yl}-4-{(1R)-1-[2-chloro-4-(hydroxymethyl)phenyl]ethoxy}-1,3-thiazole-5-carboxylic acid [221-1] (hereinafter, referred to as the compound [221-1]) as a colorless oily product.

(2) 4.6 mg of the target compound [221] was obtained as a pale yellow oily product from 13 mg of the compound [221-1] and dimethylamine according to the method of Example 209.

A spectral data of the compound [221] is presented below.
$^1$H-NMR (CDCl$_3$) δ: 8.33 (s, 1H), 8.13 (s, 1H), 7.63 (m, 2H), 7.49 (d, J=8.0 Hz, 1H), 7.34 (d, J=8.0 Hz, 1H), 7.06 (brs, 1H), 7.05 (d, J=8.0 Hz, 1H), 6.20 (q, J=6.8 Hz, 1H), 5.79 (brs, 1H), 4.58 (dd, J=12.0, 16.0 Hz, 2H), 3.72 (d, J=12.0 Hz, 1H), 2.96 (d, J=12.0 Hz, 1H), 2.60 (s, 6H), 1.85 (d, J=6.8 Hz, 3H).
mass: 486, 488 (M+1)$^+$.

Example 222

Synthesis of 4-{(1R)-1-[4-[(t-butylamino)methyl]-2-(difluoromethoxy)phenyl]ethoxy}-2-[6-(hydroxymethyl)imidazo[1,2-a]pyridin-3-yl]-1,3-thiazole-5-carboxyamide [222] (hereinafter, referred to as the compound [222])

(1) 1.8 g of ethyl 4-{(1R)-1-[4-({[t-butyl(dimethyl)silyl]oxy}methyl)-2-(difluoromethoxy)phenyl]ethoxy}-2-(6-iodoimidazo[1,2-a]pyridin-3-yl)-1,3-thiazole-5-carboxylic acid [222-1] (including impurities) (hereinafter, referred to as the compound [222-1]) was obtained as a yellow solid from 900 mg of the compound [211-3] and 750 mg of the compound [168-5] according to the method of Example 1-(4).

(2) 486 mg of ethyl 4-{(1R)-1-[4-({[t-butyl(dimethyl)silyl]oxy}methyl)-2-(difluoromethoxy)phenyl]ethoxy}-2-[6-(hydroxymethyl)imidazo[1,2-a]pyridin-3-yl]-1,3-thiazole-5-carboxylic acid [222-2] (hereinafter, referred to as the compound [222-2]) was obtained as a yellow solid from 1.8 g of the compound [222-1] according to the method of Example 211-(5).

(3) 486 mg of ethyl 2-{6-[(acetoxy)methyl]imidazo[1,2-a]pyridin-3-yl}-4-{(1R)-1-[2-(difluoromethoxy)-4-(hydroxymethyl)phenyl]ethoxy}-1,3-thiazole-5-carboxylic acid [222-3] (hereinafter, referred to as the compound [222-3]) was obtained as a yellow solid from the compound [222-2] according to the method of Example 221-(1).

(4) 4.6 mg of the target compound [222] was obtained as a yellow solid from the compound [222-3] and t-butylamine according to the method of Example 209.

A spectral data of the compound [222] is presented below.
$^1$H-NMR (DMSO-d$_6$) δ: 9.30 (s, 1H), 8.86 (brs, 2H), 8.51 (s, 1H), 7.78 (brs, 1H), 7.81 (d, J=8.8 Hz, 1H), 7.78-7.84 (m, 3H), 7.62 (d, J=8.8 Hz, 1H), 7.52 (s, 1H), 7.46-7.48 (m, 1H), 7.29 (t, J=73 Hz, 1H), 7.06 (brs, 1H), 6.50 (q, J=6.3 Hz, 1H), 4.65 (s, 2H), 4.07-4.10 (m, 2H), 1.76 (d, J=6.3 Hz, 3H), 1.32 (s, 9H).
mass: 546 (M+1)$^+$.

Example 223

Synthesis of 4-((1R)-1-{2-chloro-4-[(dimethylamino)methyl]phenyl}ethoxy)-2-{6-[(methylsulfonyl)methyl]imidazo[1,2-a]pyridin-3-yl}-1,3-thiazole-5-carboxyamide [223] (Hereinafter, referred to as the compound [223])

(1) 30 mg of 4-{(1R)-1-[2-chloro-4-(hydroxymethyl)phenyl]ethoxy}-2-{6-[(methylsulfonyl)methyl]imidazo[1,2-a]pyridin-3-yl}-1,3-thiazole-5-carboxyamide [223-1] (hereinafter, referred to as the compound [223-1]) was obtained as a pale yellow oily product from 296 mg of the compound [215-2] according to the steps of Example 210-(4) and (3) in that order.

(2) The target compound [223] was obtained as a colorless solid from the compound [223-1] and dimethylamine according to the method of Example 50.

A spectral data of the compound [223] is presented below.
$^1$H-NMR (CDCl$_3$) δ: 9.22 (s, 1H), 8.20 (s, 1H), 7.72 (d, J=8.0 Hz, 1H), 7.49 (d, J=8.0 Hz, 1H), 7.45-7.38 (m, 2H), 7.22 (d, J=8.0 Hz, 1H), 7.06 (brs, 1H), 6.52 (q, J=6.8 Hz, 1H), 5.70 (brs, 1H), 4.35 (s, 2H), 3.36 (s, 2H), 2.84 (s, 3H), 2.20 (s, 6H), 1.79 (d, J=6.8 Hz, 3H).

mass: 548, 550 (M+1)$^+$.

Example 224

Synthesis of 4-((1R)-1-{2-chloro-4-[(methylamino) methyl]phenyl}ethoxy)-2-{6-[(methylsulfonyl)methyl]imidazo[1,2-a]pyridin-3-yl}-1,3-thiazole-5-carboxyamide [224] (hereinafter, referred to as the compound [224])

The target compound [224] was obtained as a colorless solid from the compound [223-1] and methylamine according to the method of Example 50.

A spectral data of the compound [224] is presented below.
$^1$H-NMR (CDCl$_3$) δ: 9.20 (s, 1H), 8.20 (s, 1H), 7.72 (d, J=8.0 Hz, 1H), 7.50-7.40 (m, 3H), 7.25-7.15 (m, 1H), 7.08 (brs, 1H), 6.50 (q, J=6.8 Hz, 1H), 5.72 (brs, 1H), 4.34 (s, 2H), 3.72 (s, 2H), 2.83 (s, 3H), 2.44 (s, 3H), 1.78 (d, J=6.8 Hz, 3H).

mass: 534, 536 (M+1)$^+$.

Example 225

Synthesis of 3-[(1R)-1-(2-chlorophenyl)ethoxy]-5-{6-[(dimethylamino)methyl]imidazo[1,2-a]pyrazin-3-yl}thiophene-2-carboxyamide [225] (hereinafter, referred to as the compound [225])

(1) 10 g of t-butyl(5-methylpyrazin-2-yl)carbamate was dissolved in 100 mL of carbon tetrachloride, 16.9 g of N-bromosuccinimide and 1.97 g of 2,2'-azobisisobutylonitrile were added, and the mixture was stirred overnight at 90° C. under a nitrogen atmosphere. The insolubles were filtered through celite and the filtrate was concentrated under reduced pressure. The residue was dissolved in 120 mL of acetonitrile, then 9.4 g of potassium acetate and 633 mg of 18-crown-6 were added, and the mixture was stirred overnight at room temperature. The reaction solution was concentrated under reduced pressure, added with chloroform, washed with water and saturated brine in that order, and dried over anhydrous sodium sulfate. The insolubles were filtered and the filtrate was concentrated under reduced pressure. The obtained residue was dissolved in a solvent of 100 mL of tetrahydrofuran and 201 mL of methanol, then 1.0M aqueous solution of sodium hydroxide was added thereto under an ice-cold condition, and the mixture was stirred for 1 hour at room temperature. The reaction solution was concentrated under reduced pressure, added with chloroform, washed with water and saturated brine in that order, and dried over anhydrous sodium sulfate. The insolubles were filtered and the filtrate was concentrated under reduced pressure. The obtained residue was dissolved in 80 mL of N,N-dimethylformamide, then 3.9 g of imidazole was added, and 8.7 mL of t-butyldiphenylsilylchloride was then added under an ice-cold condition. The mixture was stirred for 3 hours at room temperature. The reaction solution was poured onto ice water, extracted with ethyl acetate, washed with water and saturated brine in that order, and dried over anhydrous sodium sulfate. The insolubles were filtered, the filtrate was concentrated under reduced pressure, and thus obtained residue was purified by silica gel chromatography, to obtain 12.9 g of t-butyl[5-({[t-butyl(dimethyl)silyl]oxy}methyl)pyrazin-2-yl]carbamate [225-1] (hereinafter, referred to as the compound [225-1]) as a pale yellow oily product.

(2) 3 g of the compound [225-1] was dissolved in 25 if L of chloroform, then 10 mL of trifluoroacetic acid was added, and the mixture was stirred for 2 hours at room temperature. The reaction solution was concentrated under reduced pressure, added with chloroform, washed with water and saturated brine in that order, and dried over anhydrous sodium sulfate. The insolubles were filtered, the filtrate was concentrated under reduced pressure, and thus obtained residue was purified by silica gel chromatography, to obtain 1.6 g of 5-({[t-butyl(dimethyl)silyl]oxy}methyl)pyrazine-2-amine [225-2] (hereinafter, referred to as the compound [225-2]) as a pale yellow oily product.

(3) 1.0 g of t-butyl 5-[6-({[t-butyl(dimethyl)silyl] oxy}methyl)imidazo[1,2-a]pyrazin-3-yl]-3-[(1R)-1-(2-chlorophenyl)ethoxy]thiophene-2-carboxylic acid [225-3] (hereinafter, referred to as the compound [225-3]) was obtained as a brown oily product from 836 mg of the compound [152-6Z] and the compound [225-2] according to the method of Example 152-(7).

(4) 550 mg of the compound [225-3] was dissolved in 10 mL of chloroform, then 5 if L of trifluoroacetic acid was added, and the mixture was stirred for 2 hours at room temperature. The reaction solution was concentrated under reduced pressure, added with chloroform, washed with water and saturated brine in that order, and dried over anhydrous sodium sulfate. The insolubles were filtered and the filtrate was concentrated under reduced pressure. From the obtained residue, 420 mg of 5-[6-({[t-butyl(dimethyl)silyl] oxy}methyl)imidazo[1,2-a]pyrazin-3-yl]-3-[(1R)-1-(2-chlorophenyl)ethoxy]thiophene-2-carboxyamide [225-4] (hereinafter, referred to as the compound [225-4]) was obtained as a brown oily product according to the method of Example 8.

(5) 420 mg of the compound [225-4] was dissolved in 5 mL of tetrahydrofuran, and 0.76 mL of tetrabutylammonium fluoride (tetrahydrofuran solution, 1M) was added under an ice-cold condition. After the 1 hour stirring at room temperature, the reaction mixture was added with ethyl acetate, washed with phosphate buffer (pH 6.8) and saturate brine in that order, and dried over anhydrous sodium sulfate. The insolubles were filtered, the filtrate was concentrated under reduced pressure, and thus obtained residue was purified by silica gel chromatography, to obtain 126 mg of 3-[(1R)-1-(2-chlorophenyl)ethoxy]-5-[6-(hydroxymethyl)imidazo[1,2-a] pyrazin-3-yl]thiophene-2-carboxyamide [225-2] (hereinafter, referred to as the compound [225-2]) as a pale yellow oily product.

(6) 7.0 mg of the target compound [225] was obtained as a pale yellow oily product from 12 mg of the compound [225-5] and dimethylamine according to the method of Example 50.

A spectral data of the compound [225] is presented below.
$^1$H-NMR (CDCl$_3$) δ: 9.11 (s, 1H), 8.22 (s, 1H), 7.87 (s, 1H), 7.48 (dd, J=1.6, 7.2 Hz, 1H), 7.43 (dd, J=1.2, 7.6 Hz, 1H), 7.33-7.22 (m, 3H), 6.81 (s, 1H), 6.10-5.82 (brs, 1H), 5.92 (q, J=6.8 Hz, 1H), 3.59 (s, 2H), 2.34 (s, 6H), 1.78 (d, J=6.8 Hz, 3H).

mass: 456, 457 (M+1)$^+$.

Example 226

Synthesis of 3-[(1R)-1-(2-chlorophenyl)ethoxy]-5-(6-{[(2-fluoroethyl)(methyl)amino]methyl}imidazo [1,2-a]pyrazin-3-yl)thiophene-2-carboxyamide [226] (hereinafter, referred to as the compound [226])

2.5 mg of the target compound [226] was obtained as a pale yellow solid from 10 mg of the compound [225-5] and 2-fluoroethylamine according to the methods of Example 215-(3) and (4).

A spectral data of the compound [226] is presented below.
$^1$H-NMR (CDCl$_3$) δ: 9.11 (s, 1H), 8.29 (s, 1H), 7.87 (s, 1H), 7.48 (dd, J=2.0, 7.5 Hz, 1H), 7.43 (dd, J=2.0, 7.5 Hz, 1H), 7.35-7.28 (m, 3H), 6.83 (s, 1H), 5.94 (q, J=8.0 Hz, 1H), 5.85 (brs, 1H), 4.62 (dt, J=5.0, 48 Hz, 2H), 3.79 (dd, J=14, 17 Hz, 2H), 2.87 (dt, J=5.0, 28 Hz, 2H), 2.42 (s, 3H), 1.78 (d, J=8.0 Hz, 3H).
mass: 488, 490 (M+1)$^+$.

Example 227

Synthesis of 3-{(1R)-1-[2-(difluoromethoxy)phenyl]ethoxy}-5-{6-[(dimethylamino)methyl]imidazo[1,2-a]pyrazin-3-yl}thiophene-2-carboxyamide [227] (Hereinafter, referred to as the compound [227])

(1) 2.04 g of 6-({[t-butyl(dimethyl)silyl]oxy}methyl)imidazo[1,2-a]pyrazine [227-1] (hereinafter, referred to as the compound [227-1]) was obtained as a light brown oily product from 865 mg of ethylvinylether and 2.9 g of the compound [225-2] according to the method of Example 152-(7).

(2) 1.01 g of methyl 5-[6-({[t-butyl(dimethyl)silyl]oxy}methyl)imidazo[1,2-a]pyrazin-3-yl]-3-hydroxythiophene-2-carboxylic acid [227-2] (hereinafter, referred to as the compound [227-2]) was obtained as a colorless solid from 1.8 g of the compound [227-1] according to the methods of Example 1-(1), (2), and (3).

(3) 35 mg of 3-{(1R)-1-(2-difluoromethoxy)phenyl}ethoxy}-5-[6-(hydroxymethyl)imidazo[1,2-a]pyrazin-3-yl]thiophene-2-carboxyamide [227-3] (hereinafter, referred to as the compound [227-3]) was obtained as a colorless solid from 100 mg of the compound [227-2] and the compound [196-1] according to the method of Example 20.

(4) The target compound [227] was obtained as a pale colorless solid from 10 mg of the compound [227-3] and dimethylamine according to the method of Example 50.

A spectral data of the compound [227] is presented below.
$^1$H-NMR (CDCl$_3$) δ: 9.11 (s, 1H), 8.24 (s, 1H), 7.86 (s, 1H), 7.52-7.16 (m, 5H), 6.89 (s, 1H), 6.69 (t, J=80 Hz, 1H), 5.89 (q, J=8.0 Hz, 1H), 5.85-5.75 (br, 1H), 3.58 (s, 2H), 2.32 (s, 6H), 1.78 (d, J=8.0 Hz, 3H).
mass: 488 (M+1)$^+$.

Example 228

Synthesis of 3-((1R)-1-{2-chloro-4-[(methylamino)methyl]phenyl}ethoxy)-5-imidazo[1,2-a]pyrazin-3-ylthiophene-2-carboxyamide [228] (hereinafter, referred to as the compound [228])

(1) Methyl 3-hydroxy-5-imidazo[1,2-a]pyrazin-3-yl-thiophene-2-carboxylic acid [228-1] (hereinafter, referred to as the compound [228-1]) was obtained as a dark brown solid from ethylvinylether and 2-aminopyrazine according to the methods of Example 227-(1) and (2).

(2) 50 mg of 3-{(1R)-1-[2-chloro-4-(hydroxymethyl)phenyl]ethoxy}-5-imidazo[1,2-a]pyrazin-3-yl]thiophene-2-carboxyamide [228-2] (hereinafter, referred to as the compound [228-2]) was obtained as a pale yellow oily production from 117 mg of the compound [228-1] and 153 mg of the compound [172-4] according to the method of Example 20.

(3) 6 mg of the target compound [228] was obtained as a pale yellow oily product from 16 mg of the compound [228-2] and methylamine according to the method of Example 50.

A spectral data of the compound [228] is presented below.
$^1$H-NMR (CDCl$_3$) δ: 9.15 (s, 1H), 8.18 (d, J=4.8 Hz, 1H), 7.96 (d, J=4.8 Hz, 1H), 7.89 (s, 1H), 7.42-7.40 (m, 2H), 7.27-7.20 (m, 2H), 6.81 (s, 1H), 5.89 (q, J=6.4 Hz, 1H), 5.85-5.75 (bs, 1H), 3.70 (s, 2H), 2.44 (s, 3H), 1.78 (d, J=6.4 Hz, 3H).
mass: 442, 444 (M+1)$^+$.

Example 229

Synthesis of 3-((1R)-1-{2-chloro-4-[(isopropylamino)methyl]phenyl}ethoxy)-5-imidazo[1,2-a]pyrazin-3-ylthiophene-2-carboxyamide [229] (hereinafter, referred to as the compound [229])

6 mg of the target compound [229] was obtained as a pale yellow oily product from 10 mg of the compound [228-2] and isopropylamine according to the method of Example 50.

A spectral data of the compound [229] is presented below.
$^1$H-NMR (CDCl$_3$) δ: 9.15 (d, J=4.0 Hz, 1H), 8.18 (dd, J=4.0, 8.0 Hz, 1H), 7.96 (d, J=8.0 Hz, 1H), 7.89 (s, 1H), 7.42-7.33 (m, 2H), 7.27-7.20 (m, 2H), 6.81 (s, 1H), 5.89 (q, J=8.0 Hz, 1H), 5.85-5.75 (br, 1H), 3.74 (s, 2H), 2.83 (sept, J=6.0 Hz, 1H), 1.78 (d, J=8.0 Hz, 3H), 1.08 (d, J=6.0 Hz, 6H).
mass: 470, 472 (M+1)$^+$.

Example 230

Synthesis of 3-{(1R)-1-[2-chloro-4-(hydroxymethyl)phenyl]ethoxy}-5-{6-[(4-methylpiperazini-1-yl)methyl]imidazo[1,2-a]pyrazin-3-yl}thiophene-2-carboxyamide [230] (hereinafter, referred to as the compound [230])

(1) 50 mg of methyl 3-((1R)-1-{4-[(benzoyloxy)methyl]-2-chlorophenyl}ethoxy)-5-[6-(hydroxymethyl)imidazo[1,2-a]pyrazin-3-yl]thiophene-2-carboxylic acid [230-1] (hereinafter, referred to as the compound [230-1]) was obtained as a pale yellow oily product from 100 mg of the compound [227-2] and 52 mg of the compound [202-1] according to the method of Example 197-(2).

(2) 30 mg of methyl 3-((1R)-1-{4-[(benzoyloxy)methyl]-2-chlorophenyl}ethoxy)-5-{6-[(4-methylpiperazin-1-yl)methyl]imidazo[1,2-a]pyrazin-3-yl}thiophene-2-carboxylic acid [230-2] (hereinafter, referred to as the compound [230-2]) was obtained as a pale yellow oily product from 50 mg of the compound [230-1] and N-methylpiperazine according to the method of Example 50.

(3) 16.8 mg of the target compound [230] was obtained as a pale yellow solid from 30 mg of the compound [230-2] according to the method of Example 171-(7).

A spectral data of the compound [230] is presented below.
$^1$H-NMR (DMSO-d$_6$) δ: 9.10 (d, J=1.2 Hz, 1H), 8.40 (s, 1H), 8.10 (s, 1H), 7.79 (brs, 1H), 7.62 (d, J=8.0 Hz, 1H), 7.39 (s, 1H), 7.31 (d, J=8.4 Hz, 1H), 7.30 (s, 1H), 7.13 (brs, 1H), 6.02 (q, J=6.4 Hz, 1H), 5.30 (brs, 1H), 4.45 (s, 2H), 3.64 (d, J=4.8 Hz, 2H), 2.53-2.32 (br, 8H), 2.14 (s, 3H), 1.72 (d, J=6.4 Hz, 3H).
mass: 541, 543 (M+1)$^+$.

Example 231

Synthesis of 3-((1R)-1-{2-chloro-4-[(dimethylamino)methyl]phenyl}ethoxy)-5-[6-(hydroxymethyl)imidazo[1,2-a]pyrazin-3-yl]thiophene-2-carboxyamide [231] (hereinafter, referred to as the compound [231])

10.5 mg of the target compound [231] was obtained as a pale yellow solid from 70 mg of the compound [227-2] and 43 mg of the compound [202-1] according to the methods of Example 197-(2), (3), and (4).

A spectral data of the compound [231] is presented below.
$^1$H-NMR (DMSO-$d_6$) δ: 9.13 (d, J=1.2 Hz, 1H), 8.40 (s, 1H), 8.16 (s, 1H), 7.83 (brs, 1H), 7.79 (d, J=8.0 Hz, 1H), 7.76 (d, 1.6 Hz, 1H), 7.60 (dd, J=8.0, 1.4 Hz, 1H), 7.38 (s, 1H), 7.15 (brs, 1H), 6.04 (q, J=6.4 Hz, 1H), 4.66 (d, J=1.8 Hz, 2H) 4.24 (d, J=5.2 Hz, 2H), 2.66 (d, J=4.8 Hz, 6H), 1.74 (d, J=6.4 Hz, 3H).
mass: 486, 488 (M+1)$^+$.

Example 232

Synthesis of 3-((1R)-1-{2-chloro-4-[(dimethylamino)methyl]phenyl}ethoxy)-5-{6-[(methylsulfonyl)methyl]imidazo[1,2-a]pyrazin-3-yl}thiophene-2-carboxyamide [232] (hereinafter, referred to as the compound [232])

9.9 mg of the target compound [232] was obtained as a colorless oily product from 53 mg of the compound [230-1] according to the steps of Example 210-(4), (3), and (1), in that order.

A spectral data of the compound [232] is presented below.
$^1$H-NMR (DMSO-$d_6$) δ: 9.19 (d, J=1.6 Hz, 1H), 8.80 (d, J=1.2 Hz, 1H), 8.18 (s, 1H), 7.85 (brs, 1H), 7.78 (d, J=8.0 Hz, 1H), 7.64 (d, 1.6 Hz, 1H), 7.50 (dd, J=8.3, 1.4 Hz, 1H), 7.35 (s, 1H), 7.17 (brs, 1H), 6.05 (q, J=6.0 Hz, 1H), 4.74 (s, 2H) 4.23 (s, 2H), 3.08 (s, 3H), 2.70 (s, 6H), 1.74 (d, J=6.4 Hz, 3H).
mass: 548, 550 (M+1)$^+$.

Example 233

Synthesis of 4-[(1R)-1-(2-chlorophenyl)ethoxy]-2-{6-[(dimethylamino)methyl]imidazo[1,2-a]pyrazin-3-yl}-1,3-thiazole-5-carboxyamide [233] (hereinafter, referred to as the compound [233])

(1) 10 g of 2-aminopyrazine was dissolved in 600 mL of chloroform, then 18.8 g of N-bromosuccinimide was added, and the mixture was stirred overnight at 0° C. The reaction mixture was added with chloroform, washed with water and saturated brine, and dried over anhydrous sodium sulfate. The insolubles were filtered and the filtrate was concentrated under reduced pressure to obtain 13.5 g of 2-amino-5-bromopyrazine [233-1] (hereinafter, referred to as the compound [233-1]) as a pale yellow solid.

(2) Ethyl 2-(6-bromoimidazo[1,2-a]pyrazin-3-yl)-4-hydroxy-1,3-thiazole-5-carboxylic acid [233-2] (hereinafter, referred to as the compound [233-2]) was obtained as a pale yellow solid from the compound [233-1] according to the methods of Example 211-(1), (2), and (3).

(3) 525 mg of ethyl 2-(6-bromoimidazo[1,2-a]pyrazin-3-yl)-4-[(1R)-1-(2-chlorophenyl)ethoxy]-1,3-thiazole-5-carboxylic acid [233-3] (hereinafter, referred to as the compound [233-3]) was obtained as a pale yellow oily product from 360 mg of the compound [233-2] and 171 mg of (s)-α-1-chlorophenylethyl alcohol according to the method of Example 1-(4).

(4) Ethyl 4-[(1R)-1-(2-chlorophenyl)ethoxy]-2-[6-(hydroxymethyl)imidazo[1,2-a]pyrazin-3-yl]-1,3-thiazole-5-carboxylic acid [233-4] (hereinafter, referred to as the compound [233-4]) was obtained as a brown oily product from the compound [233-3] according to the method of Example 211-(5).

(5) The target compound [233] was obtained as a pale yellow oily product from the compound [233-4] and dimethylamine according to the method of Example 209.

A spectral data of the compound [233] is presented below.
$^1$H-NMR (CDCl$_3$) δ: 9.19 (s, 1H), 9.01 (s, 1H), 8.25 (s, 1H), 7.49 (dd, J=2.0, 8.0 Hz, 1H), 7.43 (dd, J=2.0, 8.0 Hz, 1H), 7.33-7.28 (m, 2H), 7.10 (brs, 1H), 6.61 (q, J=8.0 Hz, 1H), 5.74 (brs, 1H), 3.73 (d, J=14 Hz, 1H), 3.63 (d, J=14 Hz, 1H), 2.37 (s, 6H), 1.83 (d, J=8.0 Hz, 3H).
mass: 457, 459 (M+1)$^+$.

Example 234

Synthesis of 4-((1R)-1-{2-chloro-4-[(methylamino)methyl]phenyl}ethoxy)-2-imidazo[1,2-a]pyrazin-3-yl-1,3-thiazole-5-carboxyamide [234] (hereinafter, referred to as the compound [234])

(1) 127 mg of ethyl 4-hydroxy-2-imidazo[1,2-a]pyrainz-3-yl-1,3-thiazole-5-carboxylic acid [234-1] (hereinafter, referred to as the compound [234-1]) was obtained as a pale yellow solid from 3-methoxyacronitrile and 2.3 g of 2-aminopyrazine according to the methods of Example 211-(1), (2), and (3).

(2) 10 mg of 4-{(1R)-1-[2-chloro-4-(hydroxymethyl)phenyl]ethoxy}-2-imidazo[1,2-a]pyrazin-3-yl-1,3-thiazole-5-carboxyamide [234-2] (hereinafter, referred to as the compound [234-2]) was obtained as a pale yellow oily product from 116 mg of the compound [234-1] and the compound [172-4] according to the method of Example 20.

(3) the target compound [234] was obtained as a colorless solid from 10 mg of the compound [234-2] and methylamine according to the method of Example 50.

A spectral data of the compound [234] is presented below.
$^1$H-NMR (CDCl$_3$) δ: 9.18 (s, 1H), 8.99 (dd, J=4.0, 8.0 Hz, 1H), 8.23 (s, 1H), 8.05 (d, J=4.0 Hz, 1H), 7.45 (s, 1H), 7.39 (d, J=8.0 Hz, 1H), 7.22 (d, J=8.0 Hz, 1H), 7.12-7.06 (br, 1H), 6.49 (q, J=8.0 Hz, 1H), 5.77-5.68 (br, 1H), 3.69 (s, 2H), 2.41 (s, 3H), 1.79 (d, J=8.0 Hz, 3H).
mass: 443, 445 (M+1)$^+$.

Example 235

Synthesis of 4-{(1R)-1-[2-chloro-4-(hydroxymethyl)phenyl]ethoxy}-2-{6-[(4-methylpiperazin-1-yl)methyl]imidazo[1,2-a]pyrazin-3-yl}-1,3-thiazole-5-carboxyamide [235] (hereinafter, referred to as the compound [235])

(1) 823 mg of ethyl 2-(6-bromoimidazo[1,2-a]pyrazin-3-yl)-4-{(1R)-1-[4-({[t-butyl(dimethyl)silyl]oxy}methyl)-2-chlorophenyl]ethoxy}-1,3-thiazole-5-carboxylic acid [235-1] (hereinafter, referred to as the compound [235-1]) was obtained as a brown oily product from 500 mg of the compound [233-2] and 450 mg of the compound [172-4] according to the method of Example 1-(4).

(2) 823 mg of the compound [235-1] was dissolved in 5 mL of N,N-dimethylformamide, then 445 μL of tributyl(vinyl)tin and 150 mg of tetrakis(triphenylphosphine)palladium (0) were added thereto, and the mixture was heated under stirring for 6 hours at 100° C. The reaction solution was added with an aqueous solution (10 mL) of potassium fluoride (4.8 g) and extracted with chloroform. The organic layer was washed with saturated brine and dried over anhydrous sodium sulfate. The insolubles were filtered and the filtrate was concentrated under reduced pressure. The obtained residue was purified by silica gel chromatography, and thus obtained product was dissolved in a solvent of 10 mL of tetrahydrofuran and 10 mL of ethanol. Thereto, 10 mL of a 1N aqueous sodium hydroxide solution was added and stirred overnight. The reaction solution was added with water and extracted with chloroform. The organic layer was washed with saturated brine and dried over anhydrous sodium sulfate. The insolubles were filtered and the filtrate was concentrated under reduced pressure. The obtained residue was dissolved in 20 mL of N,N-dimethylformamide, then 250 mg of ammonium chloride, 250 mg of 1-hydroxybenzotriazole, 640 μL of diisopropylethylamine, and 350 mg of 1-(3-dimethylaminopropyl)-3-ethylcarbodiimide were added thereto, and the mixture was stirred overnight at room temperature. The reaction mixture was added with water and extracted with chloroform. The organic layer was washed with saturated brine and dried over anhydrous sodium sulfate. The insolubles were filtered and the filtrate was concentrated under reduced pressure. The obtained residue was purified by silica gel chromatography, and 152 mg of thus obtained compound was dissolved in 5 mL of tetrahydrofuran, then 60 mg of 4-methylmorpholine N-oxide and 0.10 mL of osmium tetroxide (0.1M aqueous solution) were added, and the mixture was stirred overnight at room temperature. The reaction mixture was added with chloroform, washed with 10% aqueous solution of sodium sulfite and saturated brine in that order, and dried over anhydrous sodium sulfate. The insolubles were filtered and the filtrate was concentrated under reduced pressure. The obtained residue was dissolved in a solvent of 8 mL of methanol and 1 ml of water, then 120 mg of sodium periodate was added, and the mixture was stirred overnight at room temperature. The reaction mixture was added with chloroform, washed with water and saturated brine in that order, and dried over anhydrous sodium sulfate. The insolubles were filtered, the filtrate was concentrated under reduced pressure, and thus obtained residue was purified by silica gel chromatography, to obtain 99 mg of 4-{(1R)-1-[2-chloro-4-(hydroxymethyl)phenyl]ethoxy}-2-(6-formylimidazo[1,2-a]pyrazin-3-yl)-1,3-thiazole-5-carboxyamide [235-2] (hereinafter, referred to as the compound [235-2]) as a brown oily product.

(3) 2.3 mg of the target compound [235] was obtained as a pale yellow solid from 5 mg of the compound [235-2] and N-methylpiperazine according to the method of Example 109.

A spectral data of the compound [235] is presented below.
$^1$H-NMR (CDCl$_3$) δ: 9.17 (s, 1H), 8.62 (s, 1H), 8.24 (s, 1H), 7.85 (s, 1H), 7.41 (d, J=8.0 Hz, 1H), 7.12 (d, J=8.0 Hz, 1H), 7.12 (brs, 1H), 6.37 (q, J=8.0 Hz, 1H), 5.84 (brs, 1H), 4.75 (d, J=16 Hz, 1H), 4.66 (d, J=16 Hz, 1H), 4.08 (d, J=12 Hz, 1H), 3.27 (d, J=12 Hz, 1H), 3.09-1.89 (brs, 8H), 2.49 (brs, 1H), 2.32 (s, 3H), 1.80 (d, J=8.0 Hz, 3H).
mass: 542, 544 (M+1)$^+$.

Example 236

Synthesis of 4-((1R)-1-{2-chloro-4-[(dimethylamino)methyl]phenyl}ethoxy)-2-{6-[(methylsulfonyl)methyl]imidazo[1,2-a]pyrazin-3-yl}-1,3-thiazole-5-carboxyamide [236] (hereinafter, referred to as the compound [236])

(1) 99 mg of ethyl 4-{(1R)-1-[4-({[t-butyl(dimethyl)silyl]oxy}methyl)-2-chlorophenyl]ethoxy}-2-[6-(hydroxymethyl)imidazo[1,2-a]pyrazin-3-yl]-1,3-thiazole-5-carboxylic acid [236-1] (hereinafter, referred to as the compound [236-1]) was obtained as a yellow oily product from 823 mg of the compound [235-1] according to the method of Example 211-(5).

(2) 57 mg of ethyl 4-{(1R)-1-[4-({[t-butyl(dimethyl)silyl]oxy}methyl)-2-chlorophenyl]ethoxy}-2-{6-[(methylsulfonyl)methyl]imidazo[1,2-a]pyrazin-3-yl}-1,3-thiazole-5-carboxylic acid [236-2] (hereinafter, referred to as the compound [236-2]) was obtained as a pale yellow oily product from 99 mg of the compound [236-1] according to the method of Example 205-(1).

(3) 23 mg of 4-{(1R)-1-[2-chloro-4-(hydroxymethyl)phenyl]ethoxy}-2-{6-[(methylsulfonyl)methyl]imidazo[1,2-a]pyrazin-3-yl}-1,3-thiazole-5-carboxyamide [236-3] (hereinafter, referred to as the compound [236-3]) was obtained as a pale yellow oily product from 57 mg of the compound [236-2] according to the method of Example 10-(2).

(4) 4 mg of the target compound [236] was obtained as a pale yellow solid from 5 mg of the compound [23.6-3] and dimethylamine according to the method of Example 50.

A spectral data of the compound [236] is presented below.
$^1$H-NMR (CDCl$_3$) δ: 9.13 (s, 1H), 9.10 (s, 1H), 8.27 (s, 1H), 7.47 (s, 1H), 7.38 (d, J=8.0 Hz, 1H), 7.25 (d, J=8.0 Hz, 1H), 7.12 (brs, 1H), 6.52 (q, J=8.0 Hz, 1H), 5.90 (brs, 1H), 4.52 (s, 2H), 3.39 (dd, J=13, 16 Hz, 2H), 3.08 (s, 3H), 2.22 (s, 6H), 1.80 (d, J=8.0 Hz, 3H).
mass: 549, 551 (M+1)$^+$.

Example 237

Synthesis of 4-((1R)-1-{4-[(t-butylamino)methyl]-2-chlorophenyl}ethoxy)-2-{6-[(methylsulfonyl)methyl]imidazo[1,2-a]pyrazin-3-yl}-1,3-thiazole-5-carboxyamide [237] (hereinafter, referred to as the compound [237])

1.3 mg of the target compound [237] was obtained as a pale yellow solid from 5 mg of the compound [236-3] and t-butylamine according to the method of Example 50.

A spectral data of the compound [237] is presented below.
$^1$H-NMR (CD$_3$OD) δ: 9.12 (s, 1H), 9.00 (s, 1H), 8.43 (s, 1H), 7.58 (s, 1H), 7.55 (d, J=8.0 Hz, 1H), 7.36 (d, J=8.0 Hz, 1H), 6.54 (q, J=8.0 Hz, 1H), 4.82 (d, J=16 Hz, 1H), 4.61 (d, J=16 Hz, 1H), 3.79 (s, 2H), 3.16 (s, 3H), 1.82 (d, J=8.0 Hz, 3H), 1.20 (s, 9H).
mass: 577, 579 (M+1)$^+$.

Example 238

Synthesis of 4-((1R)-1-{2-chloro-4-[(dimethylamino)methyl]phenyl}ethoxy)-2-[6-(hydroxymethyl)imidazo[1,2-a]pyrazin-3-yl]-1,3-thiazole-5-carboxyamide [238] (hereinafter, referred to as the compound [238])

(1) 97 mg of the compound [236-1] was dissolved in 1 mL of chloroform, then 0.03 mL of diisopropylethylamine and 0.02 ml of benzoyl chloride were added under an ice-cold condition, and the mixture was stirred overnight at room temperature. The reaction mixture was added with water and extracted with chloroform. The organic layer was washed with saturated brine and dried over anhydrous sodium sulfate. The insolubles were filtered and the filtrate was concentrated under reduced pressure. The obtained residue was dissolved in 1 mL of tetrahydrofuran, and 0.3 ml of tetrabutylammonium fluoride ((tetrahydrofuran solution, 1M) was added under an ice-cold condition. After the 1 hour stirring at room temperature, the reaction solution was added with water and extracted with chloroform. The organic layer was washed with saturated brine and dried over anhydrous sodium sulfate. The insolubles were filtered and the filtrate was concentrated under reduced pressure. The obtained residue was purified by silica gel column chromatography to obtain 63 mg of ethyl 2-{6-[(benzoyloxy)methyl]imidazo[1,2-a]pyrazin-3-yl}-4-{(1R)-1-[2-chloro-4-(hydroxymethyl)phenyl]ethoxy}-1,3-thiazole-5-carboxylic acid [238-1] (hereinafter, referred to as the compound [238-1]) as a pale yellow oily product.

(2) 6 mg of the target compound [238] was obtained as a pale yellow solid from 10 mg of the compound [238-1] and dimethylamine according to the method of Example 209.

A spectral data of the compound [238] is presented below.
$^1$H-NMR (CDCl$_3$) δ: 9.16 (s, 1H), 8.49 (s, 1H), 8.23 (s, 1H), 7.57 (s, 1H), 7.37 (d, J=8.0 Hz, 1H), 7.13 (d, J=8.0 Hz, 1H), 7.11 (brs, 1H), 6.33 (q, J=8.0 Hz, 1H), 5.82 (brs, 1H), 4.78 (dd, J=12, 20 Hz, 2H), 3.62 (d, J=16 Hz, 1H), 3.12 (d, J=16 Hz, 1H), 2.23 (brs, 1H), 2.07 (s, 6H), 1.84 (d, J=8.0 Hz, 3H).
mass: 487, 489 (M+1)$^+$.

Example 239

Synthesis of 4-{(1R)-1-[2-(difluoromethoxy)-4-(hydroxymethyl)phenyl]ethoxy}-2-{6-[(4-methylpiperazin-1-yl)methyl]imidazo[1,2-a]pyrazin-3-yl}-1,3-thiazole-5-carboxyamide [239] (hereinafter, referred to as the compound [239])

The target compound [239] was obtained as a pale yellow solid from 800 mg of the compound [233-2] and 760 mg of the compound [168-5] according to the method of Example 235.

A spectral data of the compound [239] is presented below.
$^1$H-NMR (CDCl$_3$) δ: 9.16 (s, 1H), 8.81 (s, 1H), 8.23 (s, 1H), 7.53 (s, 1H), 7.43 (d, J=8.0 Hz, 1H), 7.13 (d, J=8.0 Hz, 1H), 7.13 (brs, 1H), 6.80 (dd, J=72, 74 Hz, 1H), 6.48 (brs, 1H), 6.41 (q, J=8.0 Hz, 1H), 4.72 (dd, J=16, 24 Hz, 2H), 3.94 (d, J=12 Hz, 1H), 3.31 (d, J=12 Hz, 1H), 2.59-2.43 (brs, 9H), 2.33 (s, 3H), 1.80 (d, J=8.0 Hz, 3H).
mass: 573 (M+1)$^+$.

Examples 240 and 241

Synthesis of 3-[(1S)-1-(2-chlorophenyl)-2-hydroxyethoxy]-5-imidazo[1,2-a]pyridin-3-ylthiophene-2-carboxyamide [240] (hereinafter, referred to as the compound [240]) and Synthesis of 3-[(2R)-2-(2-chlorophenyl)-2-hydroxyethoxy]-5-imidazo[1,2-a]pyridin-3-ylthiophene-2-carboxyamide [241] (hereinafter, referred to as the compound [241])

(1) 813 mg of lithium aluminum hydride was dissolved in 30 mL of tetrahydrofuran, then 2.0 g of (R)-2-chloromandelic acid was added, and the mixture was stirred for 7 hours at 60° C. After cooling back to room temperature, the reaction solution was added with 2.5 g of anhydrous sodium sulfate decahydrate and stirred for 3 hours. The insolubles were filtered. The filtrate was washed with 2N hydrochloric acid and saturated brine, and dried over anhydrous sodium sulfate. The insolubles were filtered and the filtrate was concentrated under reduced pressure. The obtained residue was dissolved in 20 mL of N,N-dimethylformamide, then 1.5 g of imidazole and 1.19 g of t-butyldimethylsilylchloride were added, and the mixture was stirred overnight at room temperature. The reaction solution was added with ethyl acetate, washed with water and saturated brine, and dried over anhydrous sodium sulfate. The insolubles were filtered and the filtrate was concentrated under reduced pressure. The obtained residue was purified by silica gel chromatography to obtain 1.98 g of a mixture product of (1R)-2-{[t-butyl(dimethyl)silyl]oxy}-1-(2-chlorophenyl)ethanol [240-1] (hereinafter, referred to as the compound [240-1]) and (2R)-2-{[t-butyl(dimethyl)silyl]oxy}-2-(2-chlorophenyl)ethanol [241-1] (hereinafter, referred to as the compound [241-1]) was obtained.

(2) 10.7 mg of the target compound [240] and 2.0 mg of the target compound [241] were obtained as a colorless oily product from 27 mg of the compound [1-3], and the compound [240-1] and the compound [241-1] according to the method of Example 20.

A spectral data of the compound [240] is presented below.
$^1$H-NMR (DMSO-d$_6$) δ: 8.39 (d, J=7.3 Hz, 1H), 7.84 (s, 1H), 7.78 (brs, 1H), 7.67 (d, J=8.8 Hz, 1H), 7.56-7.49 (m, 2H), 7.40-7.33 (m, 4H), 7.06 (m, 1H), 7.00 (s, 1H), 5.86 (m, 1H), 5.59 (t, J=6.3 Hz, 1H), 3.88-3.77 (m, 2H).
mass: 414, 416 (M+1)$^+$.

A spectral data of the compound [241] is presented below.
$^1$H-NMR (DMSO-d$_6$) δ: 8.74 (d, J=6.8 Hz, 1H), 7.96 (s, 1H), 7.71-7.67 (m, 3H), 7.57 (s, 1H), 7.47-7.33 (m, 4H), 7.11-7.06 (m, 2H), 6.20 (d, J=4.9 Hz, 1H), 5.32 (m, 1H), 4.45 (m, 1H), 4.24 (m, 1H).
mass: 414, 416 (M+1)$^+$.

Example 242

Synthesis of 3-[(2-chlorophenyl)(cyclopropyl)methoxy]-5-imidazo[1,2-a]pyridin-3-ylthiophene-2-carboxyamide [242] (hereinafter, referred to as the compound [242])

(1) 233 mg of 2-chlorobenzaldehyde was dissolved in 3 mL of tetrahydrofuran, cyclopropylmagnesium bromide was added dropwise at −78° C. under a nitrogen atmosphere. The mixture was stirred for 4 hours at the same temperature and further stirred overnight at room temperature. The reaction mixture was added with water and 2N hydrochloric acid, and extracted with ethyl acetate. The organic layer was washed with water and saturated brine, and dried over anhydrous sodium sulfate. The insolubles were filtered and the filtrate was concentrated under reduced pressure. The obtained residue was purified by silica gel chromatography to obtain 492 mg of (2-chlorophenyl)(cyclopropyl)methanol [242-1] (hereinafter, referred to as the compound [242-1]) as a pale yellow oily product.

(2) 80 mg of the target compound [242] was obtained as a colorless oily product from 93 mg of the compound [1-3] and 62 mg of the compound [242-1] according to the method of Example 20.

A spectral data of the compound [242] is presented below;
$^1$H-NMR (CDCl$_3$) δ: 8.25 (d, J=6.8 Hz, 1H), 7.73 (s, 1H), 7.66 (d, J=9.3 Hz, 1H), 7.52 (dd, J=1.9, 6.3 Hz, 1H), 7.43 (dd, J=1.5, 7.8 Hz, 1H), 7.35-7.23 (m, 4H), 6.87 (t, J=6.8 Hz, 1H), 6.70 (s, 1H), 5.90 (brs, 1H), 5.31 (d, J=7.8 Hz, 1H), 1.48 (m, 1H), 0.80-0.53 (m, 4H).
mass: 424, 426 (M+1)$^+$.

Example 243

Synthesis of 3-[(1R)-1-(2-chlorophenyl)ethoxy]-5-{6-[(methylsulfonyl)methyl]imidazo[1,2-b]pyridazin-3-yl}thiazole-2-carboxyamide [243] (hereinafter, referred to as the compound [243])

(1) 2.0 g of 3-amino-6-chloropyridazine was dissolved in 16 mL of hydroiodic acid (55% aqueous solution), and the solution was stirred overnight at 100° C. The reaction solution was added with ethyl acetate, and the precipitated solid was taken by filtration and washed with ethyl acetate. Thus obtained solid was dissolved in 60 mL of methanol, and then 650 mg of sodium hydroxide was added and heated for 10 minutes. After cooling back to room temperature, the solvent was distilled off, and 70 mL of water was added to the residue and stirred. The precipitated solid was taken by filtration, washed with water and diethylether, and dried under reduced pressure, to obtain 2.73 g of 3-amino-6-iodopyrazine [243-1] (hereinafter, referred to as the compound [243-1]) as a pale yellow solid.

(2) 212 mg of t-butyl 3-[(1R)-1-(2-chlorophenyl)ethoxy]-5-(6-iodoimidazo[1,2-b]pyridazin-3-yl)thiophene-2-carboxylic acid [243-2] (hereinafter, referred to as the compound [243-2]) was obtained from 275 mg of the compound [152-6Z] and 307 mg of the compound [243-1] according to the method of Example 152-(7).

(3) 66 mg of methyl 3-{5-(butoxycarbonyl)-4-[(1R)-1-(2-chlorophenyl)ethoxy]-2-thienyl}imidazo[1,2-b]pyridazin-6-carboxylic acid [243-3] (hereinafter, referred to as the compound [243-3]) was obtained as a pale yellow solid from 100 mg of the compound [243-2] according to the method of Example 45.

(4) 29 mg of t-butyl 3-[(1R)-1-(2-chlorophenyl)ethoxy]-5-[6-(hydroxymethyl)imidazo[1,2-b]pyridazin-3-yl]thiophene-2-carboxylic acid [243-4] (hereinafter, referred to as the compound [243-4]) was obtained as a pale yellow solid from 66 mg of the compound [243-3] according to the method of Example 48.

(5) 13 mg of 3-[(1R)-1-(2-chlorophenyl)ethoxy]-5-[6-(hydroxymethyl)imidazo[1,2-b]pyridazin-3-yl]thiophene-2-carboxamide [243-5] (hereinafter, referred to as the compound [243-5]) was obtained as a pale yellow solid from 29 mg of the compound [243-4] according to the method of Example 143-(7).

(6) 3 mg of the target compound [243] was obtained as a colorless solid from 6.5 mg of the compound [243-5] according to the method of Example 205-(1).

A spectral data of the compound [243] is presented below.
$^1$H-NMR (CDCl$_3$) δ: 8.10 (s, 1H), 8.07 (d, J=4.0 Hz, 1H), 7.50-7.25 (m, 6H), 7.22 (s, 1H), 5.91 (q, J=6.4 Hz, 1H), 5.85-5.75 (br, 1H), 4.55 (s, 2H), 2.91 (s, 3H), 1.78 (d, J=6.4 Hz, 3H).
mass: 491, 493 (M+1)$^+$.

Example 244

Synthesis of 3-[(1R)-1-(2-chlorophenyl)ethoxy]-5-{6-[(dimethylamino)methyl]imidazo[1,2-b]pyridazin-3-yl}thiophene-2-carboxamide[244] (hereinafter, referred to as the compound [244])

5 mg of the target compound [244] was obtained as a colorless solid from 6.5 mg of the compound [243-5] and dimethylamine according to the method of Example 50.

A spectral data of the compound [244] is presented below.
$^1$H-NMR (CDCl$_3$) δ: 7.99 (s, 1H), 7.93 (d, J=8.0 Hz, 1H), 7.50-7.25 (m, 7H), 5.92 (q, J=8.0 Hz, 1H), 5.85-5.75 (br, 1H), 3.70 (d, J=16.0 Hz, 1H), 3.65 (d, J=16.0 Hz, 1H), 2.32 (s, 6H), 1.78 (d, J=8.0 Hz, 3H).
mass: 456, 458 (M+1)$^+$.

Example 245

Synthesis of 3-[(1R)-1-(2-chlorophenyl)ethoxy]-5-imidazo[1,2-a]pyrimidin-3-ylthiophene-2-carboxamide[245] (hereinafter, referred to as the compound [245])

(1) 8.2 mg of t-butyl 3-[(1R)-1-(2-chlorophenyl)ethoxy]-5-imidazo[1,2-a]pyrimidin-3-ylthiophene-2-carboxylic acid [245-1] (hereinafter, referred to as the compound [245-1]) was obtained as a colorless solid from 30 mg of the compound [152-6Z] and 2-aminopyrimidine according to the method of Example 152-(7).

(2) 4 mg of the target compound [245] was obtained as a colorless solid from 8 mg of the compound [245-1] according to the method of Example 143-(7).

A spectral data of the compound [245] is presented below.
$^1$H-NMR (CDCl$_3$) δ: 8.61-8.58 (m, 2H), 7.94 (s, 1H), 7.48-7.42 (m, 2H), 7.33-7.22 (m, 3H), 6.94 (dd, J=4.4, 6.8 Hz, 1H), 6.74 (s, 1H), 5.91 (q, J=6.4 Hz, 1H), 5.85-5.75 (br, 1H), 1.78 (d, J=6.4 Hz, 3H).
mass: 399, 401 (M+1)$^+$.

Example 246

Synthesis of 3-((1R)-1-{4-[(t-butylamino)methyl]-2-methylphenyl}ethoxy)-5-imidazo[1,2-a]pyridin-3-ylthiophene-2-carboxamide [246] (hereinafter, referred to as the compound [246])

(1) 4.0 g of aluminum chloride was dissolved in 50 mL of methylene chloride, then 2.14 mL of acetylchloride was added, and the mixture was stirred for 15 minutes under a nitrogen atmosphere. The reaction solution was added with 4.0 g of 1-bromo-3-methylbenzene and stirred overnight. A saturated aqueous solution of ammonium chloride was slowly added dropwise until there is no release of CO$_2$ gas. The organic layer was washed with a saturated aqueous solution of ammonium chloride, filtered through celite, and then concentrated under reduced pressure. The obtained residue was purified by silica gel column chromatography to obtain 4.56 g of a mixture product of 1-(4-bromo-2-methylphenyl)ethanone [246-1] (hereinafter, referred to as the compound [246-1]) and 1-(2-bromo-4-methylphenyl)ethanone [246-2] (hereinafter, referred to as the compound [246-2]) as a colorless oily mixture.

(2) 2.65 g of (1S)-1-(4-bromo-2-methylphenyl)ethanol [246-3] (hereinafter, referred to as the compound [246-3]) was obtained as a colorless solid from 4.54 g of the mixture product of the compound [246-1] and the compound [246-2] according to the method of Example 168-(5).

(3) 2.65 g of the compound [246-3] was dissolved in a mixed solvent of 30 mL of methanol and 30 mL of N,N-dimethylformamide, then 4.3 mL of N,N-diisopropylethylamine and 1 g of [1,1'-bis(diphenylphosphino)ferrocene]dichloropalladium (I) dichloromethane adduct were added, and the mixture was stirred overnight at 90° C. under a carbon monoxide atmosphere. The reaction solution was concentrated under reduced pressure and filtered through celite. Thereafter, the obtained residue was extracted with ethyl acetate, washed with water and saturated brine, and dried over anhydrous sodium sulfate. The insolubles were filtered, the filtrate was concentrated under reduced pressure, and thus obtained residue was purified by silica gel column chromatography, to obtain 1.51 g of methyl 4-[(1S)-1-hydroxyethyl]-3-methylbenzoic acid [246-4] (hereinafter, referred to as the compound [246-4]) as a colorless oily product.

(4) 1.51 g of the compound [246-4] was dissolved in 20 mL of tetrahydrofuran, then 680 mg of lithium tetrahydroborate was added, and the mixture was heated overnight at 80° C. under reflux in a nitrogen atmosphere. The reaction solution was cooled back to room temperature, slowly added with water, further added with an aqueous solution of hydrochloric acid, and extracted with ethyl acetate. The resultant was washed with saturated brine and dried over anhydrous sodium sulfate. The insolubles were filtered, the filtrate was concentrated under reduced pressure, and thus obtained residue was purified by silica gel column chromatography, to obtain 1.19 g of (1S)-1-[4-(hydroxymethyl)-2-methylphenyl]ethanol [246-5] (hereinafter, referred to as the compound [246-5]) as a colorless oily product.

(5) 1.19 g of the compound [246-5] was dissolved in 50 mL of chloroform, then 0.90 mL of benzylchloride and 1.9 mL of 2,4,6-collidine were added at 0° C. under a nitrogen atmosphere, and stirred overnight at room temperature. The reaction solution was added with water and extracted with chloroform. The resultant solution was washed with saturated brine and dried over anhydrous sodium sulfate. The insolubles were filtered, the filtrate was concentrated under reduced pressure, and thus obtained residue was purified by silica gel column chromatography, to obtain 1.37 g of 4-[(1S)-1-hydroxyethyl]-3-methylbenzylbenzoate [246-6] (hereinafter, referred to as the compound [246-6]) as a colorless oily product.

(6) 225 mg of methyl 3-((1R)-1 {4-[(benzoyloxy)methyl]-2-methylphenyl}ethoxy]-5-imidazo[1,2-a]pyridin-3-ylthiophene-2-carboxylic acid [246-7] (hereinafter, referred to as the compound [246-7]) was obtained as a yellow oily product from 200 mg of the compound [1-3] and 220 mg of the compound [246-6] according to the method of Example 1-(4).

(7) 11.6 mg of the target compound [246] was obtained as a pale yellow solid from 225 mg of the compound [246-7] and t-butylamine according to the steps of Example 210-(3) and (1), in that order.

A spectral data of the compound [246] is presented below.
$^1$H-NMR (CDCl$_3$) δ: 8.17 (d, J=8.0 Hz, 1H), 7.61-7.51 (m, 3H), 7.35 (d, J=8.0 Hz, 1H), 7.19 (t, J=8.0 Hz, 1H), 7.09 (brs, 1H), 7.00 (t, J=8.0 Hz, 1H), 6.60 (s, 1H), 6.09 (brs, 1H), 5.56 (q, J=8.0 Hz, 1H), 4.03 (s, 1H), 2.38 (s, 3H), 1.62 (d, J=8.0 Hz, 3H), 1.50 (s, 9H).
mass: 463 (M+1)$^+$.

Example 247

Synthesis of 3-((1R)-1-{2-cyclopropyl-4-[(isopropylamino)methyl]phenyl}ethoxy)-5-imidazo[1,2-a]pyridin-3-ylthiophene-2-carboxyamide [247] (hereinafter, referred to as the compound [247])

(1) 10 g of 3-bromo-4-methylbenzoic acid was dissolved in 100 mL of methanol, then 10 mL of thionyl chloride was added at 0° C., and the mixture was heated overnight under reflux. After the reaction mixture is cooled back to room temperature and concentrated, ethyl acetate was added, the resultant was washed with water and dried over anhydrous sodium sulfate. The insolubles were filtered, the filtrate was concentrated under reduced pressure, and thus obtained residue was purified by silica gel column chromatography, to obtain 8.7 g of methyl 3-bromo-4-methyl-benzoic acid [247-1] (hereinafter, referred to as the compound [247-1]) as a colorless oily product.

(2) 8.7 g of the compound [247-1] was dissolved in 50 mL of toluene, then 10 mL of water, 450 mg of palladium acetate (II), 1.06 g of tricyclohexylphosphine, 28.2 g of potassium phosphate, and 4.2 g of cyclopropylboronic acid were added in that order, and the mixture was stirred overnight at 100° C. The reaction mixture was added with a saturated aqueous solution of sodium hydrogen carbonate, then ethyl acetate was added to be washed, and dried over anhydrous sodium sulfate. The insolubles were filtered, the filtrate was concentrated under reduced pressure, and the residue was purified by silica gel chromatography, to obtain 7.5 g of methyl 3-cyclopropyl-4-methyl-benzoic acid [247-2] (hereinafter, referred to as the compound [247-2]) as a pale yellow oily product.

(3) 3.0 g of the compound [247-2] was dissolved in 60 mL of carbon tetrachloride, then 7.0 g of N-bromosuccinimide and 230 mg of benzoyl peroxide were added, and the mixture was stirred overnight at 95° C. The reaction solution was added with sodium sulfite and ethyl acetate, washed with water, and dried over anhydrous sodium sulfate. The insolubles were filtered, the filtrate was concentrated under reduced pressure, and thus obtained residue was purified by silica gel chromatography, to obtain 2.7 g of methyl 3-cyclopropyl-4-monobromomethyl-benzoic acid [247-3] (hereinafter, referred to as the compound [247-3]) as a pale yellow oily product.

(4) 2.7 g of the compound [247-3] dissolved in 100 mL of acetonitrile, then 2.0 g of potassium-acetate and 500 mg of 18-crown-6 were added, and the mixture was stirred for 2 hours at 90° C. The insolubles were filtered and the filtrate was concentrated under reduced pressure. The obtained residue was added with ethyl acetate, washed with water, and dried over anhydrous sodium sulfate. The insolubles were filtered, the filtrate was concentrated under reduced pressure, and thus obtained residue was dissolved in 100 mL of methanol. Thereto, 1.0 g of sodium methoxide was added and stirred overnight. The reaction solution was added with ethyl acetate, washed with water, and dried over anhydrous sodium sulfate. The insolubles were filtered, the filtrate was concentrated under reduced pressure, and thus obtained residue was purified by silica gel chromatography, to obtain 948 mg of methyl 3-cyclopropyl-4-hydroxymethyl-benzoic acid [247-4] (hereinafter, referred to as the compound [247-4]) as a pale yellow oily product.

(5) 886 mg of methyl 3-cyclopropyl-4-formyl-benzoic acid [247-5] (hereinafter, referred to as the compound [247-5]) was obtained as a pale yellow oily product from 948 mg of the compound [247-4] according to the method of Example 151-(2).

(6) 342 mg of methyl 3-cyclopropyl-4-(1-hydroxyethyl)-benzoic acid [247-6] (hereinafter, referred to as the compound [247-6]) was obtained as a pale yellow oily product from 486 mg of the compound [247-5] according to the method of Example 39-(2).

(7) 624 mg of 1-hydroxymethyl-3-cyclopropyl-4-(1-hydroxyethyl)-benzene [247-7] (hereinafter, referred to as the compound [247-7]) was obtained as a pale yellow oily product from 664 mg of the compound [247-6] according to the method of Example 172-(3).

(8) 624 mg of the compound [247-7] was dissolved in 20 mL of chloroform, then 643 μL of 2,4,6-collidine and 377 μL of benzoyl chloride were added at 0° C., then the mixture was stirred for 3 hours at the same temperature. After heating the reaction solution to room temperature, the solution was stirred overnight. Thus obtained solution was added with ethyl acetate, washed with water, and dried over anhydrous sodium sulfate. The insolubles were filtered, the filtrate was concentrated under reduced pressure, and thus obtained residue was purified by silica gel chromatography, to obtain 657 mg of 3-cyclopropyl-4-(1-hydroxyethyl)-benzylbenzoate [247-8] (hereinafter, referred to as the compound [247-8]) as a pale yellow oily product.

(9) 624 mg of 4-acetyl-3-cyclopropylbenzyl benzoate [247-9] (hereinafter, referred to as the compound [247-9]) was obtained as a pale yellow oily product from 657 mg of the compound [247-8] according to the method of Example 151-(2).

(10) 733 mg of 3-cyclopropyl-4-[(1S)-1-hydroxyethyl] benzylbenzoate [247-10] (hereinafter, referred to as the compound [247-10]) was obtained as a pale yellow oily product from 763 mg of the compound [247-9] according to the method of Example 168-(5).

(11) Methyl 3-((1R)-1-{4-[(benzoyloxy)methyl]-2-cyclopropylphenyl}ethoxy)-5-imidazo[1,2-a]pyridin-3-ylthiophene-2-carboxylic acid [247-11] (hereinafter, referred to as the compound [247-11]) was obtained from 124 mg of the compound [247-10] and 115 mg of the compound [1-3] according to the method of Example 1-(4).

(12) 34.8 mg of a hydrochloride salt of the target compound [247] was obtained from the compound [247-11] and isopropylamine according to the method of Example 246-(7). A spectral data of the compound is presented below.
$^1$H-NMR (DMSO-$d_6$) δ: 8.40 (d, J=8.0 Hz, 1H), 7.85 (s, 1H), 7.11 (brs, 1H), 7.68 (d, J=12.0 Hz, 1H), 7.38-7.34 (br, 2H), 7.16 (s, 1H), 7.15 (d, J=12.0 Hz, 1H), 7.09 (brs, 1H), 7.06 (t, J=8.0 Hz, 1H), 6.93 (s, 1H), 6.20 (q, J=4.0 Hz, 1H), 3.57 (s, 2H), 2.61 (spt, J=6.0 Hz, 1H), 2.18 (m, 1H), 1.72 (d, J=8.0 Hz, 3H), 1.0-0.8 (m, 1H), 0.93 (d, J=8.0 Hz, 6H), 0.75-0.55 (m, 4H).
mass: 475 (M+1)$^+$.

Example 248

Synthesis of 3-{(1R)-1-[4-[(t-butylamino)methyl]-2-(difluoromethyl)phenyl]ethoxy}-5-imidazo[1,2-a]pyridin-3-ylthiophene-2-carboxyamide [248] (hereinafter, referred to as the compound [248])

(1) 102 mg of methyl 4-bromo-3-formylbenzoic acid [248-1] (hereinafter, referred to as the compound [248-1]) was obtained as a white solid from 140 mg of methyl 4-bromo-3-methylbenzoic acid according to the method of Example 168-(2).

(2) 4.36 g of the compound [1-3] was dissolved in 100 mL of chloroform, and 5.00 mL of diethylaminosulfur trifluoride was added at 0° C. The reaction mixture was stirred for 4 hours at room temperature under a nitrogen atmosphere, and then poured onto a saturated aqueous solution of sodium hydrogen carbonate. The reaction mixture was extracted with chloroform, and dried over anhydrous magnesium sulfate. The insolubles were filtered, the filtrate was concentrated under reduced pressure, and thus obtained residue was purified by silica gel column chromatography, to obtain 4.35 g of methyl 4-bromo-3-(difluoromethyl)benzoic acid [248-2] (hereinafter, referred to as the compound [248-2]) as a white solid.

(3) 3.38 g of [4-bromo-3-(difluoromethyl)phenyl]methanol [248-3] (hereinafter, referred to as the compound [248-3]) was obtained as a colorless oily product from 4.45 g of the compound [248-2] according to the method of Example 172-(3).

(4) 3.38 g of the compound [248-3] was dissolved in 50 mL of chloroform and cooled to 0° C. Thereafter, the solution was added with 4.00 mL of triethylamine and 2.00 mL of benzoyl chloride. The reaction mixture was stirred for 1 hour at room temperature, then washed with water and saturated brine in that order, and dried over anhydrous magnesium sulfate. The insolubles were filtered, the filtrate was concentrated under reduced pressure, and thus obtained residue was purified by silica gel column chromatography, to obtain 4.92 g of 4-bromo-3-(difluoromethyl)benzylbenzoate [248-4] (hereinafter, referred to as the compound [248-4]) as a colorless oily product.

(5) 4.58 g of the compound [248-4] was dissolved in 60 mL of acetonitrile, 4.85 mL of tributyl(1-ethoxyvinyl)tin and 940 mg of dichlorobis(triphenylphosphine)palladium (II) were added thereto, and the mixture was heated for 13 hours under reflux in an argon atmosphere. The reaction mixture was cooled back to room temperature, and then the insolubles were separated through celite by filtration and the filtrate was concentrated. The residue was purified by chromatography to obtain 3.86 g of 3-(difluoromethyl)-4-(1-ethoxyvinyl)benzylbenzoate [248-5] (hereinafter, referred to as the compound [248-5]) as a colorless oily product.

(6) 4.0 g of the compound [248-5] was dissolved in 90% acetic acid aqueous solution, and the solution was stirred for 1 hour at room temperature. The reaction mixture was concentrated, and then purified by chromatography, to obtain 3.05 g of 4-acetyl-3-(difluoromethyl)benzylbenzoate [248-6] (hereinafter, referred to as the compound [248-6]) as a colorless oily product.

(7) 2.35 g of 3-(difluoromethyl)-4-[(1S)-1-hydroxyethyl]benzylbenzoate [248-7] (hereinafter, referred to as the compound [248-7]) was obtained as a colorless oily product from 3.05 g of the compound [248-6] according to the method of Example 168-(5).

(8) 85 mg of methyl 3-{(1R)-1-[4-[(benzoyloxy)methyl]-2-(difluoromethyl)phenyl]ethoxy}-5-imidazo[1,2-a]pyridin-3-ylthiophene-2-carboxylate [248-8] (hereinafter, referred to as the compound [248-8]) was obtained as a colorless oily product from 40 mg of the compound [248-7] and the compound [1-3] according to the method of Example 1-(4).

(9) 67 mg of 3-{(1R)-1-[2-(difluoromethyl)-4-(hydroxymethyl)phenyl]ethoxy}-5-imidazo[1,2-a]pyridin-3-ylthiophene-2-carboxyamide [248-9] (hereinafter, referred to as the compound [248-9]) was obtained as a colorless amorphous substance from 85 mg of the compound [248-8] according to the method of Example 171-(7).

(10) 16 mg of a hydrochloride salt of the target compound [248] was obtained as a colorless amorphous substance from 22 mg of the compound [248-9] according to the method of Example 50.

A spectral data of the compound [248] is presented below.
$^1$H-NMR (DMSO-$d_6$) δ: 9.18 (brs, 1H), 9.11 (brs, 1H), 8.77 (d, J=7.0 Hz, 1H), 8.37 (s, 1H), 7.95 (d, J=9.0 Hz, 1H), 7.86-7.81 (m, 5H), 7.51 (t, J=54 Hz, 1H), 7.48-7.45 (m, 2H), 7.21 (brs, 1H), 6.11 (q, J=6.5 Hz, 1H), 4.13-4.10 (m, 2H), 1.72 (d, J=6.5 Hz, 3H), 1.35 (s, 9H).
mass: 499 (M+1)$^+$.

Example 249

Synthesis of 3-{(1R)-1-[2-chloro-4-(2-hydroxymethyl)phenyl]ethoxy}-5-imidazo[1,2-a]pyridin-3-ylthiophene-2-carboxyamide [249] (hereinafter, referred to as the compound [249])

(1) 132 mg of oily sodium hydride was washed with hexane, then 5 mL of tetrahydrofuran was added, and 5 mL of a tetrahydrofuran solution containing 870 mg of the compound [172-4] was added dropwise. The solution was stirred for 2 hours at room temperature, then 228 μL of chloromethylmethylether was added thereto, and the mixture was stirred for 4 hours at room temperature and overnight at 50° C. The reaction solution was added with ethyl acetate, washed with water and saturated brine in that order, and dried over anhydrous sodium sulfate. The insolubles were filtered and the filtrate was concentrated under reduced pressure. The residue was dissolved in 5 mL of tetrahydrofuran, then 3 mL of tetrabutylammonium fluoride (tetrahydrofuran solution, 1M) was added, and the mixture was stirred for 1 hour at room temperature. The reaction solution was added with ethyl acetate, washed with water and saturated brine in that order, and dried over anhydrous sodium sulfate. The insolubles were filtered, the filtrate was concentrated under reduced pressure, and thus obtained residue was purified by silica gel chromatography, to obtain 550 mg of {3-chloro-4-[(1S)-1-(methoxymethoxy)ethyl]phenyl}methanol [249-1] (hereinafter, referred to as the compound [249-1]) as a colorless oily product.

(2) 550 mg of the compound [249-1] was dissolved in 10 mL of chloroform, 833 µL of diisopropylethylamine was added, and then 278 µL of methanesulfonyl chloride was added dropwise. The mixture was stirred for 30 minutes at room temperature, added with chloroform, washed with water and saturated brine in that order, and dried over anhydrous sodium sulfate. The insolubles were filtered and the filtrate was concentrated under reduced pressure. The residue was dissolved in 5 mL of N,N-dimethylformamide, and 306 mg of potassium cyanide was added thereto. The mixture was stirred for 5 hours at room temperature, and the reaction solution was added with ethyl acetate, washed with water and saturated brine in that order, and dried over anhydrous sodium sulfate. The insolubles were filtered, the filtrate was concentrated under reduced pressure, and the residue was purified by silica gel chromatography, to obtain 354 mg of {3-chloro-4-[(1S)-1-(methoxymethoxy)ethyl]phenyl}acetonitrile [249-2] (hereinafter, referred to as the compound [249-2]) as a colorless oily product.

(3) The compound [249-2] was dissolved in a solvent of 4 mL of methanol and 1 mL of water, and 1 mL of a 5N aqueous sodium hydroxide solution was added thereto. The mixture was stirred overnight at room temperature and neutralized with a 1N aqueous hydrochloric acid solution. Thereafter, the solution was added with ethyl acetate, washed with water and saturated brine in that order, and dried over anhydrous sodium sulfate. The insolubles were filtered and the filtrate was concentrated under reduced pressure. The residue was dissolved in tetrahydrofuran, and poured onto a tetrahydrofuran solution containing 111 mg of lithium aluminum hydride under a nitrogen atmosphere. The mixture was stirred for 4 hours at 60° C., then water and a 1N aqueous hydrochloric acid solution were added, and extracted with ethyl acetate. The resultant solution was washed with water and saturated brine in that order and dried over anhydrous sodium sulfate. The insolubles were filtered, the filtrate was concentrated under reduced pressure, and the residue was purified by silica gel chromatography, to obtain 241 mg of 2-{3-chloro-4-[(1S)-1-(methoxymethoxy)ethyl]phenyl}ethanol [249-3] (hereinafter, referred to as the compound [249-3]) as a colorless oily product.

(4) 241 mg of the compound [249-3] was dissolved in 5 mL of chloroform, then 241 µL of pyridine and 232 µL of benzoyl chloride were added thereto, and the mixture was stirred for 2 hours at room temperature. The reaction solution was added with ethyl acetate, washed with water and saturated brine in that order, and dried over anhydrous sodium sulfate. The insolubles were filtered and the filtrate was concentrated under reduced pressure. The residue was dissolved in 5 mL of dichloromethane, then 133 µL of bromotrimethylsilane was added, and the mixture was stirred overnight at 0° C. The reaction solution was added with 1 mL of tetrabutylammonium fluoride (tetrahydrofuran solution, 1M) and stirred for 30 minutes at room temperature. The reaction solution was added with ethyl acetate, washed with water and saturated brine, and dried over anhydrous sodium sulfate. The insolubles were filtered, the filtrate was concentrated under reduced pressure, and the residue was purified by silica gel chromatography, to obtain 77 mg of 2-{3-choro-4-[(1S)-1-hydroxyethyl]phenyl}ethylbenzoate [249-4] (hereinafter, referred to as the compound [249-4]) as a colorless oily product.

(5) 40 mg of methyl 3-{(1R)-1-[2-chloro-4-(2-hydroxyethyl)phenyl]ethoxy}-5-imidazo[1,2-a]pyridin-3-ylthiophene-2-carboxylic acid [249-5] (hereinafter, referred to as the compound [249-5]) was obtained as a colorless oily product from 70 mg of the compound [1-3] and 77 mg of the compound [249-4] according to the method of Example 1-(4).

(6) 13 mg of the target compound [249] was obtained as a colorless solid from 40 mg of the compound [249-5] according to the method of Example 171-(7).

A spectral data of the compound [249] is presented below.
$^1$H-NMR (CDCl$_3$) δ: 8.32 (d, J=6.8 Hz, 1H), 7.76 (s, 1H), 7.71 (d, J=9.0 Hz, 1H), 7.40 (d, J=8.0 Hz, 1H), 7.31-7.18 (m, 4H), 6.92 (t, J=6.8 Hz, 1H), 6.76 (s, 1H), 5.87 (q, J=6.3 Hz, 1H), 5.67 (br, 1H), 3.88 (m, 2H), 2.84 (t, J=6.3 Hz, 2H), 1.76 (d, J=6.3 Hz, 3H)
mass: 442, 444 (M+1)$^+$.

Example 250

Synthesis of 3-((1R)-1-{2-chloro-4-[2-(methylamino)ethyl]phenyl}ethoxy)-5-imidazo[1,2-a]pyridin-3-ylthiophene-2-carboxyamide [250] (hereinafter, referred to as the compound [250])

2 mg of the target compound [250] was obtained as a colorless oily product from 6 mg of the compound [249] and methylamine according to the method of Example 50.

A spectral data of the compound [250] is presented below.
$^1$H-NMR (CDCl$_3$) δ: 8.32 (d, J=6.8 Hz, 1H), 7.75 (s, 1H), 7.67 (d, J=9.0 Hz, 1H), 7.39 (d, J=7.8 Hz, 1H), 7.27-7.22 (m, 3H), 7.16 (d, J=6.3 Hz, 1H), 6.89 (t, J=6.8 Hz, 1H), 6.76 (s, 1H), 5.85 (q, J=6.3 Hz, 1H), 5.76 (br, 1H), 2.86-2.77 (m, 4H), 2.43 (s, 3H), 1.75 (d, J=6.3 Hz, 3H).
mass: 455, 457 (M+1)$^+$.

Example 251

Synthesis of 3-{(1R)-1-[2-chloro-4-(3-hydroxypropyl)phenyl]ethoxy}-5-imidazo[1,2-a]pyridin-3-ylthiophene-2-carboxyamide [251] (hereinafter, referred to as the compound [251])

(1) 860 mg of the compound [249-1] was dissolved in 10 mL of chloroform, then 1.3 mL of diisopropylethylamine and 432 µL of methanesulfonyl chloride were added, and the mixture was stirred for 1 hour at room temperature. The reaction solution was added with chloroform, washed with water and saturated brine in that order, and dried over anhydrous sodium sulfate. The insolubles were filtered and the filtrate was concentrated under reduced pressure. The residue was dissolved in 5 mL of N,N-dimethylformamide. At the same time, 160 mg of oily sodium hydride was washed with hexane, 5 mL of tetrahydrofuran was added thereto, and 607 µL of diethyl malonate was added dropwise. The mixture was stirred for 1 hour, the previously prepared N,N-dimethylformamide solution was added dropwise thereto, and the mixture was stirred for 4 hours. The reaction solution was added with ethyl acetate, washed with water and saturated brine in that order, and dried over anhydrous sodium sulfate. The insolubles were filtered, the filtrate was concentrated under reduced pressure, and the residue was purified by silica gel chromatography, to obtain 927 mg of diethyl {3-chloro-4-

[(1S)-1-(methoxymethoxy)ethyl]benzylmalonic acid [251-1] (hereinafter, referred to as the compound [251-1]) as a colorless oily product.

(2) 927 mg of the compound [251-1] was dissolved in 7 mL of dimethylsulfoxide, then 174 mg of sodium chloride and 134 μL of water were added thereto, and the mixture was stirred overnight at 170° C. The reaction solution was added with ethyl acetate, washed with water and saturated brine in that order, and dried over anhydrous sodium sulfate. The insolubles were filtered, the filtrate was concentrated under reduced pressure, and the residue was purified by silica gel chromatography, to obtain 277 mg of ethyl 3-{3-chloro-4-[(1S)-1-hydroxyethyl]phenyl}propanoic acid [251-2] (hereinafter, referred to as the compound [251-2]) and 53 mg of ethyl 3-{3-chloro-4-[(1S)-1-(methoxymethoxy)ethyl]phenyl}propanoic acid [251-3] (hereinafter, referred to as the compound [251-3]).

(3) To a tetrahydrofuran solution containing 76 mg of lithium aluminum hydride, 5 mL of a tetrahydrofuran solution containing 277 mg of the compound [251-2] was slowly added dropwise under a nitrogen atmosphere. The mixture was stirred for 3 hours at 60° C., added with water and a 1N aqueous hydrochloric acid solution, and extracted with ethyl acetate. The organic layer was washed with water and saturated brine in that order, and dried over anhydrous sodium sulfate. The insolubles were filtered, the filtrate was concentrated under reduced pressure, and the residue was dissolved in 5 mL of chloroform. Thereto, 285 μL of collidine and 138 μL of benzoyl chloride were added at 0° C., and the mixture was stirred overnight at room temperature. The reaction solution was added with diethylether, washed with a 1N aqueous hydrochloric acid solution and saturated brine in that order, and dried over anhydrous sodium sulfate. The insolubles were filtered, the filtrate was concentrated under reduced pressure, and the residue was purified by silica gel chromatography, to obtain 241 mg of 3-{3-chloro-4-[(1S)-1-hydroxyethyl]phenyl}propylbenzoate [251-4] (hereinafter, referred to as the compound [251-4]) as a colorless oily product.

(4) 130 mg of the target compound [251] was obtained as a colorless solid from 86 mg of the compound [1-3] and 100 mg of the compound [251-4] according to the methods of Example 249-(5) and (6).

A spectral data of the compound [251] is presented below.
$^1$H-NMR (CDCl$_3$) δ: 8.30 (d, J=7.3 Hz, 1H), 7.75 (s, 1H), 7.67 (d, J=8.8 Hz, 1H), 7.37 (d, J=7.8 Hz, 1H), 7.27-7.23 (m, 3H), 7.15 (m, 1H), 6.90 (m, 1H), 6.76 (s, 1H), 5.89-5.84 (m, 2H), 3.66 (t, J=6.3 Hz, 2H), 2.70 (t, J=7.8 Hz, 2H), 1.87 (m, 2H), 1.75 (d, J=6.3 Hz, 3H).

mass: 456, 458 (M+1)$^+$.

Example 252

Synthesis of 3-((1R)-1-{2-chloro-4-[3-(methylamino)propyl]phenyl}ethoxy)-5-imidazo[1,2-a]pyridin-3-ylthiophene-2-carboxyamide [252] (hereinafter, referred to as the compound [252])

21 mg of the target compound [252] was obtained as a colorless oily product from 30 mg of the compound [251] and methylamine according to the method of Example 50.

A spectral data of the compound [252] is presented below.
$^1$H-NMR (CDCl$_3$) δ: 8.45 (d, J=6.8 Hz, 1H), 7.86 (s, 1H), 7.73 (br, 1H), 7.68 (d, J=8.8 Hz, 1H), 7.55 (d, J=7.8 Hz, 1H), 7.36 (m, 1H), 7.31 (d, J=1.5 Hz, 1H), 7.22 (d, J=7.8 Hz, 1H), 7.17 (s, 1H), 7.07 (m, 2H), 5.99 (q, J=6.3 Hz, 1H), 2.55 (m, 2H), 2.38 (t, J=6.8 Hz, 2H), 2.18 (s, 3H), 1.69 (d, J=6.3 Hz, 3H), 1.61 (m, 2H).

mass: 469, 471 (M+1)$^+$.

Example 253

Synthesis of 3-((1R)-1-{4-[1-(t-butylamino)ethyl]-2-chlorophenyl}ethoxy)-5-imidazo[1,2-a]pyridin-3-ylthiophene-2-carboxyamide [253] (hereinafter, referred to as the compound [253])

(1) 400 mg of methyl 3-{(1R)-1-[2-chloro-4-(hydroxymethyl)phenyl]ethoxy}-5-imidazo[1,2-a]pyridin-3-ylthiophene-2-carboxylic acid [253-1] (hereinafter, referred to as the compound [253-1]) was obtained as a pale yellow oily product from 200 mg of the compound [1-3] and the compound [172-4] according to the method of Example 197-(2).

(2) 0.46 mL of oxalyl dichloride was dissolved in 10 mL of dichloromethane, and 0.77 mL of dimethylsulfoxide was added at −78° C. under a nitrogen atmosphere. After the one and half hours stirring, the reaction solution was added with a solution prepared by dissolving 400 mg of the compound [253-1] to 10 mL of dichloromethane, and the mixture was stirred for 1 hour. Thereto, 2.3 mL of triethylamine was added. The mixture was heated to room temperature, added with a saturated aqueous solution of ammonium chloride, and extracted with chloroform. The organic layer was washed with water and saturated brine, and dried over anhydrous sodium sulfate. The insolubles were filtered, the filtrate was concentrated under reduced pressure, and thus obtained residue was purified by silica gel column chromatography, to obtain 230 mg of methyl 3-[(1R)-1-(2-chloro-4-formylphenyl)ethoxy]-5-imidazo[1,2-a]pyridin-3-ylthiophene-2-carboxylic acid [253-2] (hereinafter, referred to as the compound [253-2]) as a pale yellow oily product.

(3) 158 mg of methyl 3-{(1R)-1-[2-chloro-4-(hydroxyethyl)phenyl]ethoxy}-5-imidazo[1,2-a]pyridin-3-ylthiophene-2-carboxylic acid [253-3] (hereinafter, referred to as the compound [253-3]) was obtained as a pale yellow amorphous from 210 mg of the compound [253-2] according to the method of Example 39-(2).

(4) 2.2 mg of the target compound [253] was obtained as a pale yellow oily product from 33 mg of the compound [253-3] and t-butylamine according to the method of Example 209.

A spectral data of the compound [253] is presented below.
$^1$H-NMR (CDCl$_3$) δ: 8.29 (d, J=7.0 Hz, 1H), 8.27 (d, J=7.0 Hz, 1H), 7.71 (s, 2H), 7.67 (d, J=8.0 Hz, 2H), 7.54-7.52 (m, 2H), 7.40-7.38 (m, 4H), 7.26-7.23 (m, 4H), 6.89 (q, J=8.0 Hz, 2H), 6.76 (s, 1H), 6.75 (s, 1H), 5.88-5.84 (m, 4H), 4.32-4.26 (m, 1H), 3.99-3.93 (m, 1H), 1.75 (d, J=8.0 Hz, 6H), 1.62 (brs, 2H), 1.38-1.28 (brs, 3H), 1.25 (s, 3H), 1.00 (s, 9H), 0.99 (s, 9H).

mass: 497, 499 (M+1)$^+$.

Example 254

Synthesis of 3-{(1R)-1-[4-(1-aminocyclopropyl)-2-chorophenyl]ethoxy}-5-imidazo[1,2-a]pyridin-3-ylthiophene-2-carboxyamide [254] (hereinafter, referred to as the compound [254])

(1) 505 mg of the compound [172-4] was dissolved in 3 mL of chloroform, and then 0.45 mL of triethylamine, 0.23 mL of benzoyl chloride, and 50 mg of 4-dimethylaminopyridine were added in that order. The reaction mixture was stirred overnight, then 0.080 mL of benzoyl chloride was added thereto, and the mixture was heated for 2 hours under reflux. After cooling the reaction mixture back to room temperature, 0.080 mL of N,N-dimethylethane-1,2-diamine was added and stirred for 5 minutes. The reaction mixture was purified by silica gel column chromatography to obtain 615 mg of (1S)-1-[4-({[t-butyl(dimethyl)silyl]oxy}methyl)-2-chlorophenyl]ethylbenzoate [254-1] (hereinafter, referred to as the compound [254-1]) as a colorless oily product.

(2) 615 mg of the compound [254-1] was dissolved in 12 mL of tetrahydrofuran, then tetrabutylammonium fluoride (1.0M, tetrahydrofuran solution, 2.0 mL) was added at room temperature, and the mixture was stirred for 10 minutes. The reaction mixture was added with 0.12 mL of acetic acid, concentrated, and purified by silica gel column chromatography, to obtain 410 mg of (1S)-1-[2-chloro-4-(hydroxymethyl)phenyl]ethylbenzoate [254-2] (hereinafter, referred to as the compound [254-2]) as a colorless oily product.

(3) Oxalyl chloride (2.0M, dichloromethane, 2.0 mL) was diluted with 30 mL of dichloromethane, cooled to −78° C., and then added with a dichloromethane solution (5.0 mL) of 0.43 mL of dimethylsulfoxide. The reaction mixture was stirred for 15 minutes, and then a dichloromethane solution (15 mL) containing 410 mg of the compound [254-2] was added thereto. The mixture was stirred for 1 hour at −78° C., then 1.7 mL of triethylamine was added, and heated to 0° C. over 40 minutes. The reaction mixture was diluted with chloroform, then washed with water and saturated brine, and dried over anhydrous magnesium sulfate. The insolubles were filtered, the filtrate was concentrated, and thus obtained residue was purified by silica gel column chromatography, to obtain 408 mg of (1S)-1-(2-chloro-4-formylphenyl)ethylbenzoate [254-3] (hereinafter, referred to as the compound [254-3]) as a colorless oily product.

(4) 357 mg of the compound [254-3] was dissolved in 5 mL of pyridine, and 100 mg of hydroxylamine hydrochloride was added thereto. The reaction mixture was stirred for 10 minutes at 60° C., cooled to 10° C., and 0.35 mL of methanesulfonyl chloride was added. The reaction mixture was stirred for 30 minutes at 60° C., cooled to room temperature, diluted with ethyl acetate, and washed with 1M hydrochloric acid and saturated brine. The obtained ethyl acetate solution was dried over anhydrous magnesium sulfate, then the insolubles were separated by filtration and concentrated. The obtained residue was purified by silica gel column chromatography to obtain 296 mg of (1S)-1-(2-chloro-4-cyanophenyl)ethylbenzoate [254-4] (hereinafter, referred to as the compound [254-4]) as a colorless oily product.

(5) 295 mg of the compound [254-4] was dissolved in 5 mL of diethylether, cooled to −78° C., and then added with 0.33 mL of titanium tetraisopropoxide. The reaction mixture was added with ethylmagnesium bromide (3.0M, 0.76 mL), stirred for 30 minutes at −78° C., and then heated to room temperature over 30 minutes. The reaction mixture was added with 0.265 mL of a boron trifluoride diethyl ether complex, stirred for 30 minutes at room temperature, and then further added with hydrochloric acid-(1M, 3 mL) and stirred for another 10 minutes. The reaction solution was added with an aqueous solution of sodium hydroxide (1M), adjusted to pH 9, extracted with ethyl acetate, and dried over anhydrous sodium sulfate. The insolubles were separated by filtration, the filtrate was concentrated, and the residue was purified by chromatography, to obtain 192 mg of (1S)-1-[4-(1-aminocyclopropyl)-2-chlorophenyl]ethylbenzoate [254-5] (hereinafter, referred to as the compound [254-5]) as a colorless oily product.

(6) 0.20 mL of triethylamine, 0.20 g of di-t-butyldicarbonate, and 50 mg of 4-(dimethylamino)pyridine were added to the mixture of 180 mg of the compound [254-5], 4 mL of tetrahydrofuran, and 4 mL of chloroform, and the mixture solution was stirred for 2 hours at room temperature. The reaction mixture was diluted with chloroform, washed with water and saturated brine, and dried over anhydrous magnesium sulfate. The insolubles were filtered and then concentrated. The obtained residue was purified by silica gel column chromatography to obtain 65 mg of (1S)-1-(4-{1-[(t-butoxycarbonyl)amino]cyclopropyl}-2-chlorophenyl)ethylbenzoate [254-6] (hereinafter, referred to as the compound [254-6]) as a colorless oily product.

(7) A mixture of 65 mg of the compound [254-6], 1 mL of tetrahydrofuran, 1 mL of methanol, and an aqueous solution of sodium hydroxide (1M, 1 mL) was stirred for 1 hour at room temperature, then the reaction mixture was diluted with ethyl acetate, and washed with water and saturated brine. The obtained ethyl acetate solution was dried over anhydrous magnesium sulfate, the insolubles were filtered and concentrated, and the residue was purified by silica gel column chromatography, to obtain 45 mg of t-butyl(1-{3-chloro-4-[(1S)-hydroxyethyl]phenyl}cyclopropyl)carbamate [254-7] as a white solid.

(8) 78 mg of methyl 3-{(1R)-1-(4-{1-[(t-butoxycarbonyl)amino]cyclopropyl}-2-chlorophenyl)ethoxy}-5-imidazo[1,2-a]pyridin-3-ylthiophene-2-carboxylate [254-8] (hereinafter, referred to as the compound [254-8]) was obtained as a white solid from 43 mg of the compound [254-7] according to the method of Example 1-(4).

(9) 84 mg of t-butyl {1-[4-((1R)-1-{[2-(aminocarbonyl)-5-imidazo[1,2-a]pyridin-3-ylthienyl]oxy}ethyl)-3-chlorophenyl]cyclopropyl}carbamate [254-9] (hereinafter, referred to as the compound [254-9]) was obtained as a white solid from 78 mg of the compound [254-8] according to the method of Example 171-(7).

(10) 84 mg of the compound [254-9] was dissolved in 4 mL of chloroform, then 4 mL of trifluoroacetic acid was added thereto, and the mixture was stirred for 1.5 hours at room temperature. The reaction mixture was concentrated. Thereafter, the residue was dissolved in a mixed solvent of 1 mL of chloroform and 0.1 mL of methanol, and added with 0.10 mL of triethyl amine. The mixture was stirred and then concentrated. The obtained residue was purified by silica gel column chromatography, then hydrochloric acid (methanol solution, 1 mL) was added thereto, and the resultant was concentrated, to obtain 5 mg of a dihydrochloride salt of the target compound [254] as a white solid.

A spectral data of the compound [254] is presented below.

$^1$H-NMR (DMSO-$d_6$) δ: 9.00 (br, 3H), 8.77 (d, J=7.0 Hz, 1H), 8.38 (s, 1H), 7.96 (d, J=9.6 Hz, 1H), 7.88-7.84 (m, 2H), 7.70 (d, J=8.0 Hz, 1H), 7.56 (d, J=2.0 Hz, 1H), 7.47 (t, J=7.0 Hz, 1H), 7.42 (dd, J=2.0, 8.0 Hz, 1H), 7.37 (s, 1H), 7.19 (brs, 1H), 6.04 (q, J=6.4 Hz, 1H), 1.71 (d, J=6.4 Hz, 3H), 1.38 (br, 2H)), 1.23 (br, 2H).

mass: 453, 455 (M+1)$^+$.

INDUSTRIAL APPLICABILITY

The compound according to the present invention has an excellent inhibitory effect against PLK1 and cell proliferation thus is expected to serve as a useful antitumor agent in the field of medicine.

The invention claimed is:
1. A compound of Formula I:

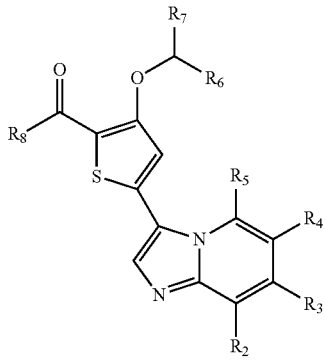

(I)

wherein:
R$_2$, R$_3$, R$_4$, and R$_5$, which may be the same or different, are each a hydrogen atom or —Y$_1$—Y$_2$—Y$_3$—Y$_4$, wherein
Y$_1$ is a single bond, CH$_2$, CH(CH$_3$), O, S, SO, SO$_2$, CO, CONH, or NHCO;
Y$_2$ is a single bond or (CW$_i$W$_i$')$_n$, wherein n is an integer of 1 to 4; i is an integer of 1 to n; and (CW$_i$W$_i$')$_n$ represents, (CW$_1$W$_1$') when n is equal to 1, (CW$_1$W$_1$')—(CW$_2$W$_2$') when n is equal to 2, (CW$_1$W$_1$')—(CW$_2$W$_2$')—(CW$_3$W$_3$') when n is equal to 3, and (CW$_1$W$_1$')—(CW$_2$W$_2$')—(CW$_3$W$_3$')—(CW$_4$W$_4$') when n is equal to 4, where W$_1$, W$_2$, W$_3$, and W$_4$, and W$_1$', W$_2$', W$_3$', and W$_4$', which may be the same or different, are each a hydrogen atom, a lower alkyl group, or a substituent selected from <substituent group β$_1$>;
Y$_3$ is a single bond, NH, NR$_a$, S, O, or COO, wherein R$_a$ is a substituent selected from the <substituent group β$_1$>, or a lower alkyl group which may be substituted with one or more of the same or different substituents selected from the <substituent group β$_1$>;
Y$_4$ is a hydrogen atom, a substituent selected from the <substituent group β$_1$>, a lower alkyl group which may be substituted with one or more of the same or different substituents selected from the <substituent group β$_1$>, R$_b$C(=O)NR$_c$—(CHZ$_1$)$_p$—, NR$_d$R$_d$'-(CHZ$_2$)$_q$—C(=O)NR$_c$—(CHZ$_1$)$_p$—, NR$_e$R$_e$'—(CHZ$_3$)$_r$—C(=O)—(CHZ$_1$)$_p$—, a cycloalkyl group, an aliphatic heterocyclic group, an aryl group, an aralkyl group, a heteroaryl group, or a lower alkyl substituted with the heteroaryl group, wherein
the cycloalkyl group, the aliphatic heterocyclic group, the aryl group, the aralkyl group, and the heteroaryl group may be substituted with one or more of the same or different substituents selected from the following:
1) a lower alkyl group,
2) a substituent selected from the <substituent group β$_1$>,
3) a lower alkyl group substituted with a substituent selected from the <substituent group β$_1$>,
4) R$_b$C(=O)NR$_c$—(CHZ$_1$)$_p$—,
5) NR$_d$R$_d$'—(CHZ$_2$)$_q$—C(=O)NR$_c$—(CHZ$_1$)$_p$—,
6) NR$_e$R$_e$'—(CHZ$_3$)$_r$—C(=O)—(CHZ$_1$)$_p$—, and
7) a cycloalkyl group which may be substituted, and two hydrogen atoms, which bind to the same carbon atom, in the aliphatic heterocyclic group may be substituted with an oxo group;

p, q, and r, which may be the same or different, are each 0, 1, or 2;
Z$_1$, Z$_2$, and Z$_3$, which may be the same or different, are each a hydrogen atom or a lower alkyl group;
R$_b$ is a substituent selected from <substituent group β$_2$>, a lower alkyl group which may be substituted with one or more of the same or different substituents selected from the <substituent group β$_2$>, or a cycloalkyl group which may be substituted;
R$_c$ is a hydrogen atom, a substituent selected from the <substituent group β$_2$>, or a lower alkyl group which may be substituted with one or more of the same or different substituents selected from the <substituent group β$_2$>;
R$_d$ and R$_d$', which may be the same or different, are each a hydrogen atom or a lower alkyl group; and
R$_e$ and R$_e$' are each a hydrogen atom or a lower alkyl group, or alternatively R$_e$ and R$_e$', together with the nitrogen atom to which they bind, form an aliphatic heterocyclic group selected from a pyrrolidinyl group, a piperidinyl group, and a piperazinyl group;
provided, however, that:
when X$_i$ (where i is one of 2, 3, 4 and 5) is a nitrogen atom, the corresponding R$_i$ (where i is one of 2, 3, 4 and 5) together with the X$_i$ forms a nitrogen atom;
R$_6$ is a hydrogen atom, a substituent selected from the <substituent group β$_1$>, a lower alkyl group which may be substituted with one or more of the same or different substituents selected from the <substituent group β$_1$>, or a cycloalkyl group;
R$_7$ is a phenyl group, wherein the phenyl group may be substituted with one or more of the same or different substituents selected from the following:
1) a substituent selected from the <substituent γ$_1$>;
2) a lower alkyl group which may be substituted with one or more of the same or different substituents selected from the <substituent γ$_4$>, wherein the lower alkyl group may be substituted with one or more halogen atom(s), and two lower alkyl groups, which bind to the same carbon atom, in the lower alkyl group may together form a ring structure having 3 to 5 carbon atoms;
3) a lower alkyl group substituted with an aliphatic heterocyclic group selected from the <substituent γ$_2$> optionally substituted with one or more of, the same or different substituents selected from the <substituent group γ$_1$> and/or a lower alkyl group;
4) —(CH$_2$)$_k$—NR$_9$R$_{10}$, wherein
k is 1, 2, or 3;
R$_9$ is a hydrogen atom or a lower alkyl group; and
R$_{10}$ is a hydrogen atom, a lower alkyl group which may be substituted with one or more of the same or different substituents selected from the <substituent group γ$_1$>, or a cycloalkyl group having 5 to 6 carbon atoms, wherein the cycloalkyl group may be substituted with one or more of, the same or different substituents selected from the <substituent group γ$_1$> and/or a lower alkyl group which may be substituted with the same or different substituents selected from the <substituent group γ$_1$>; and
5) —O—R$_{11}$, wherein R$_{11}$ is —(CH$_2$)$_l$—NR$_{12}$R$_{13}$, wherein
l is 2 or 3; and
R$_{12}$ and R$_{13}$, which may be the same or different, are each a hydrogen atom, a lower alkyl group, or a lower alkyl group substituted with one or more of the same or different substituents selected from the <substituent group $\gamma_1$>, wherein the <substituent group $\gamma_1$>, <substituent group $\gamma_2$>, and <substituent group $\gamma_4$> are defined as follows:

<substituent group $\gamma_1$>: a halogen atom, a hydroxy group, a formyl group, a nitro group, a cyano group, an amino group, a lower alkylamino group, a dilower alkylamino group, a lower alkoxy group which may be substituted with one or more halogen atom(s), a lower alkylsulfonyl group, and a carboxyl group, <substituent group $\gamma_2$>: a pyrrolidinyl group, a piperidinyl group, and a piperazinyl group; and <substituent group $\gamma_4$>: a halogen atom, a hydroxy group, a formyl group, a nitro group, a cyano group, a lower alkoxy group which may be substituted with one or more halogen atom(s), a lower alkylsulfonyl group, and a carboxyl group;

$R_8$ is an amino group or a hydroxy group; and the <substituent group a>, the <substituent group $\beta_1$>, and the <substituent group $\beta_2$> are defined as follows:

<substituent group $\alpha$>: a halogen atom, a hydroxy group, and an amino group, <substituent group $\beta_1$>: a halogen atom, a hydroxy group, a nitro group, a cyano group, a formyl group, an amino group, a lower alkylamino group, a dilower alkylamino group, a lower alkylsulfonyl group, a lower alkylsulfonylamino group, an aminosulfonyl group, an N-lower alkylaminosulfonyl group, an N,N-dilower alkylaminosulfonyl group, a lower alkoxy group, a lower alkoxycarbonyl group, a lower alkanoyl group, and a carboxyl group, <substituent group $\beta_2$>: a halogen atom, a hydroxy group, a nitro group, a cyano group, a formyl group, a lower alkoxy group, a lower alkoxycarbonyl group, a lower alkylsulfonyl group, and a lower alkanoyl group, or a pharmaceutically acceptable salt or ester thereof.

2. The compound according to claim 1 or a pharmaceutically acceptable salt or ester thereof, wherein $R_2$ and $R_5$, which may be the same or different, are each a hydrogen atom, a halogen atom, a hydroxyl group, an amino group, or a methyl group which may be substituted with 1 to 3 halogen atom(s).

3. The compound according to claim 2 or a pharmaceutically acceptable salt or ester thereof, wherein $R_8$ is an amino group.

4. The compound according to claim 3 or a pharmaceutically acceptable salt or ester thereof, wherein $R_6$ is a hydrogen atom or a methyl group.

5. The compound according to claim 4 or a pharmaceutically acceptable salt or ester thereof, wherein $R_7$ is a phenyl group substituted at least at the $2^{nd}$ position with a halogen atom, a difluoromethoxy group, or a trifluoromethyl group.

6. The compound according to claim 5 or a pharmaceutically acceptable salt or ester thereof, wherein $R_3$ and $R_4$, which may be the same or different, are each a hydrogen atom or —$Y_1$—$Y_2$—$Y_3$—$Y_4$ wherein:

$Y_1$ is a single bond, $CH_2$, or O;

$Y_2$ is a single bond or $(CW_iW_i')_n$, wherein $W_i$, $W_i'$, and n are the same as defined above;

$Y_3$ is a single bond, NH, or $N(CH_3)$;

$Y_4$ is a substituent selected from the <substituent group $\beta_1$>; a lower alkyl group which may be substituted with one or more of the same or different substituents selected from the <substituent group $\beta_1$>; an aliphatic heterocyclic group selected from an azetidyl group, a pyrrolidinyl group, a piperidinyl group, a piperazinyl group, and a morpholino group; a heteroaryl group selected from a pyrrolyl group, an imidazolyl group, a pyridyl group, and a pyrimidinyl group; or a lower alkyl group substituted with the heteroaryl group, wherein the aliphatic heterocyclic group and the heteroaryl group may be substituted with one or more of the same or different substituents selected from the following:

1) a lower alkyl group,
2) a substituent selected from the <substituent group $\beta_1$>, and
3) a lower alkyl group substituted with a substituent selected from the <substituent group $\beta_1$>; and wherein the <substituent group $\beta_1$> is: a halogen atom, a hydroxy group, an amino group, a cyano group, a lower alkylamino group, a dilower alkylamino group, a lower alkylsulfonyl group, and a carboxyl group.

7. The compound according to claim 6 or a pharmaceutically acceptable salt or ester thereof, wherein $R_7$ is a phenyl group further substituted at the $4^{th}$ position with —$CH_2OH$ or —$CH_2$—$NR_9R_{10}$, wherein $R_9$ is a hydrogen atom or a lower alkyl group; and $R_{10}$ is a lower alkyl group which may be substituted with a hydroxy group.

8. The compound according to claim 7 or a pharmaceutically acceptable salt or ester thereof, wherein $R_2$, $R_3$, and $R_5$ are all hydrogen atoms;

$R_4$ is a hydrogen atom, a substituent selected from the <substituent group $\beta_1$>, or a lower alkyl group which may be substituted with one or more of the same or different substituents selected from the <substituent group $\beta_1$>; and the <substituent group $\beta_1$> is a hydroxy group, an amino group, a cyano group, and a methylsulfonyl group.

9. A compound selected from the group consisting of
(a) 3-[1-(2-chlorophenyl)ethoxy]-5-imidazo[1,2-a]pyridin-3-ylthiophene-2-carboxyamide,
(b) 5-imidazo[1,2-a]pyridin-3-yl-3-[1-(2-nitrophenyl)ethoxy]thiophene-2-carboxyamide,
(c) 3-[(1R)-1-(2-chlorophenyl)ethoxy]-5-[6-(2-hydroxyethoxy)imidazo[1,2-a]pyridin-3-yl]thiophene-2-carboxyamide,
(d) 3-[(1R)-1-(2-chlorophenyl)ethoxy]-5-[6-(hydroxymethyl)imidazo[1,2-a]pyridin-3-yl]thiophene-2-carboxyamide,
(e) 3-[(1R)-1-(2-chlorophenyl)ethoxy]-5-[6-(piperazin-1-ylmethyl)imidazo[1,2-a]pyridin-3-yl]thiophene-2-carboxyamide,
(f) 3-{1-[2-chloro-4-(hydroxymethyl)phenyl]ethoxy}-5-imidazo[1,2-a]pyridin-3-ylthiophen-2-carboxyamide,
(g) 3-[(1R)-1-(2-chloro-4-{[(2-hydroxy-1,1-dimethylethyl)amino]methyl}phenyl)ethoxy]-5-imidazo[1,2-a]pyridin-3-ylthiophene-2-carboxyamide,
(h) 3-((1R)-1-{4-[(t-butylamino)methyl]-2-chlorophenyl}ethoxy)-5-imidazo[1,2-a]pyridin-3-ylthiophene-2-carboxyamide,
(i) 3-{(1R)-1-[4-[(t-butylamino)methyl]-2-(difluoromethoxy)phenyl]ethoxy}-5-imidazo[1,2-a]pyridin-3-ylthiophene-2-carboxyamide,
(j) 3-[(1R)-1-(2-(difluoromethoxy)-4-{[(2-hydroxy-1,1-dimethylethyl)amino]methyl}phenyl)ethoxy]-5-imidazo[1,2-a]pyridin-3-ylthiophene-2-carboxyamide,
(k) 3-[(1R)-1-(2-chloro-4-{[(2-hydroxy-1,1-dimethylethyl)amino]methyl}phenyl)ethoxy]-5-(6-cyanoimidazo[1,2-a]pyridin-3-yl)thiophene-2-carboxyamide, (l) 3-((1R)-1-{4-[(t-butylamino)methyl]-2-chlorophenyl}ethoxy)-5-(6-cyanoimidazo[1,2-a]pyridin-3-yl)thiophene-2-carboxyamide,
(m) 3-{(1R)-1-[4-[(t-butylamino)methyl]-2-(difluoromethoxy)phenyl]ethoxy}-5-(6-cyanoimidazo[1,2-a]pyridin-3-yl)thiophene-2-carboxyamide,
(n) 3-((1R)-1-{2-chloro-4-[(methylamino)methyl]phenyl}ethoxy)-5-[6-(hydroxymethyl)imidazo[1,2-a]pyridin-3-yl]thiophene-2-carboxyamide,
(o) 3-((1R)-1-{4-[(t-butylamino)methyl]-2-chlorophenyl}ethoxy)-5-[6-(hydroxymethyl)imidazo[1,2-a]pyridin-3-yl]thiophene-2-carboxyamide,
(p) 3-{(1R)-1-[4-[(t-butylamino)methyl]-2-(difluoromethoxy)phenyl]ethoxy}-5-[6-(hydroxymethyl)imidazo[1,2-a]pyridin-3-yl]thiophene-2-carboxyamide,
(q) 3-[(1R)-1-(2-chlorophenyl)ethoxy]-5-{6-[(methylsulfonyl)methyl]imidazo[1,2-a]pyridin-3-yl}thiophene-2-carboxyamide,
(r) 3-((1R)-1-{2-chloro-4-[(dimethylamino)methyl]phenyl}ethoxy)-5-{6-[(methylsulfonyl)methyl]imidazo[1,2-a]pyridin-3-yl}thiophene-2-carboxyamide,
(s) 3-((1R)-1-{4-[(t-butylamino)methyl]-2-chlorophenyl}ethoxy)-5-{6-[(methylsulfonyl)methyl]imidazo[1,2-a]pyridin-3-yl}thiophene-2-carboxyamide,
(w) 3-{(1R)-1-[2-chloro-4-(hydroxymethyl)phenyl]ethoxy}-5-{6-[(4-methylpiperazin-1-yl)methyl]imidazo[1,2-a]pyrazin-3-yl}thiophene-2-carboxyamide or a pharmaceutically acceptable salt of ester thereof.

10. A pharmaceutical composition comprising, together with a pharmaceutically acceptable carrier or diluent, at least one compound of claim 1 or a pharmaceutically acceptable salt or ester thereof as an active ingredient.

* * * * *